(12) United States Patent
Gao et al.

(10) Patent No.: US 9,511,152 B2
(45) Date of Patent: Dec. 6, 2016

(54) MULTICOLORED PH-ACTIVATABLE FLUORESCENCE NANOPLATFORM

(71) Applicant: The Board of Regents of the University of Texas System, Austin, TX (US)

(72) Inventors: Jinming Gao, Dallas, TX (US); Kejin Zhou, Dallas, TX (US); Baran D. Sumer, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 661 days.

(21) Appl. No.: 13/827,197

(22) Filed: Mar. 14, 2013

(65) Prior Publication Data

US 2013/0330278 A1 Dec. 12, 2013

Related U.S. Application Data

(60) Provisional application No. 61/620,774, filed on Apr. 5, 2012.

(51) Int. Cl.
*A61K 9/14* (2006.01)
*A61K 49/00* (2006.01)
*G01N 21/64* (2006.01)

(52) U.S. Cl.
CPC ....... *A61K 49/0054* (2013.01); *A61K 49/0032* (2013.01); *A61K 49/0082* (2013.01); *G01N 21/6486* (2013.01)

(58) Field of Classification Search
CPC .................................................. A61K 49/0054
See application file for complete search history.

(56) References Cited

U.S. PATENT DOCUMENTS

| | | |
|---|---|---|
| 2006/0034796 A1 | 2/2006 | Ashwell et al. |
| 2006/0229235 A1 | 10/2006 | Peterson |
| 2008/0081075 A1 | 4/2008 | Hsiue et al. |
| 2009/0317802 A1 | 12/2009 | Bhatia et al. |
| 2010/0069726 A1 | 3/2010 | Levinson |
| 2010/0303731 A1 | 12/2010 | Hyde et al. |
| 2010/0311903 A1 | 12/2010 | Rajagopalan |

FOREIGN PATENT DOCUMENTS

| | | |
|---|---|---|
| WO | WO 03/074026 | 9/2003 |
| WO | WO 2009/138473 | 11/2009 |
| WO | WO 2011/097384 | 8/2011 |
| WO | WO 2011-113616 | 9/2011 |
| WO | WO 2012/039741 | 3/2012 |
| WO | WO 2012/039855 | 3/2012 |
| WO | WO 2012/040513 | 3/2012 |

OTHER PUBLICATIONS

PCT International Search Report and Written Opinion in International application No. PCT/US2013/035050, dated Sep. 10, 2013.
Ding et al., "Nitrogen-doped carbon dots derived from polyvinyl pyrrolidone and their multicolor cell imaging," *Nanotechnology*, 25:205604, 2014.
European Extended Search Report issued in European Application No. 13772672.5, mailed Oct. 9, 2015.
Huang et al., "Multi-chromatic pH-activatable $^{19}$F-MRI nanoprobes with binary ON/OFF pH transitions and chemical-shift barcodes," *Angew. Chem. Int. Ed.*, 52:8074-8078, 2013.
Sharker et al., "Photo- and pH-tunable multicolor fluorescent nanoparticle-based spiropyran-and BODIPY-conjugated polymer with grapheme oxide," *Chem. Asian J.*, 9:2921-2927, 2014.
Zhou et al., "Multicolored pH-tunable and activatable fluorescence nanoplatform responsive to physiologic pH stimuli," *Journal of the American Chemical Society*, 134:7803-7811, 2012.
Alani et al., "Polymeric micelles for the pH-dependent controlled, continuous low dose release of paclitaxel," *Biomaterials*, 31:1765-772, 2010.
Albertazzi et al., "Delivery and subcellular targeting of dendrimer-based fluorescent pH sensors in living cells," *J Am Chem Soc.*, 132:18158-67, 2010.
Almutairi et al., "Biodegradable pH-sensing dendritic nanoprobes for near-infrared fluorescence lifetime and intensity imaging," *J Am Chem Soc.*, 130:444-5, 2008.
Bae et al., "Design of environment-sensitive supramolecular assemblies for intracellular drug delivery: polymeric micelles that are responsive to intracellular pH change," *Angew Chem Int Ed Engl.*, 42:4640-4643, 2003.
Bae et al., "Multifunctional polymeric micelles with folate-mediated cancer cell targeting and pH-triggered drug releasing properties for active intracellular drug delivery," *Mol BioSyst.*, 1:242-250, 2005.
Bae et al., "Preparation and Biological Characterization of Polymeric Micelle Drug Carriers with Intracellular pH-Triggered Drug Release Property: Tumor Permeability, Controlled Subcellular Drug Distribution, and Enhanced in Vivo Antitumor Efficacy," *Bioconjug Chem.*, 16:122-30, 2005.
Benjaminsen et al., "Evaluating nanoparticle sensor design for intracellular pH measurements," *ACS Nano*, 5:5864-73, 2011.
Blanco et al., "β-Lapachone-containing PEG-PLA Polymer Micelles as Novel Nanotherapeutics against NQO1-Overexpressing Tumor Cells," *J Control Release*, 122(3):365-374, 2007.
Braunecker et al., "Controlled/living radical polymerization: Features, developments, and perspectives," *Progress in Polymer Science*, 32(1):93-146, 2007.
Bütün et al., "Synthesis and aqueous solution properties of near-monodisperse tertiary amine methacrylate homopolymers and diblock copolymers," *Polymer*, 42:5993-6008, 2001.
Casey et al., "Sensors and regulators of intracellular pH," *Nat Rev Mol Cell Biol.*, 11:50-61, 2010.

(Continued)

*Primary Examiner* — Paul Dickinson
(74) *Attorney, Agent, or Firm* — Parker Highlander PLLC

(57) ABSTRACT

The present invention relates to pH-tunable, highly activatable multicolored fluorescent nanoplatforms and methods of using the nanoplatforms in a variety of applications including, but not limited to, investigating fundamental cell physiological processes such as pH regulation in endocytic vesicles, endosome/lysosome maturation, and effect of pH on receptor cycling and trafficking of subcellular organelles.

31 Claims, 77 Drawing Sheets
(59 of 77 Drawing Sheet(s) Filed in Color)

(56) References Cited

OTHER PUBLICATIONS

Chenna et al., "Preparation and cytotoxicity toward cancer cells of mono(arylimino) derivatives of beta-lapachone," *J Med Chem.*, 44:2486-2489, 2001.
De Silva et al., "Signaling recognition events with fluorescent sensors and switches," *Chem Rev.*, 97:1515-1566, 1997.
Diaz-Fernandez et al., "Micelles for the self-assembly of "off-on-off" fluorescent sensors for pH windows," *Chemistry—A European Journal*, 12(3):921-930, 2006.
Ghosh et al., "Simultaneous and reversible functionalization of copolymers for biological applications," *Macromolecules*, 39:5595-5597, 2006.
Giacomelli et al., "Specific interactions improve the loading capacity of block copolymer micelles in aqueous media," *Langmuir*, 23:6947-6955, 2007.
Gijs et al., "Thiol chemistry on well-defined synthetic polypeptides," *Chem Comm.*, 24:3612-3614, 2009.
Griset et al., "Expansile nanoparticles: synthesis, characterization, and in vivo efficacy of an acid-responsive polymeric drug delivery system," *J Am Chem Soc.*, 131:2469-2471, 2009.
Han et al., "Fluorescent indicators for intracellular pH," *Chem Rev.*, 110(5):2709-28, 2010.
Heffernan et al., "Polyketal nanoparticles: a new pH-sensitive biodegradable drug delivery vehicle," *Bioconjugate Chem.*, 16:1340-1342, 2005.
Hu et al., "Synthesis and pH-dependent micellization of 2-(diisopropylamino)ethyl methacrylate based amphiphilic diblock copolymers via RAFT polymerization," *Polymer*, 48:3437-3443, 2007.
Izumi et al., "Cellular pH regulators: potentially promising molecular targets for cancer chemotherapy," *Cancer Treat Rev.*, 29(6):541-9, 2003.
Jung et al., "pH-sensitive polymer nanospheres for use as a potential drug delivery vehicle," *Biomacromolecules*, 8:3401-7, 2007.
Kato et al., "Polymerization of methyl methacrylate with the carbon tetrachloride/dichlorotris-(triphenylphosphine)ruthedum(II)/methylaluminum bis(2,6-di-tert-butylphenoxide) initiating system: possibility of living radical polymerization," *Macromolecules*, 28:1721-1723, 1995.
Khemtong et al., "In vivo off-resonance saturation magnetic resonance imaging of $\alpha_\nu\beta_3$-targeted superparamagnetic nanoparticles," *Cancer Res.*, 69:1651-1658, 2009.
Kim et al., "Doxorubicin loaded pH-sensitive micelle: antitumoral efficacy against ovarian A2780/DOXR tumor," *Pharm Res.*, 25:2074-82, 2008.
Kim et al., "Multicenter phase II trial of Genexol-PM, a novel Cremophor-free, polymeric micelle formulation of paclitaxel, with cisplatin in patients with advanced non-small-cell lung cancer," *Ann Oncol.*, 18(12):2009-14, 2007.
Kobayashi et al., "New strategies for fluorescent probe design in medical diagnostic imaging," *Chem Rev.*, 110(5):2620-40, 2010.
Kobayashi et al., "Target-cancer-cell-specific activatable fluorescence imaging probes: rational design and in vivo applications," *Acc Chem Res.*, 44(2):83-90, 2011.
Lakowicz, "Chapter 13. Energy Transfer," *Principles of Fluorescence Spectroscopy*, 3rd ed., New York City: Springer, 2006. 443-475. Print.
Lee et al., "Activatable imaging probes with amplified fluorescent signals," *Chem Commun.*, 36:4250-60, 2008.
Lee et al., "Doxorubicin loaded pH-sensitive polymeric micelles for reversal of resistant MCF-7 tumor," *J Control Release*, 103:405-18, 2005.
Lee et al., "Poly(L-histidine)-PEG block copolymer micelles and pH-induced destabilization," *J Control Release*, 90:363-74, 2003.
Li et al., "pH-activated near-infrared fluorescence nanoprobe imaging tumors by sensing the acidic microenvironment," *Adv Funct Mater.*, 20:2222-2230, 2010.
Licciardi et al., "Synthesis of novel folic acid-functionalized biocompatible block copolymers by atom transfer radical polymerization for gene delivery and encapsulation of hydrophobic drugs," *Biomacromolecules*, 6:1085-1096, 2005.
Lopalco et al., "Catch and release microwave mediated synthesis of cyanine dyes," *Org Biomol Chem.*, 7:856-859, 2009.
Lovell et al., "Activatable photosensitizers for imaging and therapy," *Chem Rev.*, 110(5):2839-57, 2010.
Ma et al., "Well-defined biocompatible block copolymers via atom transfer radical polymerization of 2-methacryloyloxyethyl phosphorylcholine in protic media," *Macromolecules*, 36(10):3475-3484, 2003.
Marconescu, "Targeting nanoparticles to tumor vasculature," *PhD Thesis*, UT Southwestern Medical Center, Dallas, 2008.
Maxfield et al., "Endocytic recycling," *Nat Rev Mol Cell Biol.*, 5(2)121-32, 2004.
McAllister et al., "Polymeric nanogels produced via inverse microemulsion polymerization as potential gene and antisense delivery agents," *J Am Chem Soc.*, 124:15198-15207, 2002.
Moad et al., "Living radical polymerization by the RAFT process," *Australian Journal of Chemistry*, 58(6):379-410, 2005.
Modi et al., "A DNA nanomachine that maps spatial and temporal pH changes inside living cells," *Nat Nanotech.*, 4:325-330, 2009.
Nakanishi et al., "Development of the polymer micelle carrier system for doxorubicin," *J Control Release*, 74:295-302, 2001.
Nasongkla et al., "Multifunctional polymeric micelles as cancer-targeted, MRI-ultrasensitive drug delivery systems," *Nano Lett.*, 6:2427-2430, 2006.
Nishi et al., "The vacuolar (H+)-ATPases—nature's most versatile proton pumps," *Nat Rev Mol Cell Biol.*, 3(2):94-103, 2002.
Reinicke et al., "Develoment of beta-Lapachone prodrugs for therapy agains human cancer cells with elevated NAD(P)H:Quinone Oxidoreductase 1 levels," *Clin Cancer Res.*, 11:3055-3064, 2005.
Seshadri et al., "The delivery of superoxide dismutase encapsulated in polyketal microparticles to rat myocardium and protection from myocardial ischemia-reperfusion injury," *Biomaterials*, 31:1372-1379, 2010.
Srikun et al., "A dendrimer-based platform for simultaneous dual fluorescence imaging of hydrogen peroxide and pH gradients produced in living cells," *Chemical Science*, 2:1156-1165, 2011.
Sun et al., "Bright fluorescent nanoparticles for developing potential optical imaging contrast agents," *Nanoscale*, 2:548-558, 2010.
Sutton et al., "Doxorubicin and beta-lapachone release and interaction with micellar core materials: experiment and modeling," *Exp Biol Med.*, 232(8):1090-9, 2007.
Sutton et al., "Functionalized micellar systems for cancer targeted drug delivery," *Pharmaceutical Research*, 24(6):1029-1049, 2007.
Sutton, "Chapter 5: Hydrophobic prodrug strategy for the creation of polymeric micelles with pHsensitive release of beta-lapachone," *pH Sensitive RNA and Drug Delivery Systems—Ph.D. Dissertation*, Case Western Reserve University, Cleveland, 2007. 174-206.
Sy et al., "Surface functionalization of polyketal microparticles with nitrilotriacetic acid-nickel complexes for efficient protein capture and delivery," *Biomaterials*, 31:4987-4994, 2010.
Tsarevsky et al., "'Green' atom transfer radical polymerization: from process design to preparation of well-defined environmentally friendly polymeric materials," *Chem Rev.*, 107(6):2270-99, 2007.
Uchiyama et al., "Multiplexing sensory molecules map protons near micellar membranes," *Angew Chem Int Ed Engl.*, 47(25):4667-9, 2008.
Ueno et al., "Fluorescent probes for sensing and imaging," *Nat methods*, 8(8):642-5, 2011.
Urano et al., "Selective molecular imaging of viable cancer cells with pH-activatable fluorescence probes," *Nat Med.*, 15:104-109, 2009.
Vetvicka et al., "Biological evaluation of polymeric micelles with covalently bound doxorubicin," *Bioconjug Chem.*, 20:2090-2097, 2009.
Wang et al., "Controlled living radical polymerization—atom-transfer radical polymerization in the presence of transition-metal complexes," *J Am. Chem Soc.*, 117:5614-5615, 1995.
Webb et al., "Dysregulated pH: a perfect storm for cancer progression," *Nat Rev Cancer*, 11(9):671-7, 2011.

(56) References Cited

OTHER PUBLICATIONS

Ye et al., "Novel near-infrared fluorescent integrin-targeted DFO analogue," *Bioconjug Chem.*, 19:225-234, 2007.

Yezhelyev et al., "Proton-sponge coated quantum dots for siRNA delivery and intracellular imaging," *J Am Chem Soc.*, 130(28):9006-12, 2008.

Yu et al., "Overcoming endosomal barrier by amphotericin B-loaded dual pH-responsive PDMA-b-PDPA micelleplexes for siRNA delivery," *ACS Nano*, 5(11):9246-55, 2011.

Zhang et al., "Creating new fluorescent probes for cell biology," *Nat Rev Mol Cell Biol.*, 3(12):906-18, 2002.

Zhou et al., "Tunable, ultra-sensitive pH responsive nanoparticles targeting specific endocytic organelles in living cells," *Angew Chem Int Ed Engl.*, 50:6109-6114, 2011.

PCT International Preliminary Report on Patentability issued in International application No. PCT/US2011/001418, dated Apr. 4, 2013.

PCT International Preliminary Report on Patentability in International application No. PCT/US2011/047497, dated Apr. 4, 2013.

PCT International Search Report and Written Opinion issued in International application No. PCT/US2011/001418, dated Dec. 2, 2011.

PCT International Search Report and Written Opinion issued in International application No. PCT/US2011/047497, dated Oct. 21, 2011.

PCT Invitation to Pay Additional Fees issued in International application No. PCT/US2013/035050, dated Jul. 11, 2013.

U.S. Appl. No. 13/825,518 entitled "Novel Block Copolymer and Micelle Compositions and Methods of Use Thereof," submitted to the United States Patent Office on Mar. 21, 2013.

U.S. Appl. No. 13/825,524 entitled "pH-Sensitive Compositions for Delivery of Beta Lapachone and Methods of Use," submitted to the United States Patent Office on Mar. 21, 2013.

Scheme 1

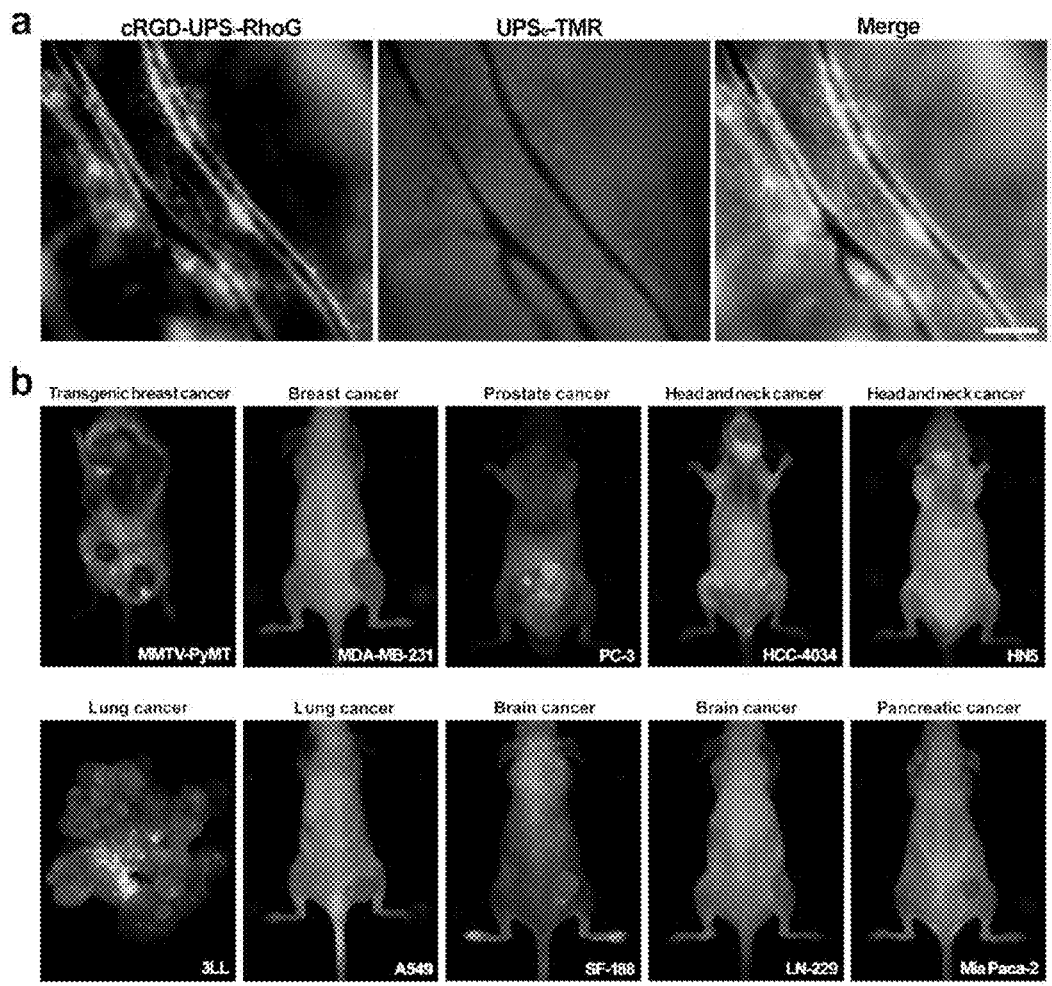
Fig. 37A-B

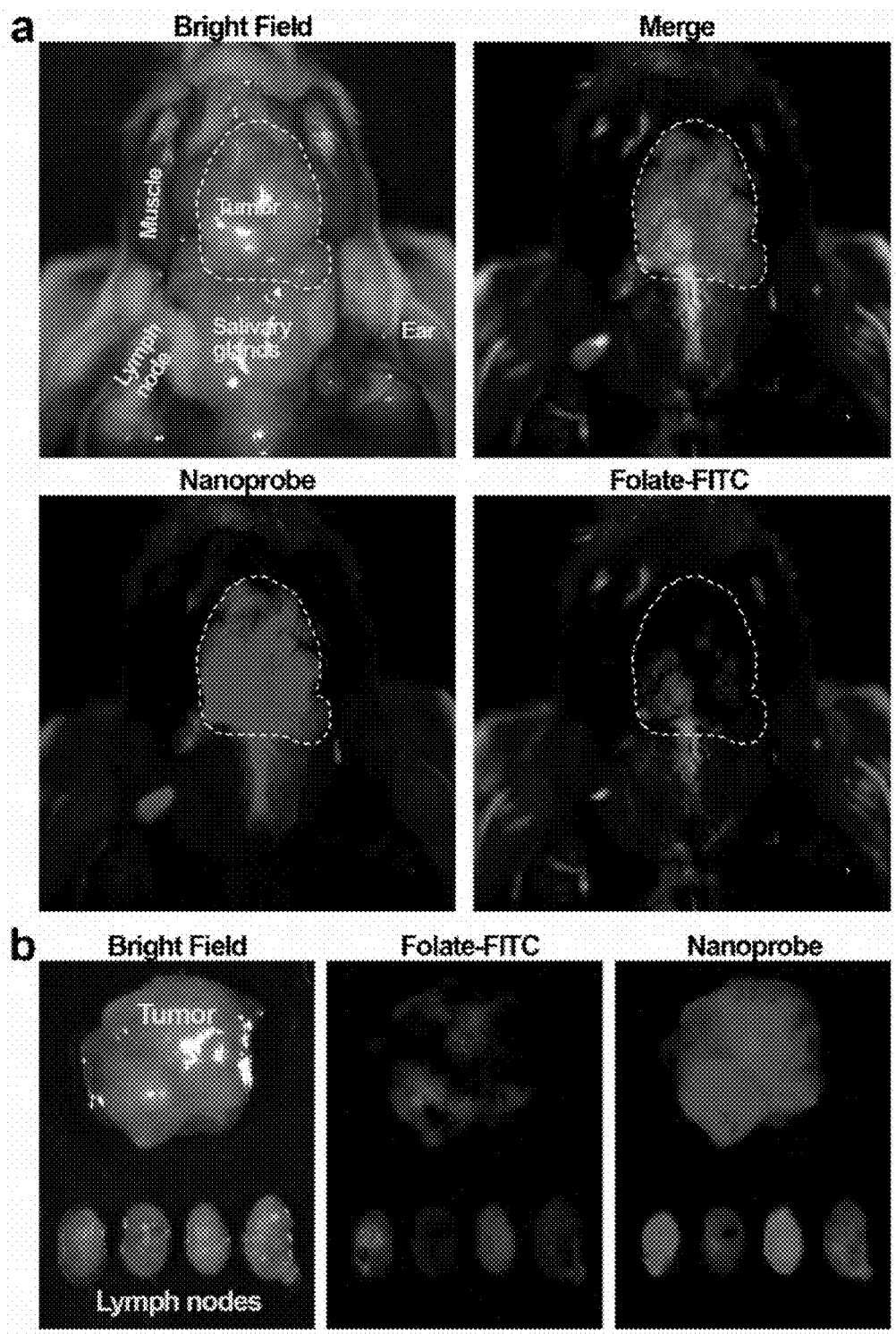
Fig. 39A-B

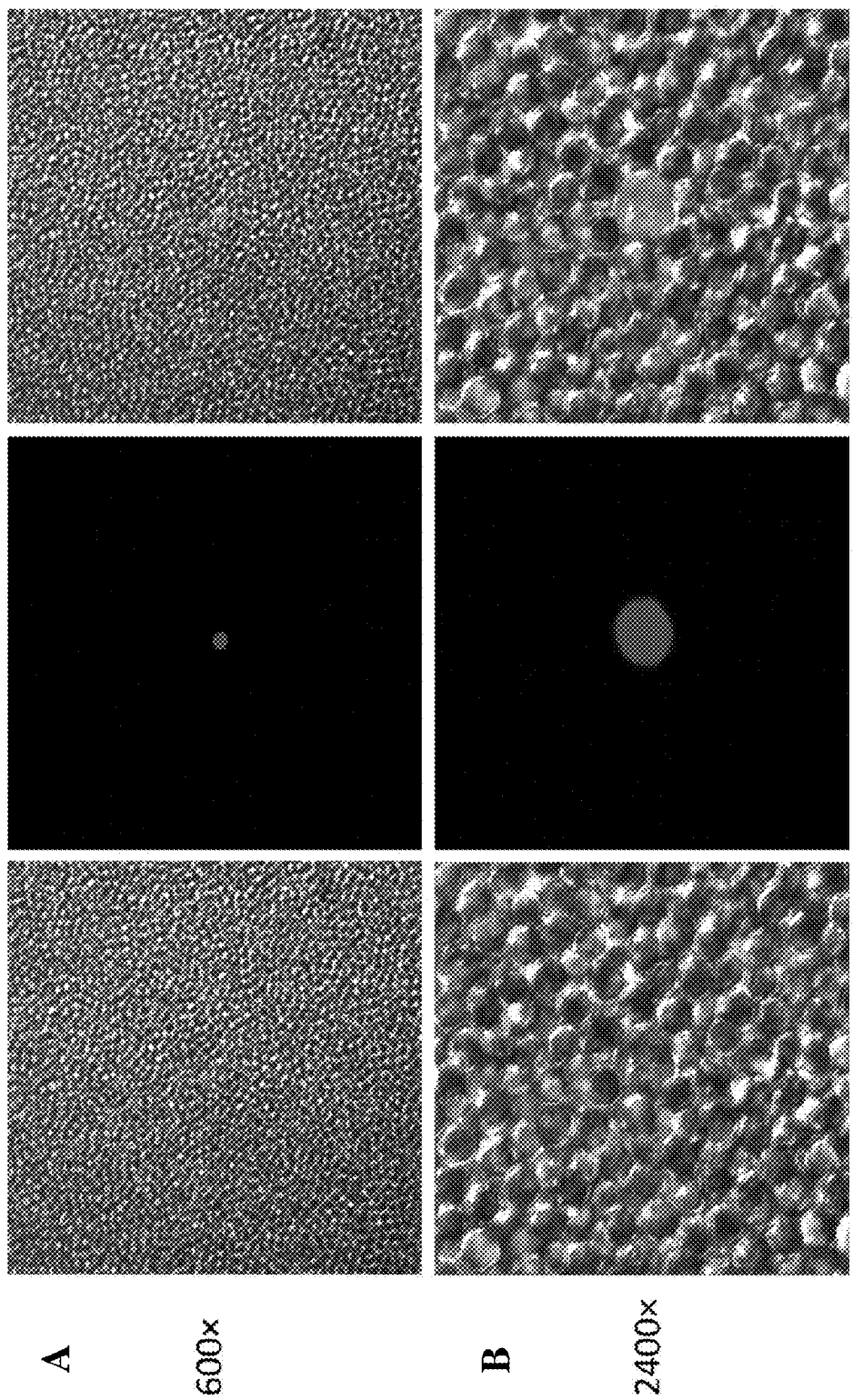
Fig. 40A-B

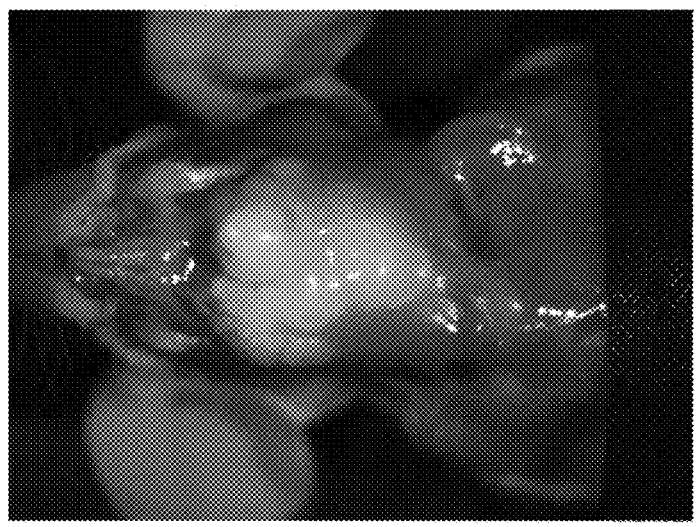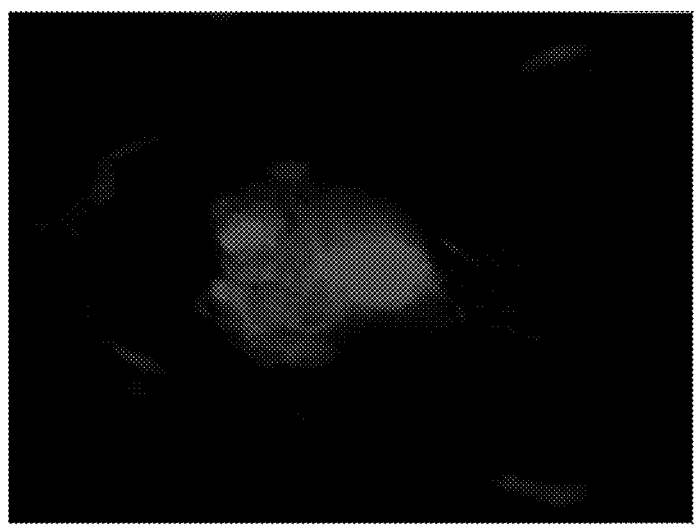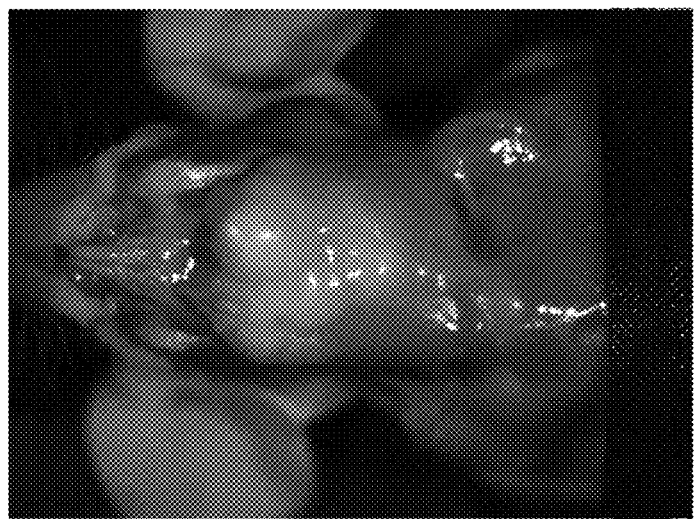
Fig. 50

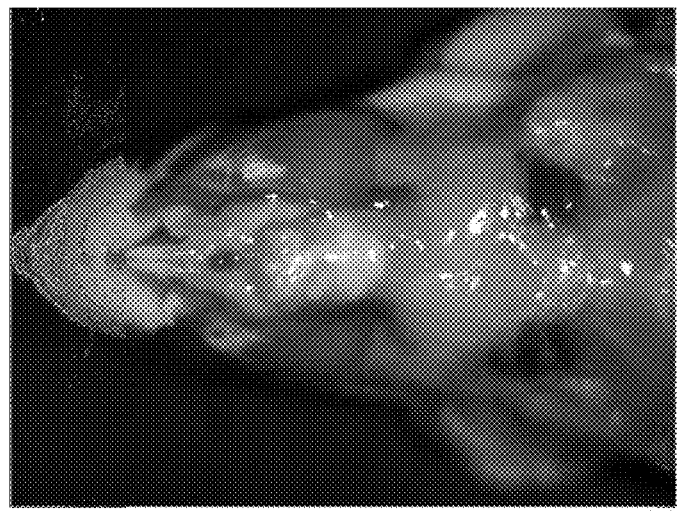
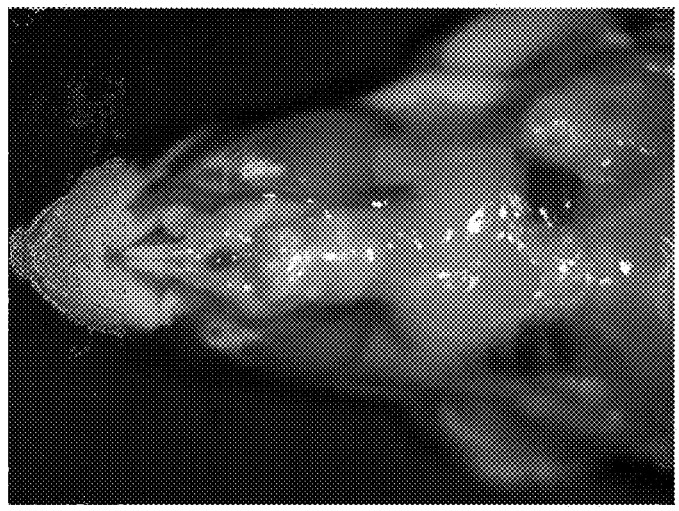
Fig. 52

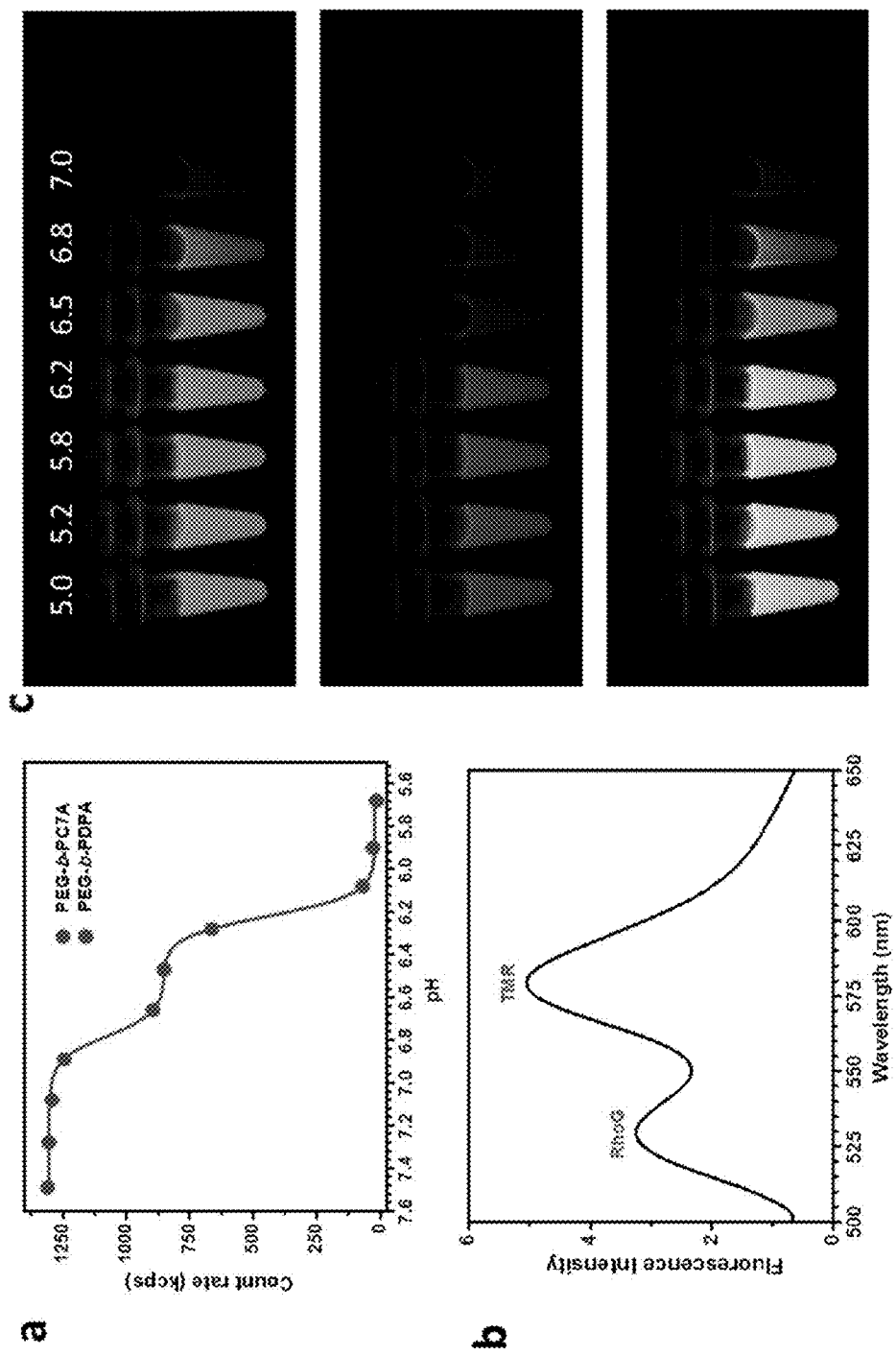
FIG. 53a-c

US 9,511,152 B2

MULTICOLORED PH-ACTIVATABLE FLUORESCENCE NANOPLATFORM

This application claims the benefit of U.S. Provisional Application Ser. No. 61/620,774, filed Apr. 5, 2012, the entirety of which is incorporated herein by reference.

This invention was made with government support under Grant Number RO1 EB013149 awarded by the National Institutes of Health. The government has certain rights in the invention.

BACKGROUND OF THE INVENTION

1. Field of the Invention

The present invention relates generally to the fields of molecular and cellular biology, nanotechnology, and fluorescence sensors. More particularly, it relates to nanoplatforms for the detection of pH changes.

2. Description of Related Art

Fluorescence imaging has become an important tool in the study of biological molecules, pathways and processes in living cells thanks to its ability to provide spatial-temporal information at microscopic, mesoscopic and macroscopic levels (see, e.g., Tsien, R. Y. *Nat. Rev. Mol. Cell. Biol.* 2003, 4, SS16; Weissleder, R., *Nature* 2008, 452, 580; Fernandez-Suarez, M., *Nat. Rev. Mol. Cell. Biol.* 2008, 9, 929). Fluorescent reporter molecules can be broadly divided into two categories: intrinsically expressed fluorescent proteins (e.g., GFP) or externally administered fluorescent probes (e.g., synthetic dyes). Fluorescent protein reporters have greatly impacted studies in basic biological sciences by specific labeling of target proteins and live cell imaging of protein functions (see, e.g., Giepmans, B. N. G. *Science* 2006, 312, 217; Gross, S., *Cancer Cell* 2005, 7, 5). External imaging probes have been extensively used in various cellular and animal imaging studies.

Recently, activatable imaging probes that are responsive to physiological stimuli such as ionic and redox potentials, enzymatic expressions, and pH have received considerable attention to probe cell physiological processes (see, e.g., de Silva, A. P., *Chem. Rev.* 1997, 97, 1515; Zhang, J., *Nat. Rev. Mol. Cell. Biol.* 2002, 3, 906; Lee, S., *Chem. Commun.* 2008, 4250; Kobayashi, H.; *Chem. Res.* 2010, 44, 83; Lovell, J. F., *Chem. Rev.* 2010, 110, 2839; Ueno, T., *Nat. Methods* 2011, 8, 642). Among these stimuli, pH stands out as an important physiological parameter that plays a critical role in both the intracellular (pHi) and extracellular (pHe) milieu (Alberts, B., *Molecular Biology of the Cell;* 5th ed.; Garland Science: New York, 2008). For example, the pH of intracellular compartments (e.g. endocytic vesicles) in eukaryotic cells is carefully controlled and directly affects many processes such as membrane transport, receptor cycling, lysosomal degradation, and virus entry into cells (Maxfield, F. R., *Nat. Rev. Mol. Cell. Biol.* 2004, 5, 121; Izumi, H., *Cancer Treat. Rev.* 2003, 29, 541; Nishi, T., *Nat. Rev. Mol. Cell. Biol.* 2002, 3, 94). Recently, dysregulated pH has been described as another hallmark of cancer because cancer cells display a "reversed" pH gradient with a constitutively increased cytoplasmic pH that is higher than the extracellular pH (pHe) (Webb, B. A., *Nat. Rev. Cancer* 2011, 11, 671).

Although various pH-sensitive fluorescent probes have been reported (Kobayashi, H., *Chem. Rev.* 2010, 110, 2620; Han, J. Y., *Chem. Rev.* 2010, 110, 2709), their pH sensitivity primarily arises from ionizable residues with pH-dependent photo-induced electron transfer (PeT) properties to the fluorophores. One potential drawback for these fluorescent agents is their broad pH response (ΔpH-2) as dictated by the Henderson-Hasselbalch equation (Atkins, P., *Physical Chemistry;* Oxford University Press, 2009). This lack of sharp pH response makes it difficult to detect subtle pH differences between the acidic intracellular organelles (e.g., <1 pH difference between early endosomes and lysosomes) (Maxfield, F. R., *Nat. Rev. Mol. Cell. Biol.* 2004, 5, 121; Casey, J. R., *Nat. Rev. Mol. Cell. Biol.* 2010, 11, 50) or pHe in solid tumors (6.5-6.9) (Webb, B. A., *Nat. Rev. Cancer* 2011, 11, 671; Zhang, X., *J. Nucl. Med.* 2010, 51, 1167.) over normal tissue environment (7.4). Moreover, simultaneous control of pH transition point and emission wavelengths (in particular, in the near IR range) is difficult for small molecular dyes.

Recent attempts to develop pH-sensitive fluorescent nanoparticles primarily employ polymers conjugated with small molecular pH-sensitive dyes (Srikun, D., *J. Chem. Sci.* 2011, 2, 1156; Benjaminsen, R. V., *ACS Nano* 2011, 5, 5864; Albertazzi, L., *J. Am. Chem. Soc.* 2010, 132, 18158; Urano, Y., *Nat. Med.* 2009, 15, 104) or the use of pH-sensitive linkers to conjugate pH-insensitive dyes (Li, C., *Adv. Funct. Mater.* 2010, 20, 2222; Almutairi, A., *J. Am. Chem. Soc.* 2007, 130, 444.). These nanoprobe designs also yield broad pH response and lack the ability to fine-tune pH transition point.

SUMMARY OF THE INVENTION

Various embodiments of the present invention provide pH-tunable, highly activatable multicolored fluorescent nanoplatforms and methods of using the nanoplatforms in a variety of application including, but not limited to, investigating fundamental cell physiological processes such as pH regulation in endocytic vesicles, endosome/lysosome maturation, and effect of pH on receptor cycling and trafficking of subcellular organelles.

In one embodiment, the present invention provides a pH-responsive system comprising: a population of first nanoparticles, wherein the first nanoparticles comprise (i) a first block copolymer comprising a hydrophilic polymer segment and a hydrophobic polymer segment and (ii) a first fluorescent dye, and further wherein the first nanoparticles have a first pH transition point and a first emission spectra. In some embodiments, the pH-responsive system further comprises a population of second nanoparticles, wherein the second nanoparticles comprise (i) a second block copolymer comprising a hydrophilic polymer segment and a hydrophobic polymer segment and (ii) a second fluorescent dye, and further wherein the second nanoparticles have a second pH transition point that differs from the first pH transition point of the first nanoparticles and a second emission spectra that differs from the first emission spectra of the first nanoparticles. In certain aspects of the invention, the pH-responsive system further comprises at least a population of third nanoparticles, wherein third nanoparticles comprise (i) a third block copolymer comprising a hydrophilic polymer segment and a hydrophobic polymer segment and (ii) a third fluorescent dye, and further wherein the third nanoparticles have a third pH transition point that differs from the pH transition points of the first and second nanoparticles and a third emission spectra that differs from the emission spectra of the first and second nanoparticles. In some embodiments, the pH-responsive system further comprises populations of at least a fourth, fifth, sixth, seventh, eighth, ninth, tenth or more nanoparticles. Each of these fourth, fifth, sixth, seventh, eighth, ninth, tenth or more nanoparticles will have pH transition points that differ from the pH transition points of the other populations of nanoparticles in the system and emission spectra that differ from the emission spectra of the other populations of nanoparticles in the system.

The hydrophilic polymer segment of the block copolymer may be any suitable hydrophilic polymer. Examples of such hydrophilic polymers include, but are not limited to, poly(ethylene oxide) (PEO), poly(methacrylate phosphatidyl choline) (MPC), and polyvinylpyrrolidone (PVP).

The hydrophobic polymer segment of the block copolymer may be any suitable hydrophobic polymer. Examples of such hydrophobic polymers include poly(2-(Diisopropyl amino)ethyl methacrylate) (PDPA), poly(2-(dibutylamino) ethyl methacrylate) (PDBA), poly(2-(hexamethyleneimino) ethyl methacrylate) (PC7A), poly(2-(pentamethyleneimino) ethyl methacrylate) (PC6A), and the hydrophilic polymers disclosed in PCT/US2011/00148 or PCT/US2011/047497.

As mentioned above, the nanoparticles comprise a block copolymer and a fluorescent dye. In certain aspects of the invention, the nanoparticles are synthesized by reacting a precursor copolymer with a hydrophobic monomer (e.g., DPA, DBA, C7A, C6A) and a monomer containing a primary amino group such as 2-aminoethyl methacrylate (AMA). Examples of precursor copolymers include, but are not limited to, $PEO_{114}$-b-P($DPA_{75}$-co-$AMA_6$), MAL-$PEO_{114}$-b-$PDPA_{88}$, $PEO_{114}$-b-P($C7A_{65}$-co-$AMA_6$), $PEO_{114}$-b-P($DPA_{74}$-co-$AMA_1$), $PEO_{114}$-b-P($DPA_{77}$-co-$AMA_3$), $PEO_{114}$-b-P($DPA_{80}$-co-$AMA_3$), $PEO_{114}$-b-P($DBA_{65}$-co-$AMA_3$), $PEO_{114}$-b-P($C7A_{65}$-co-$AMA_3$), and $PEO_{114}$-b-P($C6A_{81}$-co-$AMA_3$). In certain embodiments, the free amino groups on AMA may be conjugated to fluorescent dye molecules.

The block copolymers employed herein may be homopolymers or heteropolymers. Homopolymers may be made by the polymerization of one type of monomer subunit. Heteropolymers may be made by the polymerization of at least two different monomer subunits. As demonstrated below, copolymerizing various ratios of two or more monomers with different hydrophobicities allows one to further fine-tune the pH responses of the systems, nanoparticles, and micelles disclosed herein.

Non-limiting examples of fluorescent dyes include, rhodamine, BODIPY®, coumarin and cyanine dyes. Other non-limiting examples of fluorescent dyes include a red fluorescent squarine dye such as 2,4-Bis[1,3,3-trimethyl-2-indolinylidenemethyl]cyclobutenediylium-1,3-dioxolate, an infrared dye such as 2,4Bis[3,3-dimethyl-2-(1H-benz[e]indolinylidenemethyl)]cyclobutenediylium-1,3-dioxolate, or an orange fluorescent squarine dye such as 2,4-Bis[3,5-dimethyl-2-pyrrolyl]cyclobutenediylium-1,3-diololate, quantum dots, Alexa Fluor® dyes, AMCA, BODIPY® 630/650, BODIPY® 650/665, BODIPY®-FL, BODIPY®—R6G, BODIPY®-TMR, BODIPY®-TRX, Cascade Blue®, CyDye™, including but not limited to Cy2™, Cy3™, and Cy5™, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™ ROX™, TAMRA™, TET™, Tetramethylrhodamine, or Texas Red®.

In certain aspects of the invention, the fluorescent dye is a pH-insensitive fluorescent dyes. In some embodiments, the fluorescent dye has a small Stokes shift. In particular embodiments, the Stokes shift is $\Delta\lambda<40$ nm.

In some embodiments, nanoparticles are selected from the group consisting of PDBA-BDY, PDPA-TMR, PDPA-C55, PC7A-C55, PC6A-C75, and PDPA-CMN. As discussed in more detail below, "BDY" refers to a BODIPY® dye, "TMR" refers to a rhodamine dye, "C55" and "C75" refer to cyanine dyes, and "CMN" refers to a coumarin dye. In specific embodiments, the pH-responsive system comprises at least two, three, or all four of the PDBA-BDY, PDPA-TMR, PC7A-C55, PC6A-C75, and PDPA-CMN. As discussed in detail below, the nanoparticles may be in either monomer form or micelle form depending on the pH of their environment.

The pH-responsive system may comprise nanoparticles having pH transition points over any desired pH range. In particular embodiments, the system includes two or more populations of nanoparticles, wherein each population of nanoparticles has a pH transition point that is between pH 2.0 to pH 11.0, pH 4.0 to pH 9.0, pH 4.8 to pH 8.4, pH 5.0 to pH 8.0, pH 5.0 to pH 7.4, pH 5.2 to pH 7.2, pH 5.7 to pH 6.9, pH 5.7 to pH 6.5, or pH 6.4 to pH 8.4. In one embodiment, the system includes at least four populations of nanoparticles with pH transition points of about pH 5.2, 6.4, 6.9, and 7.2. In another embodiment the system includes at least four populations of nanoparticles with pH transition points of about pH 5.7, 5.94, 6.18, and 6.42. In other embodiments, the system includes at least two populations of nanoparticles with pH transition points of about pH 6.21 and pH 6.9.

The pH-responsive system is highly activatable. In certain aspects of the invention, the pH responses ($\Delta pH_{10\text{-}90}\%$) of the nanopraticles in the system are less than 2 pH unit, less than 1.5 pH unit, less than 1 pH unit, less than 0.75 pH unit, less than 0.5 pH unit, or less than 0.25 pH unit.

The pH-responsive system may comprise nanoparticles having fluorescent emission spectra over any desired range. In certain aspects of the invention, the fluorescent emission spectra of the nanoparticles are between 400-850 nm, 500-820 nm, or 506-808 nm. In one embodiment, the system includes at least four populations of nanoparticles with emission spectra of 506 nm, 580 nm, 707 nm, and 808 nm.

In some embodiments, the nanoparticles further comprise a targeting moiety. In some embodiments, the targeting moiety is an antibody or antibody fragment. In some embodiments, the antibody is Cetuximab. In other embodiments, the antibody fragment is the Fab' fragment of Cetuximab. In other embodiments, targeting moiety binds a cell surface receptor. In other embodiments, the targeting moiety is a signal peptide. In some embodiments, the signaling peptide is the cyclic arginine-glycine-aspartic acid peptide (cRGD) peptide. In some embodiments, the signal peptide directs the nanoparticles to the nucleus, mitochondria, endoplasmic reticulum, chloroplast, apoplast, or peroxisome. In other embodiments, the targeting moiety is a small molecule. In some embodiments, the small molecule is folic acid.

In further embodiments, the present invention comprises a pH-responsive system comprising a single nanoparticle with a block copolymer and a fluorescent dye and further wherein the nanoparticle population has a pH transition point and an emission spectrum as described above. In some embodiments, the single nanoparticle further comprises a targeting moiety.

In certain embodiments, the nanoplatform utilizes ultra-pH responsive tetramethyl rhodamine (TMR)-based nanoparticles with tunable pH transitions in the physiological range (pH 5.0-7.4). pH-induced micellization of pH responsive nanoparticles may be used in conjunction with fluorescence quenching to provide pH responsive fluorescent nanoparticles. For example, in one embodiment, a series of multicolored pH-activatable fluorescent nanoparticles is provided with independent control of emission wavelengths (500-820 nm) and pH transition points (5.0-7.4). In particular embodiment, the nanoparticles with different emission wavelengths have sharp pH response (ΔpH<0.25 between ON/OFF states).

In a further embodiment, the present invention provides a composition comprising series of at least one, two, three, four, five, six, seven, eight, nine, ten or more nanoparticle populations, each nanoparticle population having a pH transition point and an emission spectra, wherein the pH transition point and the emission spectra of each nanoparticle population in the series differs from the pH transition point and the emission spectra of the other nanoparticle populations in the series. The nanoparticles comprise a block copolymer and fluorescent dye. In one embodiment, at least one of the nanoparticle populations in the series comprises PDBA-BDY, PDPA-TMR, PDPA-C55, PC7A-C55, PC6A-C75, or PDPA-CMN. In another embodiment, the series comprises PDBA-BDY nanoparticle populations, PDPA-TMR nanoparticle populations, and PC7A-C55 nanoparticle populations. In some embodiments, the nanoparticle population contain about 10% of a maleimide containing copolymer. As discussed in detail below, the nanoparticles may be in either monomer form or micelle form depending on the pH of their environment.

The nanoparticles in the series comprise a block copolymer and a fluorescent dye. In certain aspects of the invention, the nanoparticles are synthesized by reacting a precursor copolymer with a fluorescent-dye containing compound. Examples of precursor copolymers include, but are not limited to, $PEO_{114}$-b-P($DPA_{75}$-co-$AMA_6$), MAL-$PEO_{114}$-b-$PDPA_{88}$, $PEO_{114}$-b-P($C7A_{65}$-co-$AMA_6$), $PEO_{114}$-b-P($DPA_{74}$-co-$AMA_1$), $PEO_{114}$-b-P($DPA_{77}$-co-$AMA_3$), $PEO_{114}$-b-P($DPA_{80}$-co-$AMA_6$), $PEO_{114}$-b-P($DBA_{65}$-co-$AMA_3$), $PEO_{114}$-b-P($C7A_{65}$-co-$AMA_3$), and $PEO_{114}$-b-P($C6A_{81}$-co-$AMA_3$).

In some embodiments, the nanoparticles are synthesized from a copolymer comprising:
a) a polymer according to formula:

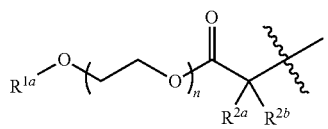

b) a monomer according to formula $A^1$; and
c) a monomer according to formula $A^2$;
or a pharmaceutically acceptable salt thereof; and stereoisomers, isotopic variants and tautomers thereof;
wherein
each $A^1$ and $A^2$ is independently selected from

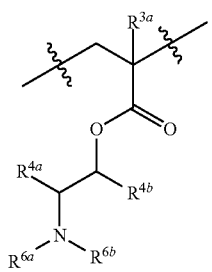

$A^1$

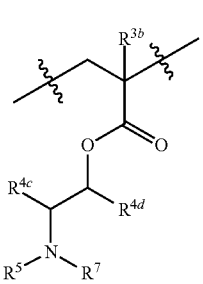

$A^2$ each $R^{1a}$ is independently H, substituted or unsubstituted alkyl, or

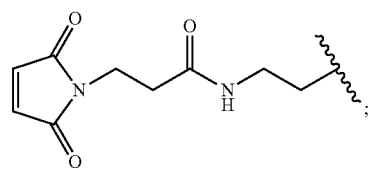 [SMILES: *CCNC(=O)CCN1C(=O)C=CC1=O]

each $R^{2a}$, $R^{2b}$, $R^{3a}$, $R^{4a}$, $R^{4b}$, $R^{4c}$, $R^{4d}$, and $R^5$ is independently H or substituted or unsubstituted alkyl;

each $R^{6a}$, and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye;

the subscript n is an integer between 10 to 200;

and wherein the copolymer is a random copolymer.

In some embodiments, $A^1$ has the formula:

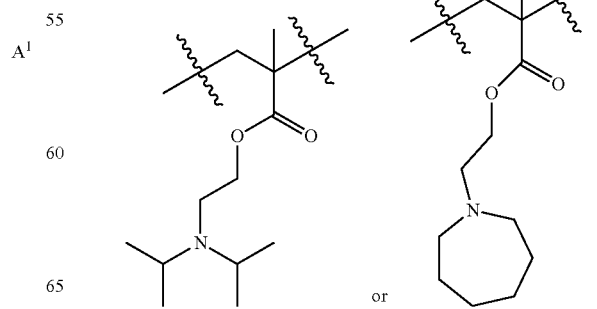

In some embodiments, $A^2$ has the formula:

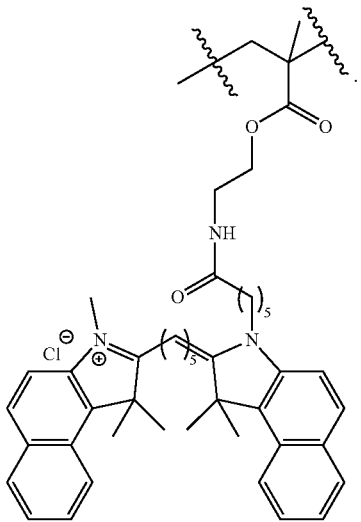

In certain aspects of the invention, the fluorescent dye is a pH-insensitive fluorescent dyes. In some embodiments, the fluorescent dye has a small Stokes shift. In particular embodiments, the Stokes shift is $\Delta\lambda<40$ nm.

The series of nanoparticle populations may comprises nanoparticles having pH transition points over any desired pH range. In particular embodiments, the series includes two or more populations of nanoparticles, wherein each population of nanoparticles has a pH transition point that is between pH 2.0 to pH 11.0, pH 4.0 to pH 9.0, pH 4.8 to pH 8.4, pH 5.0 to pH 8.0, pH 5.0 to pH 7.4, pH 5.2 to pH 7.2, pH 5.7 to pH 6.9, pH 5.7 to pH 6.5, or pH 6.4 to pH 8.4. In one embodiment, the composition includes at least four populations of nanoparticles with pH transition points of about pH 5.2, 6.4, 6.9, and 7.2. In another embodiment the composition includes at least four populations of nanoparticles with pH transition points of about pH 5.7, 5.94, 6.18, and 6.42. In another embodiments, the composition includes at least two populations of nanoparticles with pH transition points of about pH 6.21 and pH 6.9.

In certain aspects of the invention, the pH responses ($\Delta pH_{10-90}\%$) of the nanopraticles in the series are less than 2 pH unit, less than 1.5 pH unit, less than 1 pH unit, less than 0.75 pH unit, less than 0.5 pH unit, or less than 0.25 pH unit.

The series of nanoparticle populations may comprises nanoparticles having fluorescent emission spectra over any desired range. In certain aspects of the invention, the fluorescent emission spectra of the nanoparticles are between 400-850 nm, 500-820 nm, or 506-808 nm. In one embodiment, the system includes at least four populations of nanoparticles with emission spectra of 506 nm, 580 nm, 707 nm, and 808 nm.

In another aspect of the present invention, there is a composition further comprising a single nanoparticle with a copolymer and a fluorescent dye, and further wherein the nanoparticle population has a pH transition point and an emission spectrum. In some embodiments, the single nanoparticle further comprises a targeting moiety.

Another embodiment provides a composition comprising at least one, two, three, four, five, six, seven, eight, nine, ten or more micelle populations, wherein each micelle comprises a block copolymer and a fluorescent dye, and further wherein each micelle population has a pH transition point and fluorescent dye that differs from the pH transition point and fluorescent dye of the other micelle populations. As discussed in detail below, the fluorescent dye is quenched by the micelle. Thus, disassociation of the micelles results in an increase in fluorescence intensity. In certain aspects of the invention, the fluorescent dye is a pH-insensitive fluorescent dyes. In some embodiments, the fluorescent dye has a small Stokes shift. In particular embodiments, the Stokes shift is $\Delta\lambda<40$ nm. In one embodiment, at least one of the micelle populations comprises PDBA-BDY, PDPA-TMR, PDPA-C55, PC7A-C55, PC6A-C75, or PDPA-CMN. In another embodiment, the composition comprises PDBA-BDY micelle populations, PDPA-TMR micelle populations, and PC7A-C55 micelle populations. In certain aspects of the invention, the micelle populations are synthesized from a precursor copolymer selected from the group consisting of $PEO_{114}$-b-$P(DPA_{75}$-co-$AMA_6)$, MAL-$PEO_{114}$-b-$PDPA_{88}$, $PEO_{114}$-b-$P(C7A_{65}$-co-$AMA_6)$, $PEO_{114}$-b-$P(DPA_{74}$-co-$AMA_1)$, $PEO_{114}$-b-$P(DPA_{77}$-co-$AMA_3)$, $PEO_{114}$-b-$P(DPA_{80}$-co-$AMA_6)$, $PEO_{114}$-b-$P(DBA_{65}$-co-$AMA_3)$, $PEO_{114}$-b-$P(C7A_{65}$-co-$AMA_3)$, and $PEO_{114}$-b-$P(C6A_{81}$-co-$AMA_3)$.

The micelle populations may have pH transition points over any desired pH range. In particular embodiments, the composition includes two or more populations of micelles, wherein each population of micelles has a pH transition point that is between pH 2.0 to pH 11.0, pH 4.0 to pH 9.0, pH 4.8 to pH 8.4, pH 5.0 to pH 8.0, pH 5.0 to pH 7.4, pH 5.2 to pH 7.2, pH 5.7 to pH 6.9, pH 5.7 to pH 6.5, or pH 6.4 to pH 8.4. In one embodiment, the composition includes at least four populations of micelles with pH transition points of about pH 5.2, 6.4, 6.9, and 7.2. In another embodiment the composition includes at least four populations of micelles with pH transition points of about pH 5.7, 5.94, 6.18, and 6.42. In certain aspects of the invention, the pH responses ($\Delta pH_{10-90}\%$) of the micelles in the composition are less than 2 pH unit, less than 1.5 pH unit, less than 1 pH unit, less than 0.75 pH unit, less than 0.5 pH unit, or less than 0.25 pH unit.

Any of the nanoparticles or micelles disclosed herein may further comprise a targeting moiety. The targeting moiety may be used to target or bind the nanoparticle or micelle to, for example, a particular cell surface receptor (e.g., $\Delta v\beta 3$ integrin, EGFR, Her2/neu) or organelle (e.g., nucleus, mitochondria, endoplasmic reticulum, chloroplast, apoplast, or peroxisome). The targeting moiety may be, for example, an antibody or antibody fragment, a protein, a peptide (e.g., a signal peptide), a peptidomimetic ligand, a carbohydrate, an aptamer, or a small molecule. In some embodiments, the antibody is Cetuximab. In some embodiments, the antibody fragment is the Fab' fragment of Cetuximab. In some embodiments, the signaling peptide is the cRGD peptide. In some embodiments, the signal peptide directs the nanoparticles to the nucleus, mitochondria, endoplasmic reticulum, chloroplast, apoplast, or peroxisome. In some embodiments, the small molecule is folic acid.

In some embodiments, the micelle population further comprises a hybrid micelle population, wherein the micelle comprises more than one block copolymer and more than one fluorescent dye, and further wherein the micelle population has more than one pH transition point and emission spectra that differs for each pH transition point.

In some aspects, the present invention provides a single micelle with a copolymer and a fluorescent dye, and further wherein the micelle population has a pH transition point and an emission spectrum. In some embodiments, the single micelle further comprises a targeting moiety.

In one embodiment, the present invention provides a method of monitoring intracellular pH comprising: (a) contacting a cell with a pH-responsive system or composition as discussed above; and (b) detecting one or more fluorescent signals in the cell, wherein the detection of a fluorescent signal indicates that a micelle comprising a corresponding fluorescent dye has reached its pH transition point and dissociated. In certain embodiments, the method, further comprises: (c) contacting the cell with a compound of interest; (d) detecting one or more fluorescent signals in the cell; and (e) determining whether a change in the one or more fluorescent signals in the cell occurred following the contacting of the cell with the compound of interest. A compound of interest may be any compound that may be of interest with respect to its ability to affect the pH of the cell. The compound of interest may be, for example, a drug, peptide, protein, nucleic acid, or small molecule.

Another embodiment provides a method of monitoring vesicular trafficking comprising: (a) contacting a cell with a composition comprising at least a first and a second micelle population, wherein the first micelle population has a first pH transition point and a first fluorescent dye, and the second micelle population has a second pH transition point and a second fluorescent dye, and further wherein the first and second pH transition points are not identical and the first and second fluorescent dyes are not identical, under conditions whereby the cell takes up the composition by endocytosis; (b) detecting in the cell a first and/or second fluorescent signal corresponding to fluorescent emission spectra of the first and/or second fluorescent dye, wherein the detection of the first fluorescent signal indicates that the first micelle population has reached its pH transition point and disassociated, and the detection of the second fluorescent signal indicates that the second micelle population has reached its pH transition point and disassociated; and (c) determining what compartment the endocytozed micelle population was in when it dissociated based on the pH transition point of the micelle. In certain embodiments, the method further comprises determining the distribution of the fluorescent signals in the cell.

A further embodiment provides a method of monitoring vesicular trafficking comprising: (a) contacting a cell with a composition comprising at least a first and second, and third micelle population, wherein each micelle comprises a block copolymer and a fluorescent dye, and further wherein the first micelle population has a pH transition point between about pH 6.3-7.4 and a first fluorescent emission spectra, the second micelle population has a pH transition point between about pH 5.9-6.2 and a second fluorescent emission spectra, and the third micelle population has a pH transition point between about pH 5.0-5.8 and a third fluorescent emission spectra, under conditions whereby the cell takes up the composition by endocytosis; (b) detecting in the cell a first, second, and third fluorescent signal corresponding to the first, second, and third fluorescent emission spectra, wherein the detection of the first, second, and third fluorescent signals indicates that the micelle comprising a corresponding fluorescent dye has reached its pH transition point and disassociated; and (c) determining that a vesicle is an early endosome when the first fluorescent signal is detected, determining that a vesicle is a late endosome/lysosome when the second fluorescent signal is detected, and determining that a vesicle is a lysosome when the third fluorescent signal is detected. In certain embodiments, the method further comprises determining the spatial distribution of the fluorescent signals in the cell.

In another embodiment, the present invention provides a method of monitoring cell receptor cycling comprising: (a) contacting a cell with a composition comprising at least a first and a second micelle population, wherein each micelle comprises a block copolymer, a fluorescent dye, and a receptor binding moiety, and further wherein the first micelle population has a first pH transition point and a first fluorescent emission spectra and the second micelle population has a second pH transition point and a second fluorescent emission spectra that differ from the first pH transition point and the first emission spectra; (b) detecting in the cell or on its surface at least a first and/or a second fluorescent signal corresponding to the at least first and/or second fluorescent emission spectra, wherein the detection of the first and/or second fluorescent signal indicates that the micelle comprising a corresponding fluorescent dye has reached its pH transition point and disassociated; and (c) determining the distribution of the at least first and/or second fluorescent signals in the cell or on the cell surface. In some embodiments, the method further comprises a third micelle population having a third pH transition point and a third fluorescent emission spectra that differ from the first and second pH transition point and emission spectrums.

Another embodiment provides a method of monitoring endosome pH comprising: (a) contacting an endosome with a composition comprising at least a first and second micelle population, wherein each micelle comprises a block copolymer and a fluorescent dye, and further wherein the first micelle population has a pH transition point between about pH 5.7-6.3 and a first fluorescent emission spectra, the second micelle population has a pH transition point between about pH 5.7-6.3 and a second fluorescent emission spectra, wherein the first and second micelle populations have different pH transition points and different fluorescent emission spectra, under conditions whereby the endosome takes up the composition; (b) detecting in the endosome at least one of a first and second fluorescent signal corresponding to the first and second fluorescent emission spectra, wherein the detection of first and/or second fluorescent signals indicates that the micelle comprising a corresponding fluorescent dye has reached its pH transition point and disassociated; and (c) determining a pH or pH range for the endosome. In some embodiments, the method further comprises contacting the endosome with at least a third and a fourth micelle population. In certain aspects, the first micelle population has a pH transition point of about pH 5.7, the second micelle population has a pH transition point of about pH 5.94, the third micelle population has a pH transition point of about pH 6.18, and the fourth micelle population has a pH transition point of about pH 6.42.

Another embodiments provides a method of measuring extracellular pH, comprising: (a) contacting a collection of cells or their extracellular environment with a pH-responsive system or composition described above; and (b) detecting a fluorescent signals in the collection of cells, wherein the detection of a fluorescent signal indicates that a micelle comprising a corresponding fluorescent dye has reached its pH transition point and disassociated. In some embodiments, the method further comprises detecting the spatial orientation of the fluorescent signals in the collection of cells or their extracellular environment. In some embodiments, the method further comprises (a) contacting the cell or cells or their extracellular environment with a compound of interest; (b) detecting one or more fluorescent signals in and around the cell; and (c) determining whether a change in the one or more fluorescent signals in and around the cell occurred following the contacting of the cell with the compound of interest. In some embodiments, the compound of interest is a drug. In other embodiments, the compound of interest is an antibody, peptide, protein, nucleic acid, or small molecule. In some embodiments, the cell or collection of cells or their extracellular environment are a cancer cell or collection of cancer cells or their extracellular environment, a cell or collection of cells or their extracellular environment defective in lysosomal storage, a neural cell or collection of neural cells or their extracellular environment that are defective, a cell or collection of cells or their extracellular environment involved with inflammation, a cell or collection of cells or their extracellular environment involved with infection, a cell or collection of cells or their extracellular environment involved with wound healing a cell or collection of cells or their extracellular environment involved with hypoxia, a cell or collection of cells or their extracellular environment involved with radiation damage, a cell or collection of cells or their extracellular environment involved with trauma or a cell or collection of cells or their extracellular environment involved with hypoxemia.

Another embodiment provides a method of imaging angiogenic tumor vasculature comprising: (a) contacting tumor vasculature with a composition described above comprising at least two micelle populations described above, wherein each micelle comprises a block copolymer and a fluorescent dye, and further wherein the first micelle population has a pH transition point between about pH 6.5-7.4 and a first fluorescent emission spectra, the second micelle population has a pH transition point between about pH 5.9-6.4 and a second fluorescent emission spectra, and; (b) detecting in the tumor vasculature a first and second fluorescent signal corresponding to the first and second fluorescent emission spectra, wherein the detection of first and second fluorescent signals indicates that the micelle comprising a corresponding fluorescent dye has reached its pH transition point and disassociated. In some embodiments, the method further comprises determining the spatial orientation and distribution of the fluorescent signals in the tumor vasculature. In some embodiments, the method further comprising a micelle which has a targeting moiety. In some embodiments, the targeting moiety is the cRGD peptide.

Another embodiment is a method of imaging circulating tumor cells comprising: (a) contacting a circulating tumor cell in lymphatic channels or the bloodstream with a composition comprising a pH-responsive system or composition described above, wherein the micelle comprises a block copolymer and a fluorescent dye, and has a pH transition point between about pH 5.9-6.4, and; (b) detecting a fluorescent signals in the circulating tumor cells, wherein the detection of a fluorescent signal indicates that a micelle comprising a corresponding fluorescent dye has reached its pH transition point and disassociated. In some embodiments, the method further comprises determining the spatial orientation and distribution of fluorescent signals of circulating tumor cell in the lymphatic system or bloodstream. In some embodiments, the method further comprises a micelle which has a targeting moiety. In some embodiments, the targeting moiety is an antibody fragment. In some embodiments, the antibody fragment is a fragment of Cetuximab.

Another embodiments provides a method of imaging a tumor comprising: (a) contacting the tumor with a composition described above comprising at least two micelle populations, wherein each micelle comprises a block copolymer and a fluorescent dye, and further wherein the first micelle population has a pH transition point between about pH 6.5-7.4 and a first fluorescent emission spectra, the second micelle population has a pH transition point between about pH 5.9-6.4 and a second fluorescent emission spectra, and; (b) detecting in the tumor a first and second fluorescent signal corresponding to the first and second fluorescent emission spectra, wherein the detection of first and second fluorescent signals indicates that the micelle comprising a corresponding fluorescent dye has reached its pH transition point and disassociated. In some embodiments, the method further comprises determining the spatial orientation and distribution of fluorescent signals in the tumor. In some embodiments, the method further comprises a micelle which has a targeting moiety. In some embodiments, the targeting moiety is an antibody fragment. In some embodiments, the antibody fragment is a fragment of Cetuximab. In other embodiments, the targeting moiety is a small molecule. In some embodiments, the small molecule is folic acid.

Another embodiment provides a method of imaging a tumor that has metastasized to a lymph node in the regional area of the primary tumor comprising: (a) contacting the tumor with a composition described above comprising at least two micelle populations, wherein each micelle comprises a block copolymer and a fluorescent dye, and further wherein the first micelle population has a pH transition point between about pH 6.5-7.4 and a first fluorescent emission spectra, the second micelle population has a pH transition point between about pH 5.9-6.4 and a second fluorescent emission spectra, and; (b) detecting in the tumor a first and second fluorescent signal corresponding to the first and second fluorescent emission spectra, wherein the detection of first and second fluorescent signals indicates that the micelle comprising a corresponding fluorescent dye has reached its pH transition point and disassociated. In some embodiments, the method further comprises determining the spatial orientation and distribution of fluorescent signals in the tumor. In some embodiments, the method further comprises a micelle which has a targeting moiety. In some embodiments, the targeting moiety is an antibody fragment. In some embodiments, the antibody fragment is a fragment of Cetuximab. In other embodiments, the targeting moiety is a small molecule. In some embodiments, the small molecule is folic acid.

Another embodiment provides a method of imaging a sentinel node of a tumor comprising: (a) contacting the tumor with a composition described above comprising at least two micelle populations, wherein each micelle comprises a block copolymer and a fluorescent dye, and further wherein the first micelle population has a pH transition point between about pH 6.5-7.4 and a first fluorescent emission spectra, the second micelle population has a pH transition point between about pH 5.9-6.4 and a second fluorescent emission spectra, and; (b) detecting in the tumor a first and second fluorescent signal corresponding to the first and second fluorescent emission spectra, wherein the detection of first and second fluorescent signals indicates that the micelle comprising a corresponding fluorescent dye has reached its pH transition point and disassociated. (c) having the dissociated portions of the micelle including the fluorescent signal enter the lymphatic vasculature draining the tumor, and move through the lymphatic vasculature to the lymph nodes along the lymphatic vasculature. (d) detecting in the lymphatic vasculature and the lymph nodes along the lymphatic vasculature the first and second fluorescent signal corresponding to the first and second fluorescent emission spectra, wherein the detection of first and second fluorescent signals indicates that the micelle comprising a corresponding fluorescent dye has reached its pH transition point and disassociated in the primary tumor and has moved to the lymphatic vasculature and the lymph nodes along the lymphatic vasculature. In some embodiments, the method further comprises determining the spatial orientation and distribution of fluorescent signals in the tumor. In some embodiments, the method further comprises a micelle which has a targeting moiety. In some embodiments, the targeting moiety is an antibody fragment. In some embodiments, the antibody fragment is a fragment of Cetuximab. In other embodiments, the targeting moiety is a small molecule. In some embodiments, the small molecule is folic acid.

In any of the methods described herein, the fluorescent signals may be detected once or more than once over a period of time. Additionally, the distribution of the fluorescent signals may be determined once or more than once over a period of time. The time period may be over several minutes, several hours, or several days. In some embodiments, the fluorescent signals are detected over a period of zero to 12 hours, or over a period of 1 to 12 hours. In some embodiments, the distribution of the fluorescent signals is determined over a period of zero to 12 hours, or over a period of 1 to 12 hours. The detection of the fluorescent signals may be continuous or intermittent.

In any of the methods described herein, the step of detecting one or more fluorescent signals may be repeated two or more times. In certain aspects of the invention, the detecting step is repeated at least 2, 3, 4, 5, 6, 7, 8, 9, 10, 11, 12, 13, 14, 15, 16, 17, 19, 20, or more times.

In addition to monitoring intracellular or intraorganelle pH, the methods and compositions disclosed herein may also be used to detect and/or monitor extracellular pH or the pH in fluids. For example, tumors are known to have an extracellular environment that is more acidic that the extracellular environment in healthy tissue. Thus, the methods and compositions disclosed herein may be used, for example, to identify tumor margins for pathology, diagnostic, or image-guided surgical applications. In certain aspects, the addition of targeting moieties could further enhance the labeling of the relevant cells or tissues. Furthermore, using a series of pH-responsive micelles, one can achieve greater contrast between healthy and diseased tissues, because the series of pH-responsive micelles will differentially label these tissues depending on pH and/or targeting moiety. Also, a series of pH-responsive micelles may be used to deliver different compounds, such as drugs, to healthy and diseased tissues, because the series of pH-responsive micelles will differentially disassociate in healthy versus diseased tissue depending on pH and/or targeting moiety. Thus, for example, a series of micelles could be used to deliver a chemotherapeutic or radiosensitizing drug to cancer cells, while delivering a rescue drug to healthy cells. Fluorescent labeling of the series of micelles may be used to indicate when and where the drug has been released from within the micelle.

In another embodiment, the present invention provides a copolymer comprising:

a) a polymer according to formula:

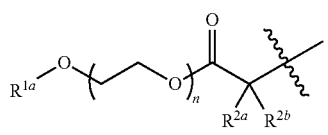

b) a monomer according to formula $A^1$; and
c) a monomer according to formula $A^2$;
or a pharmaceutically acceptable salt thereof; and stereoisomers, isotopic variants and tautomers thereof;

wherein
each $A^1$ and $A^2$ is independently selected from

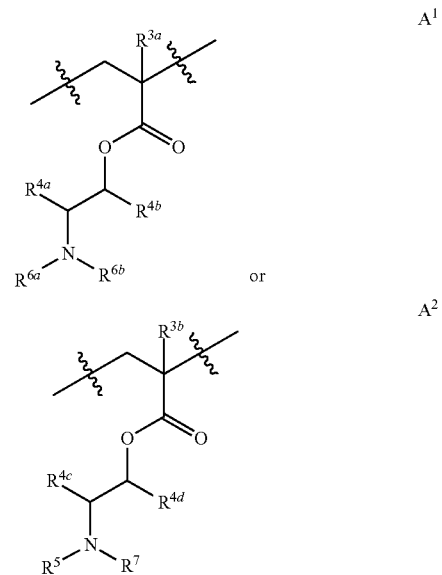

each $R^{1a}$ is independently H, substituted or unsubstituted alkyl, or

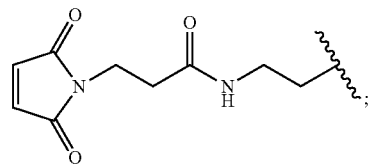 [SMILES: *CCNC(=O)CCN1C(=O)C=CC1=O]

each $R^{2a}$, $R^{2b}$, $R^{3a}$, $R^{4a}$, $R^{4b}$, $R^{4c}$, $R^{4d}$, and $R^5$ is independently H or substituted or unsubstituted alkyl;

each $R^{6a}$, and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye;

the subscript n is an integer between 10 to 200;

and wherein the copolymer is a random copolymer, with the proviso that copolymers disclosed in Zhou, K., *Angew. Chem. Int. Ed.* 2011, 50, 6109-6114, PCT/US2011/00148, and PCT/US2011/047497 are explicitly excluded.

In another embodiment, the present invention provides a copolymer according to formula I:

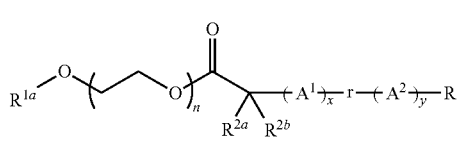

or a pharmaceutically acceptable salt thereof; and stereoisomers, isotopic variants and tautomers thereof;

wherein
each A¹ and A² is independently selected from

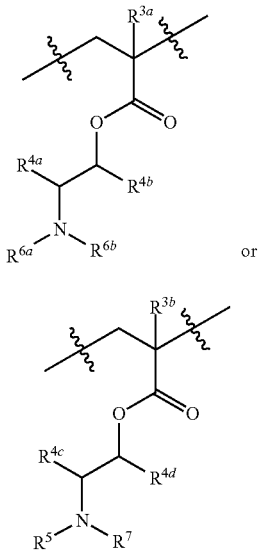

provided that both A¹ and A² are different at the same time;

each $R^{1a}$ is independently H, substituted or unsubstituted alkyl, or

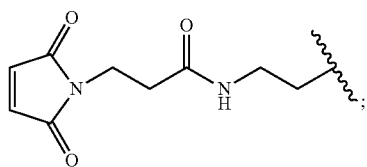 [SMILES: *CCNC(=O)CCN1C(=O)C=CC1=O]

each $R^{2a}$, $R^{2b}$, $R^{3a}$, $R^{4a}$, $R^{4b}$, $R^{4c}$, $R^{4d}$, and $R^5$ is independently H or substituted or unsubstituted alkyl;

$R^{1b}$ is H, substituted or unsubstituted alkyl, Br, or S—R;

each $R^{6a}$ and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye;

the subscript n is an integer between 10 to 200; the subscript x is an integer between 1 to 200; and the subscript y is an integer between 1 to 200;

and wherein r represents that the copolymer is in the form of random copolymer, with the proviso that copolymers disclosed in Zhou, K., Angew. Chem. Int. Ed. 2011, 50, 6109-6114, PCT/US2011/00148, and PCT/US2011/047497 are explicitly excluded.

The methods disclosed herein may be used with any cell of interest. In certain embodiments the cell is a cancer cell, a cell defective in lysosomal storage, or a defective neural cell. In some embodiments, the cell may be a cell in a tissue sample. For example, the nanoplatform may be used to demarcate the tumor and normal tissue boundaries for image-guided surgical resection and/or analysis of tumor margins after surgical resection. In some embodiments, targeting moieties may be employed to direct micelles to either tumor cells or normal cells. Alternatively, differences in pH, either intracellularly or in the extracellular matrix, may be used to distinguish tumor tissue from normal tissue using the pH-responsive nanoplatform described herein.

In some embodiments of the present invention, it is envisioned that the pH-responsive system, the composition, or the methods could be achieved using only one of the envisioned nanoparticles or micelles rather than the described two or more nanoparticles or micelles. In some embodiments, it is also envisioned that each of the nanoparticles or micelles may be used as hybrid nanoparticles or micelles as described in the examples. In some embodiments, it is also envisioned that each of the nanoparticles can be sequentially.

As used herein, "pH-responsive micelle," "pH-sensitive micelle," "pH-activatable micelle" and "pH-activatable micellar (pHAM) nanoparticle" are used interchangeably herein to indicate a micelle comprising one or more block copolymers, which disassociates depending on the pH (e.g. above or below a certain pH). As a non-limiting example, at a certain pH, the block copolymer is substantially in micellar form. As the pH changes (e.g. decreases), the micelles begin to disassociate, and as the pH further changes (e.g. further decreases), the block copolymer is present substantially in disassociated (non-micellar) form.

As used herein, "pH transition range" indicates the pH range over which the micelles disassociate.

As used herein, "pH transition value" (pHt) indicates the pH at which half of the micelles are disassociated.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

(FIG. 2A) Ultra-pH responsive properties of PDPA-TMR nanoprobe (200 μg/mL), where fluorescence activation is observed within a pH range of 6.2-6.6. The sample was excited at 545 nm, and the emission spectra were collected from 550 to 750 nm. (FIG. 2B) Normalized fluorescence intensity as a function of pH for PDPA-TMR. The inset fluorescent images of PDPA-TMR aqueous solutions (100 μg/mL) at pH 5.5 and 7.4 were taken on an Maestro instrument. The pH dependence of number-weighted hydrodynamic radius, <$R_h$>, was obtained by pH titration of PDPA-TMR using 0.02 M NaOH aqueous solution. (FIG. 2C) Molar fraction of tertiary amino groups in PDPA-TMR as a function of pH. The fluorescence transition point ($pH_t$) from FIG. 2B and the apparent pKa of the PDPA-TMR copolymer are indicated. (FIG. 2D) Fluorescence intensity ratio of PDPA-TMR samples at different pH over pH 7.4 at different polymer concentrations.

(FIG. 4A) pH dependence of the fluorescence intensity ratio of PDPA-TMR1, PDPA-TMR3 and PDPA-TMR6 aqueous solutions at different pHs to pH 7.4. Copolymer concentrations were at 200 μg/mL and maximum emission intensity was measured at 580 nm. (FIG. 4B) The UV-Vis absorption spectra with normalization to the monomer peak intensity of PDPA-TMR1, PDPA-TMR3 and PDPA-TMR6 in aqueous solution at pH 7.4 and 5.5. Copolymer concentrations were at 200 μg/mL and free TMR dye concentration was at 1.0 μg/mL. (FIG. 4C) Fluorescence intensity ratio of pH 5.5 to 7.4 as a function of weight percentage of PDPA-TMR1, PDPA-TMR3 and PDPA-TMR6 over their dye-free precursors (PDPA-$AMA_{n=1,3,6}$), respectively. (FIG. 4D) Fluorescence emission spectra of PDPA-CMN, PDPA-BDY and their molecular mixture with 1:1 weight ratio at pH 7.4. The samples were excited at CMN wavelength ($\lambda_{ex}$=408 nm). Each copolymer concentration was controlled at 200 μg/mL.

(FIG. 5A) Fluorescence intensity ratio at different pH over pH 7.4 for PDPA-PPO copolymer solution (concentration=500 μg/mL). (FIG. 5B) Fluorescence intensity ratio at pH 5.5 over 7.4 as a function of weight percentage of PDPA-PPO in the molecular mixture of PDPA-PPO and its dye-free synthetic precursor.

(FIG. 9A) pH titration curve of PEO-(PDPA-TMR) with 0.02 M NaOH aqueous solution. (FIG. 9B) Number-weighted hydrodynamic radius distribution of PEO-(PDPA-TMR) aqueous solution at pH 5.8 and 6.8 during the titration experiment.

(FIG. 13A) Fluorescence emission spectra of PDPA-BDY, PDPA-TMR and their molecular mixture with 1:1 weight ratio at pH 7.4. Each individual polymer concentration is at 200 μg/mL. The samples were excited at 498 nm and the emission spectra were collected from 505 to 750 nm. (FIG. 13B) Fluorescence emission spectra of these solutions at pH 5.5.

(FIG. 14A) Fluorescence and (FIG. 14B) UV-Vis absorption spectra of free coumarin aqueous solution at pH 7.4 and 5.5 (coumarin concentrations are 1 μg/mL). (FIG. 14C) Fluorescence emission and (FIG. 14D) UV-Vis absorption spectra of PDPA-CMN aqueous solution at pH 7.4 and 5.5 where the polymer concentration is at 200 μg/mL. (FIG. 14E) Change of the fluorescence intensity ratio at pH 5.5 over 7.4 as a function of weight percentage of PDPA-CMN in the molecular mixture of PDPA-CMN and its corresponding synthetic precursor (total polymer concentrations are at 200 μg/mL). For measurement of fluorescence emission, the samples were excited at 408 nm, and the emission spectra were collected from 420 to 700 nm.

(FIG. 15A) Fluorescence emission spectra of free PPO dye in aqueous solution at pH 7.4 and 5.5 (PPO concentration is at 15 μg/mL). (FIG. 15B) pH dependent fluorescence emission spectra of PEO-(PDPA-PPO) copolymer in aqueous solution where the copolymer concentrations are at 500 μg/mL. For fluorescence emission experiments, the samples were excited at 408 nm.

(FIG. 16A) pH dependent fluorescence emission spectra and (FIG. 16B) fluorescence intensity ratio of PC7A-C55 as a function of pH in aqueous solution (copolymer concentrations are at 200 μg/mL). The samples were excited at 690 nm, and the emission spectra were collected from 700 to 780 nm. (FIG. 16C) The absorption spectra with normalization to the monomer peak intensity of PC7A-C55 in aqueous solution at pH 7.6 and 6.2. (FIG. 16D) Change of the fluorescence intensity ratio as a function of weight percentage of PC7A-C55 in the molecular mixture of PC7A-C55 and its corresponding dye-free synthetic precursor.

(FIG. 17A) pH dependent fluorescence emission spectra and (FIG. 17B) fluorescence intensity ratio of PC6A-C75 as a function of pH in aqueous solution (copolymer concentrations are at 200 μg/mL). The samples were excited at 790 nm, and the emission spectra were collected from 800 to 900 nm. (FIG. 17C) The absorption spectra with normalization to the monomer peak intensity of PC6A-C75 in aqueous solution at pH 8.0 and 6.4. (FIG. 17D) Change of the fluorescence intensity ratio as a function of weight percentage of PC6A-C75 in the molecular mixture of PC6A-C75 and its corresponding dye-free synthetic precursor.

(FIG. 18A) pH dependent fluorescence emission spectra and (FIG. 18B) fluorescence maximum intensity ratio of PDBA-BDY in aqueous solution (copolymer concentrations are at 200 μg/mL). The samples were excited at 498 nm, and the emission spectra were collected from 505 to 650 nm. (FIG. 18C) The absorption spectra with normalization to the monomer peak intensity of PDBA-BDY in aqueous solution at pH 6.2 and 4.2. (FIG. 18D) Change of the fluorescence maximum intensity ratio as a function of weight percentage of PDBA-BDY in the molecular mixture of PDBA-BDY and its corresponding dye-free synthetic precursor.

(FIG. 21A) Synthesis of pH-activatable micellar nanoprobes. (FIG. 21B) Normalized fluorescence intensity as a function of pH for different nanoprobes. Nanoprobe concentrations are at 200 μg/mL Fmax/Fmin is up to 63-fold. (FIG. 21C) pH transition value as a function of percentage of PDBA in copolymers' component.

FIGS. 37A & 37B iUPS nanoprobes target both acidic pHe and tumor vasculature with broad tumor specificity. 37A Intravital fluorescent images show complimentary pattern of spatial activation of cRGD-UPS$_i$-RhoG (10 mg/kg, green) and UPS, TMR (10 mg/kg, red) inside tumor vasculature and parenchyma, respectively. The dual nanoprobes were co-injected intravenously and the images were taken at 6 h post-injection. 37B iUPS nanoprobes show broad tumor imaging specificity and efficacy in 10 different tumor models of different cancer types (breast, prostate, head and neck, lung, brain, and pancreatic cancers) and organ sites. In each model, high T/N ratios were observed demonstrating the success of targeting tumor microenvironment signals as a universal strategy to achieve broad tumor specificity.

FIGS. 39A & 39B Comparison of iUPS nanoprobe activation with folate-FITC conjugates in head-neck orthotopic tumors. 39A Nude mice bearing orthotopic HN5 head-neck carcinoma were intravenously co-injected with iUPS nanoprobe and folate-FITC, a small molecular probe in Phase I clinical trials. At 24 h post-injection, tumors were surgically exposed for fluorescent intraoperative imaging of tumor vasculature and acidic tumor milieu. 39B At 24 h post-injection, mice were sacrificed and excised tumor and lymph nodes were visualized. Nanoprobe is more efficacious to image the whole tumor and lymph nodes than folate-FITC. The mice autofluorescence is color coded blue while the unmixed folate-FITC and nanoprobe signal is coded green and red, respectively.

FIGS. 40A & 40B Ex vivo experiments to detect rare circulating tumor cells in whole blood using Fab'-UPS$_i$-TMR nanoprobes. 40A A microscopy image at 600× magnification of the serum. 40B A microscopy image at 2400× magnification of the serum.

FIG. 50 In vivo imaging of PDPA-TMR-Fab' nanoprobe in HN5 tumor-bearing mice showing that the probe selectively highlights the tumor preferentially.

FIG. 52 In vivo imaging of PDPA-TMR-FA nanoprobe in HN5 tumor-bearing mice showing that the probe selectively highlights the tumor preferentially.

FIGS. 53A-C. Sequential activation of multi-colored hybrid nanoprobe. 53a The mean count rate (kcps) of hybrid nanoprobes plotted as a function of pH. 53b Fluorescence spectra of hybrid nanoprobes (100 µg/mL) at pH 7.4 and excited by 490 nm. 53c Representative fluorescent images of hybrid nanoprobes (100 µg/mL) at different pH values

DESCRIPTION OF ILLUSTRATIVE EMBODIMENTS

Figure 1:
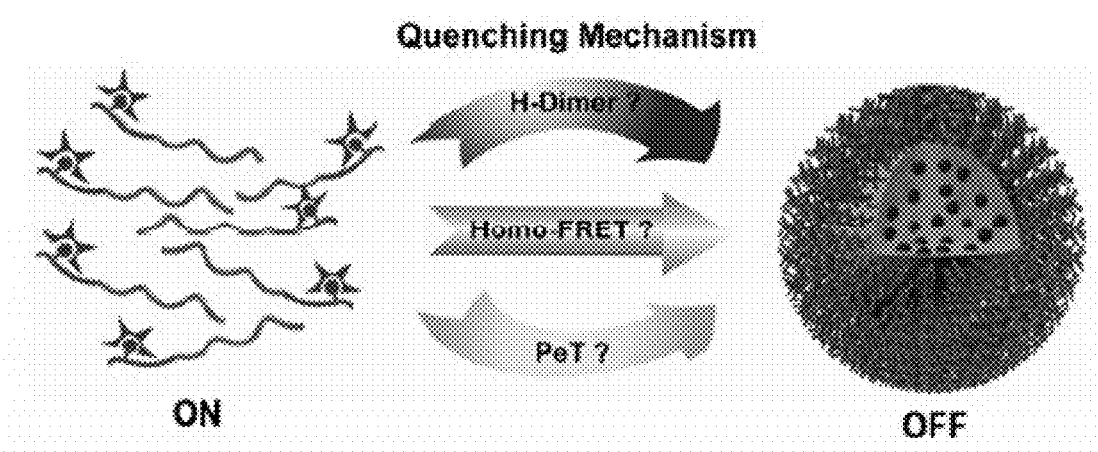
FIG. 1. Schematic illustration of three possible photochemical mechanisms for the development of pH-activatable nanoparticles: H-dimer formation, homo Förster resonance energy transfer (homo-FRET), and photo-induced electron transfer (PeT).

Various embodiments of the present invention provides pH-tunable, highly activatable multicolored fluorescent nanoparticles using fluorescent dyes. In certain embodiments, this multicolored nanoplatform utilzes ultra-pH responsive tetramethyl rhodamine (TMR)-based nanoparticles with tunable pH transitions in the physiological range (5.0-7.4). Methods of making tetramethyl rhodamine (TMR)-based nanoparticles described in Zhou, K., *Chem. Int. Ed.* 2011, 50, 6109; PCT/US2011/00148, and PCT/US2011/047497. pH-induced micellization of pH responsive nanoparticles is used in conjunction with fluorescence quenching to provide pH responsive fluorescent nanoparticles (see FIG. 1). For example, in one embodiment, a series of multicolored pH-activatable fluorescent nanoparticles is provided with independent control of emission wavelengths (500-820 nm) and pH transition points (5.0-7.4). The nanoparticles with different emission wavelengths achieved sharp pH response (ΔpH<0.25 between ON/OFF states). Incubation of a mixture of several multicolored nanoparticles with cancer cells showed a pattern of sequential activation that directly correlated with their pH transition values. The multicolored nanoplatform provides a useful nanotechnology toolset to investigate fundamental cell physiological processes such as pH regulation in endocytic vesicles, endosome/lysosome maturation, and effect of pH on receptor cycling and trafficking of subcellular organelles. While the various embodiments describe using multiple different nanoparticles or micelles, it is envisioned that similar results may be obtained using only a single nanoparticle.

A. Block Copolymers and Fluorescent Dyes

The pH-responsive micelles and nanoparticles disclosed herein comprise block copolymers and fluorescent dyes. A block copolymer comprises a hydrophilic polymer segment and a hydrophobic polymer segment. The hydrophobic polymer segment is pH sensitive. For example, the hydrophobic polymer segment may comprise an ionizable amine group to render pH sensitivity. The block copolymers form pH-activatable micellar (pHAM) nanoparticles based on the supramolecular self-assembly of these ionizable block copolymers. At higher pH, the block copolymers assemble into micelles, whereas at lower pH, ionization of the amine group in the hydrophobic polymer segment results in dissociation of the micelle. The ionizable groups may act as tunable hydrophilic/hydrophobic blocks at different pH values, which may directly affect the dynamic self-assembly of micelles.

For diagnostic or pH monitoring applications, a labeling moiety may be conjugated to the block copolymer. In some embodiments, the label (e.g. a fluorescent label) is sequestered inside the micelle when the pH favors micelle formation. Sequestration in the micelle results in a decrease in label signal (e.g. via fluorescence quenching). Specific pH conditions may lead to rapid protonation and dissociation of micelles into unimers, thereby exposing the label, and increasing the label signal (e.g. increasing fluorescence emission). The micelles of the invention may provide one or more advantages in diagnostic applications, such as: (1) disassociation of the micelle (and rapid increase in label signal) within a short amount of time (e.g. within minutes) under certain pH environments (e.g. acidic environments), as opposed to hours or days for previous micelle compositions; (2) increased imaging payloads; (3) selective targeting of label to the desired site (e.g. tumor or particular endocytic compartment); (4) prolonged blood circulation times; (5) responsiveness within specific narrow pH ranges (e.g. for targeting of specific organelles); and (6) high contrast sensitivity and specificity. For example, the micelles may stay silent (or in the OFF state) with minimum background signals under normal physiological conditions (e.g. blood circulation, cell culture conditions), but imaging signals can be greatly amplified when the micelles reach their intended molecular targets (e.g. extracellular tumor environment or cellular organelle).

Numerous fluorescent dyes are known in the art. In certain aspects of the invention, the fluorescent dye is a pH-insensitive fluorescent dyes. In some embodiments, the fluorescent dye has a small Stokes shift. In particular embodiments, the Stokes shift is $\Delta\lambda<40$ nm. The fluorescent dye may be conjugated to the copolymer directly or through a linker moiety. Methods known in the art may be used to conjugate the fluorescent dye to, for example, the hydrophobic polymer.

Examples of block copolymers and block copolymers conjugated to fluorescent dyes include:

A copolymer comprising:
a) a polymer according to formula:

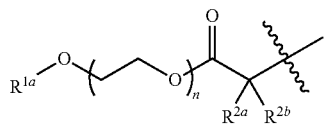

b) a monomer according to formula $A^1$; and
c) a monomer according to formula $A^2$;
or a pharmaceutically acceptable salt thereof; and stereoisomers, isotopic variants and tautomers thereof;

wherein
each $A^1$ and $A^2$ is independently selected from

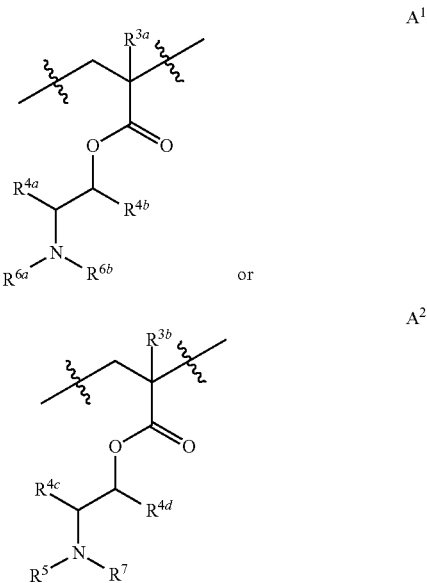

each $R^{1a}$ is independently H, substituted or unsubstituted alkyl, or

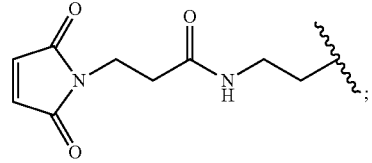 [SMILES: *CCNC(=O)CCN1C(=O)C=CC1=O]

each $R^{2a}$, $R^{2b}$, $R^{3a}$, $R^{4a}$, $R^{4b}$, $R^{4c}$, $R^{4d}$, and $R^5$ is independently H or substituted or unsubstituted alkyl;

each $R^{6a}$, and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye;
the subscript n is an integer between 10 to 200;
and wherein the copolymer is a random copolymer.

A copolymer according to formula I:

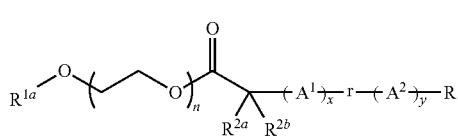

or a pharmaceutically acceptable salt thereof; and stereoisomers, isotopic variants and tautomers thereof;

wherein
each $A^1$ and $A^2$ is independently selected from

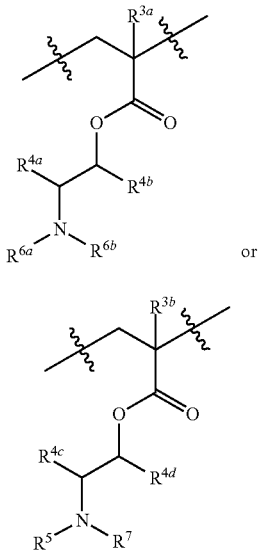

provided that both $A^1$ and $A^2$ are different at the same time;

each $R^{1a}$ is independently H, substituted or unsubstituted alkyl, or

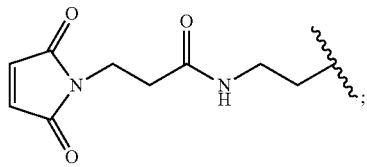 [SMILES: *CCNC(=O)CCN1C(=O)C=CC1=O]

each $R^{2a}$, $R^{2b}$, $R^{3a}$, $R^{4a}$, $R^{4b}$, $R^{4c}$, $R^{4d}$, and $R^5$ is independently H or substituted or unsubstituted alkyl;

$R^b$ is H, substituted or unsubstituted alkyl, Br, or S—R;

each $R^{6a}$ and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye;

the subscript n is an integer between 10 to 200; the subscript x is an integer between 1 to 200; and the subscript y is an integer between 1 to 200;

and wherein r represents that the copolymer is in the form of random copolymer.

A copolymer according to formula II:

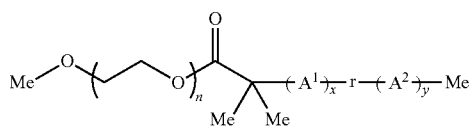

or a pharmaceutically acceptable salt thereof; and stereoisomers, isotopic variants and tautomers thereof, with the proviso that the Me at the right terminal end of the structure may be Me or Br;

wherein $A^1$, $A^2$, n, x, and y are as in claim 1;

and wherein r represents that the copolymer is in the form of random copolymer.

A copolymer according to formula III:

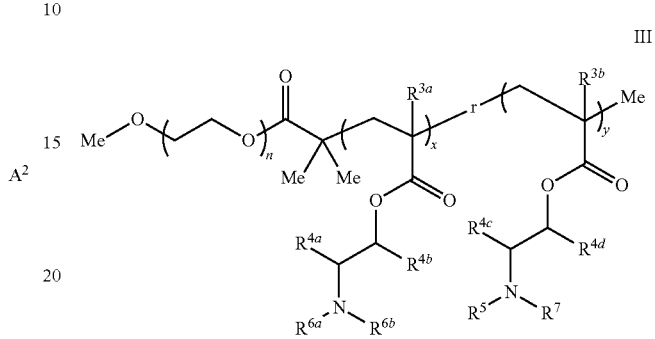

or a pharmaceutically acceptable salt thereof; and stereoisomers, isotopic variants and tautomers thereof, with the proviso that the Me on the right terminal end of the structure may be Me or Br;

wherein
each $R^{3a}$, $R^{3b}$, $R^{4a}$, $R^{4b}$, $R^{4c}$, $R^{4d}$, and $R^5$ is independently H or substituted or unsubstituted alkyl;

each $R^{6a}$, and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye;

the subscript n is an integer between 10 to 200; the subscript x is an integer between 1 to 200; the subscript y is an integer between 1 to 200;

and wherein r represents that the copolymer is in the form of random copolymer.

A copolymer according to formula IV:

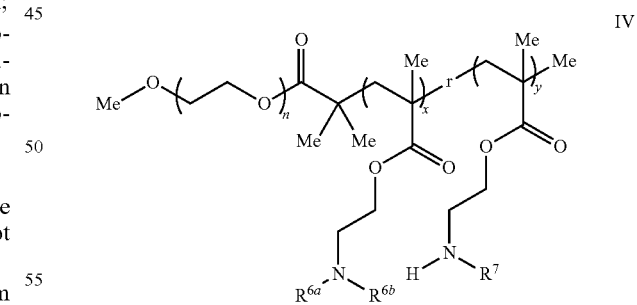

or a pharmaceutically acceptable salt thereof; and stereoisomers, isotopic variants and tautomers thereof, with the proviso that the Me on the right terminal end of the structure may be Me or Br;

wherein
each $R^{6a}$, and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye; the subscript n is an integer between 10 to 200; the subscript x is an integer between 1 to 200; the subscript y is an integer between 1 to 200;

and wherein r represents that the copolymer is in the form of random copolymer.

In certain embodiments, $R^7$ is selected from Coumarin (or CMN), DODPY (or BDY), PyPMO (or PPO), TMR, Cy5,5, and Cy7,5; and Coumarin (or CMN), DODPY (or BDY), PyPMO (or PPO), TMR, Cy5,5, and Cy7,5 are according to formula:

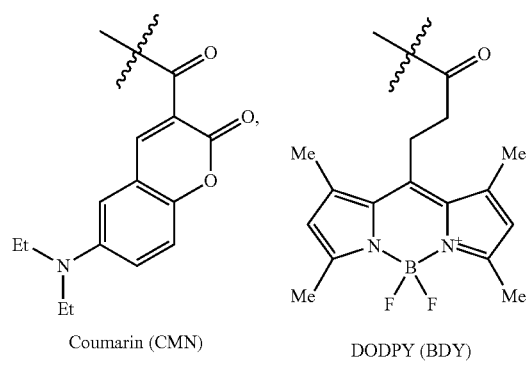

Coumarin (CMN)        DODPY (BDY)

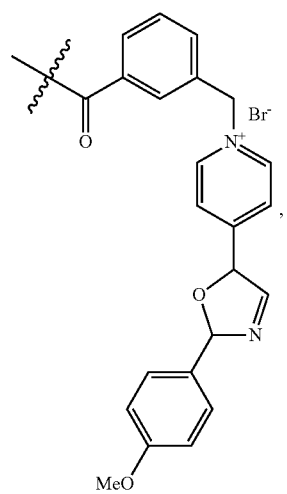

PyPMO (PPO)

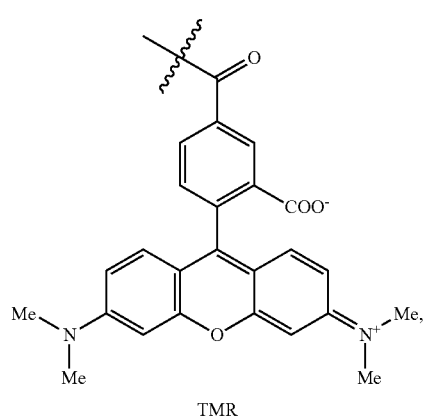

TMR

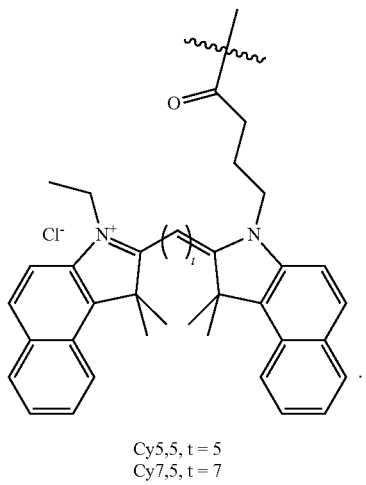

Cy5,5, t = 5
Cy7,5, t = 7

It is noted, however, that Coumarin (CMN) did not lead to fluorescence activation in the studies described herein, so its usefulness may be as a negative control or in some embodiments it may be explicitly excluded from the definition of $R^7$.

In certain embodiments, the subscript n is an integer between 80-200, 100-140, or 110-120. In some embodiments, the subscript n is 114.

In certain embodiments, the subscript x is an integer between 10-110, 40-80, 50-80, 60-80, or 70-80. In some embodiments, the subscript x is 71, 72, 77, or 80.

In certain embodiments, the subscript y is an integer between 1-20, 1-15, or 1-10. In some embodiments, the subscript y is 1, 3, 5, or 6.

A copolymer is according to formula V:

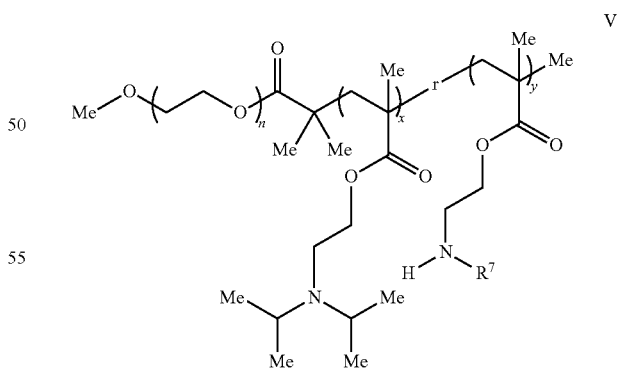

or a pharmaceutically acceptable salt thereof; and stereoisomers, isotopic variants and tautomers thereof, with the proviso that the Me at the right terminal end of the structure may be Me or Br;

wherein
R⁷ is CMN, BDY, PPO, TMR, C55, or C75:

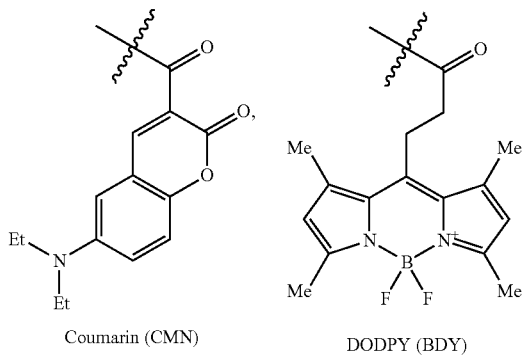

Coumarin (CMN)    DODPY (BDY)

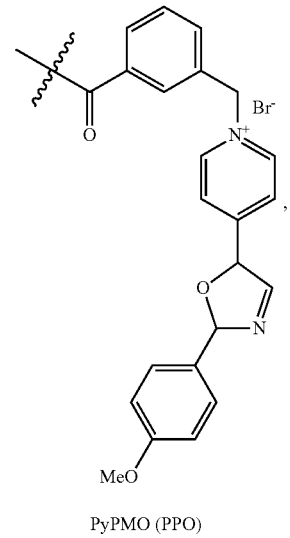

PyPMO (PPO)

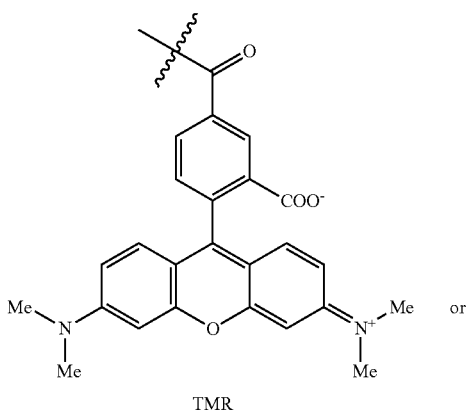

TMR    or

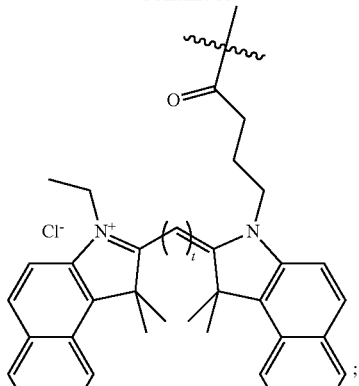

Cy5,5, (C55), t = 5
Cy7,5, (C75), t = 7 the subscript n is an integer between 110-120; the subscript x is an integer between 70 to 81; the subscript y is an integer between 1 to 10;

and wherein r represents that the copolymer is in the form of random copolymer.

A copolymer according the formula V; wherein
R⁷ is TMR;
the subscript n is 114;
the subscript x is 71; and
the subscript y is 1.

A copolymer according to formula V; wherein
R⁷ is TMR;
the subscript n is 114;
the subscript x is 77; and
the subscript y is 3.

A copolymer according the formula V; wherein
R⁷ is TMR;
the subscript n is 114;
the subscript x is 80; and
the subscript y is 6.

A copolymer according the formula V; wherein
R⁷ is CMN;
the subscript n is 114;
the subscript x is 77; and
the subscript y is 3.

A copolymer according the formula V; wherein
R⁷ is BDY;
the subscript n is 114;
the subscript x is 77; and
the subscript y is 3.

A copolymer according the formula V; wherein
R⁷ is PPO;
the subscript n is 114;
the subscript x is 77; and
the subscript y is 3.

A copolymer according to formula VI:

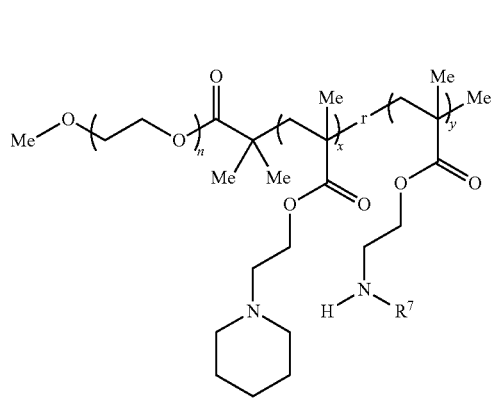

VI

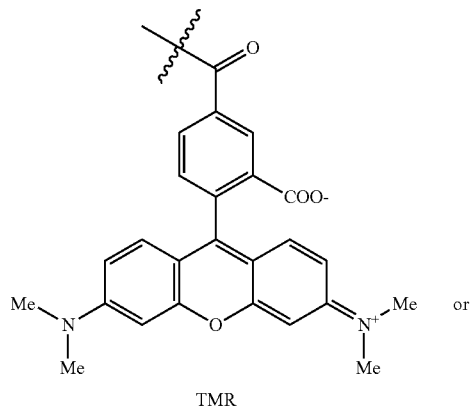

TMR or or a pharmaceutically acceptable salt thereof; and stereoisomers, isotopic variants and tautomers thereof, with the proviso that the Me on the right terminal end of the structure may be Me or Br;

wherein $R^7$ is CMN, BDY, PPO, TMR, C55, or C75:

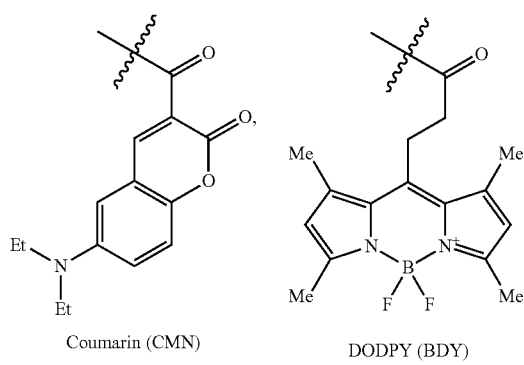

Coumarin (CMN)       DODPY (BDY)

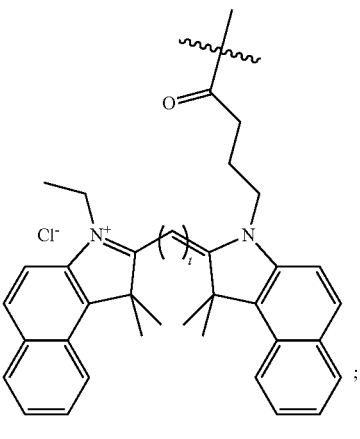

Cy5,5, (C55), t = 5
Cy7,5, (C75), t = 7

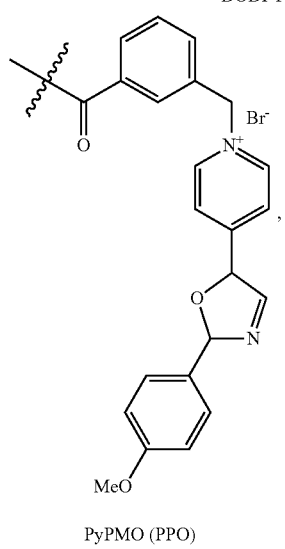

PyPMO (PPO)

the subscript n is an integer between 110-120; the subscript x is an integer between 70 to 81; the subscript y is an integer between 1 to 10;

and wherein r represents that the copolymer is in the form of random copolymer.

A copolymer according the formula VI; wherein
$R^7$ is C75;
the subscript n is 114;
the subscript x is 81; and
the subscript y is 3.

A copolymer according the formula VI; wherein
$R^7$ is C55;
the subscript n is 114;
the subscript x is 65; and
the subscript y is 3.

A copolymer according to formula VII:

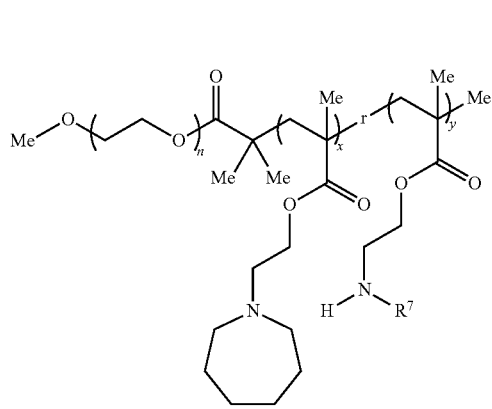

VII

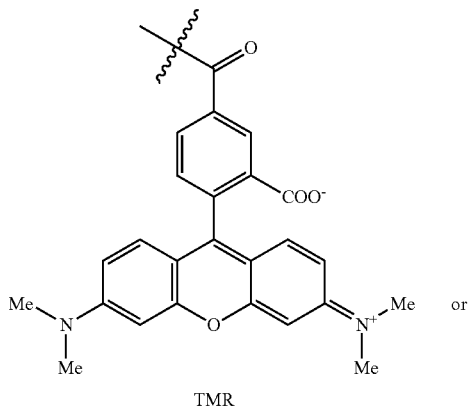

TMR or a pharmaceutically acceptable salt thereof; and stereoisomers, isotopic variants and tautomers thereof, with the proviso that the Me on the right terminal end of the structure may be Me or Br;

wherein $R^7$ is CMN, BDY, PPO, TMR, C55, or C75:

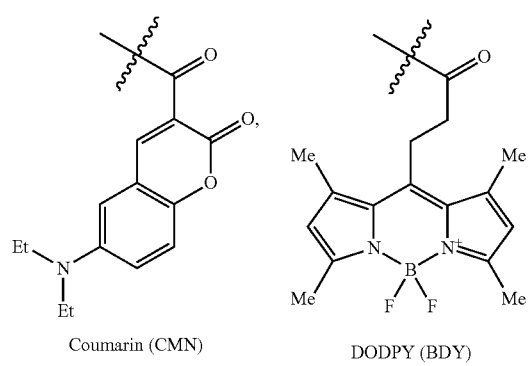

Coumarin (CMN)        DODPY (BDY)

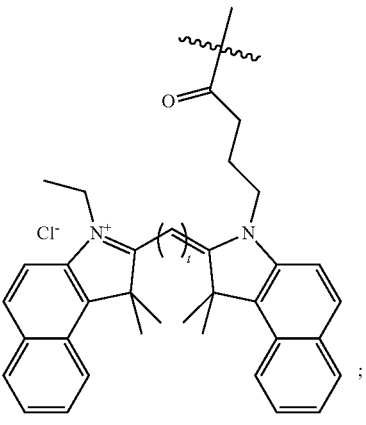

Cy5,5, (C55), t = 5
Cy7,5, (C75), t = 7

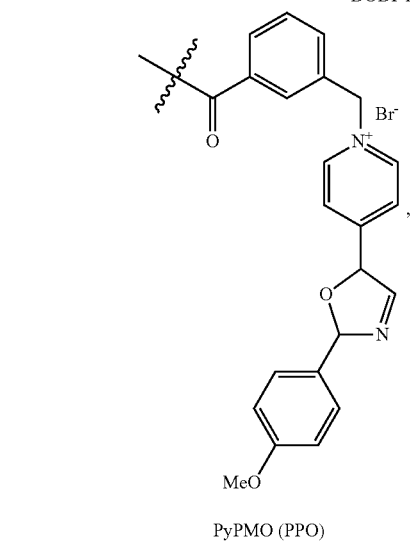

PyPMO (PPO)

the subscript n is an integer between 110-120; the subscript x is an integer between 70 to 81; the subscript y is an integer between 1 to 10;

and wherein r represents that the copolymer is in the form of random copolymer.

A copolymer according to formula VII; wherein $R^7$ is C75;

the subscript n is 114;

the subscript x is 81; and the subscript y is 3.

A copolymer according to formula VII; wherein $R^7$ is C55;

the subscript n is 114;

the subscript x is 65; and the subscript y is 3.

A copolymer according to formula VIII:

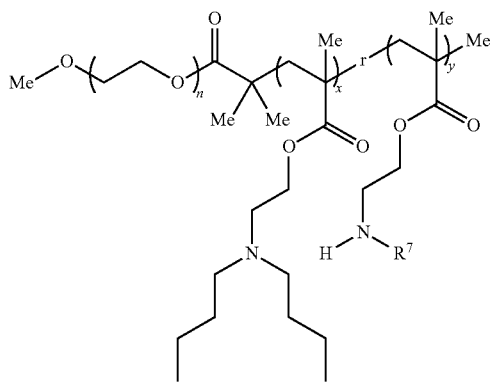

VIII or a pharmaceutically acceptable salt thereof; and stereoisomers, isotopic variants and tautomers thereof;
wherein
R⁷ is CMN, BDY, PPO, TMR, C55, or C75:

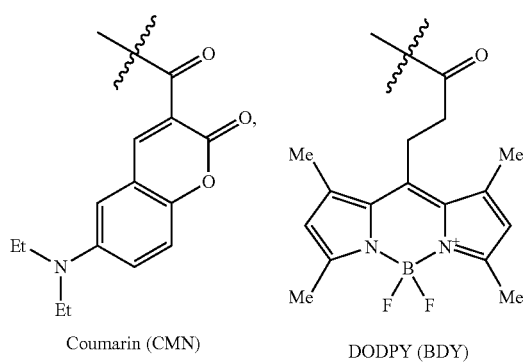

Coumarin (CMN)          DODPY (BDY)

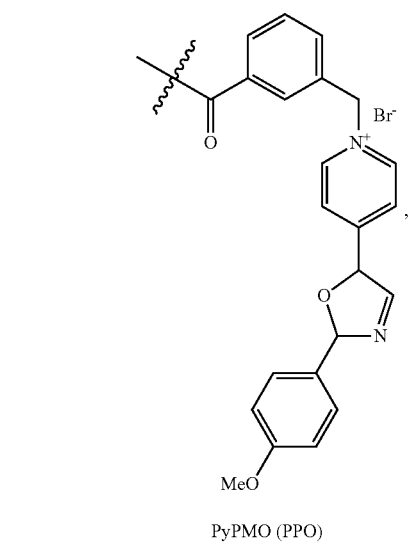

PyPMO (PPO)

[TMR structure]

TMR

[Cy structure]

Cy5,5, (C55), t = 5
Cy7,5, (C75), t = 7 the subscript n is an integer between 110-120; the subscript x is an integer between 70 to 81; the subscript y is an integer between 1 to 10;
and wherein r represents that the copolymer is in the form of random copolymer.

In some embodiments, the copolymer is PDBA-BDY; and wherein
A copolymer according the formula VIII; wherein
R⁷ is BDY;
the subscript n is 114;
the subscript x is 77; and
the subscript y is 3.

Additional examples of block copolymers are described in Zhou, K., *Chem. Int. Ed.* 2011, 50, 6109; PCT/US2011/00148, and PCT/US2011/047497, each of which is incorporated herein by reference.

B. Micelle Systems and Compositions

The systems and compositions disclosed herein utilize either a single micelle or a series of micelles tuned to different pH levels. Furthermore, the micelles have a narrow pH transition range. In some embodiments, the micelles have a pH transition range of less than about 1 pH unit. In various embodiments, the micelles have a pH transition range of less than about 0.9, less than about 0.8, less than about 0.7, less than about 0.6, less than about 0.5, less than about 0.4, less than about 0.3, less than about 0.25, less than about 0.2, or less than about 0.1 pH unit. The narrow pH transition range advantageously provides a sharper pH response that can result in complete turn-on of the fluorophores with subtle changes of pH.

Accordingly, a single or series of pH-tunable, multicolored fluorescent nanoparticles having pH-induced micellization and quenching of fluorophores in the micelle core provide mechanisms for the independent control of pH transition (via polymers) and fluorescence emission (dyes with small Stoke shifts). The fluorescence wavelengths can be fine tuned from, for example, green to near IR emission range (500-820 nm). Their fluorescence ON/OFF activation can be achieved within 0.25 pH units, which is much narrower compared to small molecular pH sensors. This multicolored, pH tunable and activatable fluorescent nanoplatform provides a valuable tool to investigate fundamental cell physiological processes such as pH regulation in endocytic organelles, receptor cycling, and endocytic trafficking, which are related to cancer, lysosomal storage disease, and neurological disorders.

The size of the micelles will typically be in the nanometer scale (i.e. between about 1 nm and 1 μm in diameter). In some embodiments, the micelle has a size of about 10 to about 200 nm. In some embodiments, the micelle has a size of about 20 to about 100 nm. In some embodiments, the micelle has a size of about 30 to about 50 nm.

C. Targeting Moieties

The micelles and nanoparticles may further comprise a targeting moiety. The targeting moiety may be used to target the nanoparticle or micelle to, for example, a particular cell surface receptor, cell surface marker, or to an organelle (e.g., nucleus, mitochondria, endoplasmic reticulum, chloroplast, apoplast, or peroxisome). Such targeting moieties will be advantageous in the study of receptor recycling, marker recycling, intracellular pH regulation, endocytic trafficking.

The targeting moiety may be, for example, an antibody or antibody fragment (e.g., Fab' fragment), a protein, a peptide (e.g., a signal peptide), an aptamer, or a small molecule (e.g., folic acid). The targeting moiety may be conjugated to the block copolymer (e.g., conjugated to the hydrophilic polymer segment) by methods known in the art. The selection of targeting moiety will depend on the particular target. For example, antibodies, antibody fragments, small molecules, or binding partners may be more appropriate for targeting cell surface receptors and cell surface markers, whereas peptides, particularly signal peptides, may be more appropriate for targeting organelles.

D. Fluorescence Detection

Various aspects of the present invention relate to the direct or indirect detection of micelle disassociation by detecting an increase in a fluorescent signal. Techniques for detecting fluorescent signals from fluorescent dyes are known to those in the art. For example, fluorescence confocal microscopy as described in the Examples below is one such technique.

Flow cytometry, for example, is another technique that can be used for detecting fluorescent signals. Flow cytometry involves the separation of cells or other particles, such as microspheres, in a liquid sample. The basic steps of flow cytometry involve the direction of a fluid sample through an apparatus such that a liquid stream passes through a sensing region. The particles should pass one at a time by the sensor and may categorized based on size, refraction, light scattering, opacity, roughness, shape, fluorescence, etc.

The measurements described herein may include image processing for analyzing one or more images of cells to determine one or more characteristics of the cells such as numerical values representing the magnitude of fluorescence emission at multiple detection wavelengths and/or at multiple time points.

E. Kits

The present invention also provides kits. Any of the components disclosed herein may be combined in a kit. In certain embodiments the kits comprise a pH-responsive system or composition as described above.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed. However, various combinations of components may be comprised in a container. In some embodiments, all of the micelle population in a series are combined in a single container. In other embodiments, some or all of the micelle population in a series are provided in separate containers.

The kits of the present invention also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

F. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

1. Relationships Between pH-Induced Micellization and Fluorescence Activation.

The block copolymer poly(ethylene oxide)-bpoly[2-(diisopropylamino)ethyl methacrylate-co-2-aminoethyl methacrylate hydrochloride], PEO-b-P(DPA-co-AMA) (PDPA-AMA, Table 1), was synthesized using the atom transfer radical polymerization method.

TABLE 1

Characterization of PEO-b-(PR-co-AMA) diblock copolymers.

| Copolymer | $M_n$, $^1$H NMR (kD)$^a$ | $M_{n,GPC}$ (kD)$^b$ | $M_{w,\,GPC}$ (kD)$^b$ | PDI$^b$ |
|---|---|---|---|---|
| PEO$_{114}$-b-P(DPA$_{74}$-co-AMA$_1$) | 20.9 | 19.7 | 23.8 | 1.21 |
| PEO$_{114}$-b-P(DPA$_{77}$-co-AMA$_3$) | 21.9 | 20.2 | 24.2 | 1.20 |
| PEO$_{114}$-b-P(DPA$_{80}$-co-AMA$_6$) | 23.0 | 21.3 | 25.3 | 1.19 |
| PEO$_{114}$-b-P(DBA$_{65}$-co-AMA$_3$) | 21.1 | 20.0 | 23.6 | 1.18 |
| PEO$_{114}$-b-P(C7A$_{65}$-co-AMA$_3$) | 19.6 | 18.4 | 21.5 | 1.17 |
| PEO$_{114}$-b-P(C6A$_{81}$-co-AMA$_3$) | 21.4 | 20.5 | 25.4 | 1.24 |

$^a$Number-averaged molecular weight ($M_n$) as determined by $^1$H NMR.
$^b$Number-averaged molecular weight ($M_n$), weight-averaged molecular weight ($M_w$), and polydispersity index (PDI = $M_w/M_n$) as determined by GPC using THF as the eluent.

5-Carboxytetramethylrhodamine succinimidyl ester was used to conjugate the dye to the primary amino groups to yield PDPA-TMR copolymer (Zhou, K., *Chem. Int. Ed.*

Figures 2A, 2B, 2C, 2D:
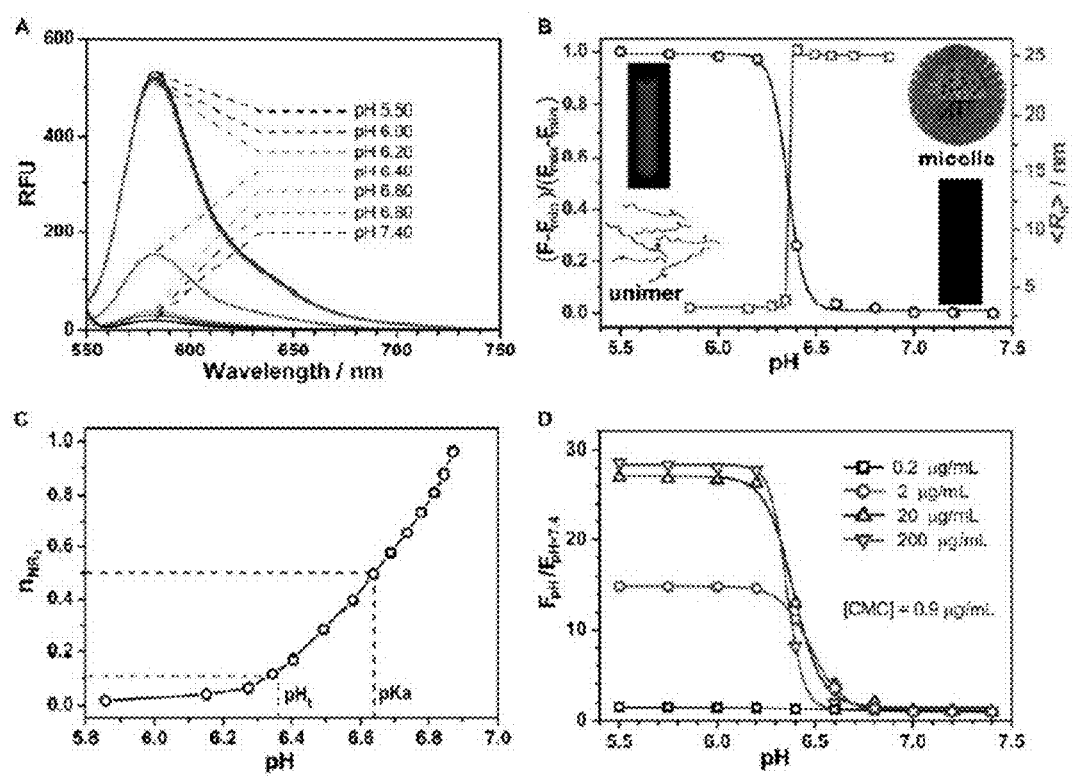
FIGS. 2A-2D.

2011, 50, 6109). The pH-dependent fluorescence properties of PDPA-TMR aqueous solution are shown in FIG. 2A. To quantitatively assess the pH responsive properties, normalized fluorescence intensity (NFI=[F−Fmin]/[Fmax−Fmin]) was plotted as a function of pH, where F is the fluorescence intensity of the nanoparticle at any given pH, and Fmax and Fmin are the maximal and minimal fluorescence intensities at the ON/OFF states, respectively. To quantify the sharpness of pH response, ΔpH10-90%, the pH range in which the NFI value varies from 10% to 90%, was measured. For PDPA-TMR (FIG. 2B), the ΔpH10-90% was 0.20 pH unit, representing a <2-fold change in proton concentration ([H+]). For pH-sensitive small molecular dyes (Urano, Y., Nat. Med. 2009, 15, 104), ΔpH10-90% is typically 2 pH units, corresponding to a 100-fold change in [H+] (Atkins, P., Physical Chemistry; Oxford University Press, 2009).

Amino groups have previously been introduced in polymers as ionizable groups to render pH sensitivity (Dai, S., Soft Matter 2008, 4, 435; Gil, E. S., Prog. Polym. Sci. 2004, 29, 1173). In the nanoparticle design (FIG. 3), tertiary amines with hydrophobic constituents were introduced as the ionizable hydrophobic block and poly(ethylene glycol) as the hydrophilic block. In this system, micelle formation is thermodynamically driven by two delicate balances: the first is the pH-dependent ionization equilibrium between the positively charged tertiary ammonium groups (i.e., —NHR$_2^+$) and the neutral hydrophobic tertiary amines (—NR$_2$); and the second is the micelle self-assembly process after a critical threshold of hydrophobicity is reached in the tertiary amine segment (Zhou, K., Macromolecules 2008, 41, 8927; Riess, G., Prog. Polym. Sci. 2003, 28, 1107; Lee, E. S., Controlled Release 2003, 90, 363).

Figures 9A, 9B:
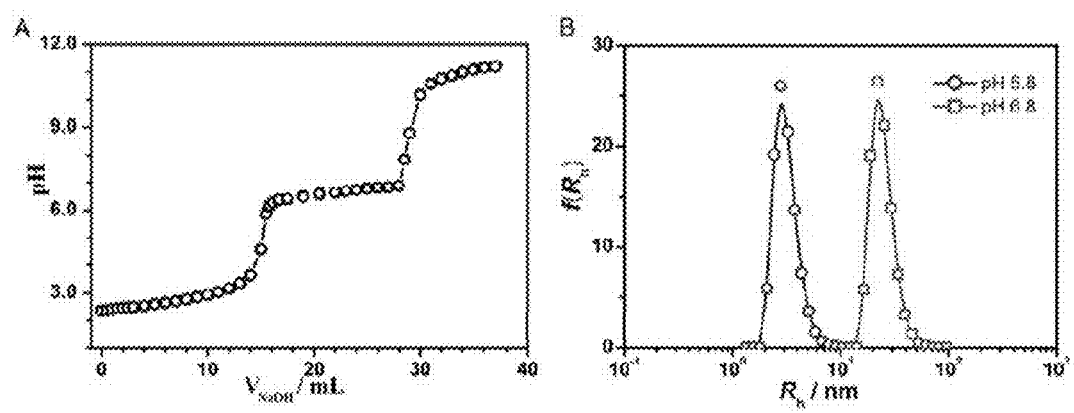
FIG. 9A-9B.

To mechanistically understand the correlation between pH-dependent fluorescence activation and pH-induced micellization, the fluorescence activation curve was compared with micelle formation from dynamic light scattering (DLS) experiment. Hydrodynamic radius, $<R_h>$, was used as the primary parameter to indicate the unimer (3 nm) to micelle (24 nm) transition (FIG. 2B, FIG. 9B). FIG. 2B shows that micellization pH coincides with fluorescence activation pH, where both curves meet at pH 6.36 at 50% point. Interestingly, fluorescence pH transition value occurs before the apparent pKa (6.64, where 50% of ammonium groups are deprotonated) of the PDPA-TMR copolymer (FIG. 2C). These data indicate that fluorescence quenching happens at the early phase of pH titration, where micelles are formed when a relatively small portion (~10 mol %) of ammonium groups are deprotonated to reach sufficient hydrophobicity of the PDPA segment for micelle formation. This was further supported by transmission electron microscopy analysis, which showed unimer state at pH 5.8, and formation of micelles at pH 6.8.

Figure 10:
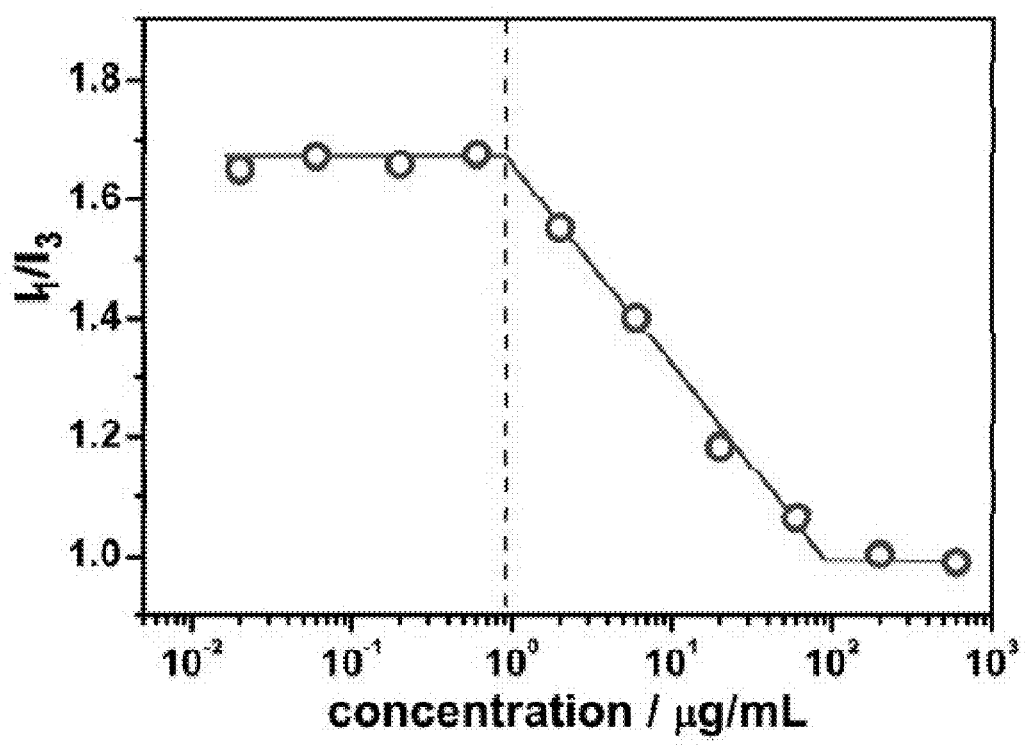
FIG. 10. Measurement of critical micelle concentration (CMC) of $PEO_{114}$-b-(PDPA77-co-AMA3) copolymer. The $I_1/I_3$ fluorescence ratio of pyrene is plotted as a function of $PEO_{114}$-b-($PDPA_{77}$-co-$AMA_3$) concentration. CMC is indicated by the dashed line at 0.9 μg/mL.

Approximately 0.5 pH unit (pH 6.4-6.9) was needed to change the ionization state of tertiary amines from 10 to 90%, suggesting micelle-induced cooperative deprotonation process compared to small ionizable molecules. Similar cooperative response was observed by Nie and coworkers with Au nanoparticles coated with carboxylic acids (Kairdolf, B. A., J. Am. Chem. Soc. 2011, 133, 7268). To further corroborate the micelle-induced fluorescence activation mechanism, the pH-dependent fluorescence intensity at copolymer concentrations above and below the critical micelle concentration (CMC) was investigated (see Ananthapadmanabhan, K. P., Langmuir 1985, 1, 352; Ruckenstein, E., J. Phys. Chem. 1975, 79, 2622). In this study, the PDPAAMA synthetic precursor was used to measure CMC instead of PDPATMR to avoid possible interference of TMR dye. Data showed that the CMC is approximately 0.9 μg/mL at pH 7.4 in 0.2 M phosphate buffer (FIG. 10). Results in FIG. 2D showed the extent of fluorescence activation decreased at lower copolymer concentrations. When the copolymer concentration is at 0.2 μg/mL (i.e., <CMC), almost no pH response is observed (free TMR dye is also pH insensitive in this pH range). These data suggest that the ultra-pH response (ΔpH10-90%<0.25 pH unit) of these fluorescent nanoparticles is a unique nanoscale phenomena, where pH-induced micellization is directly responsible for the observed fluorescence activation. In addition to imaging applications, these ultra-pH responsive nanoparticles can also be used as nano-scaled "proton sponges," which can assist the endosomal escape of siRNA or DNA molecules for more effective delivery of drugs (see Yezhelyev, M. V., J. Am. Chem. Soc. 2008, 130, 9006; Yu, H., J. ACS Nano 2011, 5, 9246).

2. Investigation of the Photochemical Mechanisms for Micelle-Induced Fluorescence Quenching.

Three common photochemical mechanisms may contribute to the observed fluorescence quenching in the micelle nanoenvironment (FIG. 1): (1) formation of H-type dimer (H-dimer) between dye molecules in the micelle core, (2) Förster resonance energy transfer between dye molecules (homoFRET), which facilitates the fluorescence decay through faster diffusion of excitons to fluorophores in sites with fast decay, and (3) photo-induced electron transfer (PeT) between the micelle core (e.g. electron-donating tertiary amines) and the fluorophore (de Silva, A. P., Chem. Rev. 1997, 97, 1515; Kobayashi, H., Acc. Chem. Res. 2010, 44, 83; Kobayashi, H., Chem. Rev. 2010, 110, 2620; Valeur, B., Molecular fluorescence: principles and applications, Wiley-VCH, 2002; Lakowicz, J. R., Principles of Fluorescence Spectroscopy; 3rd ed., Springer: New York City, 2006; Demchenko, A. P., Introduction to Fluorescence Sensing, Springer Science: New York, 2008; Lee, S., Curr. Top. Med. Chem. 2010, 10, 1135). These mechanisms have been reviewed in the design of activatable fluorescent molecular dyes (de Silva, A. P., Chem. Rev. 1997, 97, 1515; Kobayashi, H., Chem. Rev. 2010, 110, 2620). For small molecular pH-sensitive dyes, PeT has been the predominant mechanism, where a window of 2 pH unit is reported for ON/OFF activation.

Figure 3:
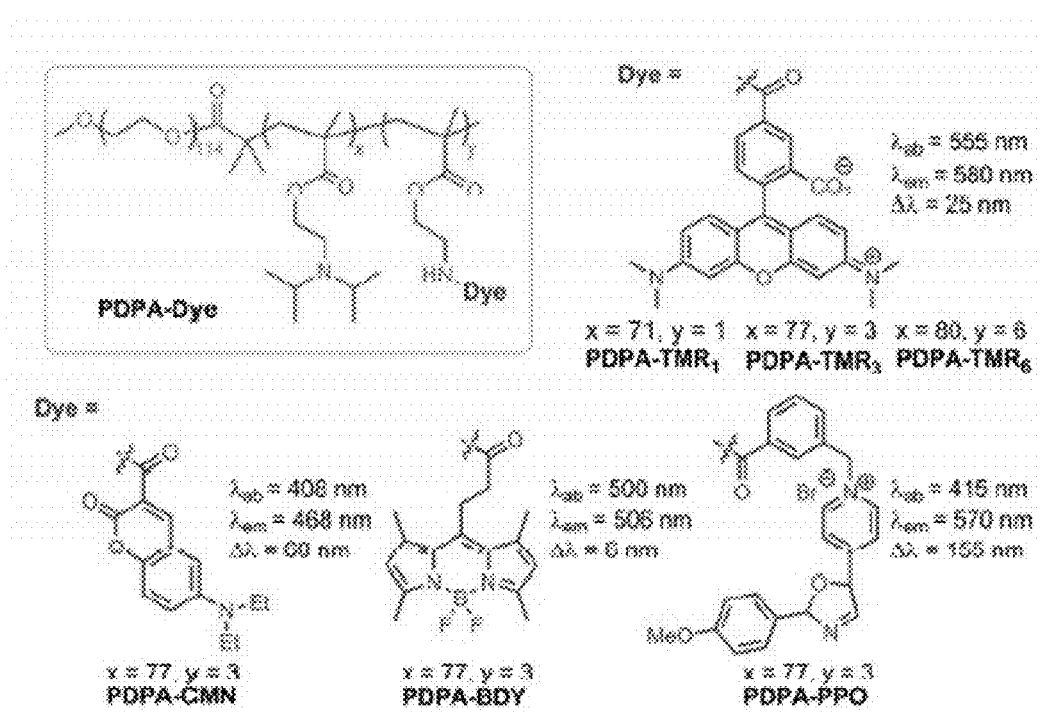
FIG. 3. Chemical structures of PDPA-TMR1, PDPA-TMR3, PDPA-TMR6, PDPA-CMN, PDPA-BDY, PDPA-PPO and their corresponding fluorescence properties.

To investigate the relative contribution from the above three mechanisms, a series of diblock copolymers with different densities and types of the dye molecules were systematically synthesized (FIG. 3). Several types of fluorophores, such as rhodamine, BODIPY and cyanine derivatives, can easily form H-type dimers at relatively high local concentrations with quenched fluorescence signal (West, W., Phys. Chem. 1965, 69, 1894; Lopez Arbeloa, I., Chem. Phys. Lett. 1982, 87, 556; Valdes-Aguilera, O., Acc. Chem. Res. 1989, 22, 171; Packard, B. Z., Phys. Chem. B 1997, 101, 5070; Ogawa, M., ACS chem. biol. 2009, 4, 535). H-dimer is a ground state complex where two dye molecules are in a sandwich-type arrangement (Valeur, B., Molecular fluorescence: principles and applications, Wiley-VCH, 2002; Johansson, M. K., Chem. Eur. J. 2003, 9, 3466; Scheibe, G. Z., Angew. Chem. 1936, 49, 563; Jelley, E. E. Nature 1936, 138, 1009). In a H-type dimer, the transition to the lower energy excited state is forbidden, which leads to its absorption blue-shifted and fluorescence diminished with respect to monomer (West, W., Phys. Chem. 1965, 69, 1894; Jelley, E. E. Nature 1936, 138, 1009).

Figures 4A, 4B, 4C, 4D:
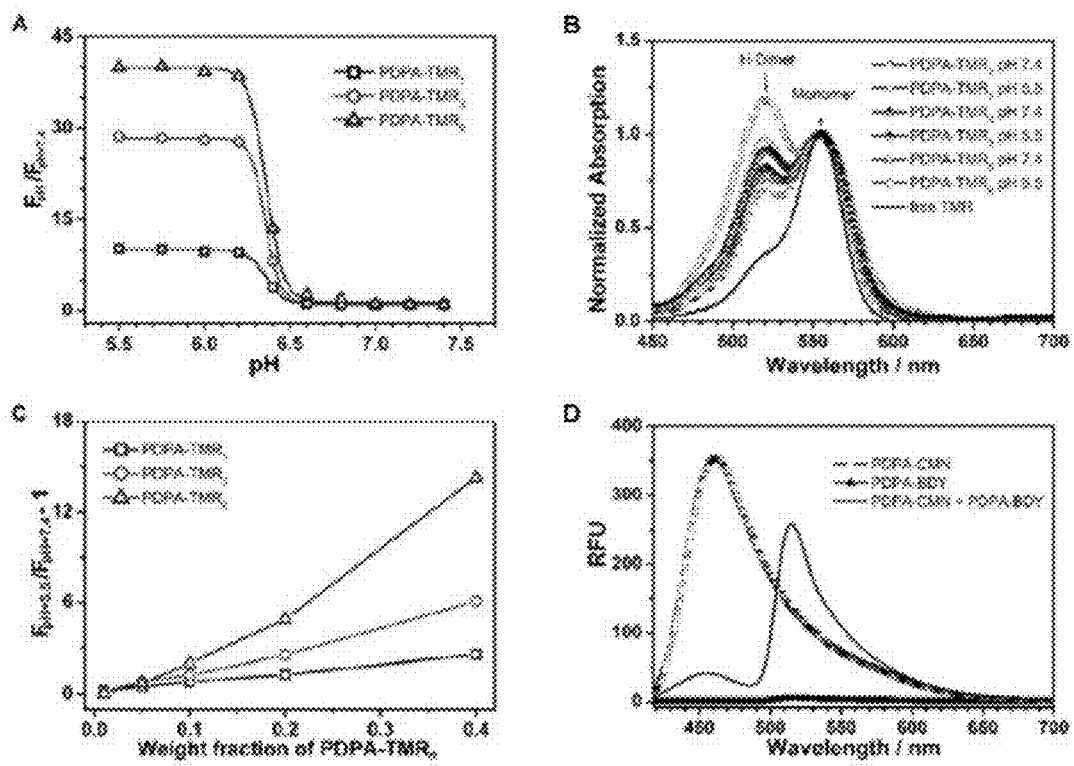
FIGS. 4A-D.
Figure 11:
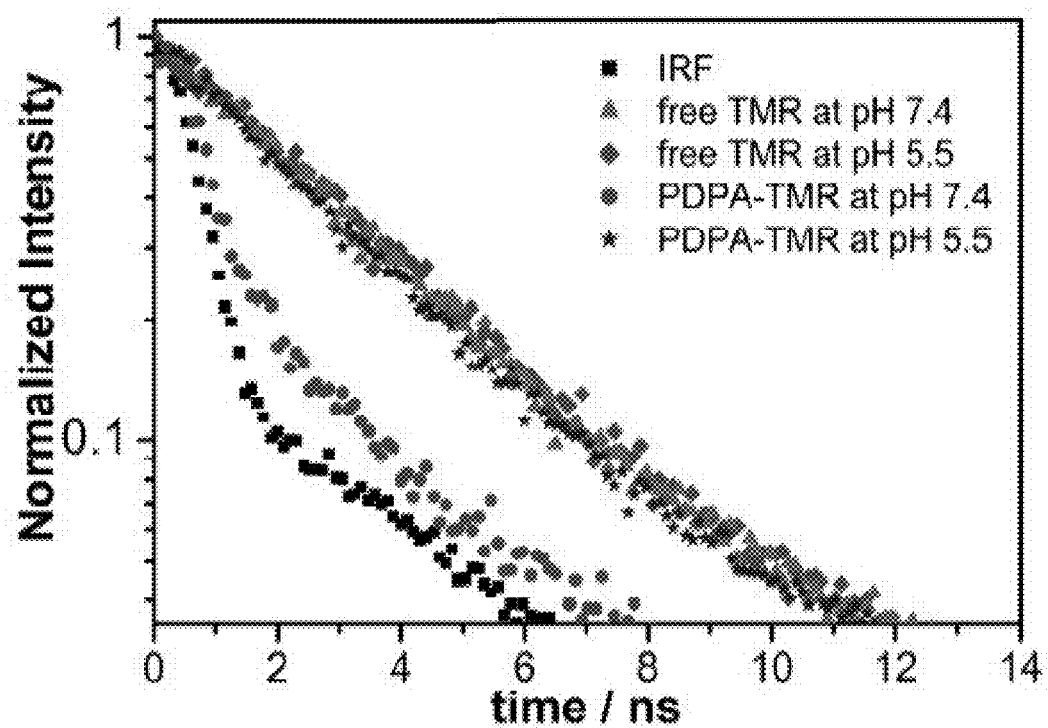
FIG. 11. Fluorescence intensity decay of free TMR dye and PEO-(PDPA-TMR) in aqueous solution at pH 7.4 and 5.5.

First, the contribution of H-dimer formation to the pH-activatable fluorescence of PDPA-TMR copolymer was determined. A series of PDPA-TMR copolymers where the number of TMR molecules per polymer chain was increased from 1 to 3 to 6 were synthesized (Table 1). Increase in TMR number resulted in increased fluorescence activation ratio, RF (RF=Fmax/Fmin) from 10 to 28 to 40 fold, respectively (FIG. 4A). Examination of the UV-Vis spectra of all three copolymers showed that higher percentages of H-dimers were formed at the lower pH (i.e., pH=5.5, unimer state) than those at higher pH (i.e. pH=7.4, micelle state) as indicated by the higher intensity of absorption peak at 520 nm (FIG. 4B). This result indicates that H-dimer formation is not a predominant mechanism that caused the fluorescence quenching at the micelle state. The slight increase of H-dimers at pH 5.5 may be a result of the increased mobility of the polymer chains at the unimer state, which facilitates TMR dimerization. Since H-type dimers are a ground-state complex, their formation does not affect the fluorescence lifetimes (Lakowicz, J. R., *Principles of Fluorescence Spectroscopy;* 3rd ed., Springer: New York City, 2006; Berezin, M. Y., *Chem. Rev.* 2010, 110, 2641). The short fluorescence lifetime ($\tau$~0.4 ns) of PDPA-TMR$_3$ at pH 7.4 compared to free dye ($\tau$~2 ns, FIG. 11) further supports that H-dimer formation is not the primary cause for the fluorescence quenching at the micelle state.

Next, the contribution of the PeT and homo-FRET mechanisms to the micelle-induced fluorescence quenching was investigated. PeT occurs when HOMO energy level of the electron donors (e.g., tertiary amines from the micelle core segment) is between LUMO and HOMO energy levels of fluorescence acceptor and when they are close in proximity (de Silva, A. P., *Chem. Rev.* 1997, 97, 1515; Weller, A. *Pure Appl. Chem.* 1968, 16, 115; Wasielewski, M. R. *Chem. Rev.* 1992, 92, 435). For FRET to occur, three specific conditions must be met (Lakowicz, J. R., *Principles of Fluorescence Spectroscopy;* 3rd ed., Springer: New York City, 2006; Vogel, S. S., *Sci. STKE* 2006, 2006, re2.): (i) the emission spectrum of the donor fluorophore must overlap with the acceptor's absorption spectrum (with homo-FRET, the donor and acceptor are identical and therefore the dye must have a small Stokes shift); (ii) the donor and acceptor must be in the proper physical orientation; (iii) the dye-pair must be close to each other. FRET efficiency has a sixth power dependence on the separation distance, which is the most frequently manipulated parameter in its implementation in fluorescence imaging studies. It should be noted that homoFRET itself does not directly result in non-radiative decay of fluorophores. However, the process can increase the diffusion of excitons among the dye molecules. When a fraction of fluorophores are trapped in a fast decay environment, homoFRET can facilitate the fluorescence decay of the overall population of fluorophores through the exchange process.

Amino groups are known to quench fluorophores through the PeT mechanism (de Silva, A. P., *Chem. Commun.* 1996, 2399; Dale, T. J., *J. Am. Chem. Soc.* 2006, 128, 4500; Diaz-Fernandez, Y., *Chem. Eur. J.* 2006, 12, 921; Tal, S., *Chem. Eur. J.* 2006, 12, 4858; Petsalakis, I. D., *J. Mol. Struct.: THEOCHEM* 2008, 867, 64). In the PDPA-TMR solution at higher pH, its weak fluorescence signal could be caused by these electron-rich tertiary amine groups in PDPA-TMR copolymers via the PeT mechanism. To distinguish the relative contributions of PeT and homo-FRET in fluorescence quenching, the distance between TMR dyes (or TMR density in the micelle core) were systematically varied while keeping the core nanoenvironment constant. More specifically, the PDPA-TMR$_{n=1,3,6}$ copolymers were blended with their dye-free precursor copolymers, (PDPA-AMA$_{n=1,3,6}$), at different weight fractions. We plotted ($R_F$-1), the ratio of fluorescence intensity at pH 7.4 and 5.5 minus 1, as a function of weight fractions. With the PeT-dominant mechanism, ($R_F$-1) is expected to be independent of the mixed percentage and the Y-intercept reflects the PeT quenching efficiency. With homoFRET-dominant mechanism, ($R_F$-1) is expected to depend on mixed percentage with the Y-intercept approaching 0. FIG. 4C clearly shows that ($R_F$-1) approaches 0 as the mixed weight percentage decreases to zero, regardless of the TMR number in the PDPA block. Increase of TMR concentration in the micelle core (either through the increase of TMR per polymer chain, or higher molar fraction of TMR-conjugated copolymer) leads to significantly increased fluorescence quenching (i.e., higher RF values). These results indicate that homo-FRET is the predominant mechanism for the fluorescence quenching in the PDPA-TMR system with a negligible contribution from PeT.

Figure 12:
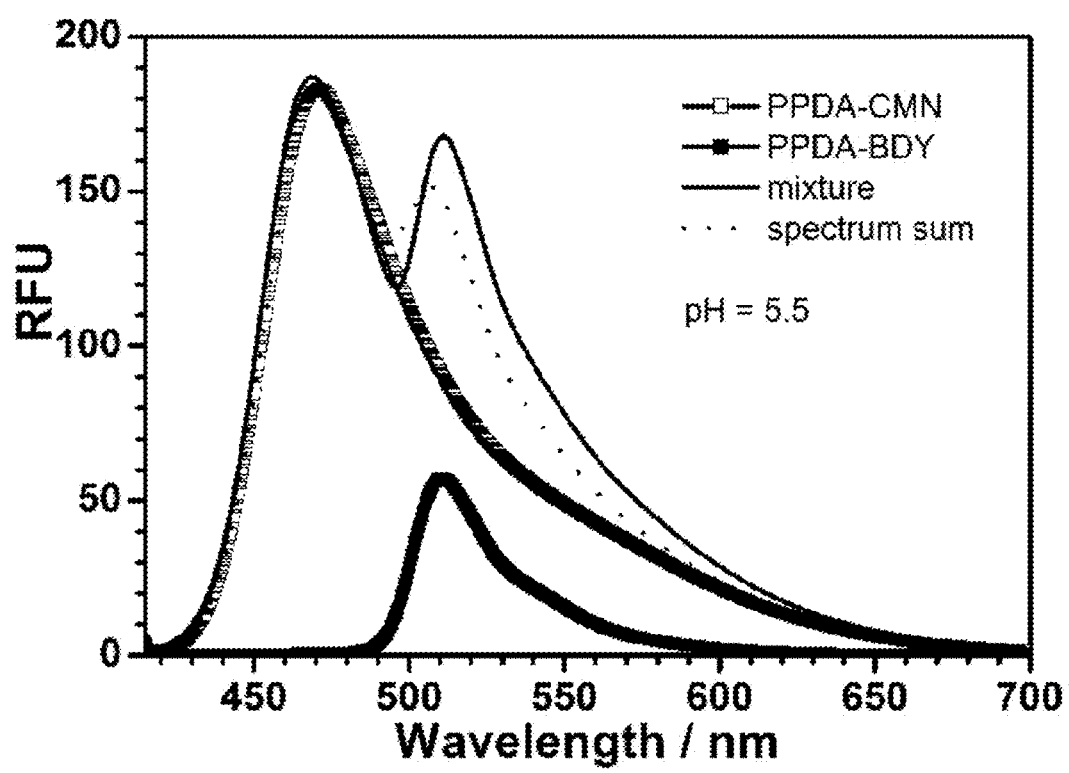
FIG. 12. Fluorescence emission spectra of PDPA-CMN, PDPA-BDY and their molecular mixture at pH 5.5 (unimer states). Each polymer concentration is controlled at 200 μg/mL. The samples were excited at 408 nm and the emission spectra were collected from 420 to 700 nm.
Figure 13A:
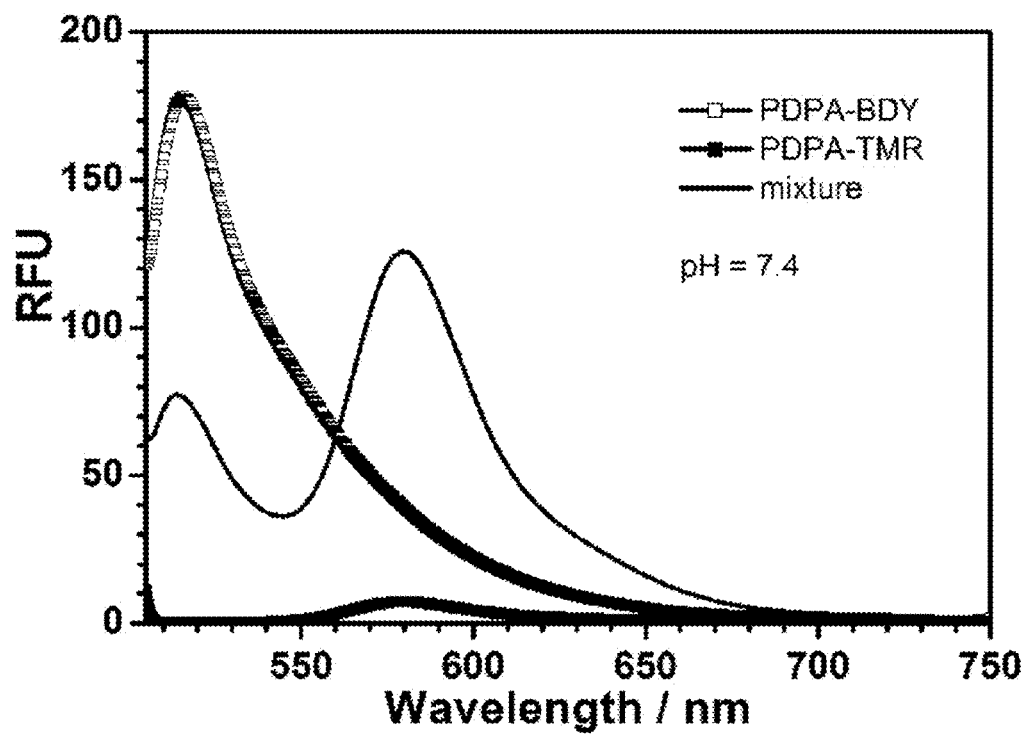
FIG. 13A-13B.
Figure 13B:
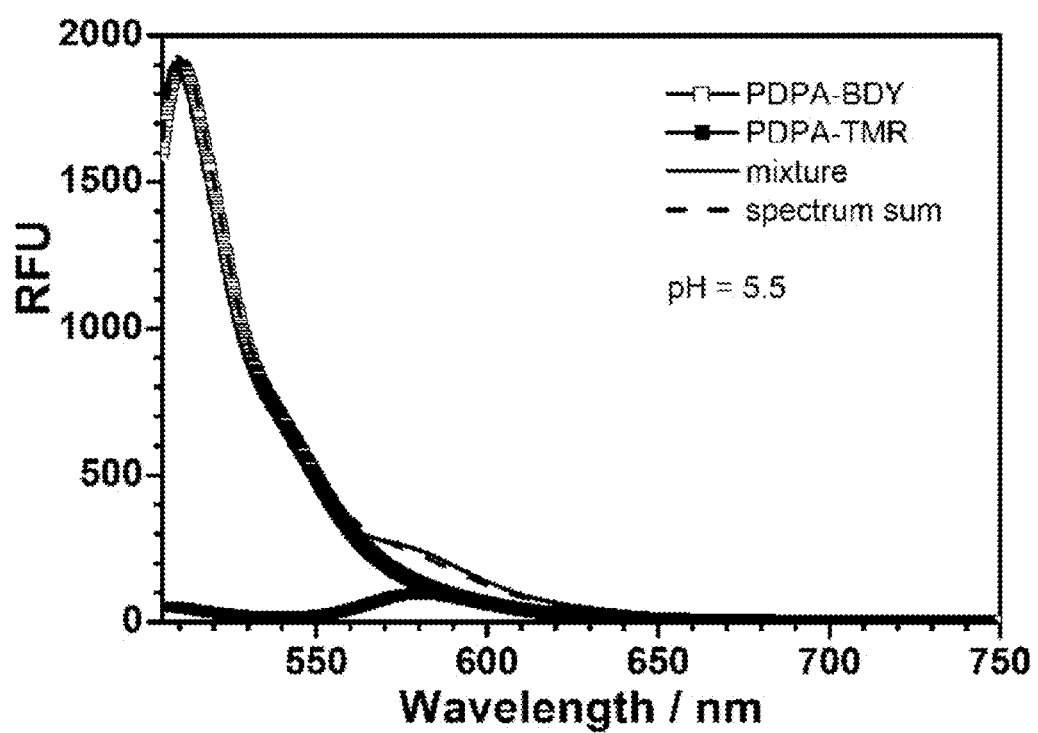
Figure 14A:
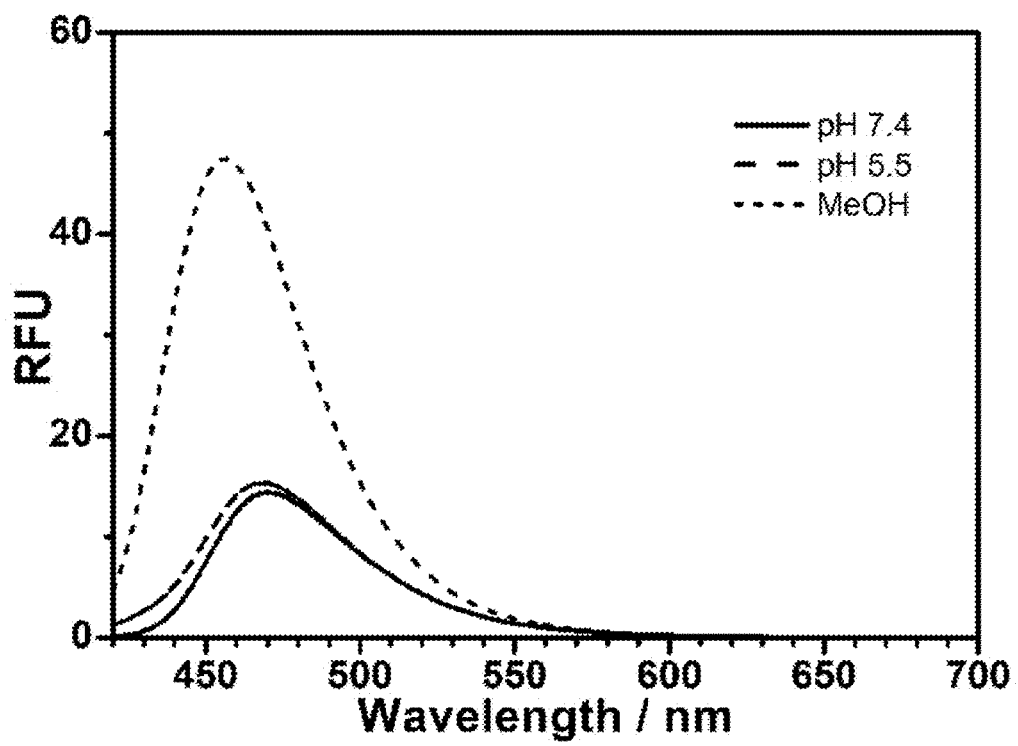
FIG. 14A-14E.
Figure 14B:
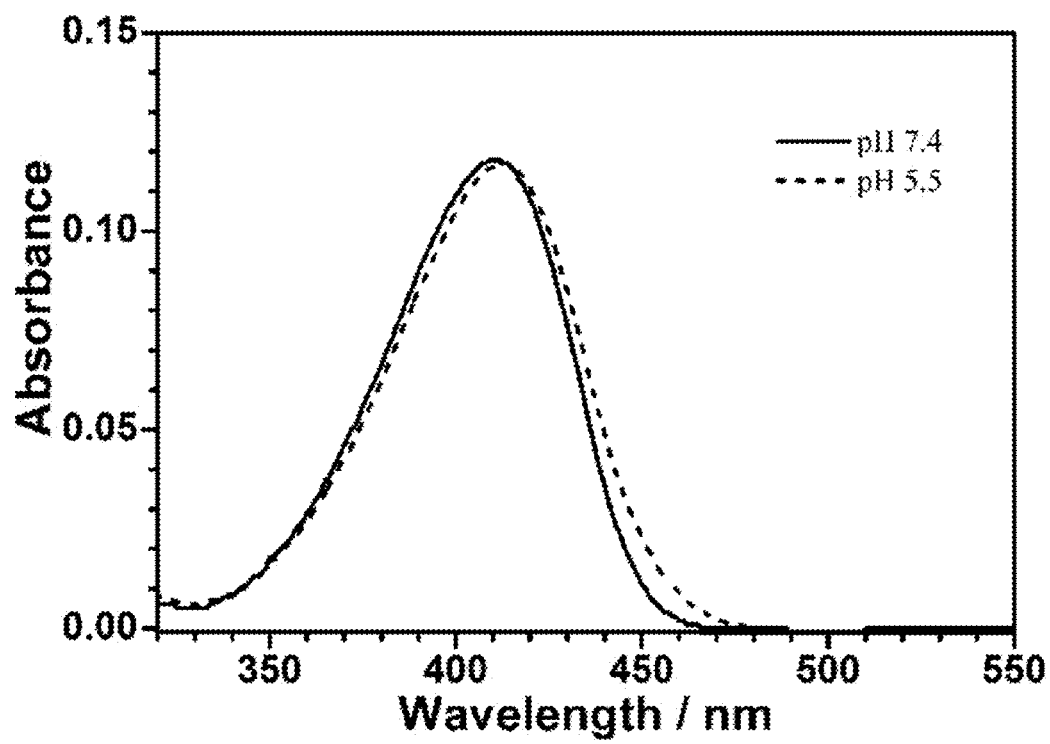
Figure 14C:
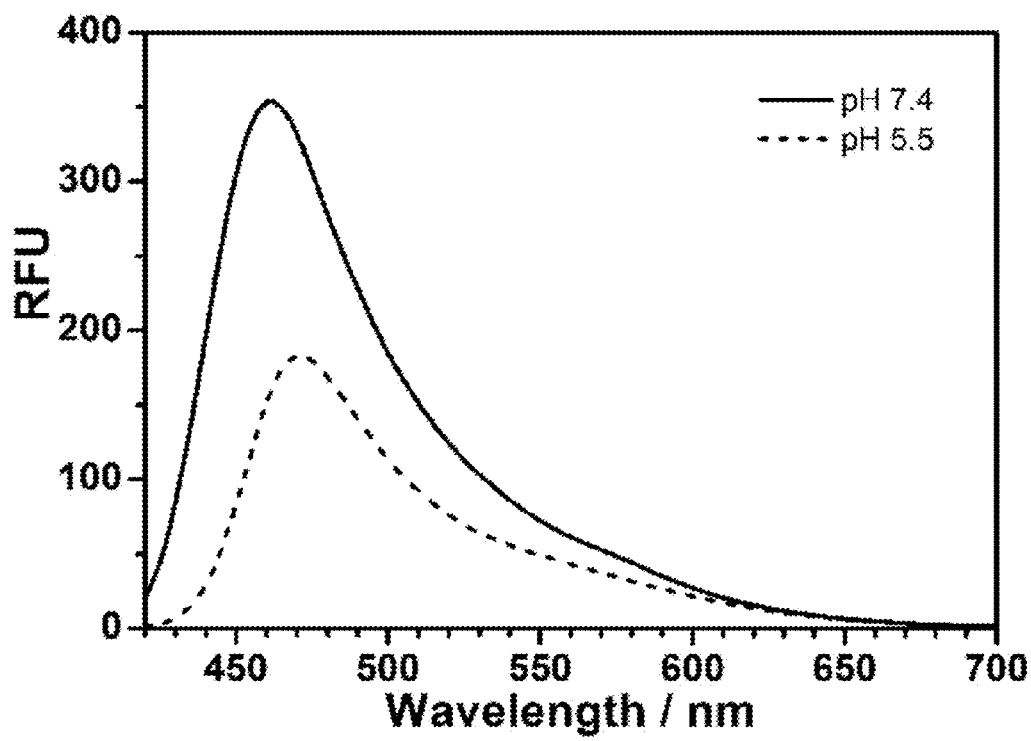
Figure 14D:
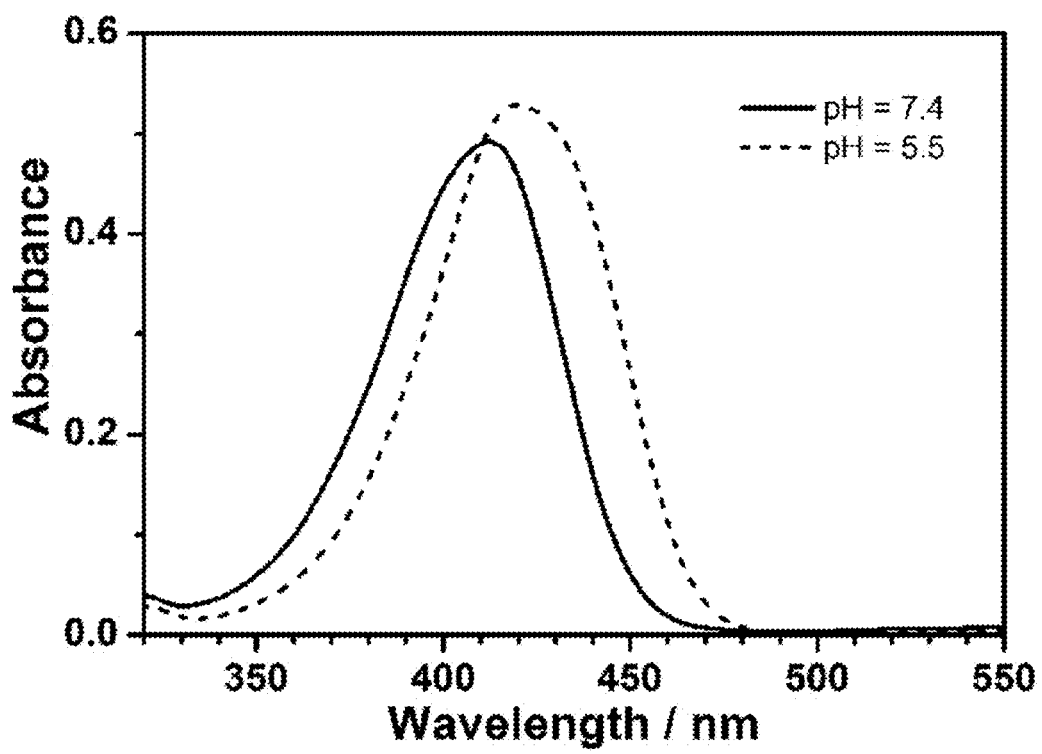
Figure 14E:
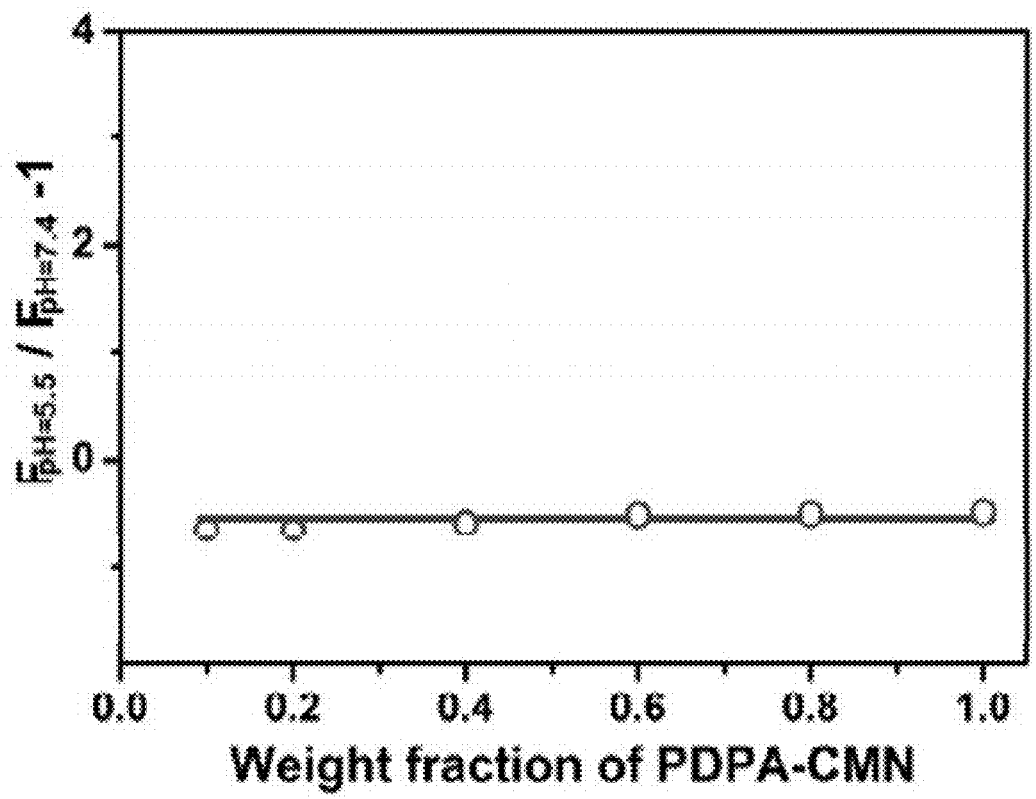
Figure 15A:
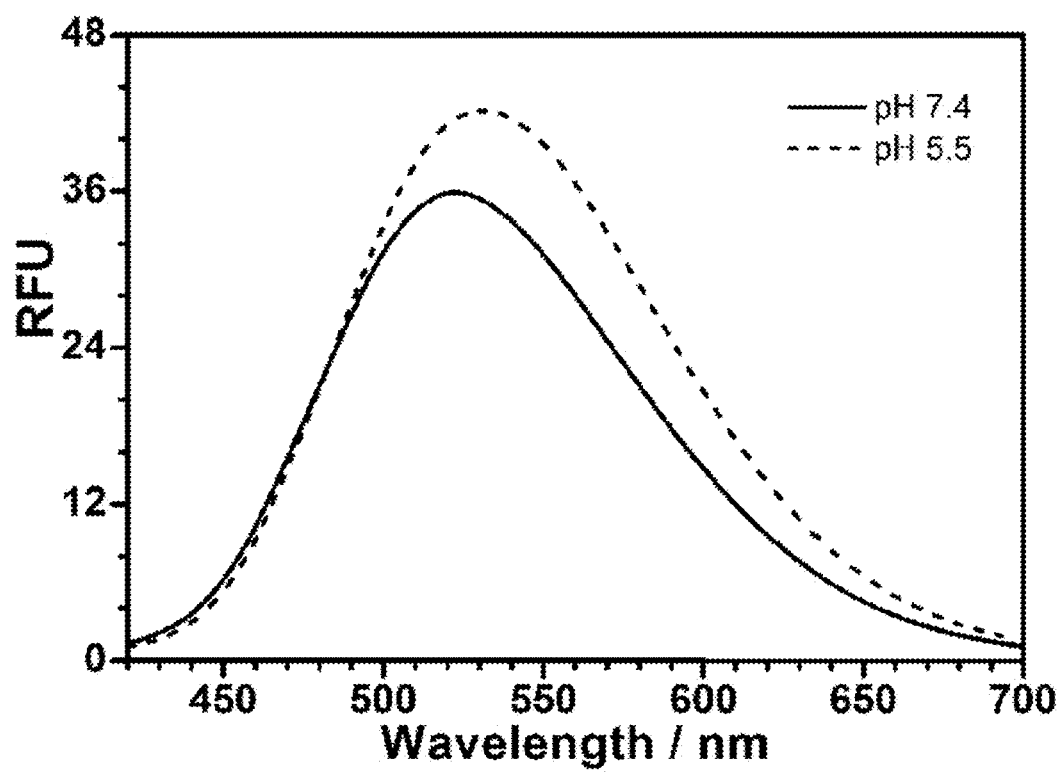
FIG. 15A-15B.
Figure 15B:
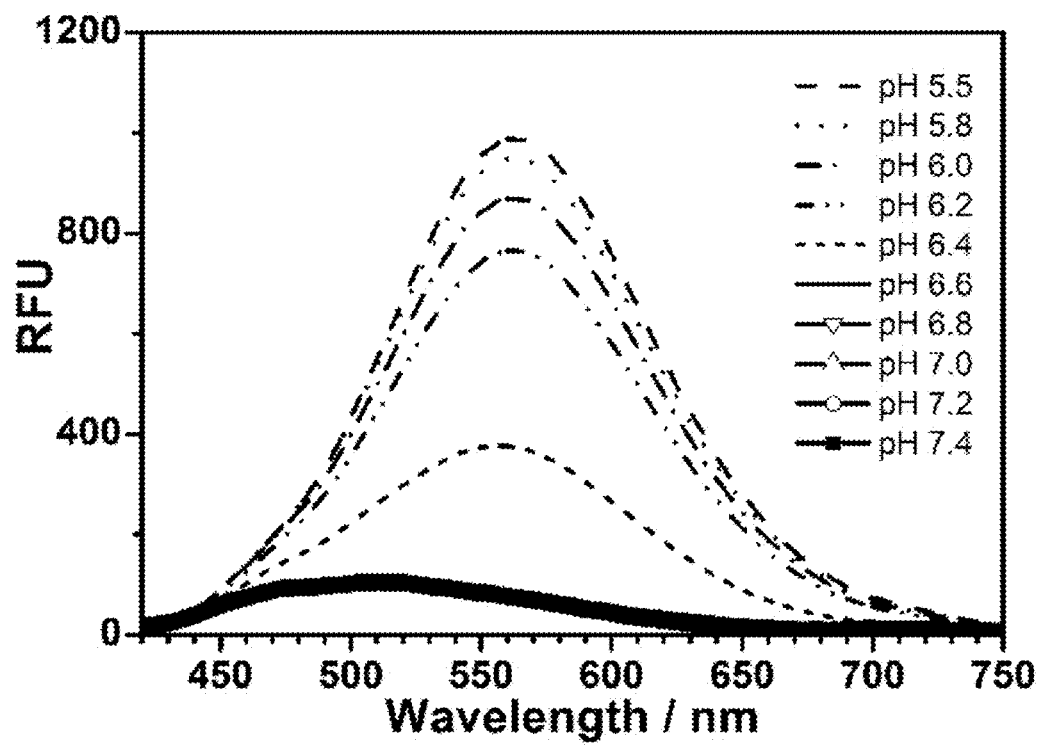

To further verify the homo-FRET mechanism, the fluorescence transfer effect from copolymers was examined with two sets of established hetero-FRET dyes: (a) PDPA-CMN and PDPA-BDY, (b) PDPA-BDY and PDPA-TMR (see their structures and fluorescence properties in FIG. 3). Each pair of copolymers was dissolved in their good solvent, THF, to make them molecularly mixed and then was added dropwise into water to make a molecular mixture of micelles. In the pair of PDPA-CMN and PDPABDY, the fluorescence spectrum of Coumarin dye overlaps the absorption spectrum of BODIPY dye for the hetero-FRET effect. Compared to PDPA-CMN alone micelle solution, the fluorescence intensity at Coumarin emission wavelength (i.e. 468 nm) in the mixed micelle solution decreased over 8 fold (FIG. 4D). Moreover, the fluorescence intensity at BODIPY emission (506 nm) increased over 53 fold for mixed micelle solution over PDPA-BDY alone micelle solution. These results clearly demonstrate that there is a strong fluorescence energy transfer from Coumarin to BODIPY dye in the mixed micelle of PDPA-CMN and PDPA-BDY at pH 7.4. No fluorescence energy transfer is observed between them at pH 5.5 (FIG. 12). Similar observation was made in the pair of PDPA-BDY and PDPA-TMR (FIG. 13).

Figures 5A, 5B:
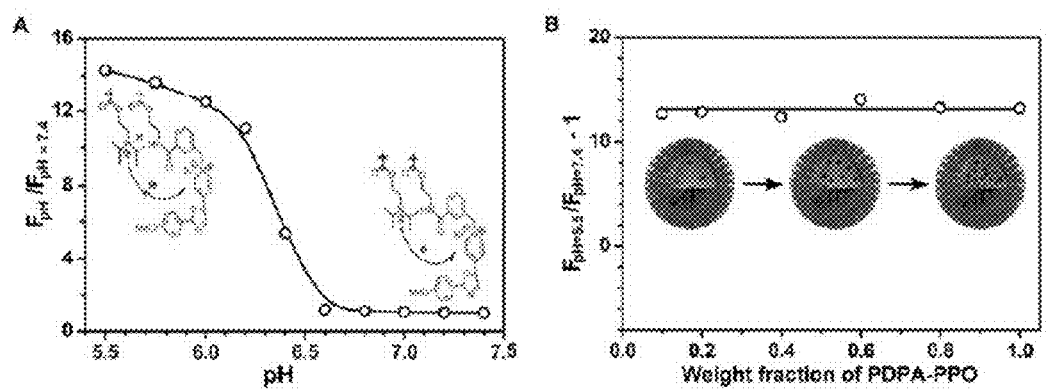
FIG. 5A-5B.

As mentioned above, homo-FRET only occurs between two identical dyes with small Stokes shift. When dye molecules with large Stokes shift are introduced into PDPA-AMA copolymer, no homo-FRET effect should be observed because their absorption spectra do not overlap with emission spectra. As shown in FIG. 14, there was almost no pH responsive fluorescence behavior for PDPA-CMN where $\lambda ex=408$ nm, $\lambda em=468$ nm and $\Delta\lambda=60$ nm. For PDPA-PPO ($\lambda ex=415$ nm, $\lambda em=570$ nm and $\Delta\lambda=155$ nm), a 14-fold increase in $R_F$ response is observed (FIG. 5A). Further examination (FIG. 5B) showed that ($R_F$-1) was independent of dye concentration and therefore distance in the micelle core. These data demonstrate that homo-FRET does not contribute to pH-induced fluorescence response of PDPA-PPO. Instead, fluorescence quenching in the micelle state is mostly due to the PeT mechanism as indicated by the large Y-intercept ($R_F$=14).

3. Development of a Multicolored pH-Tunable Fluorescence Nanoplatform.

Although PeT mechanism can lead to pH-responsive activation of nanoparticles as shown in PDPA-PPO, PeT efficiency is highly dependent on the matching of the HOMO of the electron-donating amino groups and LUMO of the fluorophore. This inter-dependence may limit the choice of the dye molecules as well as polymers with different tertiary amines, which will make it difficult to independently control the emission wavelengths of the nanoparticles and their pH transition. Finally, the protonation/deprotonation state of amino groups will also affect the PeT efficiency (Dale, T. J., *J. Am. Chem. Soc.* 2006, 128, 4500; Tal, S., *Chem. Eur. J.* 2006, 12, 4858; Petsalakis, I. D., *J. Mol. Struct.: THEOCHEM* 2008, 867, 64) and will lead to broadened pH response as demonstrated by the PDPA-PPO nanoparticles (FIG. 5A).

Figure 6:
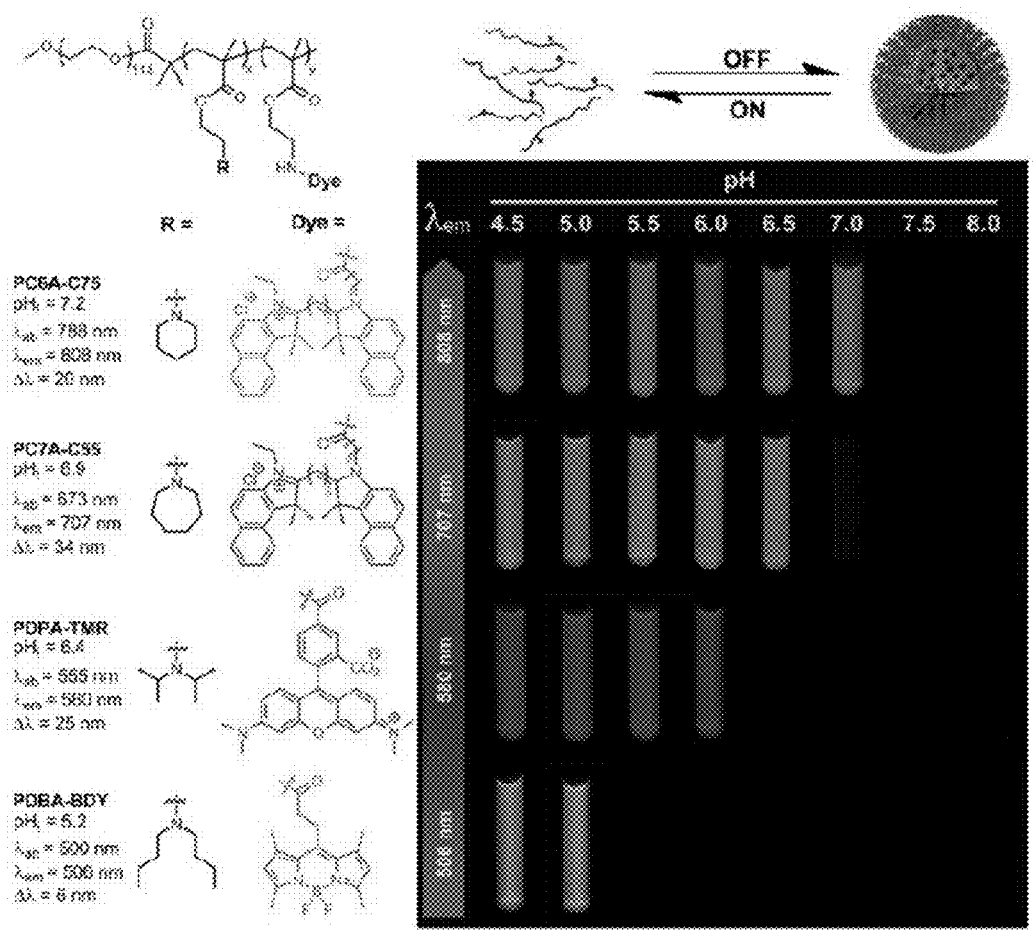
FIG. 6. Chemical structures of PBDA-BDY, PDPA-TMR, PC7A-C55, and PC6A-C75 and their corresponding fluorescence data. The representative fluorescent images of their aqueous solutions at the same polymer concentration (100 μg/mL) but different pH values were shown. Pseudo colors were used for PC7A-C55 and PC6A-C75 nanoprobes due to their near IR emissions.
Figure 7:
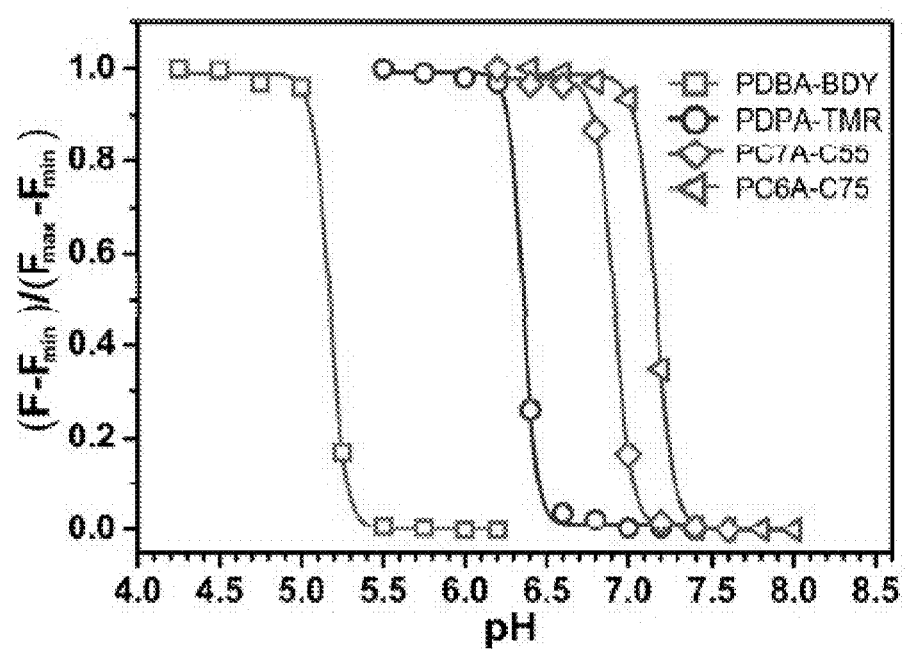
FIG. 7. Normalized fluorescence intensity as a function of pH for PBDA-BDY, PDPA-TMR, PC7A-C55, and PC6A-C75. The excitation and emission conditions for each nanoparticle are shown in FIG. 6.
Figure 16A:
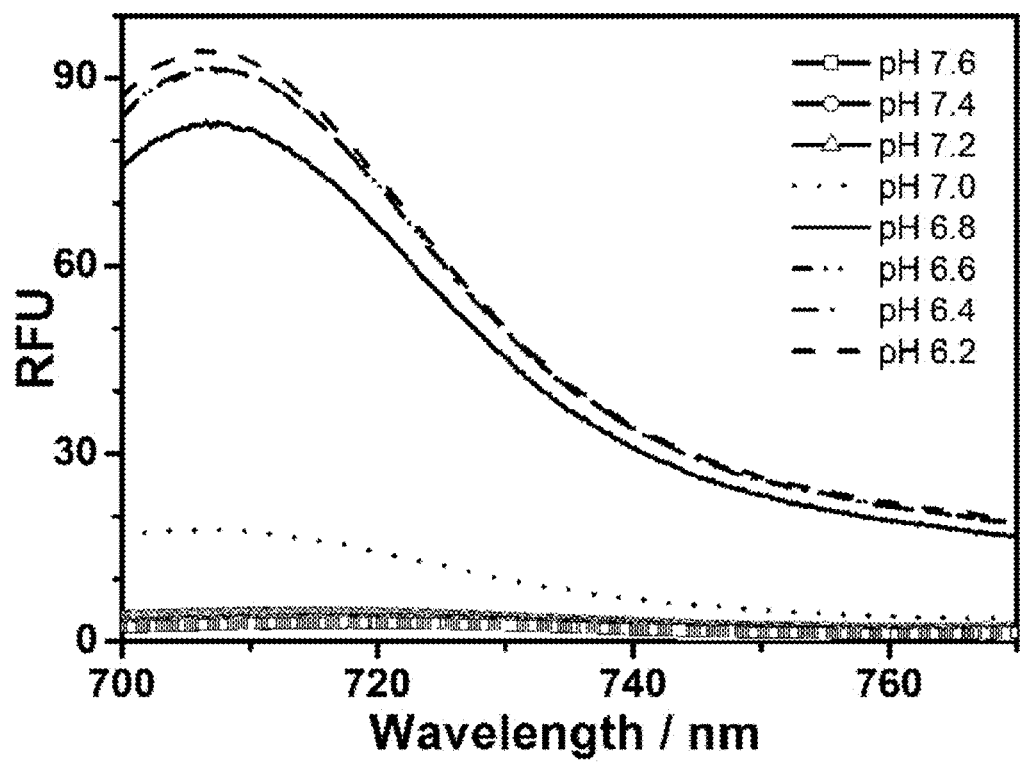
FIG. 16A-16D.
Figure 16B:
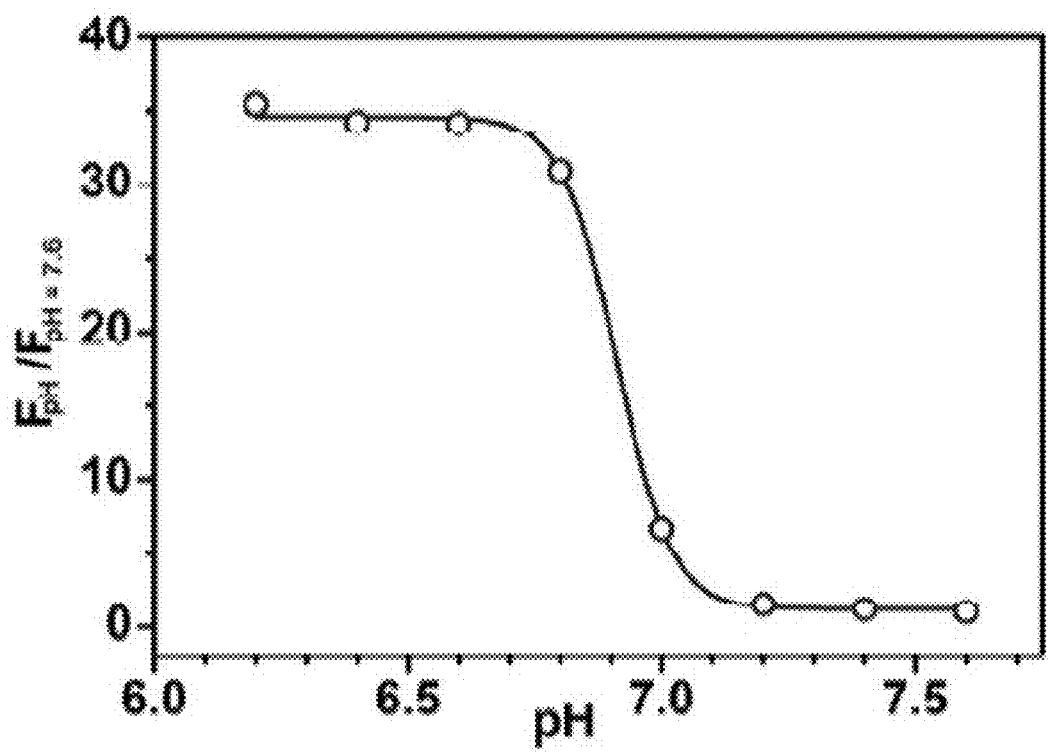
Figure 16C:
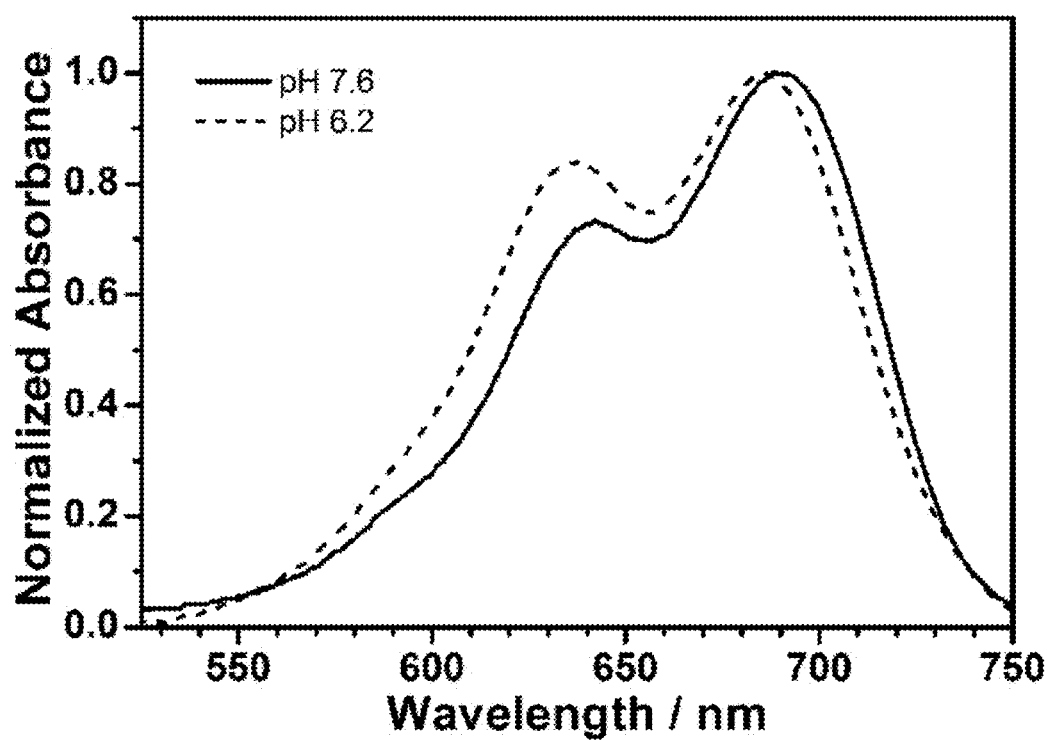
Figure 16D:
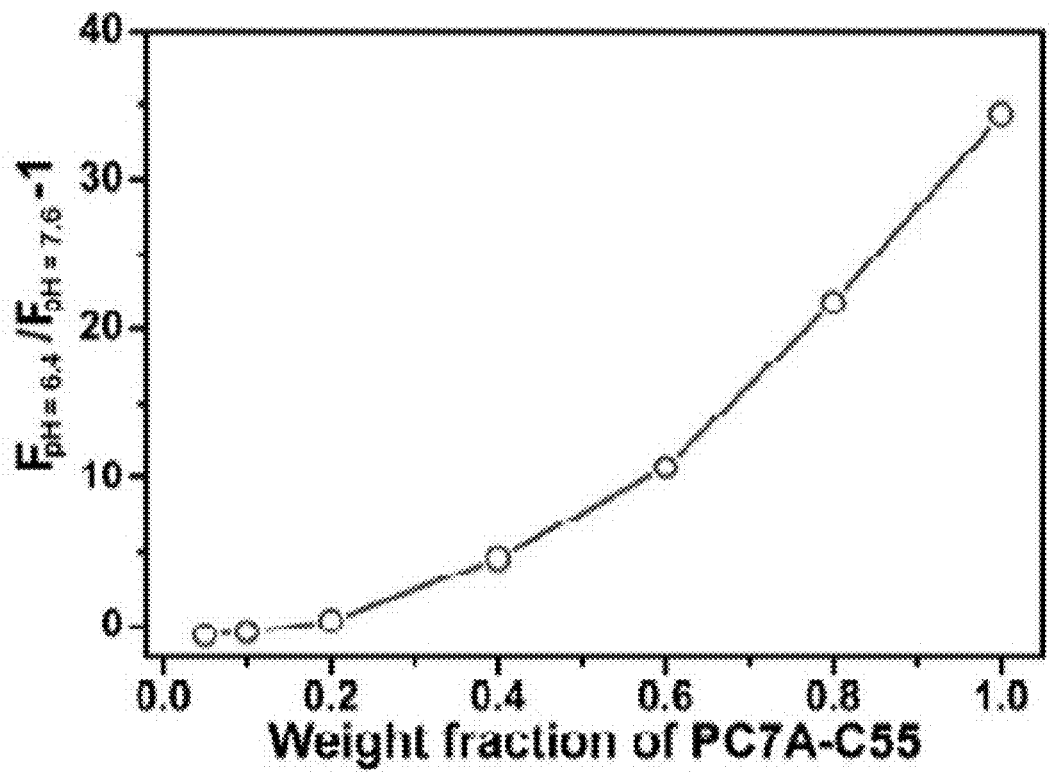
Figure 17A:
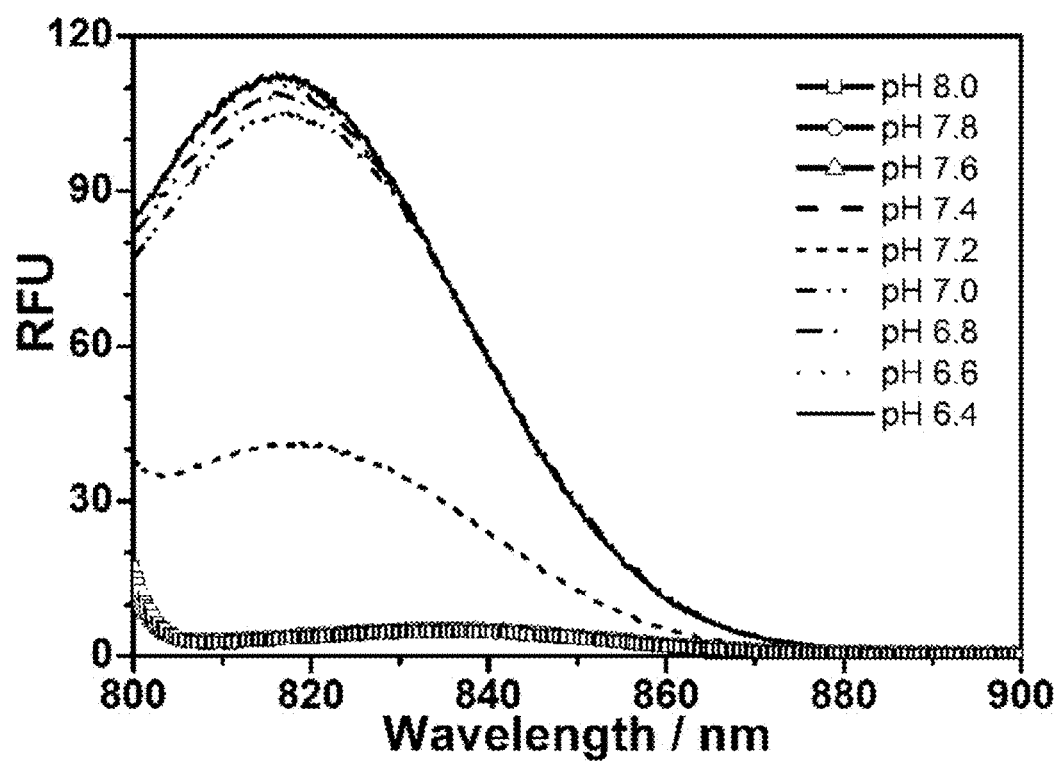
FIG. 17A-17D.
Figure 17B:
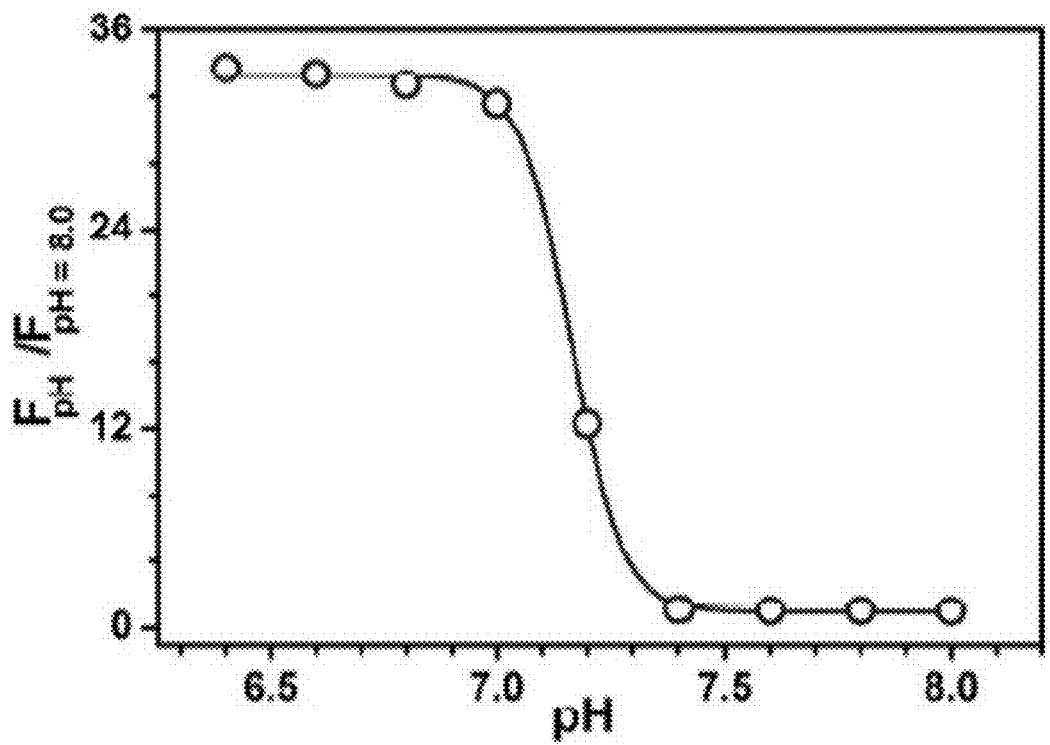
Figure 17C:
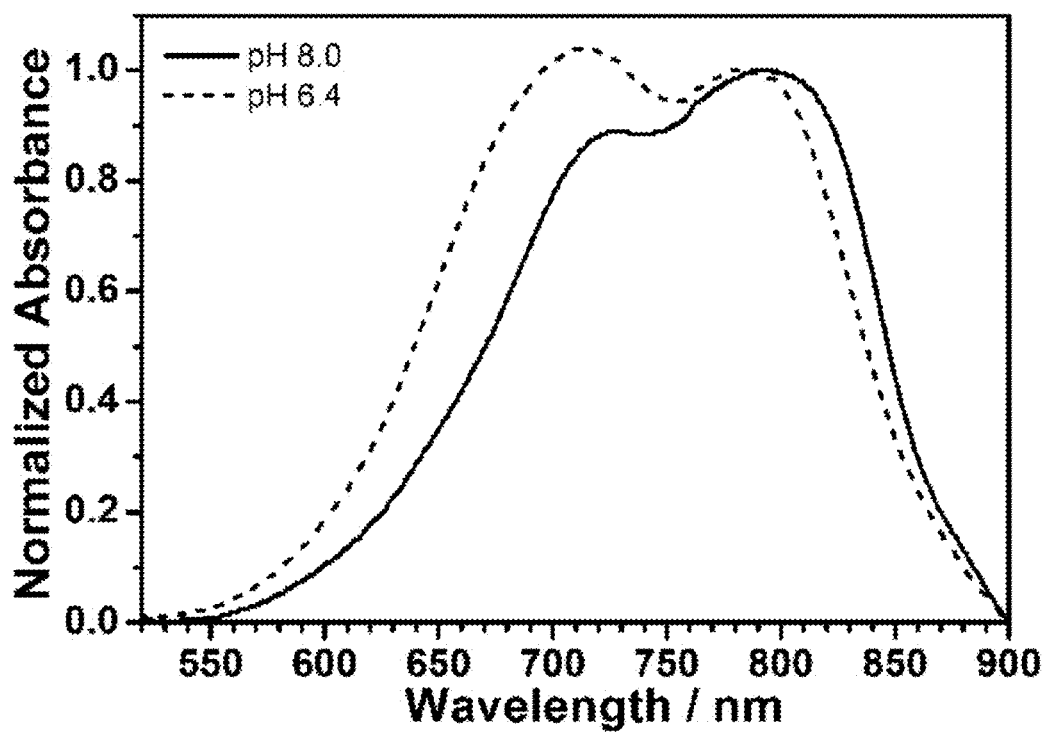
Figure 17D:
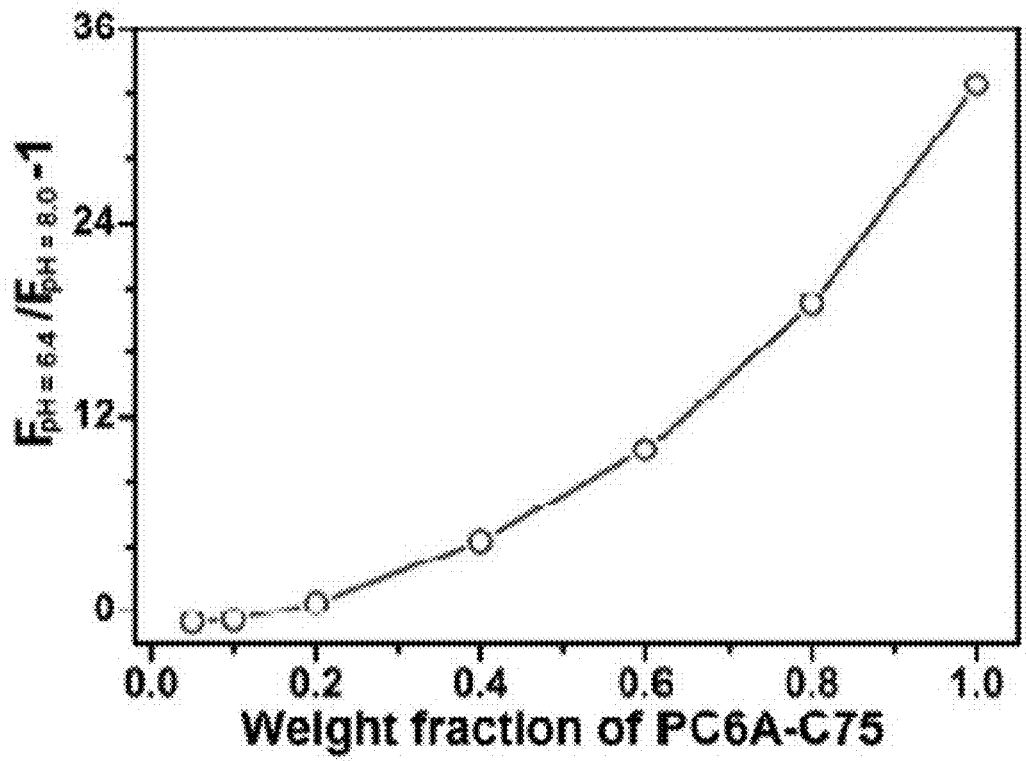
Figure 18A:
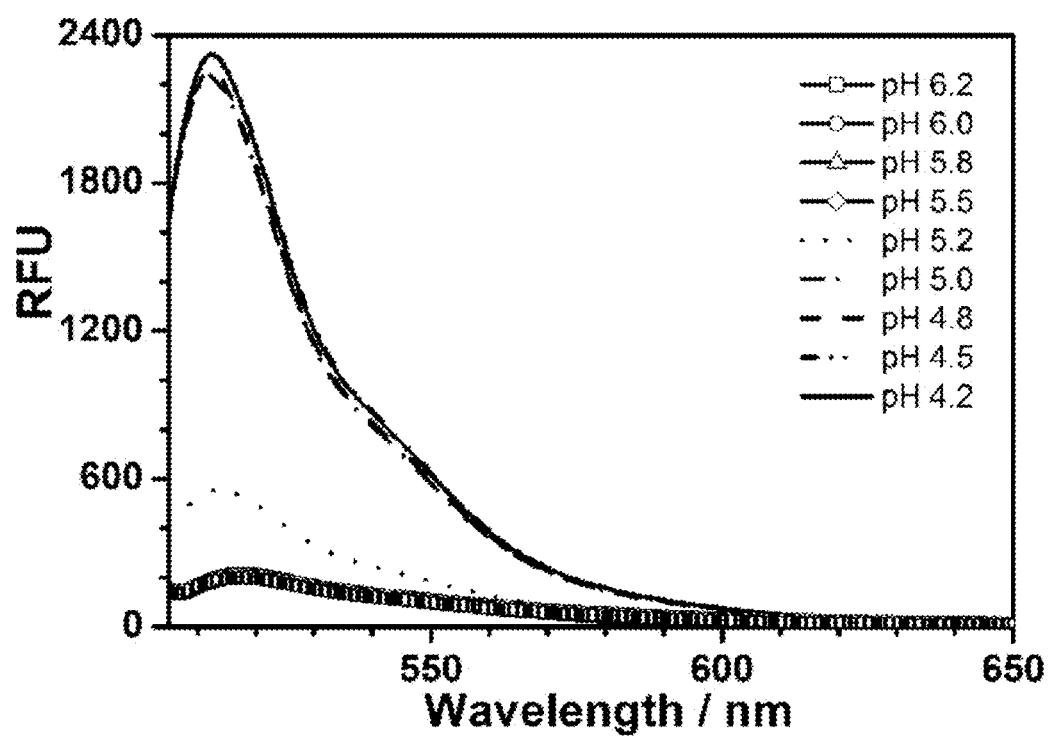
FIG. 18A-18D.
Figure 18B:
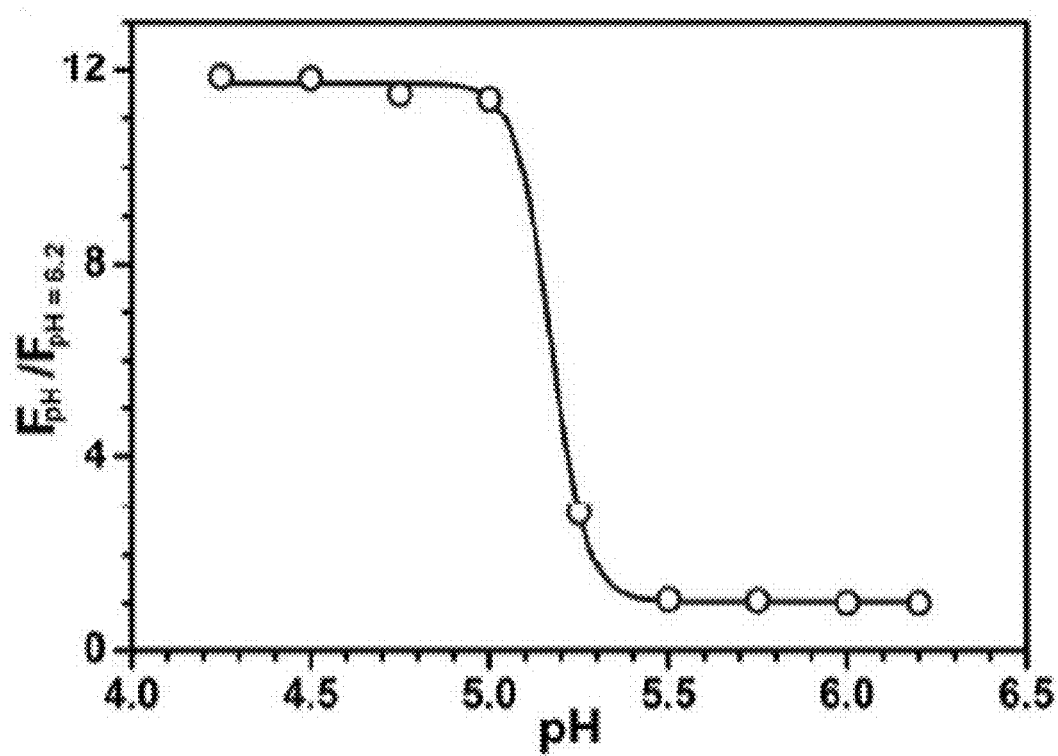
Figure 18C:
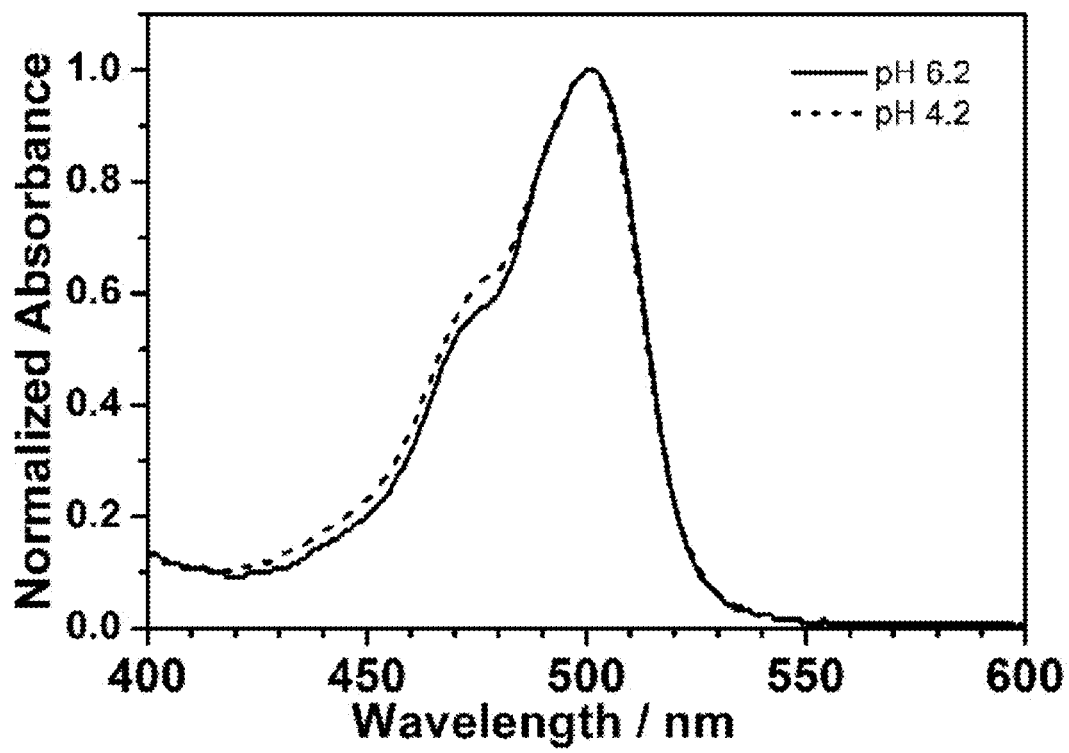
Figure 18D:
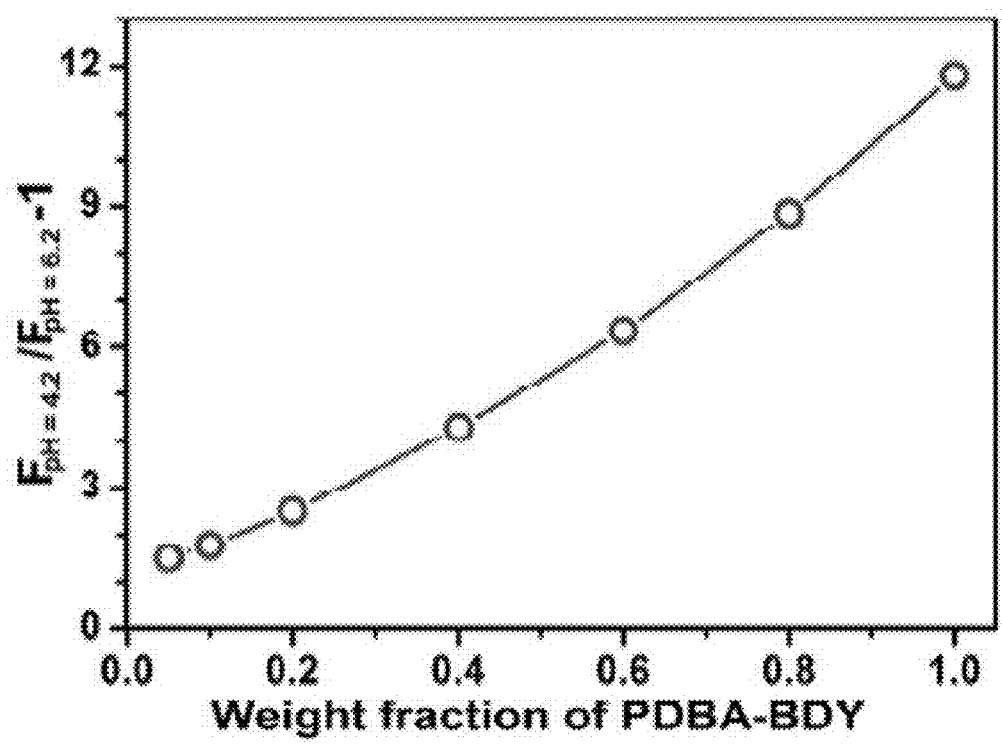

Due to the above reasons, a homo-FRET combined with pH-induced micellization was proposed to provide a more facile and robust strategy for the creation of multi-colored, pH-tunable fluorescence nanoplatform. Fluorophores with a small Stokes shift (Δλ<40 nm) can be selected from a variety of commonly available dye molecules with a wide range of emissions. This strategy has the additional advantage of independent control of pH sensitivity and emission wavelengths without direct energy/electron transfer between the polymers and fluorophores. Based on this rationale, a series of pH-tunable nanoparticles with emission wavelengths ranging from green to near IR were established. FIG. 6 shows the fluorescent images of a series of multichromatic nanoparticle solutions at different pH illustrating the sharp fluorescence transition for each nanoparticle. Quantitative data analysis show the $\Delta pH_{10-90}\%$ values are 0.22, 0.20, 0.23, and 0.24 and their pH transition points 5.2, 6.4, 6.9 and 7.2 for PDBA-BDY, PDPATMR, PC7A-C55 and PC6A-C75, respectively (FIG. 7). For the PDPA-TMR, PC7A-C55, and PC6A-C75 (FIG. 4C; FIG. 16D; FIG. 17D), only homo-FRET contributed to the fluorescence quenching mechanisms. For PC7A-C55, and PC6AC75, 33 and 34-fold fluorescence activation ratio were achieved, respectively. For PDBA-BDY, PeT contributed to 2.5-fold fluorescence activation and homo-FRET contributed 5.2-fold (FIG. 18D).

Figure 19:
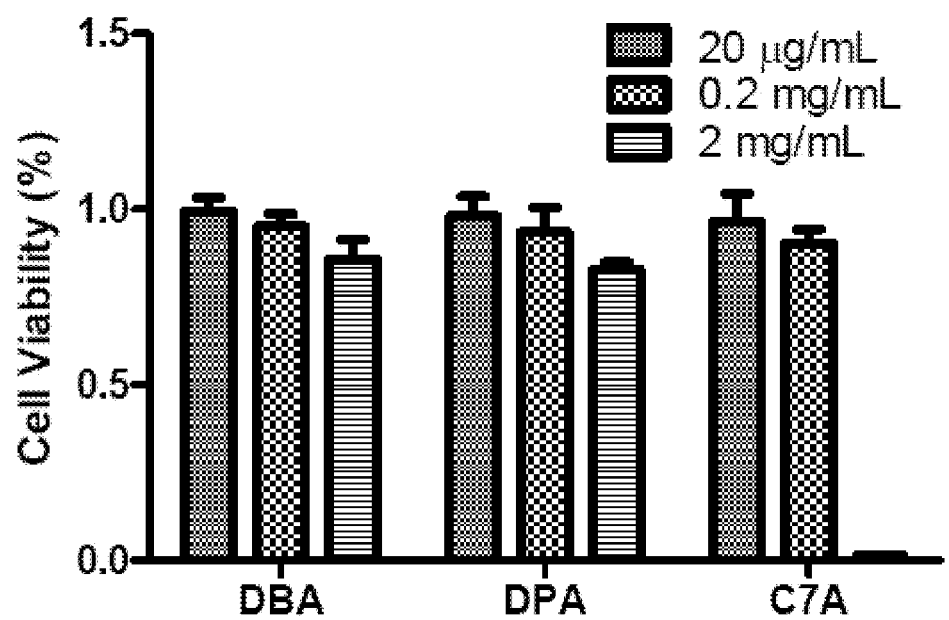
FIG. 19. Dependence of nanoparticle cytotoxicity in H2009 cells on nanoparticle composition at different doses. H2009 cells were incubated with increasing concentrations of PEG-PDBA, PEG-PDPA or PEG-PC7A nanoparticle solutions for 1 h at 37° C. Their cytotoxicity was assessed with MTT viability assay after 12 h in cell culture medium. Error bars represent standard deviation of six replicate samples.

The proposed strategy applies to several classes of commonly available fluorophores, including BODIPY, rhodamine, and cyanine families of derivatives for fine tuning of emission wavelengths. The strategy has the additional advantage of mix-matching different fluorophores with pH-sensitive polymer segments to create nanoparticles with desired color and pH transition point for biological studies. Furthermore, cell cytotoxicity study by the MTT assay has shown that these nanoparticle compositions are safe for imaging studies at 200 μg/mL (cell viability >90%, FIG. 19).

4. Sequential Activation of Multicolored Nanoparticles with Different pH Transitions Inside Endocytic Vesicles.

Vesicular trafficking is an essential process in eukaryotic cells for the delivery of membrane proteins or soluble cargos between intracellular compartments (Maxfield, F. R., *Nat. Rev. Mol. Cell. Biol.* 2004, 5, 121). Vesicular pH is a critical parameter that directly affects the membrane recycling, endo/lysosome maturation, and intracellular transport of endocytic vesicles (Izumi, H., *Cancer Treat. Rev.* 2003, 29, 541; Casey, J. R., *Nat. Rev. Mol. Cell. Biol.* 2010, 11, 50). Vesicular pH is precisely regulated by various membrane pumps or transporters such as vacuolar ($H^+$)-ATPase, $N^+/H^+$ exchanger, and $Cl^-$ channel (Nishi, T., *Nat. Rev. Mol. Cell. Biol.* 2002, 3, 94.; Ohgaki, R., *Biochemistry* 2010, 50, 443,)

Figure 8:
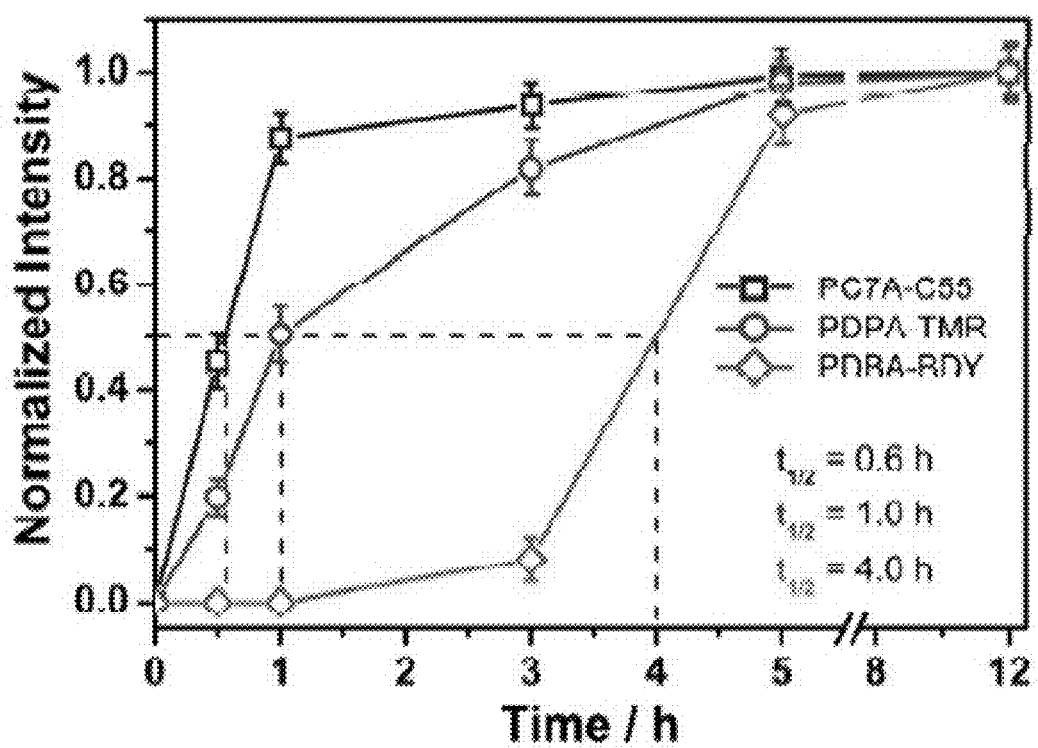
FIG. 8. Sequential activation of multicolored nanoparticles with different pH transitions over time. The quantitative data was analyzed from confocal images. The fluorescence intensity inside each cell was normalized to that at 12 hrs. The time ($t_{1/2}$) to achieve half of the maximum intensity was estimated for each nanoparticle.

In this study, the multicolored nanoparticles with different pH transitions were applied simultaneously and their spatial-temporal pattern of activation inside human H2009 lung cancer cells was investigated. The nanoparticle set consisted of a mixed nanoparticle solution of PDBA-BDY ($pH_t$=5.2), PDPA-TMR ($pH_t$=6.4), and PC7A-C55 ($pH_t$=6.9). Each nanoparticle was controlled at the same concentration (200 μg/mL) in the same culture medium and live cell imaging was performed by confocal laser scanning microscopy using three emission wavelengths. After one-hour incubation, the mixed nanoparticle solution was removed and replaced with fresh medium. Because each nanoparticle was "silent" in the external cell culture medium at pH 7.4, the kinetics of nanoparticle uptake and activation inside the H2009 cells could be monitored over time by confocal microscopy. The PC7A-C55 ($pH_t$=6.9) nanoparticles were first activated and their fluorescence intensity increased and reached a plateau after the PDPA-TMR ($pH_t$=6.4) fluorescence started to emerge in the first hour and steadily increased over a 3 hour span. Most of the punctate fluorescent dots observed for PDPA-TMR ($pH_t$=6.4) were colocalized with a subset of the PC7A-C55 ($pH_t$=6.9) fluorescent dots. Finally, PDBA-BDY ($pH_t$=5.2) nanoparticles were the last to be activated. Little fluorescence from PDBA-BDY ($pH_t$=5.2) was observed in the first three hours of incubation, but after 5 hours, the activated fluorescence of PDBA-BDY ($pH_t$=5.2) was fully visible, and interestingly, the location of the fluorescence was a further subset of the location of the PDPA-TMR fluorescence. To further quantify the time-course of intracellular activation of these nanoparticles, the fluorescence intensity for each nanoparticle over time is normalized to that at 12 hours (FIG. 8), at which time we anticipated full activation of all the nanoparticles. The half times of fluorescence activation for PC7A-C55, PDPA-TMR, and PDBA-BDY were determined to be 0.6, 1 and 4 hours, respectively, indicating sequential activation of these nanoparticles.

The sequential activation pattern of the multicolored nanoparticles directly correlated with their pH transitions, where nanoparticles with higher pH transition were activated earlier than those with lower pH transition. This data is consistent with the tendency of pH value change along the endocytic trafficking pathway where the vesicular pH gradually decreases from pH 7.4 (cell periphery) to 5.9-6.2 (early endosomes), then to 5.0-5.5 (late endosomes/lysosomes) (Maxfield, F. R., *Nat. Rev. Mol. Cell. Biol.* 2004, 5, 121; Casey, J. R., *Nat. Rev. Mol. Cell. Biol.* 2010, 11, 50; Modi, S., *Nat. Nanotech.* 2009, 4, 325). Moreover, the intracellular location of the nanoparticle activation for PDBA-BDY ($pH_t$=5.2 for specific activation in lysosomes (Zhou, K., *Angew. Chem. Int. Ed.* 2011, 50, 6109) is consistent with the peri-nuclear distribution of lysosomes. These data demonstrate the strong potential of the ultra-pH responsive, multicolored nanoplatform to detect small pH differences between the different endocytic organelles.

In summary, a robust and general system for creating series of pH-tunable, multicolored fluorescent nanoparticles through the use of commonly available pH-insensitive dyes was developed. pH-induced micellization and homo-FRET quenching of fluorophores in the micelle core provide mechanisms for the independent control of pH transition (via polymers) and fluorescence emission (dyes with small Stoke shifts). The fluorescence wavelengths can be fine tuned from, for example, green to near IR emission range (500-820 nm). Their fluorescence ON/OFF activation can be achieved within 0.25 pH units, which is much narrower compared to small molecular pH sensors. This multicolored, pH tunable and activatable fluorescent nanoplatform provides a valuable tool to investigate fundamental cell physiological processes such as pH regulation in endocytic organelles, receptor cycling, and endocytic trafficking, which are related to cancer, lysosomal storage disease, and neurological disorders.

5. Materials and Methods 2-(Pentamethyleneimino) ethanol (C6A) and N,N,N',N",N"-pentamethyldiethylenetriamine (PMDETA) were purchased from Sigma-Aldrich. 2-(Hexamethyleneimino) ethanol (C7A) and 2-(dibutylamino) ethanol (DBA) were purchased from Alfa Aesar Company and TCI America Inc., respectively. 4,4-Difluoro-1,3,5,7-tetramethyl-4-bora-3a,4a-diaza-8-indacene-8-propionic acid, succinimidyl ester (BDIPY-NHS), 7-diethylaminocoumarin-3-carboxylic acid succinimidyl ester (Coumarin-NHS),1-(3-(succinimidy-loxycarbonyl)benzyl)-4-(5-(4-methoxyphenyl)oxazol-2-yl) pyridinium bromide (PyPMO-NHS) and tetramethyl rhodamine NHS ester (NHS-TMR) were purchased from Invitrogen Company. Cy5.5 and Cy7.5 NHS esters were purchased from Lumiprobe Company. 2-(Diisopropyl amino)ethyl methacrylate (DPA) and 2-aminoethyl methacrylate (AMA) were purchased from Polyscience Company. AMA was recrystallized twice with isopropanol and ethyl acetate (3:7). Monomers of 2-(dibutylamino) ethyl methacrylate (DBA), 2-(hexamethyleneimino) ethyl methacrylate (C7A), 2-(pentamethyleneimino) ethyl methacrylate (C6A), and PEG macroinitiator (MeO-PEG114-Br) were prepared according to procedures in the literature (Zhou, K., *Angew. Chem. Int. Ed.* 2011, 50, 6109-6114). Other solvents and reagents were used as received from Sigma-Aldrich or Fisher Scientific Inc.

Figure 20:
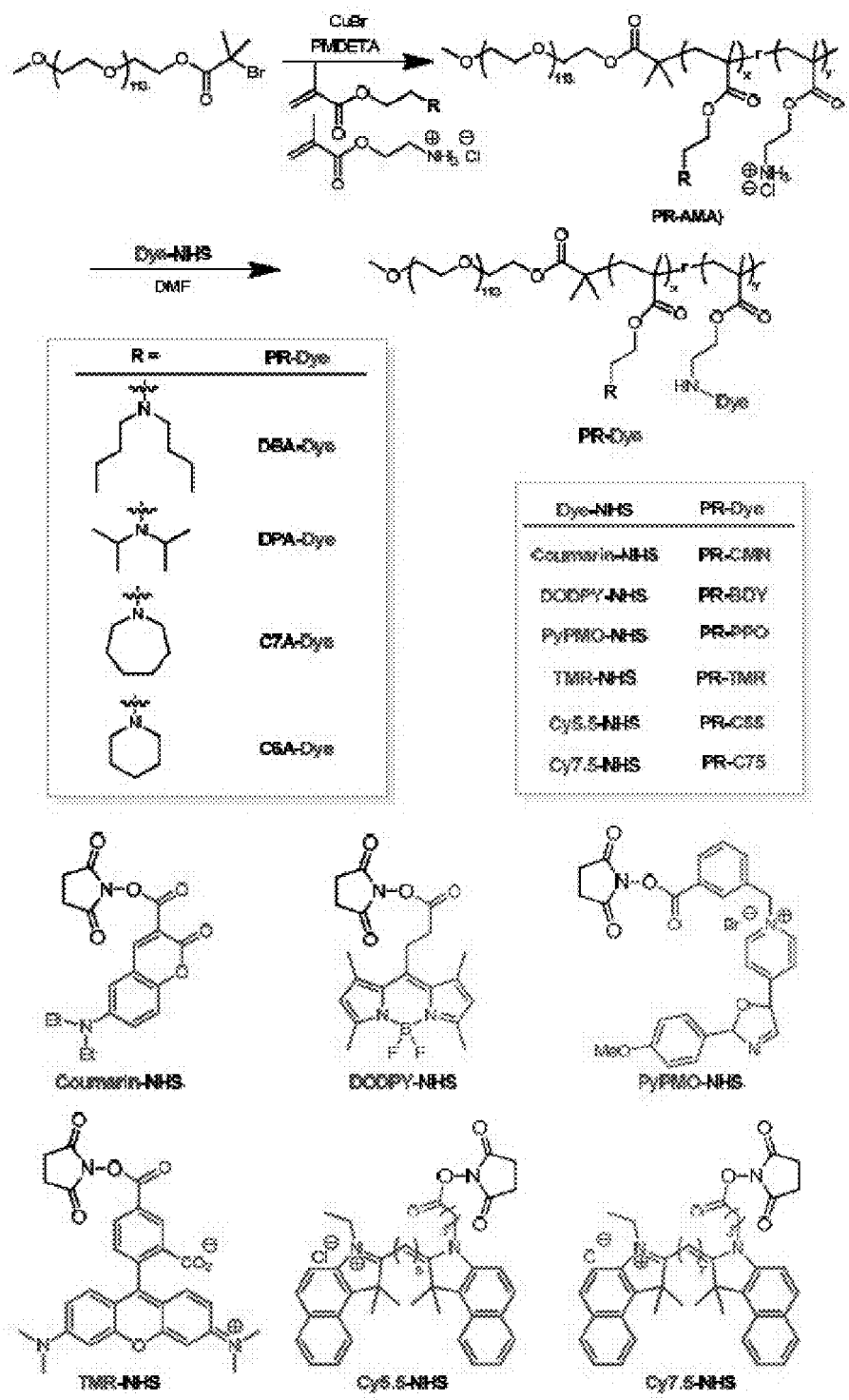
FIG. 20. Scheme for the syntheses of PEO-(PR-Dye) block copolymers.

Syntheses of PEO-(PR-Dye) block copolymers. PEO-b-(PR-co-AMA) copolymers (Scheme 1 in FIG. 20) were first synthesized by atom transfer radical polymerization (ATRP) method. The primary amino groups were introduced into each polymer chain by controlling the feeding ratio of the AMA monomer to the initiator (ratio=1, 3, or 6). The dye-free copolymers were used in polymer characterizations (Table 1). PEO-b-P(DPA-co-AMA) was used as an example to illustrate the procedure. First, DPA (1.7 g, 8 mmol), AMA (51 mg, 0.31 mmol), PMDETA (25 µL, 0.12 mmol), and MeO-PEG114-Br (500 mg, 0.1 mmol) were charged into a polymerization tube. Then a mixture of 2-propanol (2 mL) and DMF (2 mL) was added to dissolve the monomer and initiator. After three cycles of freeze-pump-thaw to remove oxygen, CuBr (16 mg, 0.11 mmol) was added into the reaction tube under nitrogen atmosphere, and the tube was sealed in vacuo. The polymerization was carried out at 50° C. for 8 hours. After polymerization, the reaction mixture was diluted with 10 mL THF, and passed through an $Al_2O_3$ column to remove the catalyst. The THF solvent was removed by rotovap. The residue was dialyzed in distilled water and lyophilized to obtain a white powder. The resulting PEO-b-PR copolymers were characterized by 500 MHz $^1$H NMR, gel permeation chromatography (Viscotech GPC-max, PLgel 5 µm MIXED-D columns by Polymer Labs, THF as eluent at 1 mL/min). Table 1 lists molecular weights ($M_n$ and $M_w$ and polydispersity index (PDI) of each copolymer.

Syntheses of dye-conjugated copolymers followed a representative procedure described below. For TMR conjugation, PEO-b-(PR-co-AMA) (50 mg) was first dissolved in 2 mL DMF. Then NHS-TMR ester (1.5 equivalents to the molar amount of the primary amino group) was added. The reaction mixture was stirred at room temperature for two days. The copolymers were purified by preparative gel permeation chromatography (PLgel Prep 10 µm 10E3Å 300×25 mm columns by Varian, THF as eluent at 5 mL/min) to remove the free dye molecules. The produced PEO-(PR-TMR) copolymers were lyophilized and kept at −20° C. for storage.

Preparation of the micelle nanoparticles. Micelles were prepared following a solvent evaporation method as previously published (Nasongkla, N., *Nano. Lett.* 2006, 6, 2427-24). In the example of PDPA-TMR micelle solution, 10 mg of the copolymer was first dissolved in 0.5 mL THF and then added into 4 mL distilled water dropwise under sonication. The THF was removed through ultrafiltration with (100 kD) membrane for several times. Then the distilled water was added to adjust the polymer concentration to 5 or 10 mg/mL as a stock solution. After micelle formation, the nanoparticles were characterized by transmission electron microscopy (TEM, JEOL 1200 EX model) for micelle size and morphology, and dynamic light scattering (DLS, Malvern MicroV model, He—Ne laser, λ=632 nm) for hydrodynamic radius ($R_h$).

For the preparation of molecularly mixed micelle, a mixture of PDPA-TMR and PEO-b-P(DPA-co-AMA) with 1:1 weight ratio was used as an example. PDPA-TMR copolymer (5 mg) and PEO-b-P(DPA-co-AMA) (5 mg) were first dissolved in 0.5 mL THF and then added into 4 mL distilled water dropwise under sonication. The THF was removed through ultrafiltration with (100 kD) membrane for several times. Then the distilled water was added to adjust the polymer concentration to 5 or 10 mg/mL as a stock solution for subsequent studies.

CMC measurement of PEO-(PDPA-AMA). Critical micelle concentration (CMC) of PEO-(PDPA-AMA) copolymer was measured in the 0.2 M sodium phosphate buffer at pH 7.4. First, the copolymer stock solution (5 mg/mL) was diluted to different concentrations with the same buffer. In each solution, 5 µL pyrene in THF solution ($2\times10^{-4}$ mol/L) was added to 2 mL polymer solution to produce the final pyrene concentration at $5\times10^{-7}$ mol/L. The fluorescence spectra were recorded on a Hitachi fluoremeter (F-7500 model) with the excitation wavelength of 339 nm and the excitation and emission slits at 10.0 nm and 1.0 nm, respectively. The $I_1$ and $I_3$ values were measured as the maximum emission intensity at ca. 372 and 382 nm, respectively. $I_1/I_3$ ratio was plotted as a function of polymer concentration at different pH values. $I_1/I_3$ ratio reflects the polarity of the pyrene environment where partition of pyrene in the hydrophobic micelle core leads to decreased $I_1/I_3$ values.3,4 CMC values were measured as the threshold polymer concentration at which micelles were formed in solution (Kalyanasundaram, K., *J. Am. Chem. Soc.* 1977, 99, 2039-2044; Winnik, F. M., *Chem. Rev.* 1993, 93, 587-614). To avoid TMR interference, PEO-b-PR copolymers without TMR conjugation were used in these studies.

pH titration of PDPA-TMR. PDPA-TMR copolymer (80 mg) was first dissolved in 5 mL 0.1 M HCl and diluted to 2 mg/mL with DI water. The pH titration was carried out by adding small volumes (0.05-0.1 mL increments) of 0.02 M NaOH solution under stirring. The pH increase in the range of 2 to 11 was monitored as a function of total added volume of NaOH ($V_{NaOH}$). The pH values were measured using a Mettler Toledo pH meter with a microelectrode. During the titration experiment, ~1 mL solutions of a series of pH points was taken and filtered with 0.45 µm Nylon filter. Then its hydrodynamic radius was measured by DLS. At pH 5.8 and 6.8, the solutions were characterized by TEM.

Fluorescence and UV-Vis characterization. The fluorescence emission spectra were obtained on a Hitachi fluorometer (F-7500 model). The UV-Vis spectroscopy study was performed on a Shimadzu UV-Vis spectrophotometer (UV-1800 model). For each copolymer, the sample was initially prepared in MilliQ water at the concentration of 6 mg/mL. Then the stock solution was diluted in 0.2 M citric-phosphate buffers with different pH values. The terminal polymer concentration was controlled at 0.2 or 0.5 mg/mL. For fluorescence lifetime measurements, the fluorescence decays of PDPA-TMR at 0.1 mg/mL were measured at pH=7.4 and 5.5 (above and below the $pH_t$, respectively) in sodium phosphate/citric acid buffers. The fluorescence decays of free TMR dye (5 μg/mL) was also measured at pH=7.4 and 5.5. These studies were carried out on a Laser-Strobe fluorescence lifetime instrument (Photon Technology International, Inc., Birmingham, N.J.), which consists of a nitrogen laser (GL-3300) linked to a dye laser (GL 302) and a stroboscopic detector. C-540A (Exciton, Inc., Dayton, Ohio) dye solution was used to generate an excitation wavelength of 540 nm. The decay curves were analyzed at the wavelength of 580 nm. The emission monochromator slit was at 4 nm. All measurements were conducted at room temperature. The IRF (instrument response function) was determined by measuring scattered light from a solution of glycogen. The fluorescence intensity decay data were analyzed by using the software supplied with the PTI instrument.

For the fluorescent images of PDBA-BDY, PDPA-TMR, C7A-C55 and C6A-C75 solutions at different pH values (100 μg/mL for each sample), the Maestro imaging system (CRI, Inc., Woburn, Mass.) was used by choosing a proper band pass excitation filter and a proper long-pass emission filter according to the instrument manual.

Cell culture and Confocal imaging study of micelle uptake. Human lung carcinoma H2009 cells were cultured in RPMI 1640 medium (Invitrogen, CA) supplemented with 5% fetal bovine serum (FBS), 100 IU/mL penicillin and 100 μg/mL streptomycin at 37° C. in 5% $CO_2$ atmosphere.

Prior to confocal imaging studies, H2009 cells were plated in glass bottom cell culture dishes (MatTek, MA) in 2 mL complete RPMI medium and incubated with mixed nanoparticles of PDBA-BDY, PDPA-TMR and C7A-C55 where each nanoparticle concentration was at 0.2 mg/mL in phenol-free RPMI 1640 medium. The medium was changed after one-hour incubation. Confocal images were captured at different time points. The images were processed and analyzed under identical conditions by the Image-J software. Five independent measurements were analyzed and averaged as the mean±standard deviation. Images were captured at designated time points by a Nikon ECLIPSE TE2000-E confocal microscope with a 100× objective lens. PDBA-BDY, PDPA-TMR and C7A-C55 were excited at 488, 543 and 623 nm, respectively. The FITC, TRITC and Cy5 filters were used for PDBA-BDY, PDPA-TMR and C7A-C55 imaging, respectively.

In vitro cytotoxicity evaluations of micelle nanoparticles. Cytotoxicity of different micelle nanoparticles (PEG-PDBA, PEG-PDPA, PEG-PC7A) was assessed by incubating H2009 cells (10,000 cells/well in 96-well plates seeded 12 h prior to experiments) with 20 μg/mL, 0.2 mg/mL or 2 mg/mL of different micelle nanoparticles in complete RPMI 1640 medium supplemented with 5% FBS for 1 h. After washing with medium to remove extracellular particles, the cells were further cultured in the complete medium for 12 h. At the endpoint, MTT stock solution was then added to each well to give a final concentration of 0.5 mg/mL for additional 4 h. After cell treatment with 100 μL DMSO, the absorbance at 490 nm was measured using a microplate reader. Cell viability was measured as the ratio of UV absorbance for treated cells over untreated control. Standard deviations were calculated from six replicate samples.

6. Fine Tuning Ultra-pH Responsive Nanoparticles for Applications in High Throughput Screening of Small Molecular Modulators of Endosomal pH.

pH plays a critical role in the endocytic trafficking and recycling of cell surface receptors (e.g. LDL receptors), which are highly related to a variety of human diseases and metabolic disorders. Small molecules that can regulate pH inside subcellular organelles are promising drug candidates to remedy the deficiency in endosome functions. High throughput screening (HTS) is a powerful method to identify lead molecules from a compound library. For HTS to work, an effective cell-based assay is essential. This study reports the syntheses of a series of fine tuning ultra-pH responsive nanoparticles, of which the fluorescent signal can be turned "on" and "off" with subtle change in pH in the early endosomal range (pH 5.7-6.3). The data demostrate the feasibility of these nanoparticles in detecting the change of early endosomal pH by confocal laser scanning microscopy. These results also demonstrate the feasibility of these nanoparticles for application in HTS of small molecules that can modulate endosomal pH.

Methods: A series of copolymers with different pH transitions were synthesized from poly(ethylene oxide) (PEO) and monomers containing tertiary amines by atom-transfer radical polymerization. The pH transition of copolymers were fine tuned by controlling the ratio of 2-(dibutyl amino) ethyl methacrylate (DBA) to 2-(diisopropyl amino)ethyl methacrylate (DPA). Tetramethyl rhodamine (TMR) was used as a fluorophore and conjugated to the copolymer. Preparative gel permeation chromatography (PLgel Prep 10 μm 10E3 Å300×25 mm columns by Varian, THF as eluent at 5 mL/min) was used to purify the polymer samples. $^1$H NMR spectra of the polymers were obtained on a Varian 1H 500 MHz NMR. Fluorescence intensities were obtained on a Hitachi fluorometer (F7000 model).

Figures 21A, 21B, 21C:
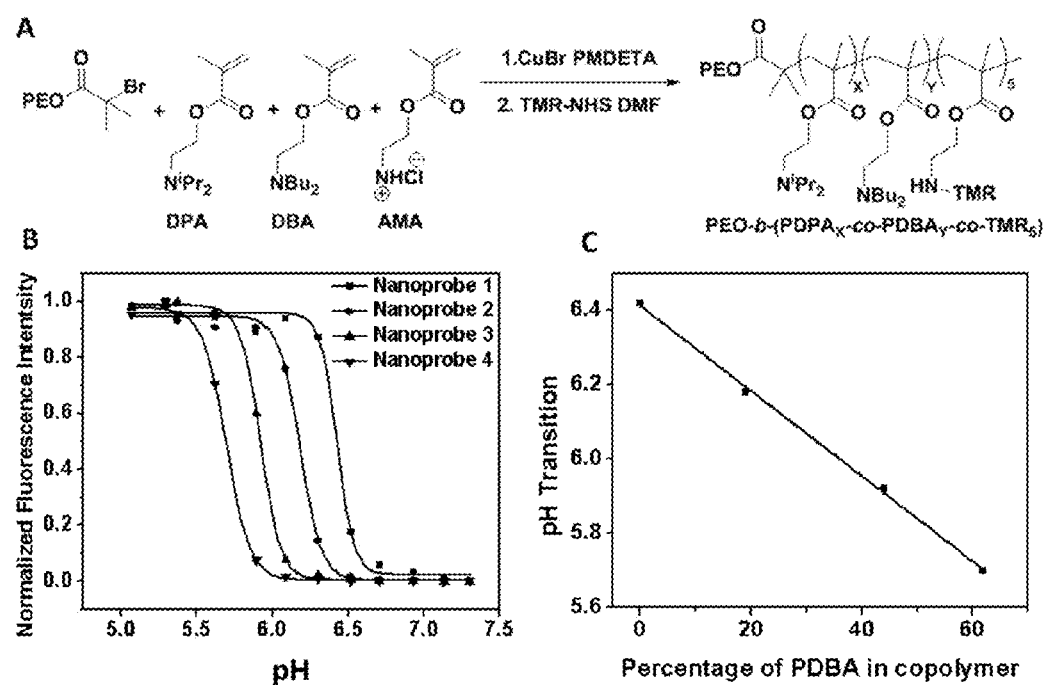
FIGS. 21A-21C.

Results: A series of ultra-pH responsive nanoparticles were synthesized (nanoprobes 1-4) with sharp pH transitions (ΔpH<0.25 between ON/OFF states). A synthesis scheme is shown in FIG. 21A. By varying the monomer ratios of DBA and DPA, the pH transition points were finely controlled at pH 6.42 (1), 6.18 (2), 5.94 (3) and 5.70 (4) (FIG. 21B; Table 2). These subtle differences revealed a linear relationship between the percentage of DBA in copolymers' component and pH transition points which can be used to fine tune pH transition to a specific value by changing the ratio of starting materials (FIG. 21C). Incubation of nanoprobes and small molecular modulators (e.g. nigericin) of endosomal pH with HeLa cell line showed earlier activation time compared to those without these small molecular modulators by confocal laser scanning microscopy. Nanoprobe (3) with a pH transition of 5.94 showed more specific activation for the detection of endosomal pH in the presence of small pH modulators as compared to other nanoprobes. These data showed feasibility of the nanoparticles in high throughput screening of small molecules that can modulate endosomal pH.

TABLE 2 pH Transition Points for Nanoprobes by using Varied Monomer Ratios

| | X | Y | pHt |
|---|---|---|---|
| Nanoprobe 1 | 75 | 0 | 6.42 |
| Nanoprobe 2 | 51 | 12 | 6.18 |
| Nanoprobe 3 | 47 | 37 | 5.92 |
| Nanoprobe 4 | 27 | 44 | 5.70 |

In summary, the feasibility of using fine tuning ultra-pH responsive nanoparticles for detection of small pH changes in early endosomes was demonstrated. The pH transition points can be fine tuned by the variation of the molar fractions of two monomers with different hydrophobicities. Different activation time windows were established by different nanoprobes, which can be further used to screen molecules with acidification or inhibition of acidification of endocytic organelles.

7. UPS Nanoprobes for Specific $pH_e$ and $pH_i$ Imaging

Figure 22:
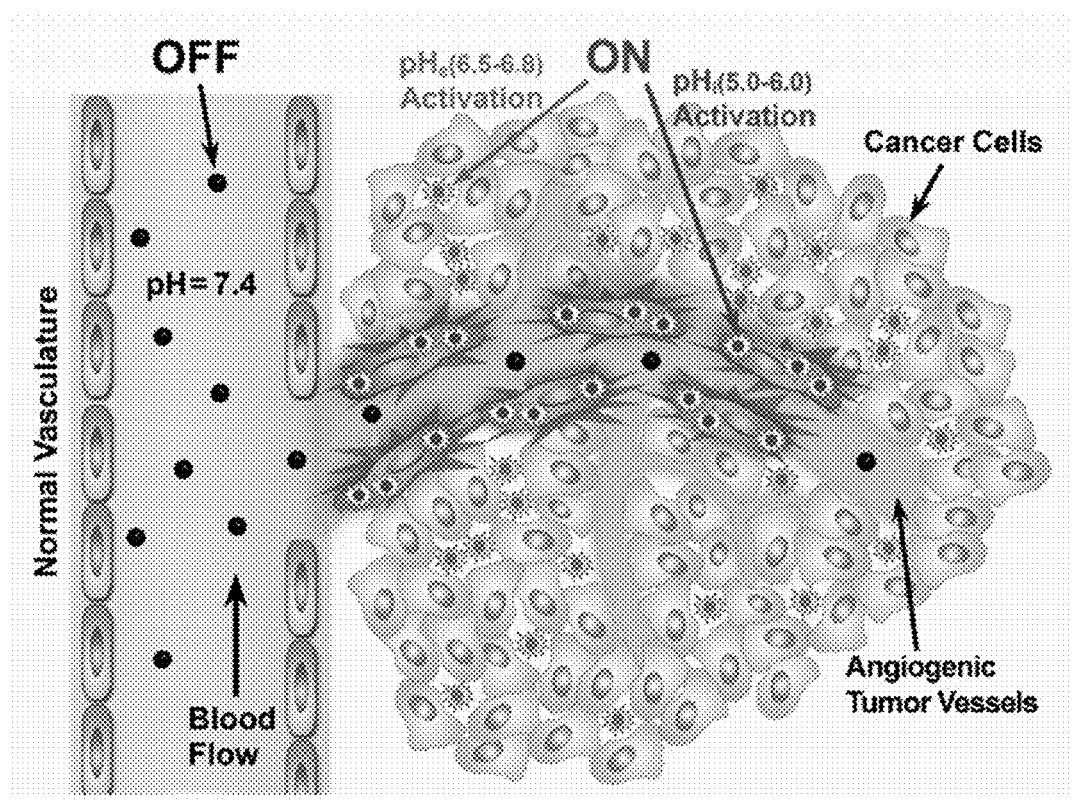
FIG. 22. Schematic of imaging tumor microenvironment by ultra-pH sensitive (UPS) nanoprobes. The UPS nanoprobes stay 'OFF' at pH 7.4 during blood circulation. After reaching tumors, the UPS nanoprobes are turned ON by acidic extracellular $pH_e$ (6.5-6.8) in the tumor milieu, or endocytic organelles ($pH_i$, 5.0-6.0) in the tumor endothelial cells after receptor-mediated endocytosis.

Tumor microenvironment is emerging as a new paradigm for cancer diagnosis and therapeutic intervention over conventional cancer cell-centric strategies (Hanahan & Weinberg, 2011). The tumor microenvironment has startling complexity and heterogeneity at the molecular, cellular, and tissue levels (Gatenby & Gillies, 2008, Swartz, et. al., 2012, Joyce, 2005). Among many microenvironment signals, two recognized hallmarks, tumor angiogenesis (Weis & Cheresh, 2011, Folkman, 2007) and low extracellular pH ($pH_e$) (Webb, et. al., 2011), are ubiquitous in solid tumors, regardless of cancer types. In this study, we will test the hypothesis that nanoprobes targeting acidic tumor $pH_e$ and angiogenic vasculature can lead to a robust strategy to broaden the specificity of tumor detection (FIG. 22).

Figure 23:
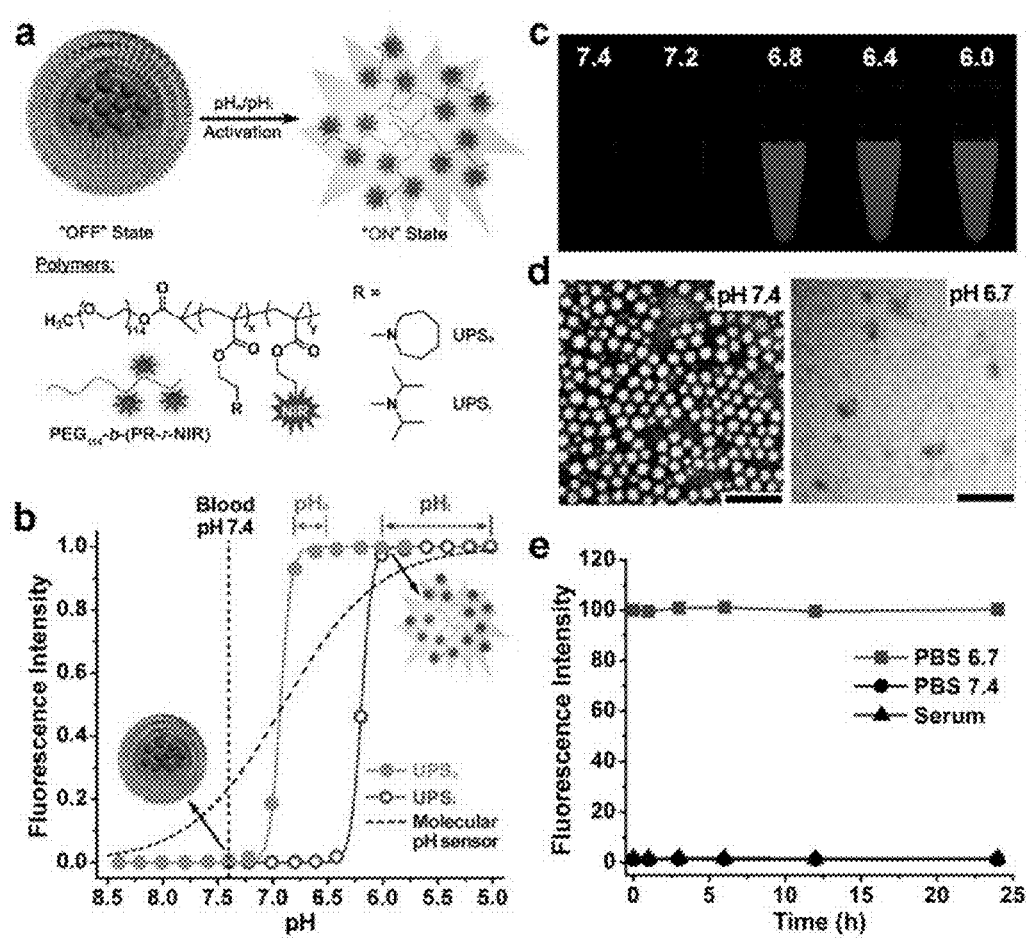
FIGS. 23A-E Syntheses and characterization of UPS nanoprobes. 23A Structural composition of two types of nanoprobes, $UPS_e$ and $UPS_i$ with pH transitions at 6.9 and 6.2, respectively. The $UPS_i$ is specifically designed to activate at acidic tumor extracellular fluid ($pH_e$=6.5-6.8). The UPS, can be activated inside acidic endocytic organelles (e.g. $pH_i$=5.0-6.0). Cy5.5 is used as the NIR fluorophore in most of the animal studies. 23B Normalized fluorescence intensity as a function of pH for $UPS_e$ and $UPS_i$ nanoprobes. At high pH (e.g. 7.4), both probes stay silent. At pH below their transitions (i.e. 6.9 and 6.2), the nanoprobes can be activated as a result of micelle dissociation. The blue dash-line simulates the pH response of a small molecular pH sensor with a $pK_a$ of 6.9 based on Henderson-Hasselbach equation. For the nanoprobes, the pH response (ΔpH10-90%) is extremely sharp (<0.25 pH unit between ON/OFF states) with >100-fold signal amplification. In contrast, small molecular pH sensors require 3 pH units for comparable signal change. 23C Fluorescent images of $UPS_e$-Cy5.5 nanoprobe solution in different pH buffers (λex=675 nm, λem=710 nm). 23D Transmission electron micrographs of $UPS_e$ nanoprobes at pH 7.4 and 6.7 (polymer concentration=1 mg/mL, scale bar=100 nm). 23E $UPS_e$ nanoprobes remain stable in fresh mouse serum over 24 h at 37° C.

To distinguish the small pH differences between acidic tumor $pH_e$ (6.5-6.8) (Webb, et. al., 2011) and blood (7.4), it is essential to establish an ultra pH-responsive nanoprobe that can maximally turn on fluorescent signals in this pH span. For this purpose, a $UPS_e$ nanoprobe from poly(ethylene glycol)-b-poly(2-(hexamethyleneimino)ethyl methacrylate) copolymers (FIG. 23a, Table 3) was synthesized. A near-infrared dye, Cy5.5 ($\lambda_{ex}$=675 nm, $\lambda_{em}$=710 nm), was conjugated to the ionizable block of the copolymer. The $UPS_e$ nanoprobe had a pH transition at 6.9 with an extremely sharp pH response ($\Delta pH_{10-90}$%, the pH difference between 10% to 90% fluorescence activation was 0.23). The fluorescence activation ratio was 102-fold for the $UPS_e$ nanoprobe between pH 6.7 and 7.4. In contrast, theoretical calculation based on the Henderson-Hasselbach equation for a small molecular pH sensor ($pK_a$=6.9) yielded only 2.6-fold fluorescence increase in this pH range (FIG. 23b). At blood pH, $UPS_e$ nanoprobes were present as self-assembled micelles with a diameter of 25.3±1.5 nm and a spherical morphology (left panel, FIG. 23d). HomoFRET-induced fluorescence quenching was responsible for complete silence of the fluorophores in the micelle state (FIG. 23c) (Zhou, et. al., 2012). Micelle dissociation at acidic $pH_e$ (right panel, FIG. 23d) resulted in dramatic increase in fluorescence signals (FIGS. 23c, e).

Figure 24:
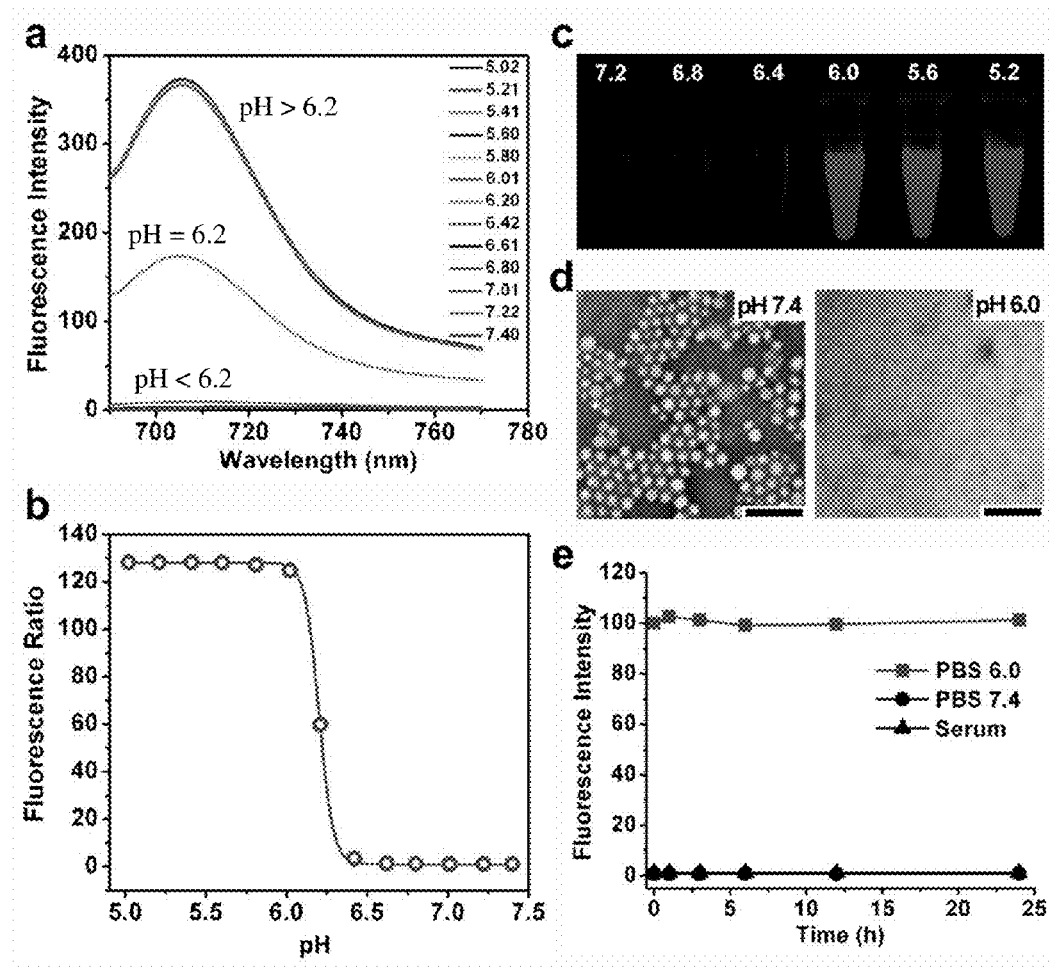
FIGS. 24A-E Characterization of cRGD-UPS, nanoprobes. 24A pH-dependent fluorescence spectra of cRGD-UPS, nanoprobes. Each sample is excited at 675 nm, and emission spectra are collected from 690 to 780 nm. The polymer concentrations were 0.1 mg/mL. 24B Fluorescence ratio as a function of pH for cRGD-UPS, nanoprobes. The pH response ($ΔpH_{10-90}$%) is 0.21 pH unit and signal amplification is 128-fold. 24C Fluorescence signal amplification of cRGD-UPS, nanoprobes as a function of pH. Fluorescence images were captured on Maestro in vivo imaging system (CRI) using the "orange" filter (640-820 nm). 24D Transmission electron microscopes of cRGD-UPS, nanoprobes in pH 7.4 and 6.0 buffers at the polymer concentration of 1 mg/mL. Scale bar is 100 nm. 24E cRGD-UPS, nanoprobes remain stable in fresh mouse serum over 24 h at 37° C.

To achieve specific activation in the acidic endocytic organelles (e.g. endosomes and lysosomes, $pH_i$=5.0-6.0) in the cells, a $UPS_i$ nanoprobe from poly(ethylene glycol)-b-poly(2-(diisopropyl amino)ethyl methacrylate) copolymers (FIG. 23a) was generated. The $UPS_i$ nanoprobe had a pH transition at 6.2 with $\Delta pH_{10-90}$% value of 0.21. The fluorescence ON/OFF activation ratio was 128-fold (FIG. 24b and Table 4). For imaging of $\alpha_v\beta_3$-expressing

TABLE 3

Characterization of the Diblock Copolymers

| Copolymer | Yield (%) | $M_{n,GPC}$ (kDa)[a] | $M_{w,GPC}$ (kDa)[a] | $M_n$, $^1$H-NMR (kDa)[b] | PDI[a] |
|---|---|---|---|---|---|
| PEG$_{114}$-b-P(C7A$_{65}$-co-AMA$_6$) | 78 | 18.7 | 22.4 | 19.6 | 1.19 |
| PEG$_{114}$-b-P(DPA$_{75}$-co-AMA$_6$) | 82 | 20.1 | 23.1 | 21.0 | 1.15 |
| MAL-PEG$_{114}$-b-PDPA$_{88}$ | 62 | 22.8 | 27.8 | 23.9 | 1.22 |

[a]Number-averaged ($M_n$), weight-averaged molecular weight ($M_w$) and polydispersity index (PDI = $M_w/M_n$) were determined by GPC using THF as the eluent;
[b]Determined by $^1$H-NMR.

TABLE 4

Characterization of UPS Nanoprobes

| Nanoprobes | Particle Size (nm)[a] | Zeta potential (mV) | $R_F$ ($F_{max}/F_{min}$)[b] | $\Delta pH_{10-90\%}$ | $pH_t$ |
|---|---|---|---|---|---|
| $UPS_e$ | 25.3 ± 1.5 | −0.72 ± 1.07 | 102 | 0.23 | 6.90 |
| $UPS_i$ | 24.9 ± 0.8 | −3.52 ± 0.60 | 135 | 0.21 | 6.21 |
| cRGD-$UPS_i$ | 24.5 ± 1.1 | −2.79 ± 0.30 | 128 | 0.21 | 6.21 |

[a]Measured from TEM, mean ± s.d.;
[b]Determined by Cy5.5 fluorescence emission intensity.

angiogenic tumor endothelial cells, the $UPS_i$ surface was functionalized with 10% cRGDfK (cRGD) peptide through thiol-maleimide linkage, shown in the scheme below. The

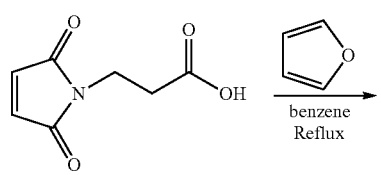

1

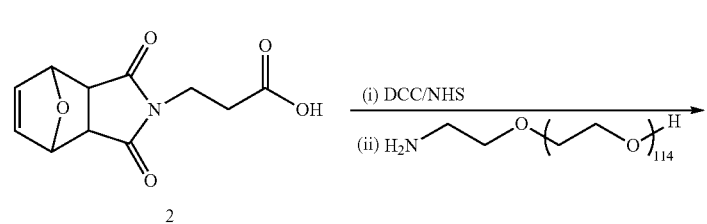 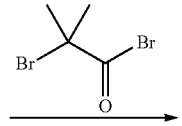

2

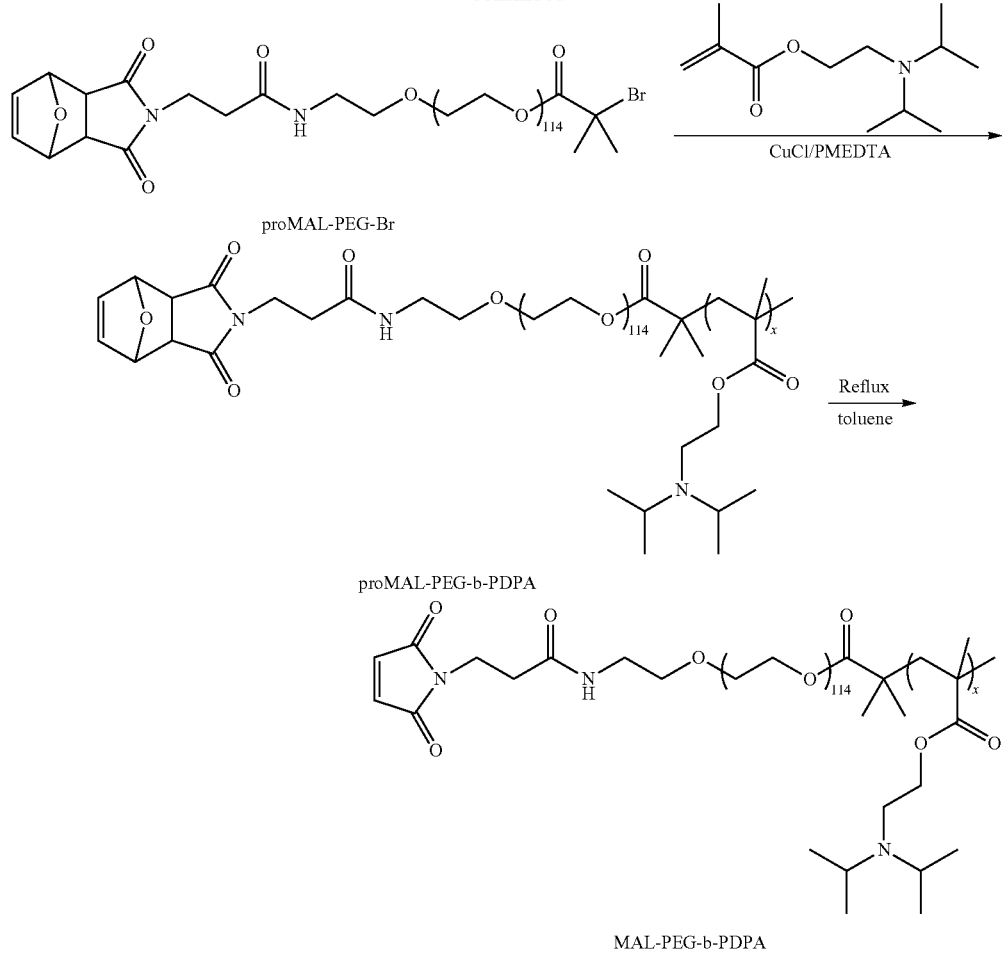

cRGD-encoded UPS$_i$ nanoprobes (24.5±1.1 nm) were stable at blood pH and acidic tumor pH$_e$, but can be selectively activated inside the lysosomes of tumor endothelial cells upon receptor-mediated endocytosis (see data below). Both UPS$_e$ and UPS$_i$ nanoprobes were stable in freshly prepared mouse serum as indicated by the negligible change in fluorescence intensity over 24 h of incubation (FIGS. 23e and 24e).

a. Imaging Acidic pH$_e$ in Tumor-Bearing Mice by the UPS$_e$ Nanoprobes

Figure 25:
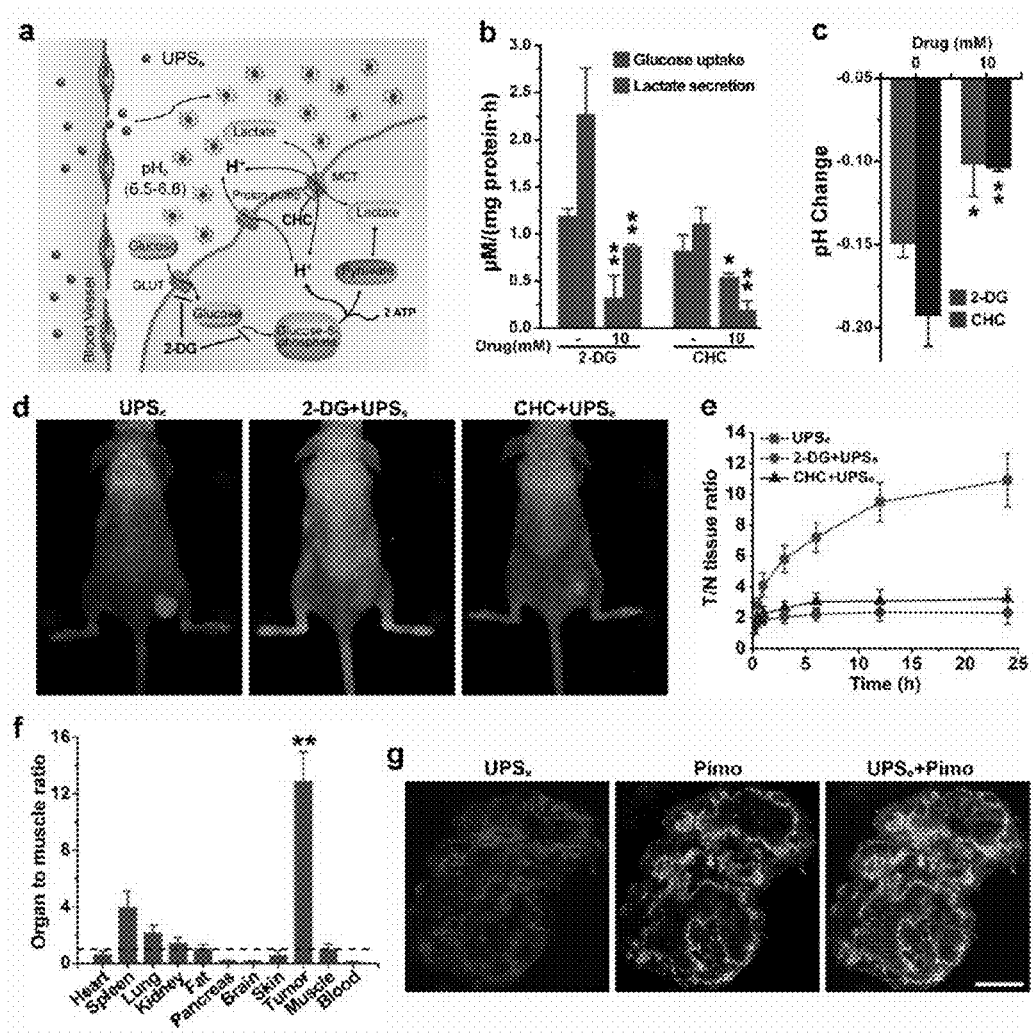
FIGS. 25A-G $UPS_e$ nanoprobes can specifically image acidic tumor $pH_e$. 25A Aerobic glycolysis of glucose and production of lactic acids by the cancer cells. 2-DG and CHC are metabolic inhibitors for glucose uptake and lactic acids secretion, respectively. 25B Effect of 2-DG or CHC on the rate of glucose uptake and lactic acid secretion in A549 cells. 25C Acidification of A549 cell culture medium in the presence of 2-DG or CHC after 24 h incubation. 25D Overlaid fluorescent images of A549 tumor-bearing mice at 24 h post-injection of $UPS_e$ nanoprobes (10 mg/kg). In the control groups, 2-DG (250 mg/kg) or CHC (250 mg/kg) was injected 12 h before $UPS_e$ nanoprobe administration. Cy5.5 (red) and autofluorescence (green) are separately shown in the composite images. 25E NIR fluorescence intensity ratio between tumor and normal tissues (T/N ratio) as a function of time after $UPS_e$ injection. Data are presented as mean±s.d. (n=4). 25F Organ to muscle ratios of fluorescence intensity at 24 h post-injection of $UPS_e$. Data are presented as mean±s.d. (n=4). **P<0.01, compared with other organs. 25G Hypoxia bands correlate with activation pattern of $UPS_e$ in A549 tumor xenograft. Whole mount images of tumor slices stained for hypoxia (green) and tumor vessels (CD31, green). All images were obtained from the adjacent sections at ×200 magnification. Scale bar is 2 mm.

To investigate the specificity of UPS$_e$ nanoprobes for pH$_e$ imaging, two inhibitors of tumor glycolysis and examined their effects on extracellular pH in cell culture were evaluated. The first agent, 2-deoxy-D-glucose (2-DG), competitively inhibits glucose uptake through cell surface glucose transporters (GLUT) and subsequent phosphorylation by hexokinases; the second agent, α-cyano-4-hydroxycinnamate (CHC), is a suicide inhibitor of monocarboxylate transporter (MCT) that prevents the secretion of lactic acid from cancer cells (FIG. 25a) (Sonveaux, et. al., 2008). In vitro cell culture experiments show that both agents significantly decreased glucose uptake and lactate secretion in A549 lung cancer cells (FIG. 25b). Moreover, 2-DG and CHC treatment retarded the acidification of cell culture medium (ΔpH are 0.15 vs. 0.10 for 2-DG, 0.19 vs. 0.10 for CHC, FIG. 25c).

For in vivo tumor imaging studies, UPS$_e$ nanoprobes (10 mg/kg) were injected intravenously in mice bearing subcutaneous A549 lung cancer xenografts (n=4 for each group). For the control groups, 2-DG (250 mg/kg) or CHC (250 mg/kg) was injected 12 h before the UPS$_e$ administration. Near IR imaging ($\lambda_{ex}$=675 nm, $\lambda_{em}$=710 nm) of tumor-bearing mice showed steady increase of fluorescence signals in tumors over 24 h after UPS$_e$ injection with background suppression in normal tissues (FIGS. 25d, e). The NIR fluorescence intensity in the tumor increased 10.9±1.7 fold from 5 min to 24 h (FIGS. 25d, e). In contrast, pretreatment with metabolic inhibitors resulted in significant signal decrease in tumors compared to UPS$_e$ alone (e.g. 2.3±0.7 fold for 2-DG (P=0.004), and 3.2±0.6 fold for CHC (P=0.007)).

Figure 26:
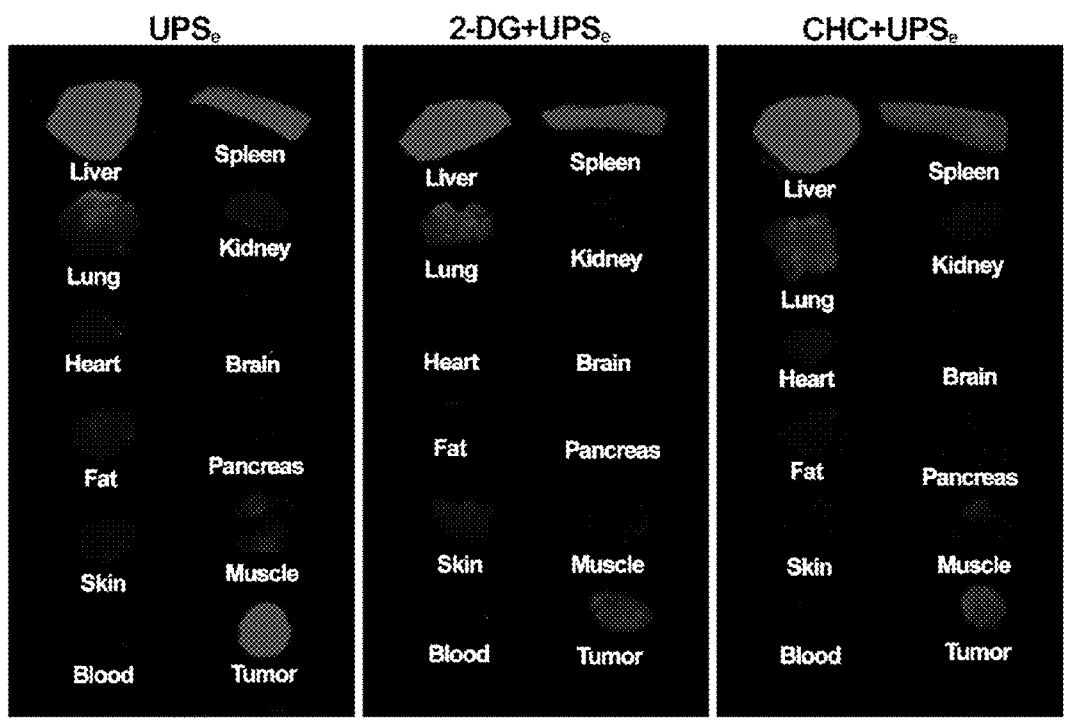
FIG. 26 Representative ex vivo fluorescence images of dissected tumors and organs of A549 tumor-bearing mice sacrificed at 24 h post-injection. A549 tumor-bearing mice were intravenously administered with $UPS_e$ nanoprobes at a dose of 10 mg/kg and, 24 h later, organs were collected for NIR imaging. In the control groups, 2-DG (250 mg/kg) or CHC (250 mg/kg) was injected 12 h before the $UPS_e$ nanoprobe administration.

After 24 h, mice were sacrificed and the excised organs were imaged. Quantification of ex vivo images showed that the T/N ratio (fluorescence intensity of tumors over normal muscles) of UPS$_e$ alone was 12.9 (FIG. 25f). The fluorescence intensity in brain, heart, skin, muscle, fat, and pancreas were comparable to muscle. The 2-DG and CHC control groups showed similar low fluorescence intensities in the ex vivo organs (FIG. 26), while the tumor intensities were 4- and 3-fold lower than that from mice with UPS$_e$ injection alone, respectively, consistent with the in vivo imaging results (FIG. 25e). These data strongly support the hypothesis that UPS$_e$ nanoprobes can specifically detect acidic tumor pH$_e$, and that the probes can sense metabolic alterations within 24 h after initiating therapy.

Figure 27:
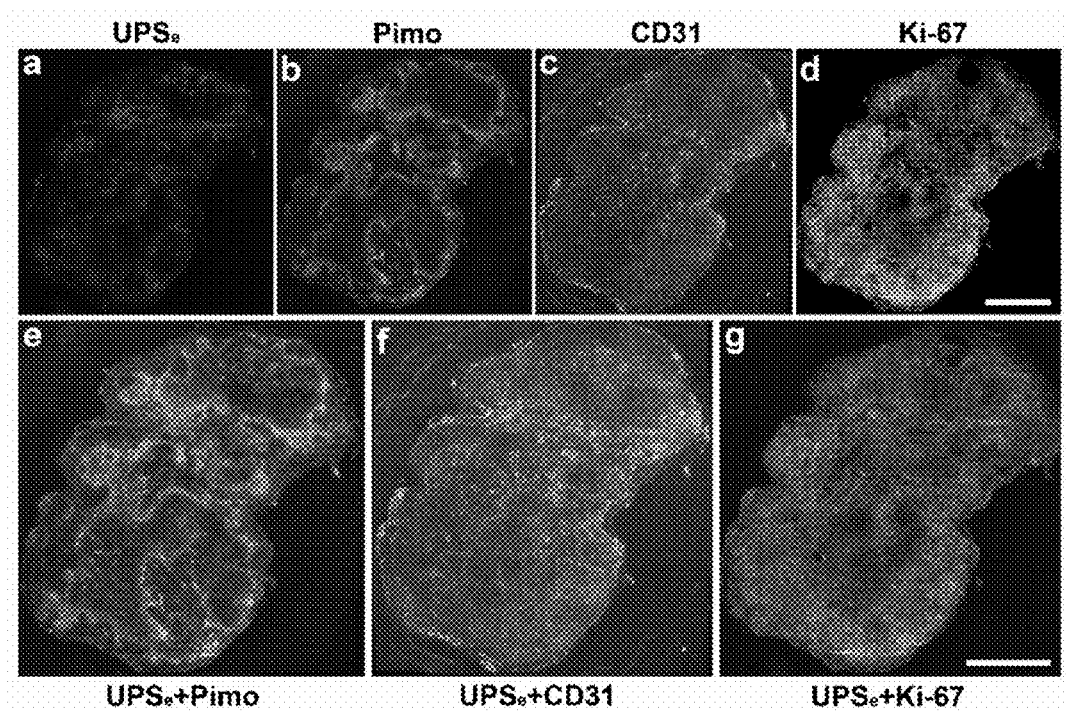
FIGS. 27A-G Representative correlation of UPS$_e$ nanoprobe images with histologically stained whole mount cryosections. Top (from left to right), 27A UPS$_e$ nanoprobe signals, 27B pimonidazole for hypoxia staining, 27C tumor vasculature stained with CD31 antibody, 27D Ki-67 for cell proliferation staining. Bottom, merged images (from left to right), 27E UPS$_e$ nanoprobe (red) and pimonidazole (green); 27F UPS$_e$ nanoprobe (red) and CD31 (green); 27G UPS$_e$ nanoprobe (red) and Ki-67 (green). All images were obtained from the adjacent sections at ×200 magnification. Scale bar is 2 mm.

Immunostaining of the whole-mount tumor sections (FIG. 25g) showed a good correlation between the nanoprobe signals (red) with hypoxia stain by pimonidazole, which agrees with previous report that hypoxic regions of the tumors are more acidic (Gatenby & Gillies, 2004). Interestingly, the nanoprobe activation profile did not correlate with tumor vascular density (CD31 stain), which was high at the periphery of the tumors (FIG. 27).

Figure 28:
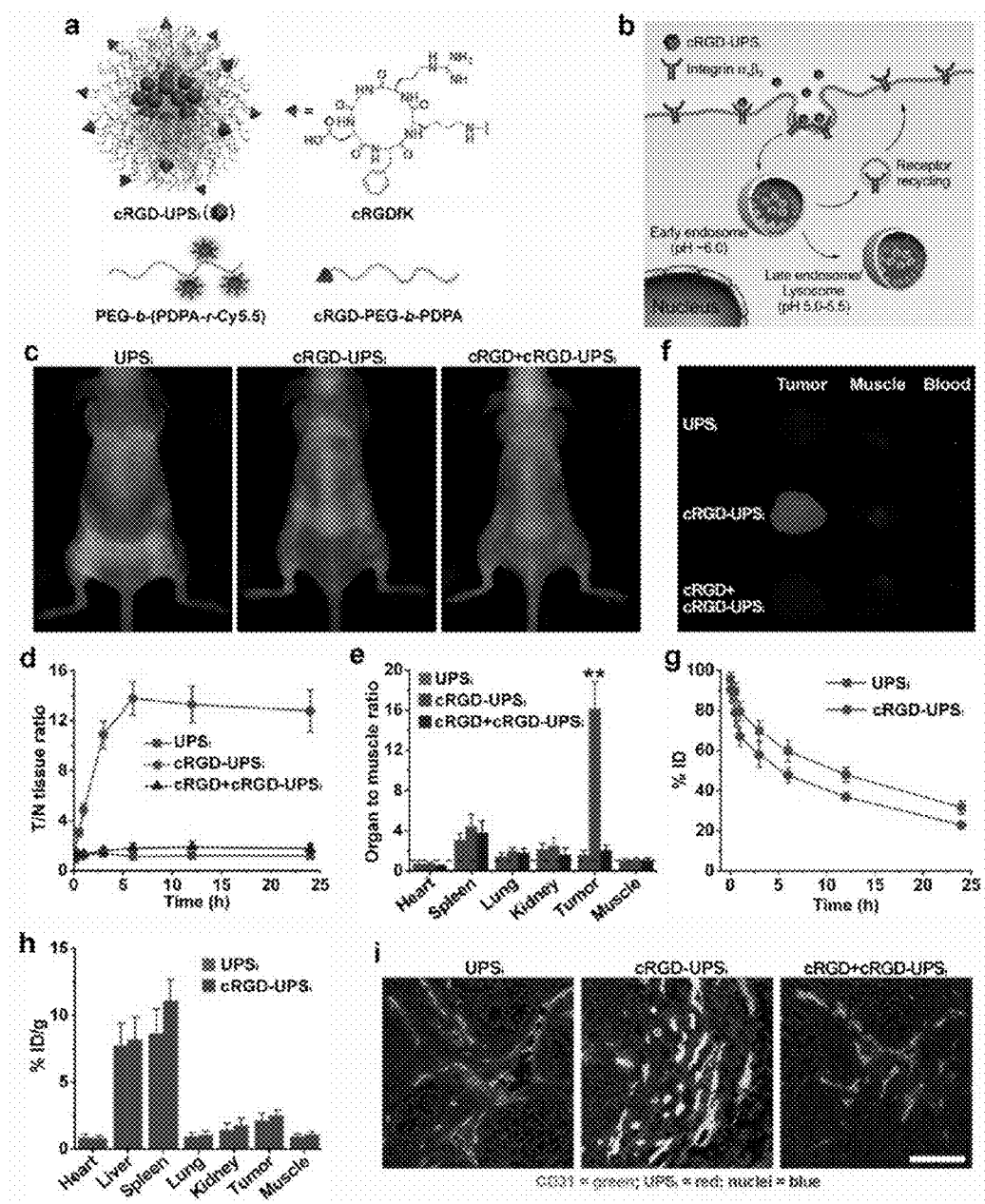
FIGS. 28A-I cRGD-UPS, nanoprobes can specifically image angiogenic tumor vasculature. 28A Design of cRGD-UPS, nanoprobe. 28B Schematic of internalization and activation of cRGD-UPS, nanoprobes after αvβ3-mediated endocytosis in tumor endothelial cells. The nanoprobes are accumulated in the endosomes or lysosomes, where the acidic pH activates the nanoprobes. 28C Superimposed fluorescent images of A549 tumor-bearing mice at 6 h post-injection of cRGD-UPS, or UPS, nanoprobe (10 mg/kg). In the competition group, a blocking dose of cRGD peptide (25 mg/kg) was injected 30 min before cRGD-UPSi administration. Cy5.5 (Red) and autofluorescence (Green) are separately shown in the composite images. 28D T/N ratio after injection of nanoprobes as a function of time. Data are presented as mean±s.d. (n=4). 28E Organ to muscle ratios of fluorescence intensity at 6 h post-injection of nanoprobe. Data are presented as mean±s.d. (n=4). P<0.01, compared with tumors treated with UPS, or cRGD blocking groups. 28F Representative images of ex vivo tumors, muscles, and blood at 6 h post-injection of nanoprobes. 28G Plasma concentration versus time curves (n=4) for cRGD-UPS$_i$ and UPS$_i$ nanoprobes. 28H Biodistribution profiles (n=4) of cRGD-UPS$_i$ and UPS$_i$ nanoprobes 6 h after intravenous injection. 28I** Correlation of nanoprobe activation with tumor vasculature (anti-CD31). The co-localization between nanoprobe and tumor vasculature is indicated by the yellow color in the merged images (green: blood vessels; red: nanoprobes; blue: nuclei. Scale bar=100 µm).
Figure 29:
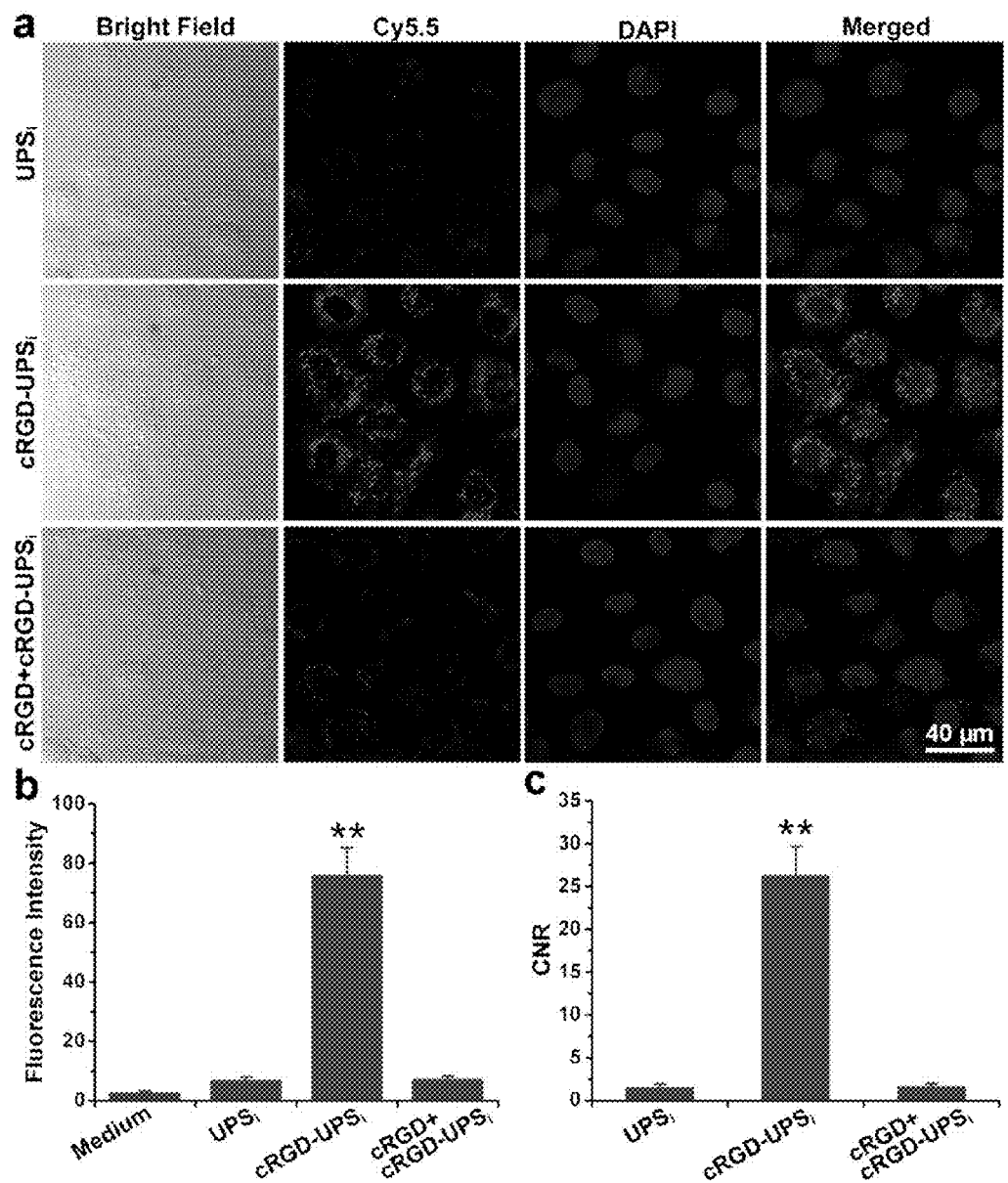
FIGS. 29A-C Fluorescence activation of cRGD-UPS, nanoprobes in HUVEC cells. 29A Representative confocal images of "activated" cRGD-UPS, nanoprobes in HUVEC cells. UPS, and free cRGD block were used as controls. 29B Fluorescence intensity of HUVEC cells treated with different nanoprobes (N>100 for each group) and cell culture medium. 29C Contrast to noise ratio (CNR) of HUVEC cells treated with cRGD-UPS, over the UPS, and free cRGD+ cRGD-UPS$_i$ controls. **P<0.01, compared with other two groups.
Figure 30:
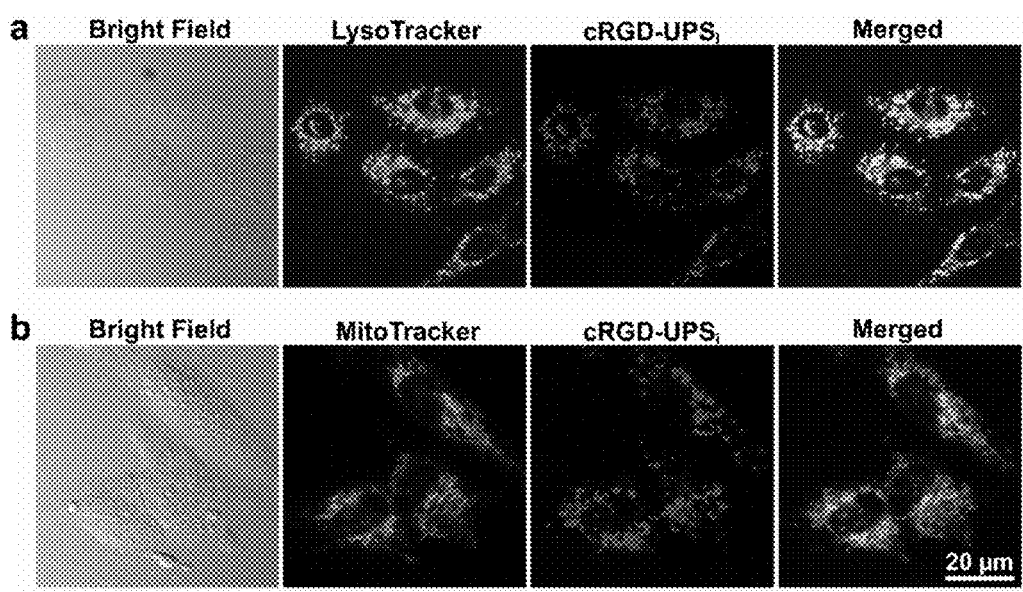
FIGS. 30A-B Subcellular activation and distribution of cRGD-UPS, nanoprobes in HUVECs. HUVECs were incubated in the presence of cRGD-UPS$_i$ for 3 h. Confocal images of cells stained with either 30A LysoTracker DND-26 (green) or 30B MitoTracker Green FM (green) were captured and the pictures were superimposed. Red color represents the nanoprobe signals. Yellow color is an indication for colocalization of nanoprobes with lysosomes.

Moreover, the nanoprobe activation map extended beyond the region of hypoxia detected by pimonidazole, likely because low pH, particularly <6.8, significantly reduces pimonidazole binding to cancer cells (Kleiter, et. al., 2006).

b. Specific Imaging of Angiogenic Tumor Vasculature by cRGD-UPS$_i$ Nanoprobes cRGD-encoded UPS$_i$ nanoprobes (cRGD-UPS$_i$ FIG. 28a) were constructed to specifically image angiogenic tumor vasculature through non-linear signal amplification of $\alpha_v\beta_3$ integrins, an established angiogenic biomarker of tumor endothelial cells. cRGD peptides bind to $\alpha_v\beta_3$ integrins, resulting in receptor-mediated endocytosis of cRGD-UPS$_i$ into the acidic endocytic organelles for fluorescence activation (FIG. 28b). Human umbilical vein endothelial cells (HUVECs) were treated with cRGD-UPS$_i$, cRGD-free UPS$_i$ (UPS$_i$), and a 50-fold molar excess of free cRGD peptide followed by cRGD-UPS$_i$ nanoprobes to demonstrate the proof of concept. Because the nanoprobes were 'silent' in cell culture medium, directly measurement of the kinetics of nanoprobe internalization and activation without removing the medium was possible. Thirty minutes after cRGD-UPS$_i$ incubation, punctate fluorescence activation was observed inside the HUVEC cells. At 3 h, an 11-fold fluorescence increase in cRGD-UPS$_i$ group was observed over the UPS$_i$ and free cRGD control groups (FIG. 29). Almost all the fluorescent punctates in cells treated with cRGD-UPS$_i$ colocalized with LysoTracker dyes (FIG. 30), demonstrating that cRGD-UPS$_i$ nanoprobes became activated in the late endosomes and lysosomes.

Figure 31:
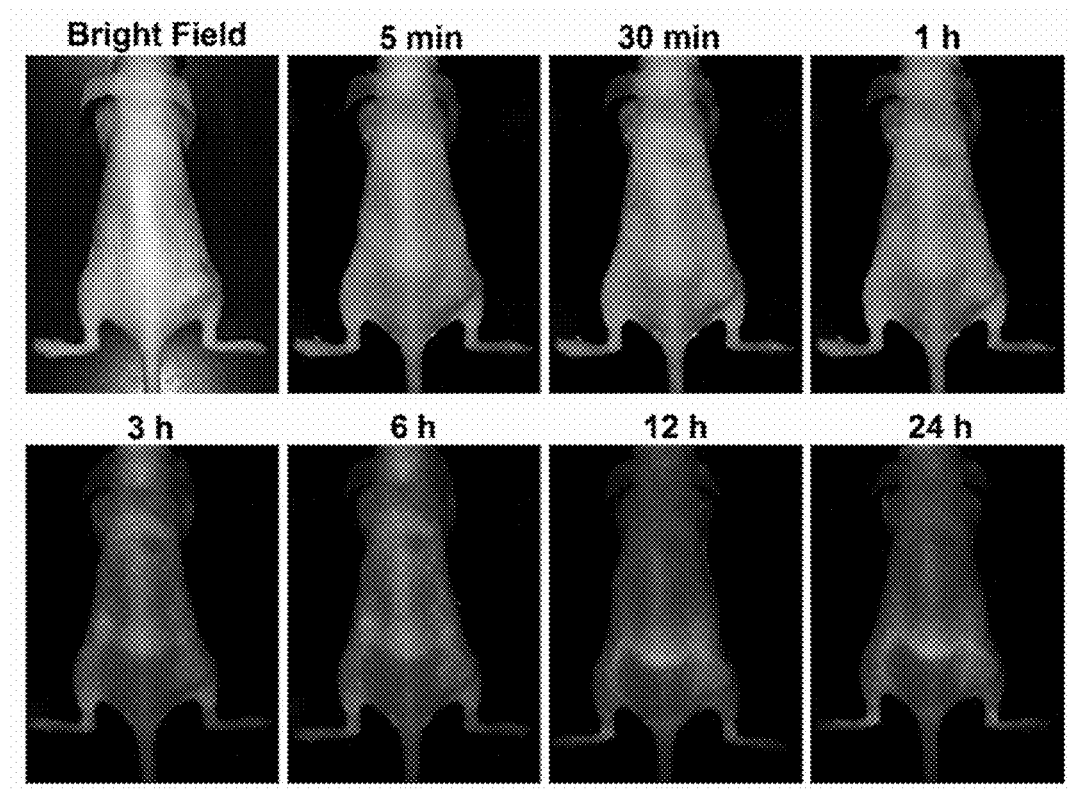
FIG. 31 Specific signal amplification of cRGD-UPS, nanoprobes for A549 tumor imaging in vivo. Athymic (nu/nu) mice bearing A549 tumors were injected with a dosage of 10 mg/kg nanoprobe and, NIR fluorescence images at selected time points were captured. The mice autofluorescence is color coded green while the unmixed nanoprobe signal is coded red.
Figure 32:
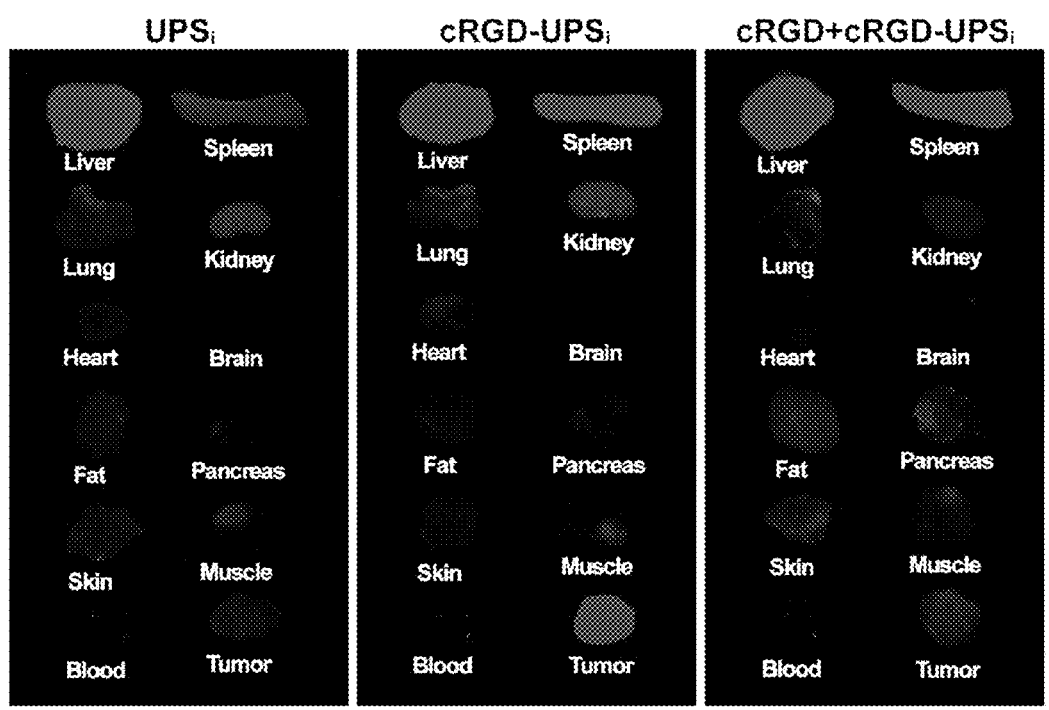
FIG. 32 Representative ex vivo fluorescence images of dissected tumors and organs of A549 tumor-bearing mice sacrificed at 6 h post-injection. A549 tumor-bearing mice were intravenously injected with cRGD-UPS, or UPS, at a dose of 10 mg/kg and, 6 h later, tumors and organs were collected for NIR imaging. In the competition group, a blocking dose of cRGDfK peptide (25 mg/kg) was injected 30 min prior to the cRGD-UPS, nanoprobe administration.
Figure 33:
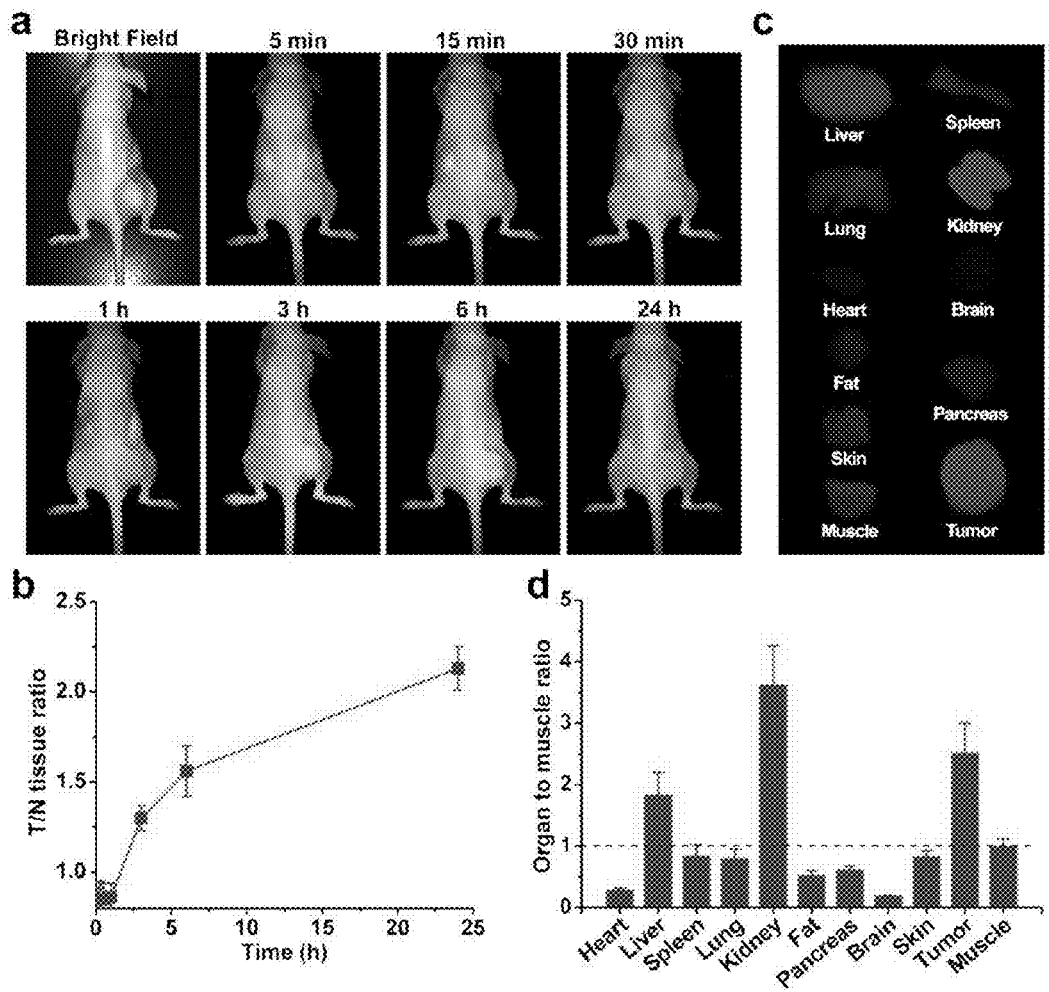
FIG. 33A-D IRDye® 800CW-cRGD Optical Probe for A549 tumor imaging in vivo and ex vivo. 33A Athymic (nu/nu) mice bearing A549 tumors were injected with a dosage of 2 nmol/mouse IRDye® 800CW RGD probe and, NIR fluorescence images at selected time-points were captured. The mice autofluorescence is color coded green while the unmixed probe signal is coded red. 33B In vivo time-dependent average fluorescence intensity ratio between tumor and normal tissue after the probe injection. 33C At 24 h post-injection, mice were sacrificed and collected organs were visualized. 33D Organ to muscle ratios for IRDye® 800CW RGD probe in A549 tumor-bearing mice. The fluorescent signal of organs was normalized to the fluorescent signal in the muscle. Data are presented as mean±s.d. (n=3).

For in vivo tumor imaging studies, cRGD-UPS$_i$ or UPS$_i$ (10 mg/kg) were injected intravenously into A549 tumor-bearing mice (n=4 for each group). As a control, a blocking dose of cRGD peptide (25 mg/kg) was injected 30 min before the cRGD-UPS$_i$ nanoprobe administration. At 30 min post-injection, the cRGD-UPS$_i$ group produced significantly higher fluorescence signals in tumors over the two control groups. The NIR fluorescence intensity in the tumor increased 12.3±1.8 fold from 5 min to 6 h post-injection (FIG. 28c). Compared to cRGD-UPS$_i$, UPS$_i$ and free cRGD pretreatment controls had minimal fluorescence increase in the tumor over 6 h span (1.4±0.2 fold, P=0.002 and 1.8±0.4 fold, P=0.003, respectively). FIG. 28d shows the in vivo kinetics of fluorescence activation of nanoprobes in tumors versus normal tissues. The T/N ratio of cRGD-UPS$_i$ increased steadily and reached a peak value of 13.8±1.4 at 6 h (FIG. 31), whereas the UPS$_i$ reached its peak value of 1.4±0.2 at 3 h. Ex vivo imaging showed that T/N ratio of cRGD-UPS$_i$ was 16.1, while UPS$_i$ controls produced <2-fold signal enhancement (FIGS. 28e, f and FIG. 32) despite comparable tumor accumulation percentages (e.g. 2.49±0.44% vs. 2.11±0.59% ID/g at 6 h post-injection, respectively, FIG. 28h). The strategy of signal amplification by the cRGD-UPS$_i$ nanoprobes in angiogenic tumor vasculature was more markedly illustrated when compared to a commercial 'always ON' cRGD-NIR Dye 800CW conjugate, where a maximum of 2-fold T/N ratio was observed within a 24 h span with strong background fluorescence signals (FIG. 33).

Figure 34:
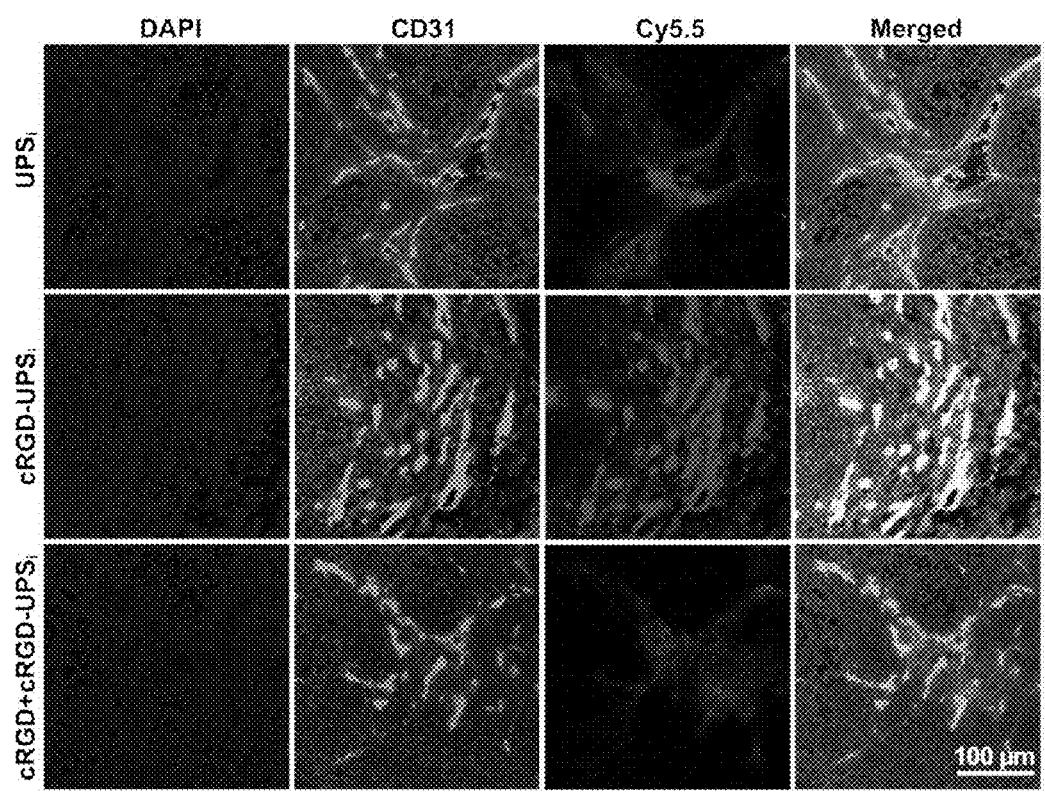
FIG. 34 Histopathological analysis of cRGD-UPS, nanoprobes homing and activation in tumor vasculature. Tumor tissue sections from UPS, group and cRGD-UPS, group (6 h) were subjected to CD31 staining. Tumor vasculature staining (anti-CD31) is shown in green. The nanoprobe signal is shown in red. The cell nucleus is shown in blue. Scale bar is 100 µm.
Figure 35:
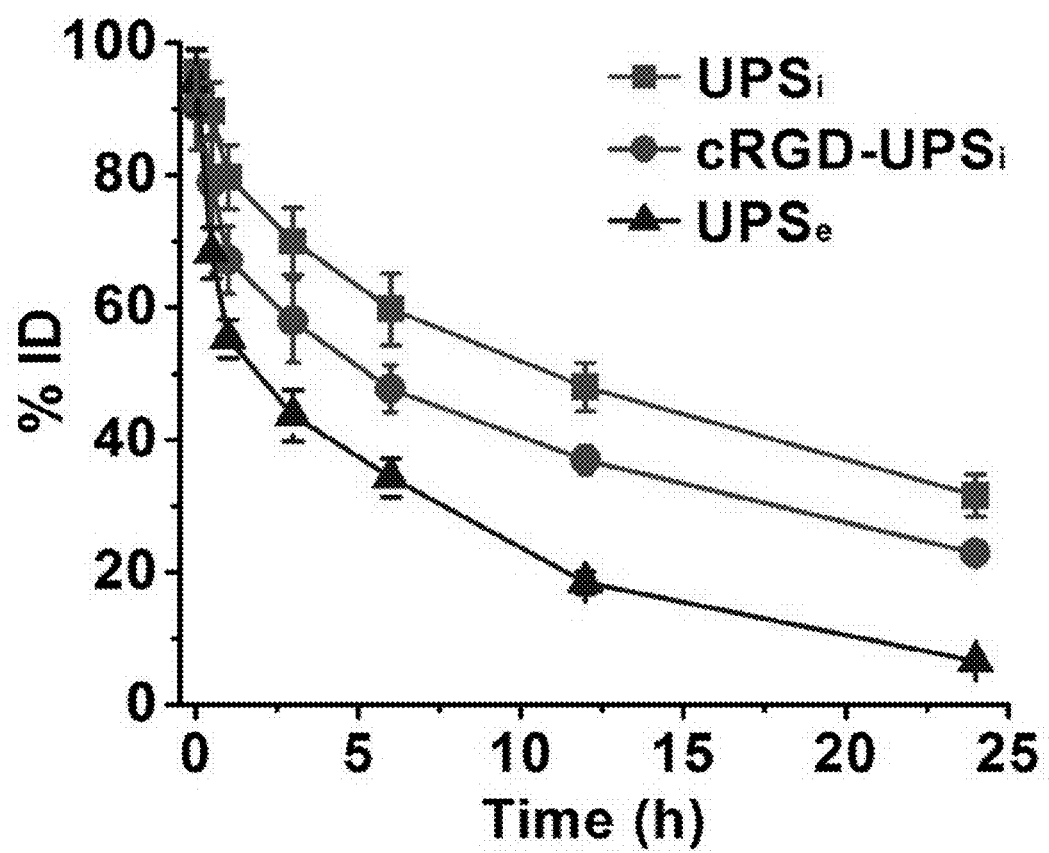
FIG. 35 In vivo pharmacokinetic studies of $^3$H-labeled UPS nanoprobes in A549 tumor-bearing mice. Plasma concentration versus time curves of UPS$_e$, cRGD-UPS$_i$ and UPS, nanoprobes (n=4-5 per group) were obtained.

Immunostaining of tumor sections (FIG. 28i and FIG. 34) was performed to verify the locations of cRGD-UPS$_i$ activation. Tumor vessels were stained with Alexa 488-labeled anti-CD31. For cRGD-UPS$_i$, the majority of nanoprobe activation was found to co-localize with tumor vasculature (light color in FIG. 28i). In contrast, low levels of nanoprobe activation were observed in the UPS$_i$ and free cRGD blocking control groups. In these tumor sections, sporadic spots of nanoprobe activation were found outside the tumor vasculature, suggesting that non-vascular cells may also pick up a small population of nanoprobes through $\alpha_v\beta_3$-independent pathways.

c. Evaluation of Pharmacokinetics, Biodistribution and Safety of UPS$_e$ and UPS$_i$ Nanoprobes To characterize the pharmacokinetic and biodistribution of UPS$_e$/UPS$_i$ nanoprobes, $^3$H-labeled nanoprobes were synthesized through acetylation (—COCT$_3$) of the free amino groups in the corresponding copolymers (Table 4). $^3$H-labeled UPS$_e$, cRGD-UPS$_i$ and UPS$_i$ nanoprobes were injected at the same dose (10 mg/kg, or 2.0 mCi/kg) for imaging studies (n=5 for each group). For all three compositions, plasma concentration-time curves showed a two-phase behavior over 24 h (FIG. 28g and FIG. 35). The $\alpha$-phase half-lives ($t_{1/2,\alpha}$) were 1.0±0.2, 2.3±0.5 and 4.3±0.7 h for UPS$_e$, cRGD-UPS$_i$ and UPS$_i$ respectively. The $\beta$-phase half-lives ($t_{1/2,\alpha}$ were 7.5±0.3, 17.0±1.8 and 19.6±2.1 h for UPS$_e$, cRGD-UPS$_i$ and UPS$_i$ respectively. For UPS$_i$ cRGD surface functionalization resulted in decreased blood half-lives, consistent with other cRGD-encoded nanoparticle systems (Huang, et. al., 2010).

Biodistribution studies show that tumor uptakes (2-3% ID/g tissue) of UPS$_e$/UPS$_i$ nanoparticles were higher than most normal tissues (heart, lung, kidney, and muscle, FIG. 28h and Tables 5-7). Among the three nanoprobe compositions, statistically significant differences in tumor distribution were not observed (e.g. 2.4±0.7%, 3.4±1.1%, 3.0±1.3% ID/g for UPS$_e$, cRGD-UPS$_i$ and UPS$_i$ at 24 h post-injection, respectively. P>0.05 for each paired comparisons). The RES system (i.e. liver and spleen) was responsible for the uptake of the majority of nanoprobes (20-50% ID/g). When tumor and blood NIR fluorescence intensities were normalized over UPS concentrations from $^3$H-labelling experiments, over

TABLE 5

Biodistribution and Tissue Fluorescence of the UPS$_e$ nanoprobes (n = 4) at 24 h

| Organs | NIRF signal | % ID/g tissue | NIRF signal/(% ID/g) ratio[a] |
|---|---|---|---|
| Blood | 4 ± 1 | 6.62 ± 0.14 | 1 |
| Heart | 26 ± 11 | 0.54 ± 0.11 | 74 |
| Liver | 1071 ± 276 | 32.1 ± 2.82 | 52 |
| Spleen | 166 ± 50 | 19.9 ± 4.34 | 13 |
| Lung | 91 ± 25 | 1.57 ± 0.23 | 90 |
| Kidney | 60 ± 17 | 1.90 ± 0.21 | 49 |
| Tumor | 545 ± 88 | 2.42 ± 0.73 | 355 |
| Muscle | 42 ± 15 | 1.03 ± 0.21 | 64 |
| Pancreas | 9 ± 2 | 0.21 ± 0.06 | 63 |

[a]Tumor and organ NIRF signal/(% ID/g) ratios were normalized to blood.

TABLE 6

Biodistribution and tissue fluorescence of the UPS$_i$ nanoprobes (n = 4) at 6 & 24 h

| Organs | NIRF signal (6 h) | % ID/g tissue (6 h) | % ID/g tissue (24 h) | NIRF signal/(% ID/g) ratio[a] |
|---|---|---|---|---|
| Blood | 22 ± 5 | 59.1 ± 5.42 | 31.6 ± 3.18 | 1 |
| Heart | 27 ± 13 | 0.83 ± 0.28 | 1.02 ± 0.18 | 88 |
| Liver | 864 ± 189 | 7.71 ± 1.71 | 7.92 ± 1.78 | 299 |
| Spleen | 122 ± 28 | 8.63 ± 1.83 | 10.92 ± 2.13 | 37 |

TABLE 6-continued

Biodistribution and tissue fluorescence of the UPS$_i$ nanoprobes (n = 4) at 6 & 24 h

| Organs | NIRF signal (6 h) | % ID/g tissue (6 h) | % ID/g tissue (24 h) | NIRF signal/(% ID/g) ratio[a] |
|---|---|---|---|---|
| Lung | 56 ± 17 | 0.89 ± 0.35 | 2.18 ± 1.01 | 168 |
| Kidney | 84 ± 24 | 1.39 ± 0.56 | 2.57 ± 0.95 | 162 |
| Tumor | 62 ± 19 | 2.11 ± 0.59 | 3.04 ± 1.25 | 78 |
| Muscle | 40 ± 8 | 0.90 ± 0.22 | 1.44 ± 0.47 | 119 |

[a]Tumor and organ NIRF signal/(% ID/g) ratios were normalized to blood at 6 h.

TABLE 7

Biodistribution and tissue fluorescence of the cRGD-UPS$_i$ nanoprobes (n = 4) at 6 and 24 h

| Organs | NIRF signal (6 h) | % ID/g tissue (6 h) | % ID/g tissue (24 h) | NIRF signal/(% ID/g) ratio[a] |
|---|---|---|---|---|
| Blood | 24 ± 7 | 47.7 ± 3.57 | 22.9 ± 1.39 | 1 |
| Heart | 32 ± 8 | 0.80 ± 0.19 | 1.04 ± 0.33 | 80 |
| Liver | 1049 ± 302 | 8.16 ± 1.70 | 10.07 ± 2.74 | 257 |
| Spleen | 213 ± 61 | 11.1 ± 1.60 | 16.12 ± 3.07 | 38 |
| Lung | 94 ± 19 | 1.02 ± 0.32 | 1.92 ± 0.77 | 184 |
| Kidney | 117 ± 43 | 1.74 ± 0.59 | 2.00 ± 0.31 | 134 |
| Tumor | 783 ± 136 | 2.49 ± 0.44 | 3.42 ± 1.08 | 628 |
| Muscle | 49 ± 12 | 1.07 ± 0.24 | 1.32 ± 0.51 | 91 |

[a]Tumor and organ NIRF signal/(% ID/g) ratios were normalized to blood at 6 h.

Figure 36:
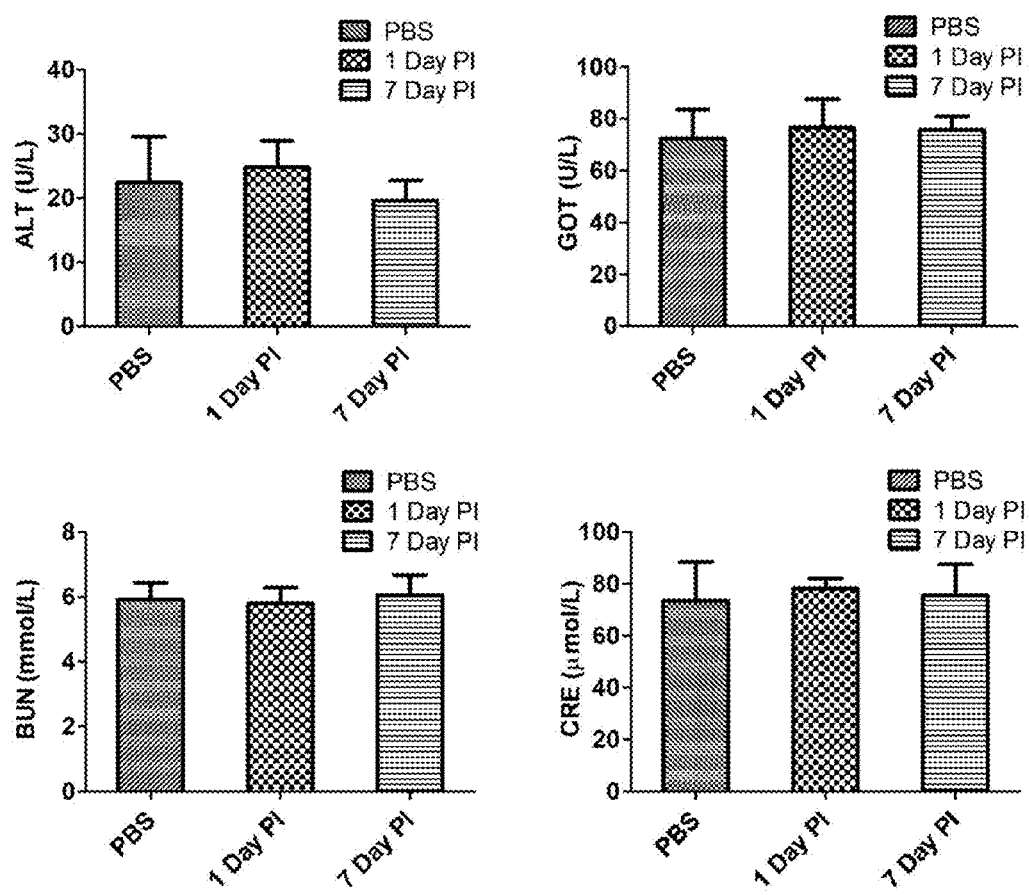
FIG. 36 Blood test parameters for athymic nude mice with intravenous administration of iUPS nanoprobes (10 mg/kg) or PBS. The results show no abnormalities in liver and kidney function over 7 day period following treatment. Data are presented as mean±s.d. (n=5). Abbreviations: ALT, aspartate transaminase; GOT, glutamic oxaloacetic transaminase; BUN, blood urea nitrogen; CRE, creatinine.
Figure 38A:
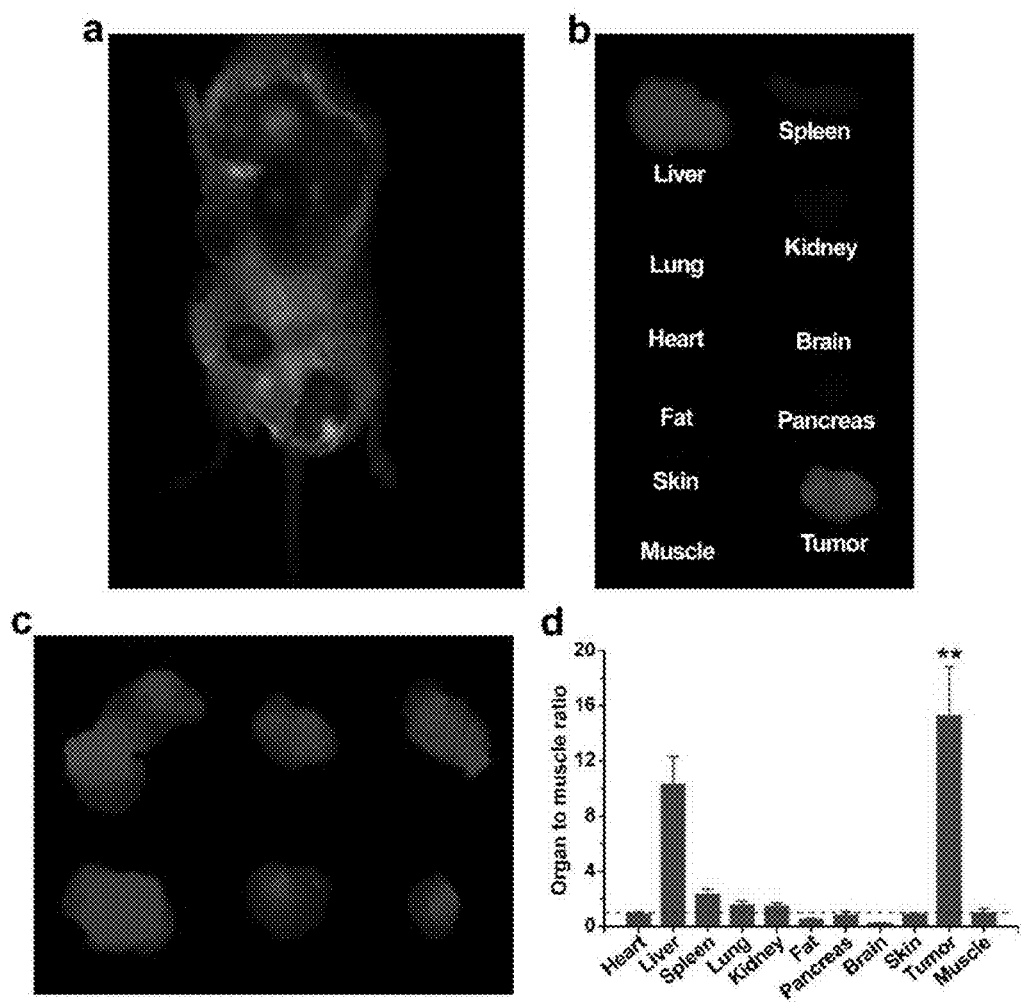
FIGS. 38Aa-d iUPS nanoprobes can clearly illuminate multifocal MMTV-PyMT transgenic mammary tumors with minimal background signals. 38Aa MMTV-PyMT transgenic mice bearing multiple mammary tumors were injected with a dosage of 10 mg/kg iUPS nanoprobe and, NIR fluorescence images at 24 h were captured using Maestro CRI imaging system. The mice autofluorescence is color-coded green while the unmixed nanoprobe signal is coded red. 38Ab At 24 h post-injection, mice were sacrificed and collected organs were visualized. 38Ac Fluorescence imaging of multiple mammary tumor nodules. 38Ad Organ to muscle ratios of fluorescence intensity at 24 h post-injection of nanoprobe. The fluorescent signal of organs was normalized to the fluorescent signal in muscle. Data are presented as mean±s.d. (n=4). **P<0.01, compared with other organs except liver.
Figure 38B:
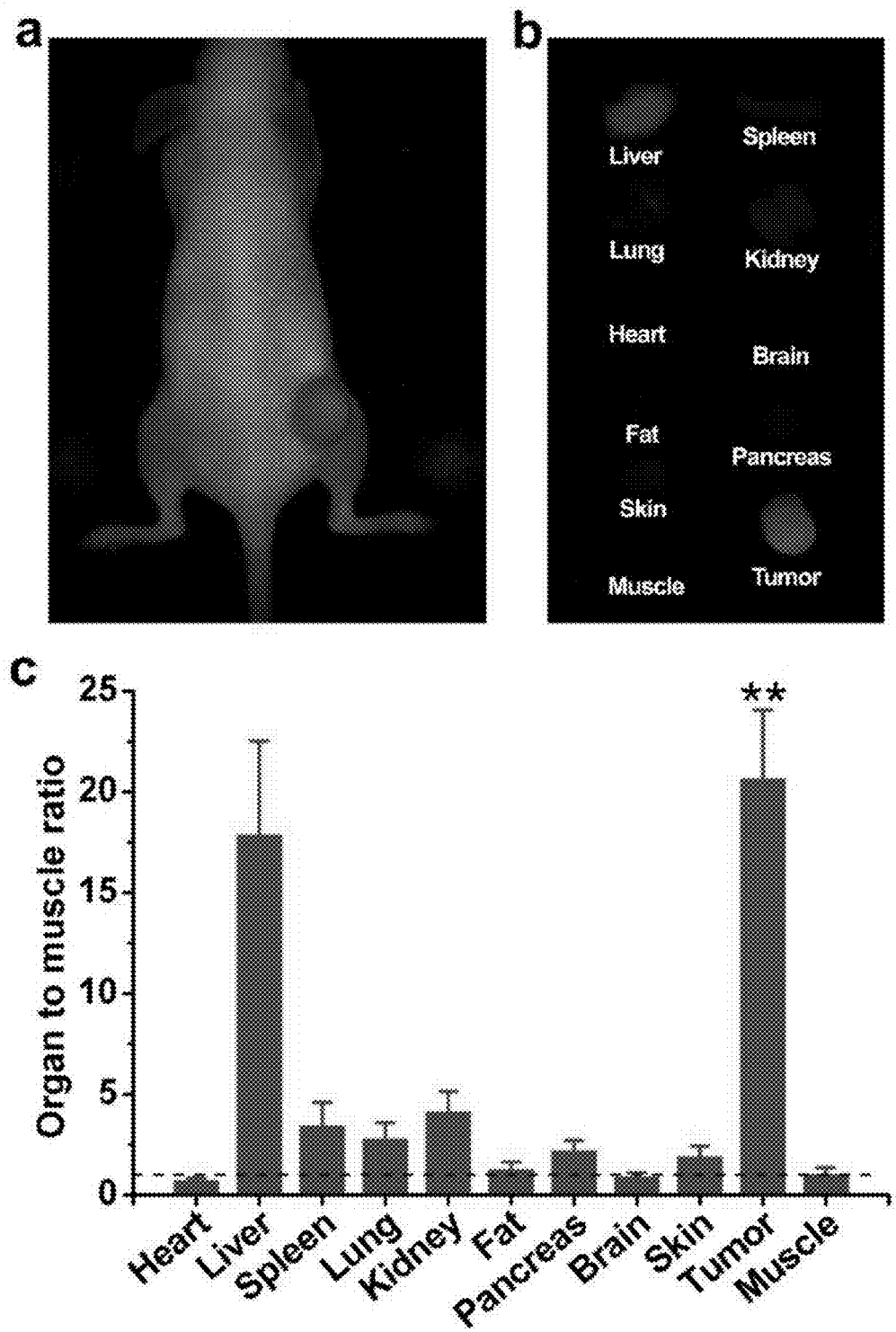
FIGS. 38Ba-c iUPS nanoprobes illuminate MDA-MB-231 tumor xenografts with high T/N ratio. 38Ba Nude mice bearing human MDA-MB-231 tumor xenografts were injected with a dosage of 10 mg/kg iUPS nanoprobe and, NIR fluorescence images at 24 h were captured using Maestro CRI imaging system. The mice autofluorescence is color coded green while the unmixed nanoprobe signal is coded red. 38Bb At 24 h post-injection, mice were sacrificed and collected organs were visualized. 38Bc Organ to muscle ratios of fluorescence intensity at 24 h post-injection of nanoprobe. The fluorescent signal of organs was normalized to the fluorescent signal in muscle. Data are presented as mean±s.d. (n=4). **P<0.01, compared with other organs except liver.
Figure 38C:
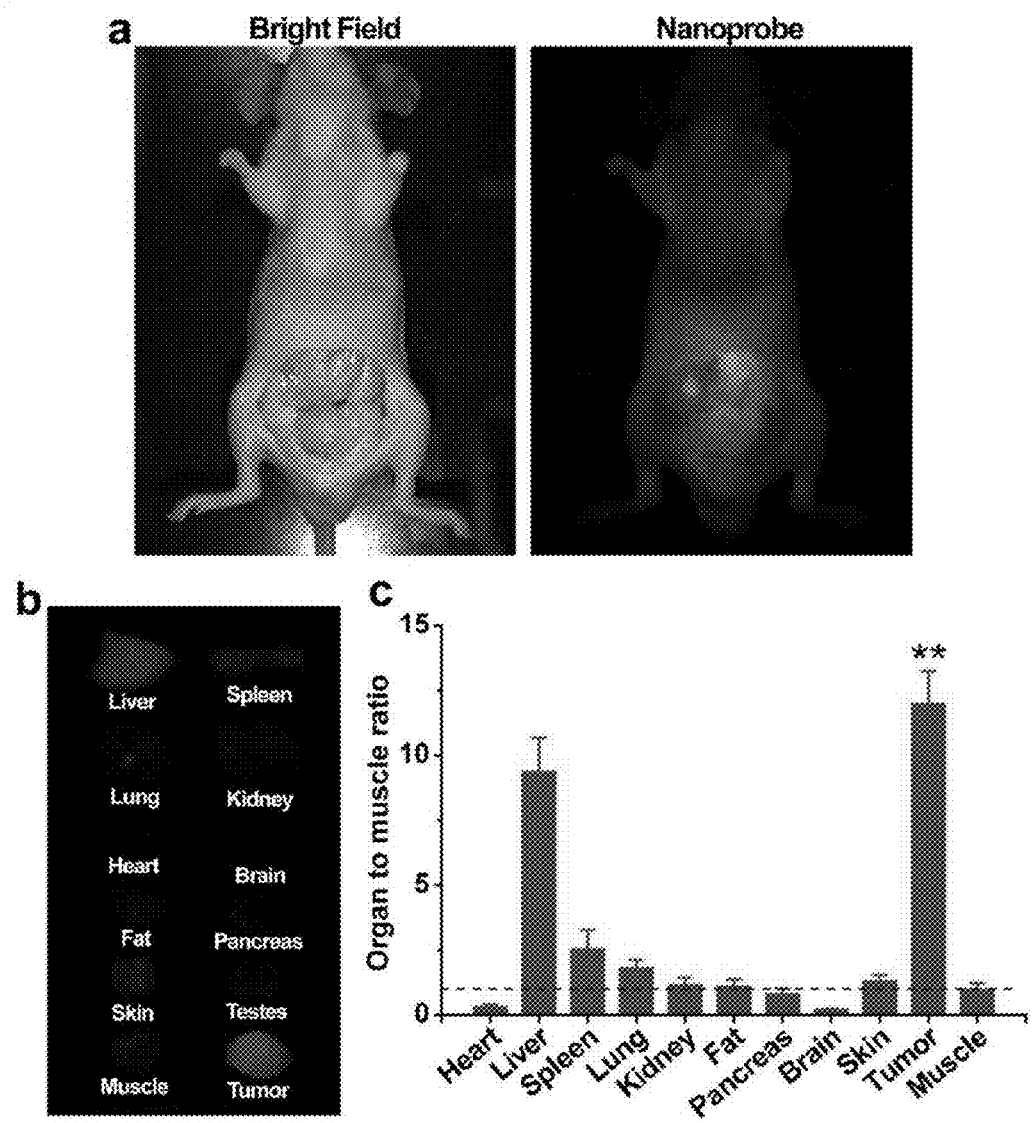
FIGS. 38Ca-c iUPS nanoprobes illuminate orthotopic PC-3 prostate carcinoma with high T/N contrast. 38Ca Nude mice bearing orthotopic PC-3 prostate tumors were injected with a dosage of 10 mg/kg iUPS nanoprobe and, NIR fluorescence images at 24 h were captured using Maestro CRI imaging system. The mice autofluorescence is color coded green while the unmixed nanoprobe signal is coded red. 38Cb At 24 h post-injection, mice were sacrificed and collected organs were visualized. 38Cc Organ to muscle ratios of fluorescence intensity at 24 h post-injection of nanoprobe. The fluorescent signal of organs was normalized to the fluorescent signal in muscle. Data are presented as mean±s.d. (n=4). **P<0.01, compared with other organs except liver.
Figure 38D:
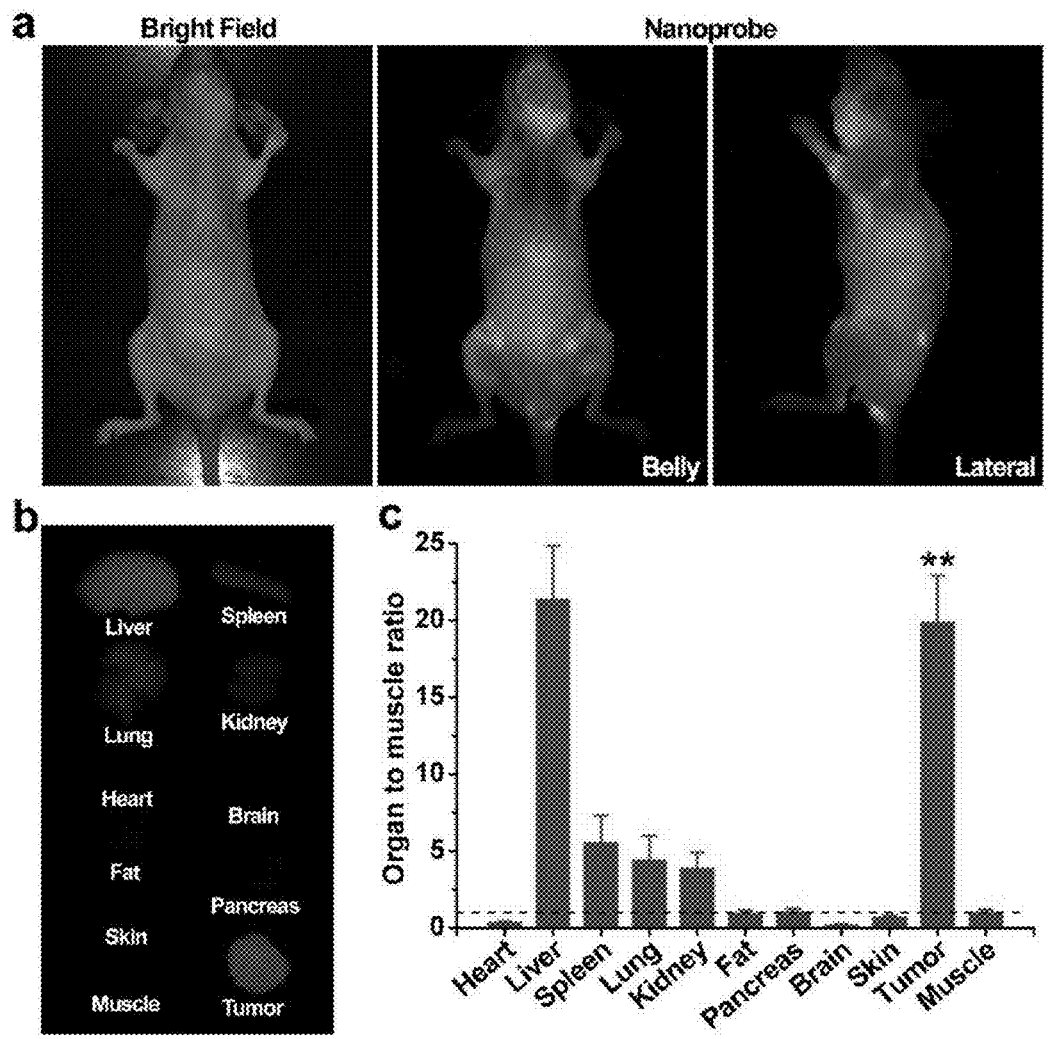
FIGS. 38Da-c iUPS nanoprobes illuminate orthotopic HCC4034 head-neck tumors with high imaging contrast. 38Da Nude mice bearing orthotopic HCC4034 head-neck tumors were injected with a dosage of 10 mg/kg iUPS nanoprobe and, NIR fluorescence images at 24 h were captured using Maestro CRI imaging system. The mice autofluorescence is color coded green while the unmixed nanoprobe signal is coded red. 38Db At 24 h post-injection, mice were sacrificed and collected organs were visualized. 38Dc Organ to muscle ratios of fluorescence intensity at 24 h post-injection of nanoprobe. The fluorescent signal of organs was normalized to the fluorescent signal in muscle. Data are presented as mean±s.d. (n=4). **P<0.01, compared with other organs except liver.
Figure 38E:
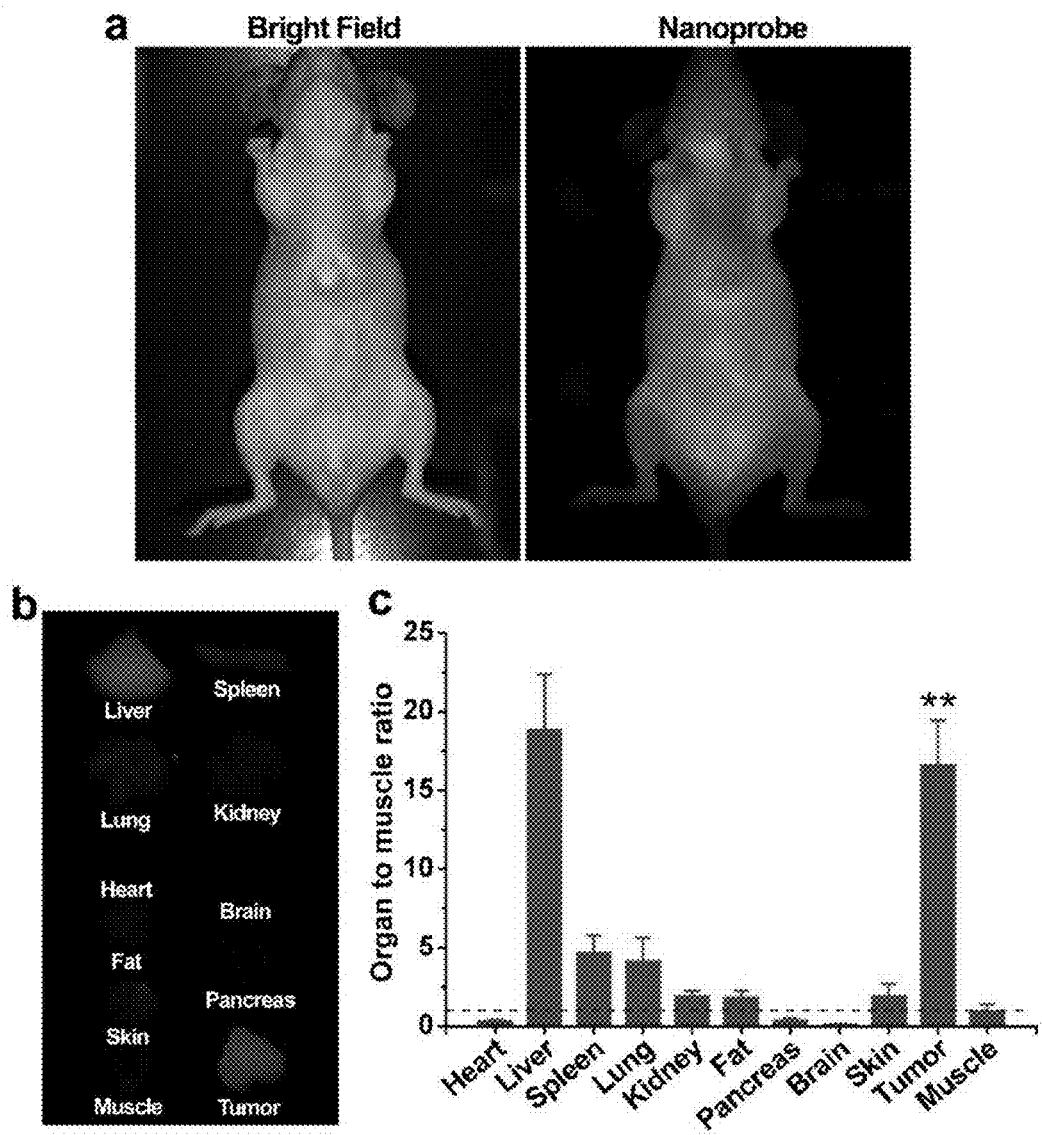
FIGS. 38Ea-c iUPS nanoprobes illuminate orthotopic HN5 head-neck tumors with high imaging contrast. 38Ea Nude mice bearing orthotopic HN5 head-neck carcinomas were injected with a dosage of 10 mg/kg iUPS nanoprobe and, NIR fluorescence images at 24 h were captured using Maestro CRI imaging system. The mice autofluorescence is color coded green while the unmixed nanoprobe signal is coded red. 38Eb At 24 h post-injection, mice were sacrificed and collected organs were visualized. 38Ec Organ to muscle ratios of fluorescence intensity at 24 h post-injection of nanoprobe. The fluorescent signal of organs was normalized to the fluorescent signal in muscle. Data are presented as mean±s.d. (n=4). **P<0.01, compared with other organs except liver.
Figure 38F:
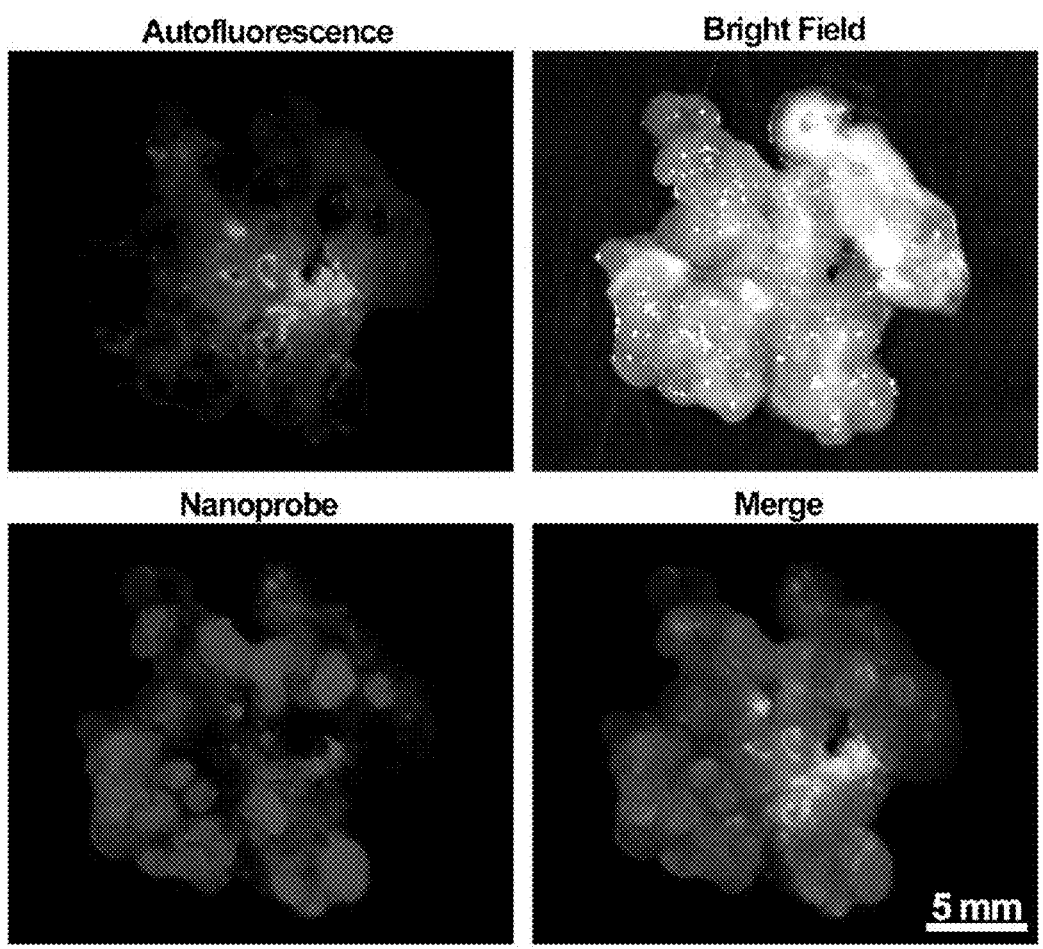
FIG. 38F iUPS nanoprobes illuminate many 3LL Lewis lung cancer foci with minimal background signals. Nude mice bearing orthotopic 3LL Lewis lung cancers were injected with a dosage of 10 mg/kg cRGD-UPS$_e$ nanoprobe and, NIR fluorescence images of excised lungs at 24 h were captured using Maestro CRI imaging system. The autofluorescence is color coded green while the unmixed nanoprobe signal is coded red. Scale bar is 5 mm. High resolution NIR images of the multiple tumor nodules (~1 mm) were visualized.
Figure 38G:
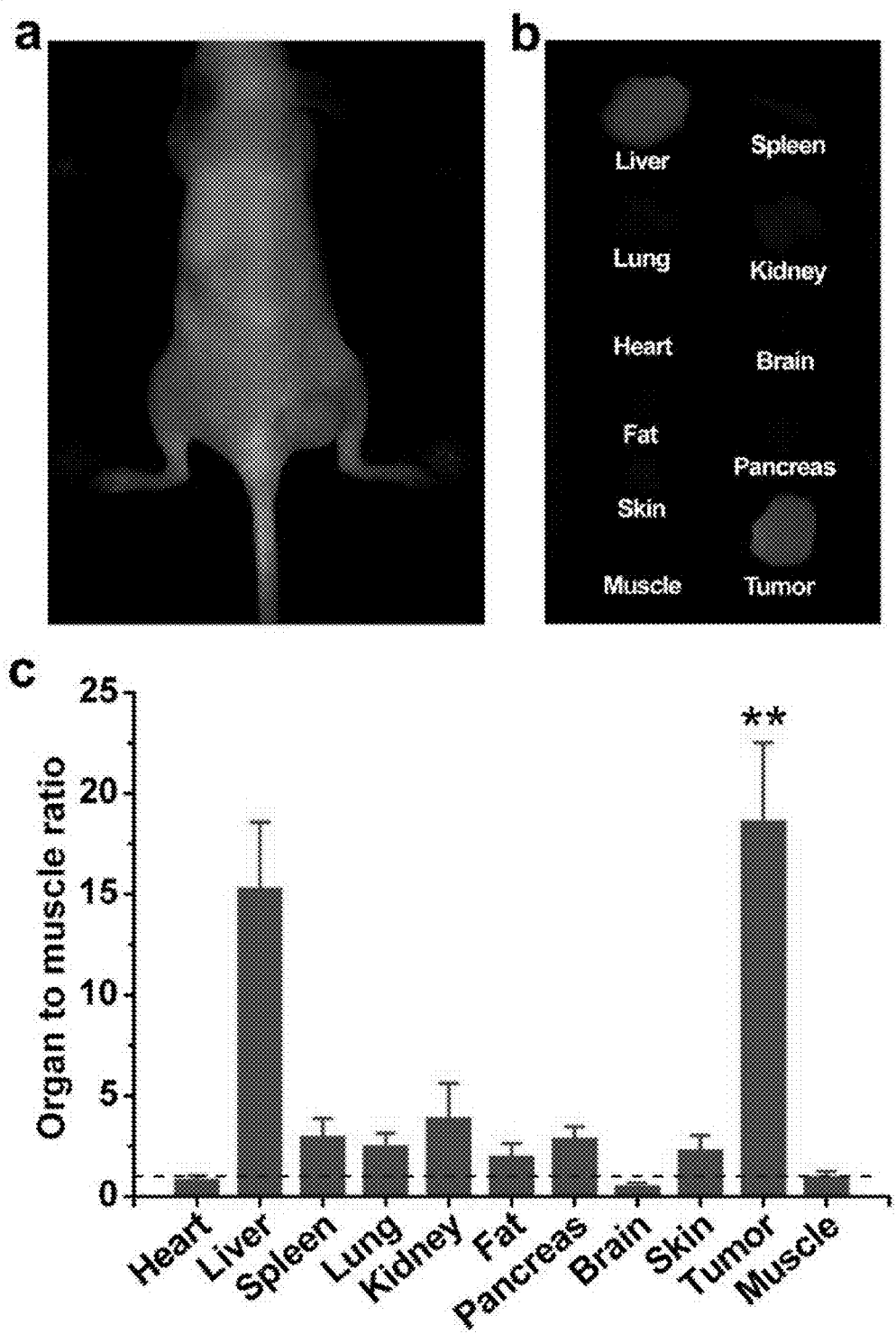
FIGS. 38Ga-c iUPS nanoprobes illuminate A549 lung cancer xenografts with high imaging contrast. 38Ga Nude mice bearing human A549 lung tumors were injected with a dosage of 10 mg/kg iUPS nanoprobe and, NIR fluorescence images at 24 h were captured using Maestro CRI imaging system. The mice autofluorescence is color coded green while the unmixed nanoprobe signal is coded red. 38Gb At 24 h post-injection, mice were sacrificed and collected organs were visualized. 38Gc Organ to muscle ratios of fluorescence intensity at 24 h post-injection of nanoprobe. The fluorescent signal of organs was normalized to the fluorescent signal in muscle. Data are presented as mean±s.d. (n=4). **P<0.01, compared with other organs except liver.
Figure 38H:
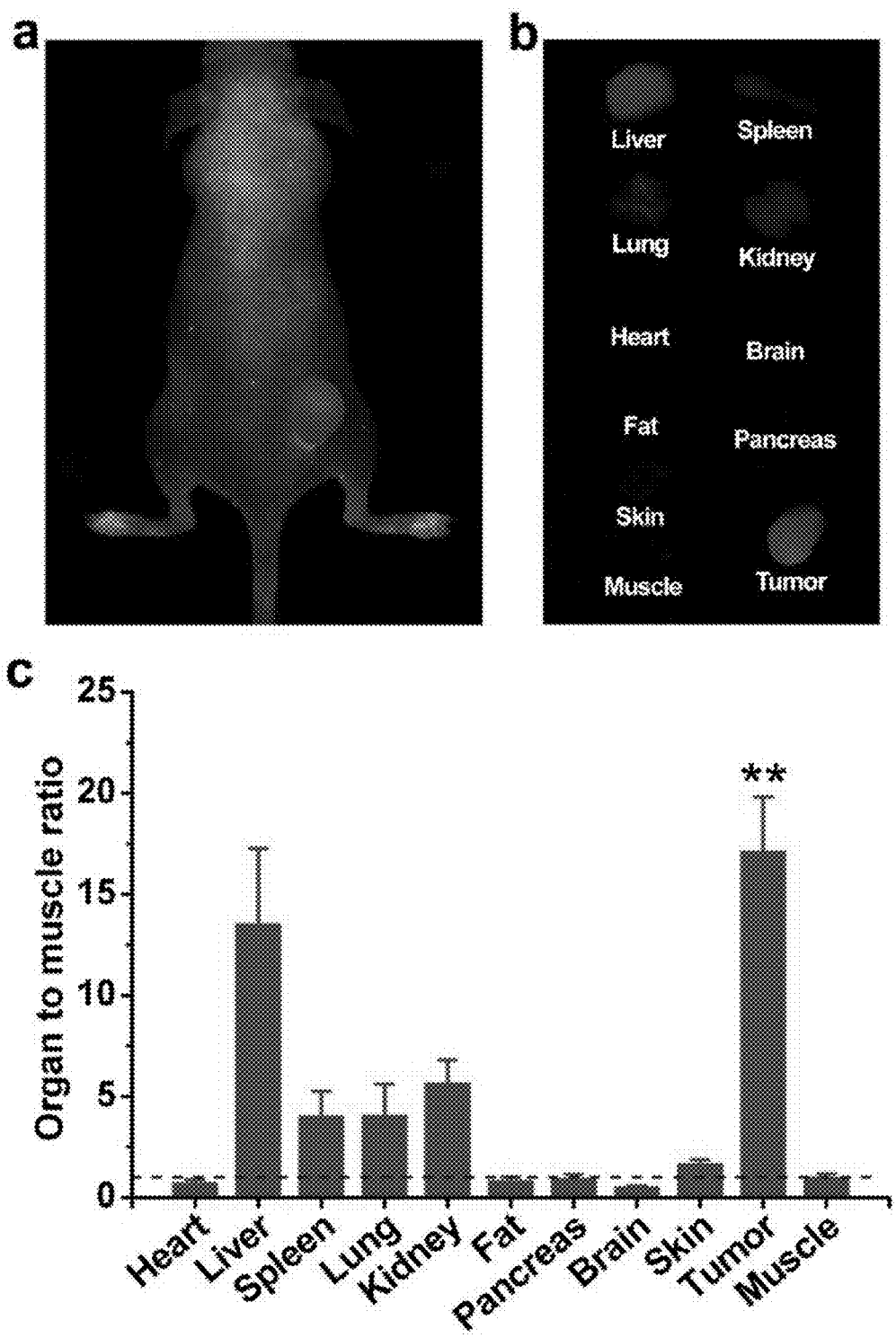
FIGS. 38Ha-c iUPS nanoprobes illuminate SF-188 brain cancer xenografts with high imaging contrast. 38Ha Nude mice bearing human SF-188 gliomas were injected with a dosage of 10 mg/kg iUPS nanoprobe and, NIR fluorescence images at 24 h were captured using Maestro CRI imaging system. The mice autofluorescence is color coded green while the unmixed nanoprobe signal is coded red. 38Hb At 24 h post-injection, mice were sacrificed and collected organs were visualized. 38Hc Organ to muscle ratios of fluorescence intensity at 24 h post-injection of nanoprobe. The fluorescent signal of organs was normalized to the fluorescent signal in muscle. Data are presented as mean±s.d. (n=4). **P<0.01, compared with other organs except liver.
Figure 38I:
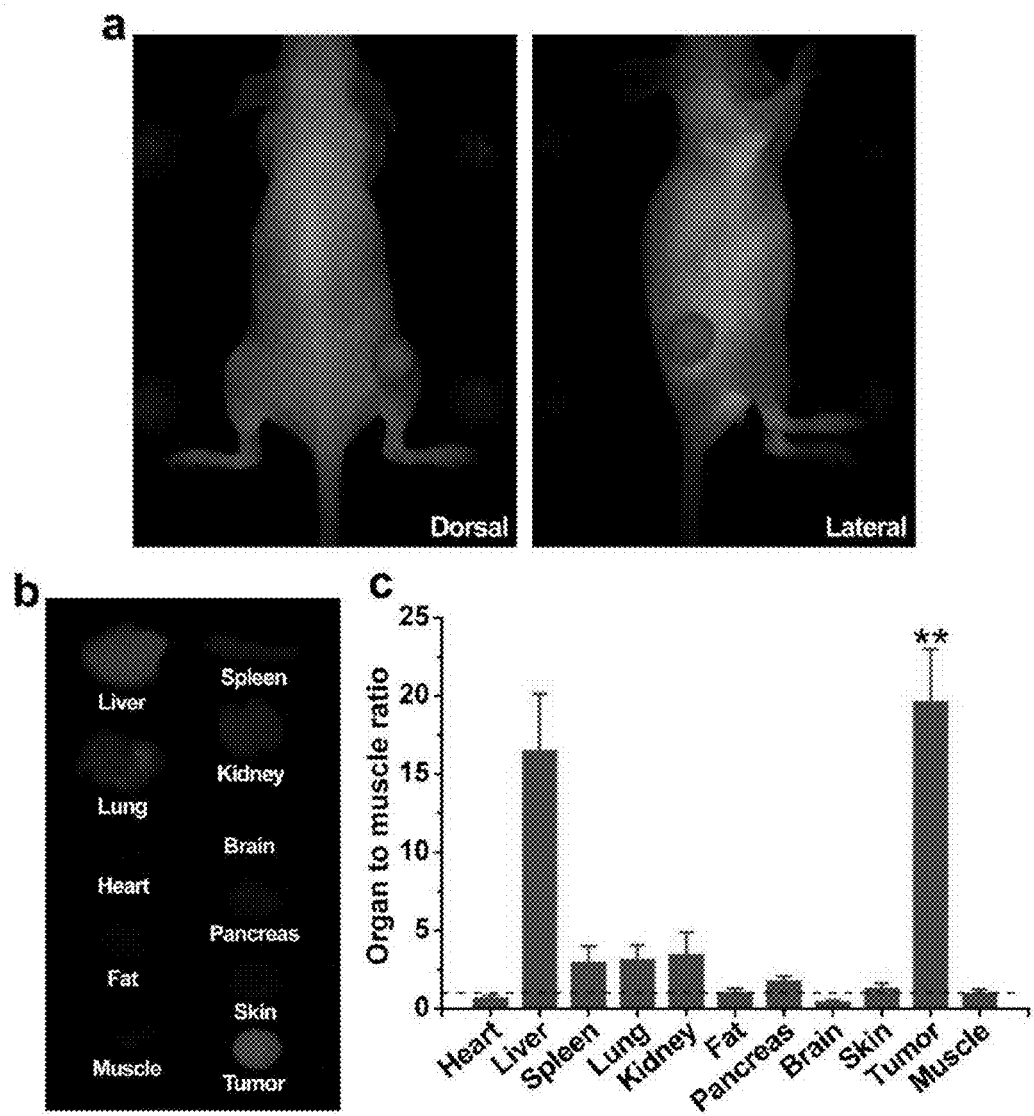
FIGS. 38Ia-c iUPS nanoprobes illuminate LN-229 brain cancer xenografts with high imaging contrast. 38Ia Nude mice bearing human LN-229 gliomas were injected with a dosage of 10 mg/kg iUPS nanoprobe and, NIR fluorescence images at 24 h were captured using Maestro CRI imaging system. The mice autofluorescence is color coded green while the unmixed nanoprobe signal is coded red. 38Ib At 24 h post-injection, mice were sacrificed and collected organs were visualized. 38Ic Organ to muscle ratios of fluorescence intensity at 24 h post-injection of nanoprobe. The fluorescent signal of organs was normalized to the fluorescent signal in muscle. Data are presented as mean±s.d. (n=4). **P<0.01, compared with other organs except liver.
Figure 38J:
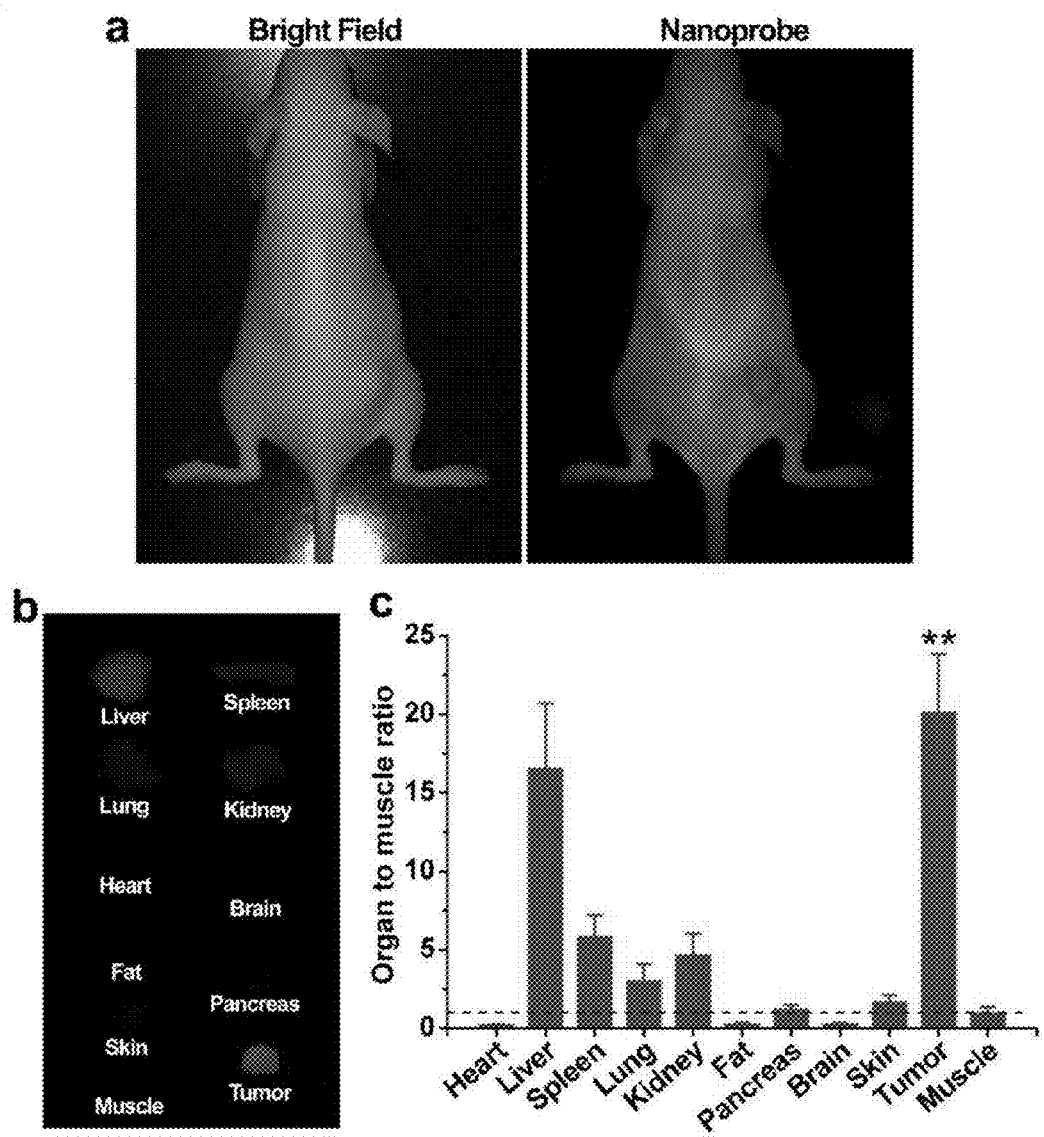
FIGS. 38Ja-c iUPS nanoprobes illuminate MiaPaca-2 pancreatic cancer xenografts with high imaging contrast. 38Ja Nude mice bearing human MiaPaca-2 pancreatic tumors were injected with a dosage of 10 mg/kg iUPS nanoprobe and, NIR fluorescence images at 24 h were captured using Maestro CRI imaging system. The mice autofluorescence is color coded green while the unmixed nanoprobe signal is coded red. 38Jb At 24 h post-injection, mice were sacrificed and collected organs were visualized. 38Jc Organ to muscle ratios of fluorescence intensity at 24 h post-injection of nanoprobe. The fluorescent signal of organs was normalized to the fluorescent signal in muscle. Data are presented as mean±s.d. (n=4). **P<0.01, compared with other organs except liver.

300-fold difference was found between tumors and blood in UPS$_e$ and cRGD-UPS$_i$ nanoprobes (Tables 5-7). To evaluate nanoprobe toxicity, the changes in animal body weight, liver and kidney functions, and histology of RES at 24 h and 7 d after nanoprobe injection (10 mg/kg) were systematically investigated. Results showed no weight loss, statistically insignificant changes of hepatic and kidney functions (e.g. aspartate transaminase and glutamic oxaloacetic transaminase, FIG. 36) and normal RES histology (data not shown), demonstrating the safety of these nanoparticles.

d. Integrated Nanoprobes (iUPS) for Combined Acidic pH$_e$ and Tumor Vasculature Imaging After establishing the mechanism of UPS$_e$ and cRGD-UPS$_i$ activations, the spatial pattern of UPS$_e$ and cRGD-UPS$_i$ activation in the tumor microenvironment was investigated. Intravital microscopy and subcutaneous A549 lung tumor xenograft in mice were utilized as our model system. To differentiate the two nanoprobes, tetramethyl rhodamine (TMR, $\lambda_{ex}/\lambda_{em}$=550/580 nm) and rhodamine G (RhoG, $\lambda_{ex}/\lambda_{em}$=502/527 nm) were used to label the UPS$_e$ and cRGD-UPS$_i$ respectively. The dual nanoprobes were co-injected intravenously and imaged over time. FIG. 37a shows complementary spatial activation patterns at 6 h post-injection: cRGD-UPS$_i$-RhoG activation was mostly restricted to tumor vessels, whereas UPS$_e$-TMR was illuminated in the interstitial space in the tumor parenchyma. Neither nanoprobe showed observable fluorescence inside tumor vasculature, demonstrating they remained 'silent' in blood.

To exploit the synergy of pH$_e$ and tumor vasculature activation, an integrated cRGD-UPS$_e$-Cy5.5 nanoprobe (iUPS) was constructed and its tumor imaging efficacy in 10 different tumor models was investigated. These models include a transgenic MMTV-PyMT breast cancer, several orthotopic cancers (lung, head and neck, prostate) and various subcutaneous cancer models (brain, pancreatic cancers). In all of the 10 tumor models, universal nanoprobe activation in the tumor microenvironment over surrounding normal tissues/organs (FIG. 37b and FIG. 38a-j) were observed. In many models, higher T/N ratios (~20) were obtained due to the additive effect of combining both pH$_e$ and tumor vasculature signals. Finally, the imaging efficacy of iUPS nanoprobes with a small molecular folate-FITC conjugate (Phase I clinical trials) in mice bearing orthotopic HN5 head and neck carcinoma were compared. The iUPS nanoprobe and folate-FITC were co-injected intravenously into tumor-bearing mice. At 24 h post-injection, only a small region of orthotopic HN5 tumors was visualized by folate-FITC, whereas the iUPS nanoprobe illuminated the whole tumor as well as local nodal metastasis (FIG. 39). The folate-FITC result is consistent with the fact that many head and neck cancer cells do not express folate receptors. These data highlight the success of targeting tumor microenvironment as a more robust and universal strategy to achieve broad tumor specificity.

e. Materials and Methods

Materials. Cyclic RGDfK (cRGDfK) peptide was purchased from Peptides International Inc. (Kentucky, USA). LysoTracker® Green, MitoTracker® Green, Hoechest 33342, fetal bovine serum, penicillin streptomycin, and cell culture media were obtained from Invitrogen Inc. (OR, USA). Amicon ultra-15 centrifugal filter tubes (MWCO=100 K) were from Millipore. Cy5.5 NHS ester was obtained from Lumiprobe company. Monomers 2-(di-isopropyl amino) ethyl methacrylate (DPA-MA), 2-aminoethyl methacrylate (AMA) were from Polyscience Company. 2-(Hexamethyleneimino) ethyl methacrylate (C7A-MA) and PEG macroinitiator (MeO-PEG5k-Br) were prepared according to the method described Zhou et. al., 2011, which is incorporated herein by reference. Other organic solvents were analytical grade from Sigma-Aldrich or Fisher Scientific Inc.

Syntheses of dye-conjugated block copolymers. Two different block copolymers (i.e. PEG-b-(PR-co-AMA)) (shown in the scheme below.) were synthesized by atom transfer radical polymerization (ATRP) method. The dye-free copolymers were used in polymer characterizations (Table 8). For the conjugation of near infrared fluorescent dye (Cy5.5) or tritium ($^3$H or T) labeling, aminoethyl methacrylate (AMA) was used in the copolymer synthesis. Six primary amino groups were introduced into each polymer chain by controlling

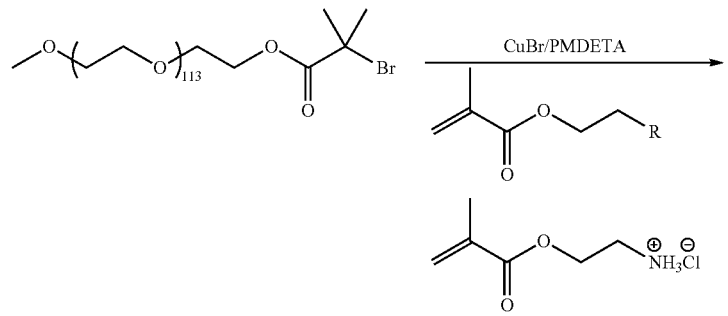

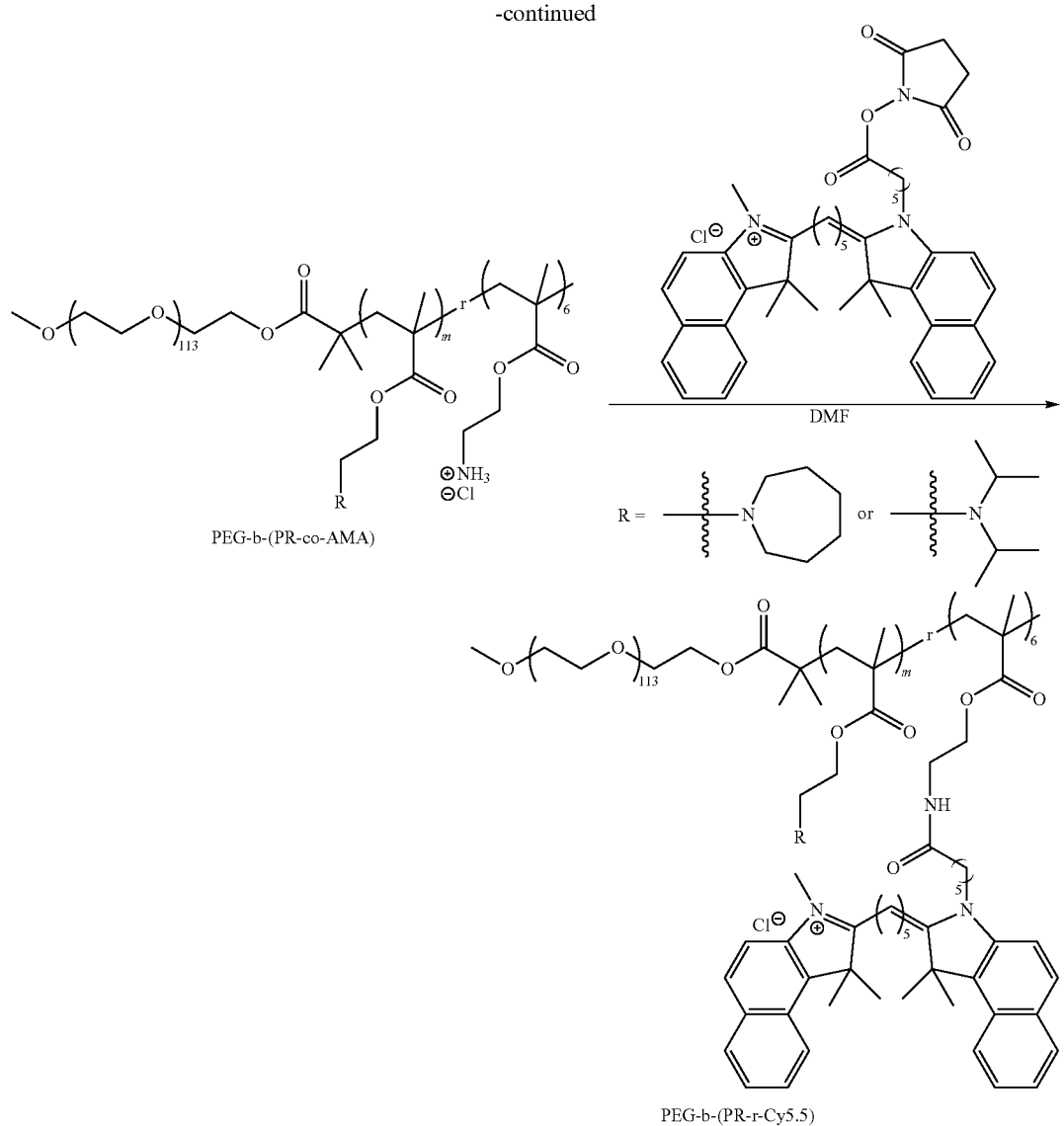

PEG-b-(PR-co-AMA)

PEG-b-(PR-r-Cy5.5)

the feeding ratio of the AMA monomer to the initiator (molar ratio=6). PEG-b-P(DPA-co-AMA) is used as an example to illustrate the procedure. First, diisopropylaminoethyl methacrylate (DPA, 1.71 g, 8 mmol), AMA (100 mg, 0.6 mmol), PMDETA (21 µL, 0.1 mmol), and MeO-PEG$_{114}$-Br (0.5 g, 0.1 mmol) were charged into a polymerization tube. Then a mixture of 2-propanol (2 mL) and DMF (2 mL) was added to dissolve the monomer and initiator. After three cycles of freeze-pump-thaw to remove oxygen, CuBr (14.4 mg, 0.1 mmol) was added into the reaction tube under nitrogen atmosphere, and the tube was sealed in vacuo. The polymerization was carried out at 40° C. for 12 h. After polymerization, the reaction mixture was diluted with 10 mL THF, and passed through an Al$_2$O$_3$ column to remove the catalyst. The THF solvent was removed by rotovap. The residue was dialyzed in distilled water and lyophilized to obtain a white powder. The resulting PEG-b-P(DPA-co-AMA) copolymers were characterized by $^1$H 500 MHz NMR, gel permeation chromatography (Viscotech GPCmax, PLgel 5 µm MIXED-D columns by

TABLE 8

Characterization of the diblock copolymers

| Copolymer | Yield (%) | $M_{n,GPC}$ (kDa)[a] | $M_{w,GPC}$ (kDa)[a] | $M_n$, $^1$H-NMR (kDa)[b] | PDI[a] |
|---|---|---|---|---|---|
| PEG$_{114}$-b-P(C7A$_{65}$-co-AMA$_6$) | 78 | 18.7 | 22.4 | 19.6 | 1.19 |
| PEG$_{114}$-b-P(DPA$_{75}$-co-AMA$_6$) | 82 | 20.1 | 23.1 | 21.0 | 1.15 |
| MAL-PEG$_{114}$-b-PDPA$_{88}$ | 62 | 22.8 | 27.8 | 23.9 | 1.22 |

[a]Number-averaged ($M_n$), weight-averaged molecular weight ($M_w$) and polydispersity index (PDI = $M_w/M_n$) were determined by GPC using THF as the eluent;
[b]Determined by $^1$H NMR.

Polymer Labs, THF as eluent at 1 mL/min). Table 8 enlists the yield, molecular weights ($M_n$ and $M_w$) and polydispersity index (PDI) of each copolymer.

For Cy5.5 conjugation, 50 mg of PEG-b-P(DPA-co-AMA$_6$) or PEG-b-(PC7A-co-AMA$_6$) was first dissolved in 2 mL of anhydrous DMF. Then, Cy5.5 NHS ester (1.5 equivalents to the molar amount of the primary amino group) was added. The reaction mixture was stirred at room temperature for two days. The polymer conjugates were purified by preparative gel permeation chromatography (PL-gel Prep 10 μm 10E3 Å, 300×25 mm column by Varian, THF as eluent at 5 mL/min) to remove the free dye molecules. The resulting polymer conjugates were lyophilized and stored at −20° C.

Synthesis of maleimide-terminated poly(ethylene glycol)-b-poly(2-(diisopropylamino) ethyl methacrylate) (MAL-PEG-b-PDPA). First, N-Maleoyl-β-alanine 1 (250 mg, 1.5 mmol) and furan (2.2 mL, 30 mmol) were dissolved in 10 mL benzene. The solution was refluxed overnight. After reaction, the solution was concentrated and then purified by flash chromatography to yield compound 2. $^1$H NMR (TMS, CDCl$_3$, ppm): 6.52 (2H, =CHCH(O—))—), 5.28 (2H, =CHCH(O—))—), 3.66 (2H, —NCH2CH2-), 2.87 (2H, —(—O)CHCH(CH)—), 2.55 (2H, —NCH2CH2-). Yield: 65%. Then, compound 2 (48 mg, 0.20 mmol) and N-hydroxymaleimide (25 mg, 0.22 mmol) were dissolved in 5 mL dichloromethane (DCM). N,N'-dicyclohexylcarbodiimide (50 mg, 0.24 mmol) was added to the above solution. After the solution was stirred for 2 h at room temperature, HO-PEG$_{5K}$-NH$_2$ (500 mg, 0.1 mmol) was added and the reaction solution was stirred continuously overnight. The reaction solution was filtered and the filtrate was poured into 50 mL cold diethyl ether. The precipitation was collected and dried for next reaction. The above product was dissolved in 5 mL DCM with the addition of triethylamine (70 μL, 0.5 mmol). Then α-bromoisobutyryl bromide (65 μL, 0.5 mmol) was added and the solution was stirred overnight. The reaction solution was poured into 50 mL cold diethyl ether and the precipitate was collected. The product was further purified by two dissolve-and-precipitation cycles and then dried. $^1$H NMR (TMS, CDCl$_3$, ppm): 6.52 (2H, =CHCH(O—))—), 5.26 (2H, =CHCH(O—))—), 4.33 (2H, —CH2OC(O)2-), 3.93~3.30 (460H, —NCH2CH2O(CH2CH2O)$_{114}$—) 2.87 (2H, —(—O)CHCH(CH)—), 2.55 (2H, —NCH2CH2-), 1.92 (6H, —C(O)C(CH3)2Br). Yield: 59%. DPA (479 mg, 2.24 mmol), PMDETA (7.0 μL, 0.034 mmol), and proMAL-PEG$_{114}$-Br (150 mg, 0.028 mmol) were charged into a polymerization tube. Then a mixture of 2-propanol (0.50 mL) and DMF (0.50 mL) was added to dissolve the monomer and initiator. After three cycles of freeze-pump-thaw to remove oxygen, CuBr (4.5 mg, 0.031 mmol) was added into the reaction tube under nitrogen atmosphere, and the tube was sealed in vacuum. The polymerization was carried out at 50° C. for 8 h. After polymerization, the reaction mixture was diluted with 10 mL THF, and passed through an Al$_2$O$_3$ column to remove the catalyst. The THF solvent was removed by rotovap. The residue was dialyzed in distilled water and lyophilized to obtain a white powder with 65% yield. The proMAL-PEG-b-PDPA copolymer were characterized by $^1$H NMR (500 MHz), gel permeation chromatography (Viscotech GPCmax, PLgel 5 μm MIXED-D columns by Polymer Labs, THF as eluent at 1 mL/min). Molecular weights (M$_n$ and M$_w$) and polydispersity index (PDI) of the copolymer was shown in Table 8. Finally, 200 mg proMAL-PEG-b-PDPA copolymer was dissolved in 10 mL toluene. The reaction solution was refluxed overnight. The toluene was removed. The residue was dialyzed in distilled water and lyophilized to obtain a white powder with 95% yield.

Syntheses and characterization of UPS nanoprobes. Dye-conjugated MeO-PEG-b-PDPA and MeO-PEG-b-PC7A, and maleimide-terminated block copolymers were synthesized by atom transfer radical polymerization (ATRP) method (described above). cRGD-UPS$_i$ nanoprobes were prepared following a previously published procedure (Nasongkla, et. al., 2006, which is incorporated herein by reference). In a typical procedure, 2 mg of MAL-PEG-b-PDPA and 18 mg of MeO-PEG-b-PDPA-Cy5.5 were dissolved in 1 mL THF. Then, the mixture was slowly added into 4 mL of Milli-Q water under sonication. The mixture was filtered 4 times to remove THF using the micro-ultrafiltration system. After micelle formation, an excess amount of cRGDfK and 0.05 M hydroxylamine in 0.05 M HEPES/0.01 M EDTA aqueous solution was added into micelle solution. The conjugation was allowed to occur for 4 h followed by filtration to remove any precipitates in micelle solution. The cRGD-UPS$_i$ nanoprobe was filtered for 6 times to remove the free cRGDfK peptide. To prepare the UPS$_i$ or UPS$_e$ nanoprobes, 20 mg of MeO-PEG-b-PDPA-Cy5.5 or MeO-PEG-b-PC7A-Cy5.5 were dissolved in 1 mL THF. The solution was slowly added into 4 mL of Milli-Q water. Then, the mixture was filtered for 4 times to remove THF, followed by filtration to remove precipitates in solution. $^1$H-NMR was used to confirm the formation of core-shell structure and conjugation of cRGD peptide to micelle surface. The successful conjugation of cRGD on the surface of micelles was validated by the appearance of phenyl protons of cRGD at 7.4 ppm. Transmission electron microscopy was carried out with 1% phosphotungstic acid negative staining and visualized on a JEOL 1200EX electron microscope (JEOL 1200EX).

Fluorescence activation of UPS nanoprobes. The fluorescence emission spectra of UPS nanoprobes in different pH buffer solutions were obtained on a Hitachi fluorometer (F-7500 model). For each UPS nanoprobe, the sample (5 mg/mL) was prepared in Milli-Q water. Then, the solution was diluted in 50 mM phosphate buffered saline (PBS) with different pH values. The final polymer concentration was controlled at 0.1 mg/mL. The nanoprobe was excited at 675 nm, and the emission spectra were collected from 690 to 770 nm. The emission intensity at 710 nm was used to quantify the signal amplification for UPS nanoprobes. The fluorescent images of UPS$_i$ and UPS$_e$ nanoprobe solutions (0.1 mg/mL) at different pH were captured on Maestro in vivo imaging system (CRI. Inc. Woburn, Mass.) using the "orange" filter (645-820 nm).

In vitro serum stability. Fresh mouse serum was collected and filtered through 0.22 μm syringe filters. Then, 0.2 mL of cRGD-UPS$_i$ or UPS$_e$ nanoprobe (2 mg/mL) was added into 2 mL of serum. The mixture was incubated at 37° C. in a humidified chamber. At each designated time point, 100 μL aliquots of serum mixture were collected and immediately imaged by Maestro in vivo imaging system under identical settings to quantify the fluorescence intensity.

Cell culture. The tumor cell lines used for in vivo implantation include A549 lung carcinoma, MDA-MB-231 breast cancer, HN5 and HCC4034 head-neck cancer, SF-188 glioma, LN-229 glioma, 3LL lung carcinoma, Mia Paca-2 pancreatic cancer and PC-3 prostate cancer cells. Cells were cultured in DMEM with 10% fetal bovine serum and antibiotics.

Animal models. Female athymic nu/nu mice (18-22 g) were purchased from Charles River (Wilmington, Mass.). Mice were inoculated s.c. on the right flank with A549 cells (5×10$^6$/mouse). Three to four weeks after implantation, animals with tumor size of 200-300 mm$^3$ were used for pharmacokinetic, biodistribution, and imaging studies. To demonstrate the universal imaging applications of the integrated nanoprobe, orthotopic tumor models, including HN5 and HCC4034 head-neck cancers, PC-3 prostate cancer and 3LL Lewis lung carcinoma were developed. MMTV-PyMT transgenic mice bearing multifocal mammary tumors were established by the Dr. DeBerardinis lab. Subcutaneous tumor models, including MDA-MB-231 breast cancer, SF-188 glioma, LN-229 glioma, and Mia Paca-2 pancreatic carcinoma were established.

Pharmacokinetic and biodistribution studies. $^3$H-labeled cRGD-UPS$_i$ were prepared from 90% MeO-PEG-b-PDPA-C(O)CT$_3$ and 10% MAL-PEG-b-PDPA. UPS$_i$ and UPS$_e$ were prepared from MeO-PEG-b-PDPA-C(O)CT$_3$ and MeO-PEG-b-PC7A-C(O)CT$_3$, respectively. For pharmacokinetic experiment, mice bearing A549 tumors were randomly divided into three groups (n=4-5 for each group) for cRGD-UPS$_i$ UPS$_i$ and UPS$_e$. The mice were injected intravenously with micelle solutions. Blood was collected at 2 min, 30 min, 1, 3, 6, 12, and 24 h after injection. Plasma (20 µL) was isolated by centrifugation at 5,000 g for 10 min. Plasma was subsequently mixed with a tissue solubilizer solution (1 mL, BTS-450; Beckman) at room temperature for 12 h followed by addition of a liquid scintillation mixture (10 mL, Ready Organic, Beckman) for 24 h. Amount of radioactive isotope was measured by a liquid scintillation counter (Beckman LS 6000 IC). Biodistribution of cRGD-UPS$_i$ UPS$_i$ and UPS$_e$ nanoprobes in tumor and other organs was performed in a separate group of A549 tumor-bearing mice (n=4 for each group). Mice were perfused with PBS buffer (30 mL) at pre-designated time points (6 and 24 h). Dissected organs were weighed, homogenized, and treated with scintillation mixtures. The nanoprobes distribution in different organs/tissues was calculated as the percentage of injected dose per gram of tissue (% ID/g).

In vivo and ex vivo NIR fluorescence imaging. For tumor vasculature imaging, cRGD-UPS$_i$ or UPS$_i$ (10 mg/kg) was administrated intravenously into the A549 tumor-bearing mice (n=4 for each group). Time-course fluorescent images were captured on Maestro in vivo imaging system using the "orange" filter. To elucidate the role of $\alpha_v\beta_3$-mediated endocytosis, a group of mice were injected with cRGDfK (25 mg/kg) 30 min before cRGD-UPS$_i$ injection.

For pH$_e$ imaging, UPS$_e$ (10 mg/kg) was injected into A549 tumor-bearing mice (n=4 for each group). Time-lapse NIR images were captured on Maestro system using the "orange" filter. As controls, 2-DG (250 mg/kg) or CHC (250 mg/kg) was injected 12 h before the UPS$_e$ nanoprobe administration. Then, the mice were monitored at pre-designated time points.

Ten tumor models described above were used to demonstrate the universal application of cRGD-UPS$_e$-Cy5.5 integrated nanoprobe in tumor microenvironment imaging. Integrated nanoprobe (10 mg/kg) was administrated intravenously into tumor-bearing mice (n=4 for each tumor model). Fluorescent images were captured on Maestro system using the "orange" filter at 24 h post-injection.

Tumor/normal tissue (T/N) ratios were determined by comparing the average fluorescence intensities in the tumor and the whole body except the tumor site. At the end of imaging, the mice were sacrificed. Tumor and selected organs were excised, and imaged by Maestro system. The fluorescence intensities of ex vivo tumors were quantified and normalized to the value of the muscle and blood.

Intravital imaging. Mice bearing A549 tumors were anesthetized with isoflurane and fixed under a Nikon ECLIPSE intravital microscope (Nikon, Japan) with a two-channel method in which one channel was used to image the activation of cRGD-UPS$_i$ nanoprobe in tumor vasculature and the other channel was used to probe the signal amplification of UPS$_e$ nanoprobe in acidic tumor microenvironment. Mixtures of cRGD-UPS$_i$-RhoG (10 mg/kg, green) and UPS$_e$-TMR (10 mg/kg, red) were intravenously injected into tumor bearing mice (n=4). Images were captured with a resolution of 1024×768 pixels with 10× Nikon objectives.

Immunofluorescence staining. In tumor vasculature imaging studies, the mice were sacrificed at 6 h post-injection. Tumors were snap frozen and cut into 8-µm sections. The slices were fixed in cold acetone and rinsed with PBS three times, and blocked with 10% BSA for 1 h at room temperature. Subsequently, the slices were incubated with rat anti-mouse CD31 antibody (1:50, BD Biosciences) at 4° C. overnight. Then, Alexa Flour® 488 dye-conjugated secondary antibody (1:100) was added to stain the slices. The slides were mounted with DAPI-containing medium. The images were captured on a fluorescence microscope (Nikon ECLIPSE TE2000-E, Japan).

In pH$_e$ imaging studies, the tumor-bearing mice were intravenously injected with UPS$_e$ (10 mg/kg). At 5 h post-injection, the animals were injected with pimonidazole (60 mg/kg). One hour later, tumors were collected, frozen and cut into 8-µm sections. Adjacent tumor sections were exposed to primary antibody diluted in blocking solution for 1 h at room temperature. Primary antibodies used were as follows: FITC-conjugated murine antipimonidazole monoclonal antibody (HPI Inc.) diluted 1:50; rat anti-mouse CD31 antibody diluted 1:50; and rabbit anti-mouse Ki-67 antibody (Millipore). Sections were washed thrice with PBS and incubated with the appropriate secondary antibodies for 1 h. CD31 was detected with an Alexa Flour® 488-conjugated secondary antibody (1:100). Ki-67 was detected with Cy$_2$-conjugated goat anti-rabbit antibody (1:100). The sections were scanned on an image analysis system consisting of Nikon fluorescence microscope using a computer-controlled motorized stage with a digital camera. All images were scanned at ×200 magnification. Composite images of sections were generated by the software from individual microscopic images.

Statistical analysis. Data were expressed as mean±s.d. Differences between groups were assessed using the paired, two-sided Student t-test. *$P<0.05$ was considered significant, and **$P<0.01$ was considered highly significant.

In vitro metabolic studies. Stock solutions of alpha-cyano-4-hydroxycinnamic acid (CHC, 1 M) and 2-deoxyglucose (2-DG, 1 M) dissolved in DMSO and PBS buffer, respectively, were used. Metabolism studies were performed as previously described with minor modifications$^2$. Briefly, A549 cells ($1.2\times10^6$/well) were seeded in 6 well plates and incubated for 24 h before inhibition studies. Media were removed and replaced at the beginning of experiments with media containing inhibitors or vehicle controls. Concentrations of glucose and lactate in the culture media were subsequently measured with an automated electrochemical analyzer (BioProfile Basic-4 analyzer, NOVA). Protein concentrations were analyzed from cell pellets using a Pierce BCA protein assay kit. Metabolic assays were conducted 6 h after inhibitor addition. The pH of the media was measured with a pH meter (Mettler-Toledo International Inc., Columbus, Ohio) at 24 h after inhibitor addition.

Fluorescence activation of UPS$_i$ nanoprobes and their localization in HUVEC cells. Human umbilical vein endothelial cells (HUVECs) were obtained from Lonza and maintained in EBM with EGM singlequots. HUVECs were used in exponential growth phase, and all the experiments were conducted at passage <6. Confocal scanning microscopy was used to investigate the cellular uptake and intracellular distribution of cRGD-UPS$_i$ nanoprobe in HUVECs. Toward this, cells were plated in glass bottom dishes (MatTek, MA) in 2 mL complete medium and incubated with cRGD-UPS$_i$ or UPS$_i$ at a polymer concentration of 0.2 mg/mL at pH 7.4. Confocal images were captured at 3 h after addition of micelles. In the competitive experiment, HUVECs were pretreated with a 20-fold molar excess of cRGDfK, and the cRGD-UPS$_i$ were subsequently incubated with the cells for 3 h. The images were analyzed using Image-J software. Five independent measurements were presented as the mean±standard deviation. For colocalization experiments, cells were incubated with LysoTracker® green (50 nM) or MitoTracker® green (100 nM) for 15 min at the end of uptake study for lysosome and mitochondria labeling, respectively. The cells were then washed thrice with PBS. The cells were imaged by a Nikon ECLIPSE TE2000-E confocal microscope with identical settings for each confocal study.

Acute toxicity. Fifteen athymic nude mice (20-24 g, 6-8 weeks) were randomly divided into two groups. The control group contains 5 mice and the experiment group contains 10 mice. iUPS integrated nanoprobes (10 mg/kg) were intravenously administered to the mice in the experiment group via tail vein. Following exposure, the vital signs and mortality of mice in each group were recorded. Half of the mice in the experiment group were sacrificed on day 1 and the remaining half were killed on day 7. The blood samples (~0.8–1 mL/mouse) were centrifuged at 5,000 g for 10 min to separate serum. Liver function was evaluated based on the serum levels of alanine transaminase (ALT) and glutamic oxaloacetic transaminase (GOT). Nephrotoxicity was determined by blood urea nitrogen (BUN) and creatinine (Cr). The tissues of heart, liver, spleen, lung, and kidney were collected and immediately fixed in 10% formalin for histopathological examinations.

8. Real-Time Imaging of Tumor Cell Trafficking in Lymphatic Channels and Bloodstream using Ultra-pH Sensitive Nanoprobes Tumor metastasis leads to the migration of cancer cells from one part of the body to another part of the body often leading to the formation of a new metastatic tumor or a metastasis. The principle cause of cancer patients is tumor metastasis. There are three principles ways that tumor can migrate and spread to other portions of the body or distinct organs: through the circulatory (blood) system, known as hematogenous, through the lymphatic system, and through the body wall into the abdominal and chest cavities, known as transcoelomic. Both lymphatic and circulatory migration appears to be dominate modes of migration, while transcoelomic is relatively uncommon. The circulatory system is often the common model for bone and soft tissue tumors such as sarcomas while the lymphatic system is the common transportation method for melanoma, breast, lung and gastrointestinal tumors. Because the methesis of tumors is of utmost importance in clinical progression of cancer, UPS nanoprobes could be useful in real-time fluorescence imaging of tumor cell trafficking in the bloodstream and lymphatic vessels.

In order to study the use of UPS nanoprobes towards this goal, ex vivo studies were carried out using A549 cells (EGFR$^{++}$) spiked into whole blood at different concentrations. The study was trying if a rare, circulating tumor cell could be identified in mouse blood. Different concentrations of cells in blood (10, 100, and 1000 CTC/mL blood) were tested using the Fab'-UPS$_i$-TMR nanoprobe with a $F_{ratio} \geq 100$ with a nanoprobe concentration of 200 µg/mL. The spiked whole blood was incubated with the nanoprobe for 3 hours and the cells were visualized using a Nikon confocal microscope.

Figure 41:
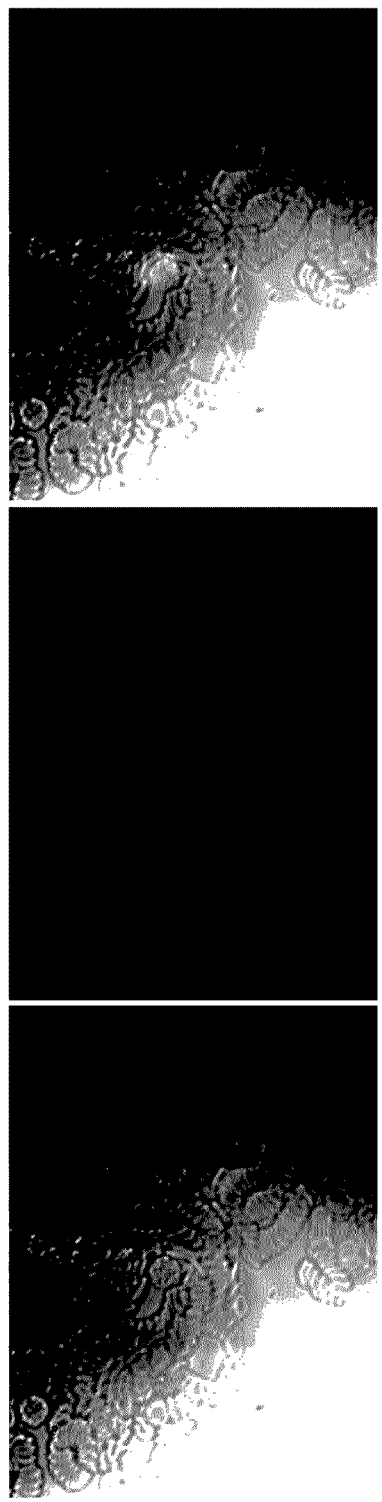
FIG. 41 Microscopy image at 600× magnification of Human HNC patient showing a circulating tumor cell.
Figure 42:
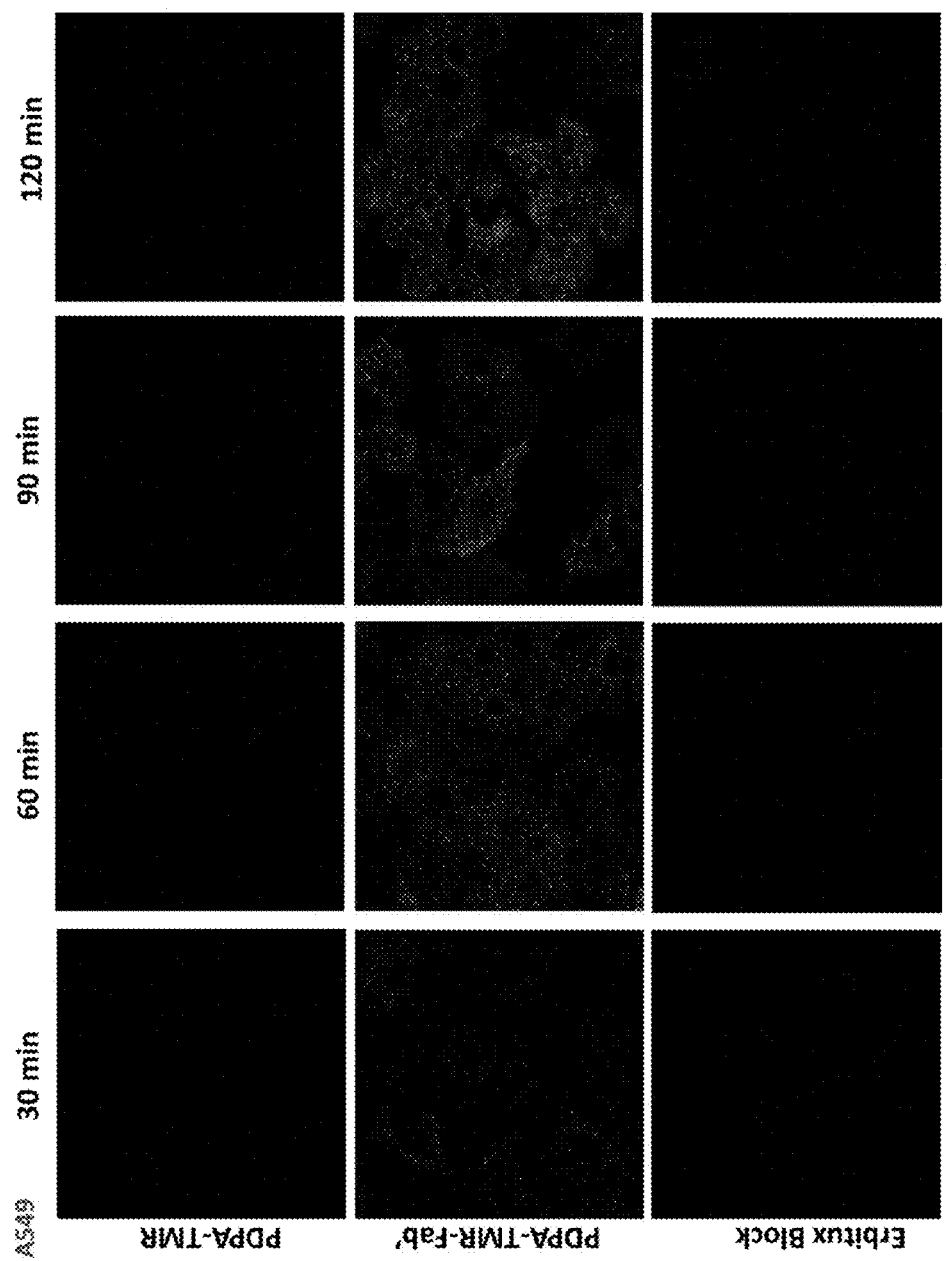
FIG. 42 Staining of A549 cells at 30, 60, 90 and 120 minutes after exposure to a Fab' containing nanoprobe. The top row shows cells exposure to the nanoprobe without the Fab' fragment conjugated and the middle row shows cells exposure to the nanoprobe which contains a conjugated Fab' fragment. The bottom row shows cells exposure to a mixture of Erbitux antibody and the nanoprobe containing the Fab' fragment.
Figure 43:
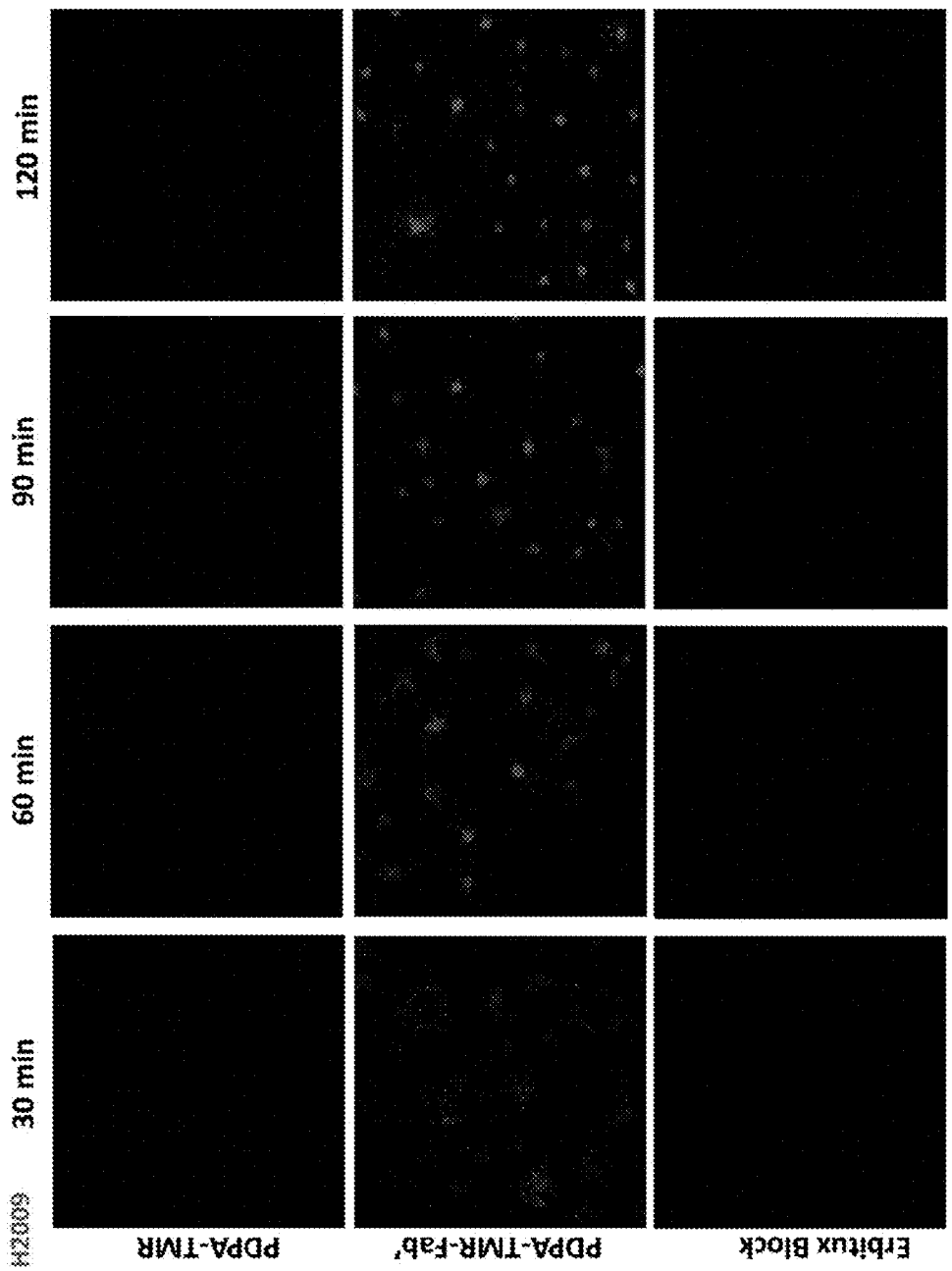
FIG. 43 Staining of H2009 cells at 30, 60, 90 and 120 minutes after exposure to a Fab' containing nanoprobe. The top row shows cells exposure to the nanoprobe without the Fab' fragment conjugated and the middle row shows cells exposure to the nanoprobe which contains a conjugated Fab' fragment. The bottom row shows cells exposure to a mixture of Erbitux antibody and the nanoprobe containing the Fab' fragment.
Figure 44:
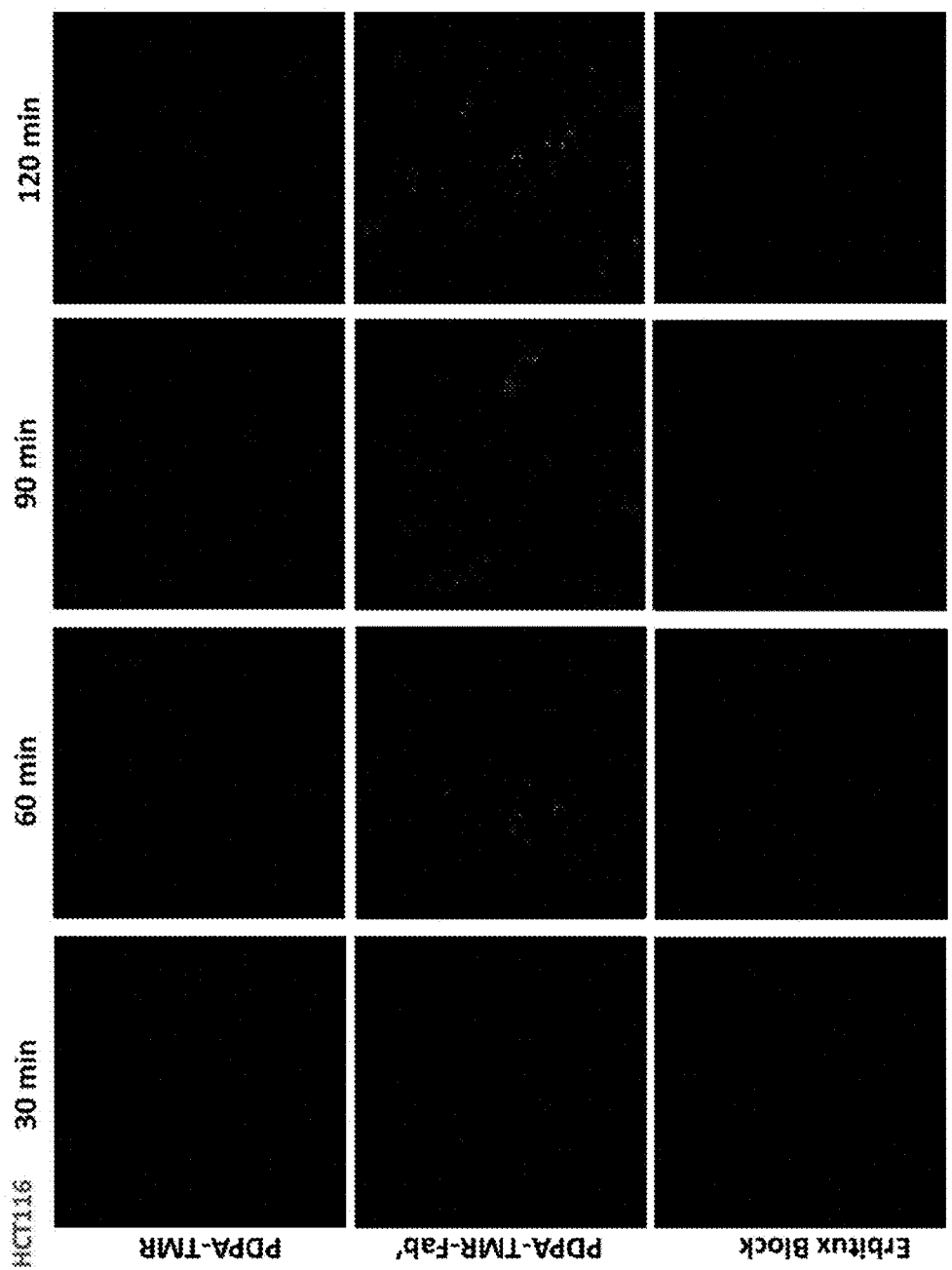
FIG. 44 Staining of HCT116 cells at 30, 60, 90 and 120 minutes after exposure to a Fab' containing nanoprobe. The top row shows cells exposure to the nanoprobe without the Fab' fragment conjugated and the middle row shows cells exposure to the nanoprobe which contains a conjugated Fab' fragment. The bottom row shows cells exposure to a mixture of Erbitux antibody and the nanoprobe containing the Fab' fragment.
Figure 45:
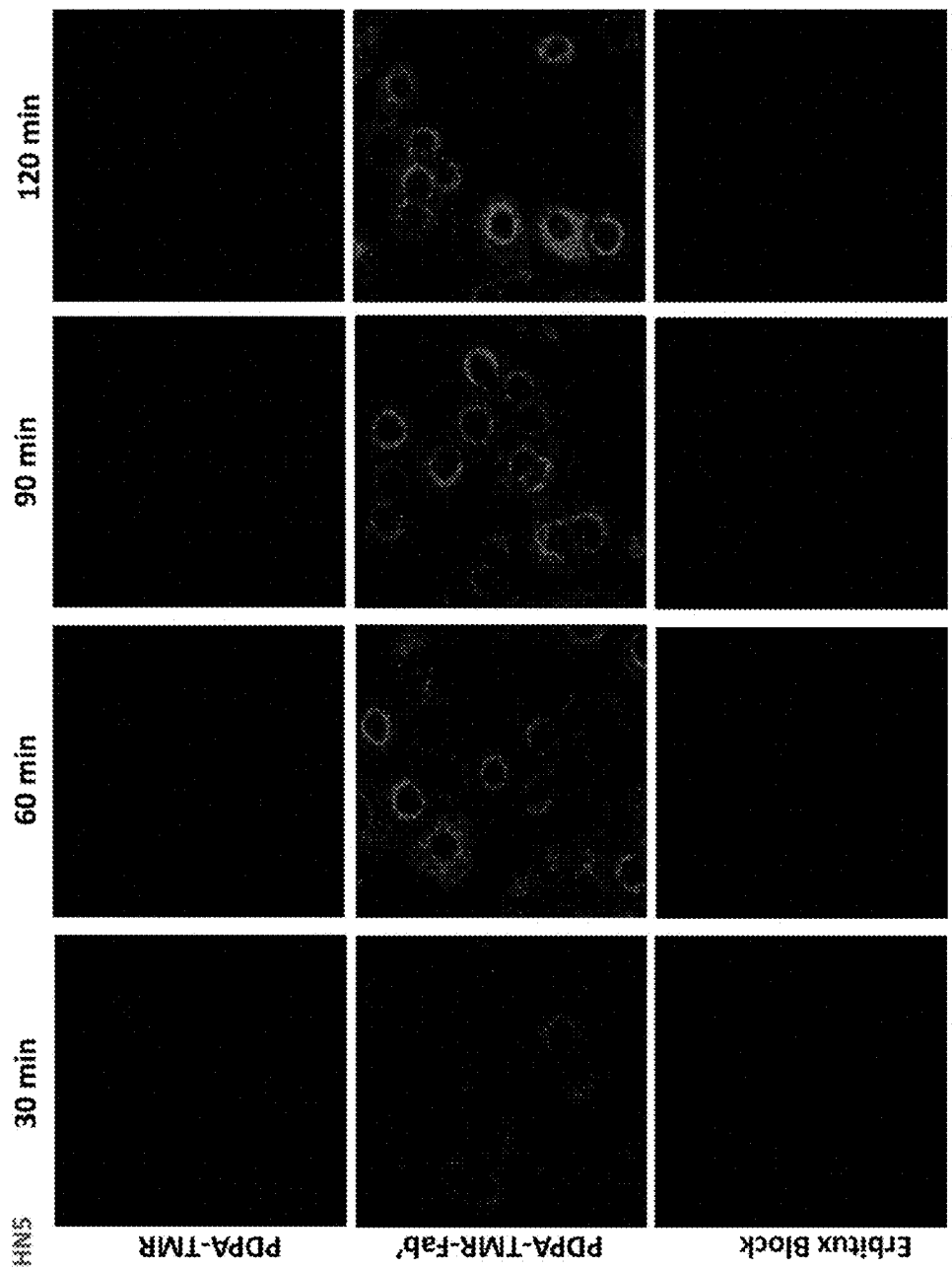
FIG. 45 Staining of HN5 cells at 30, 60, 90 and 120 minutes after exposure to a Fab' containing nanoprobe. The top row shows cells exposure to the nanoprobe without the Fab' fragment conjugated and the middle row shows cells exposure to the nanoprobe which contains a conjugated Fab' fragment. The bottom row shows cells exposure to a mixture of Erbitux antibody and the nanoprobe containing the Fab' fragment.
Figure 46:
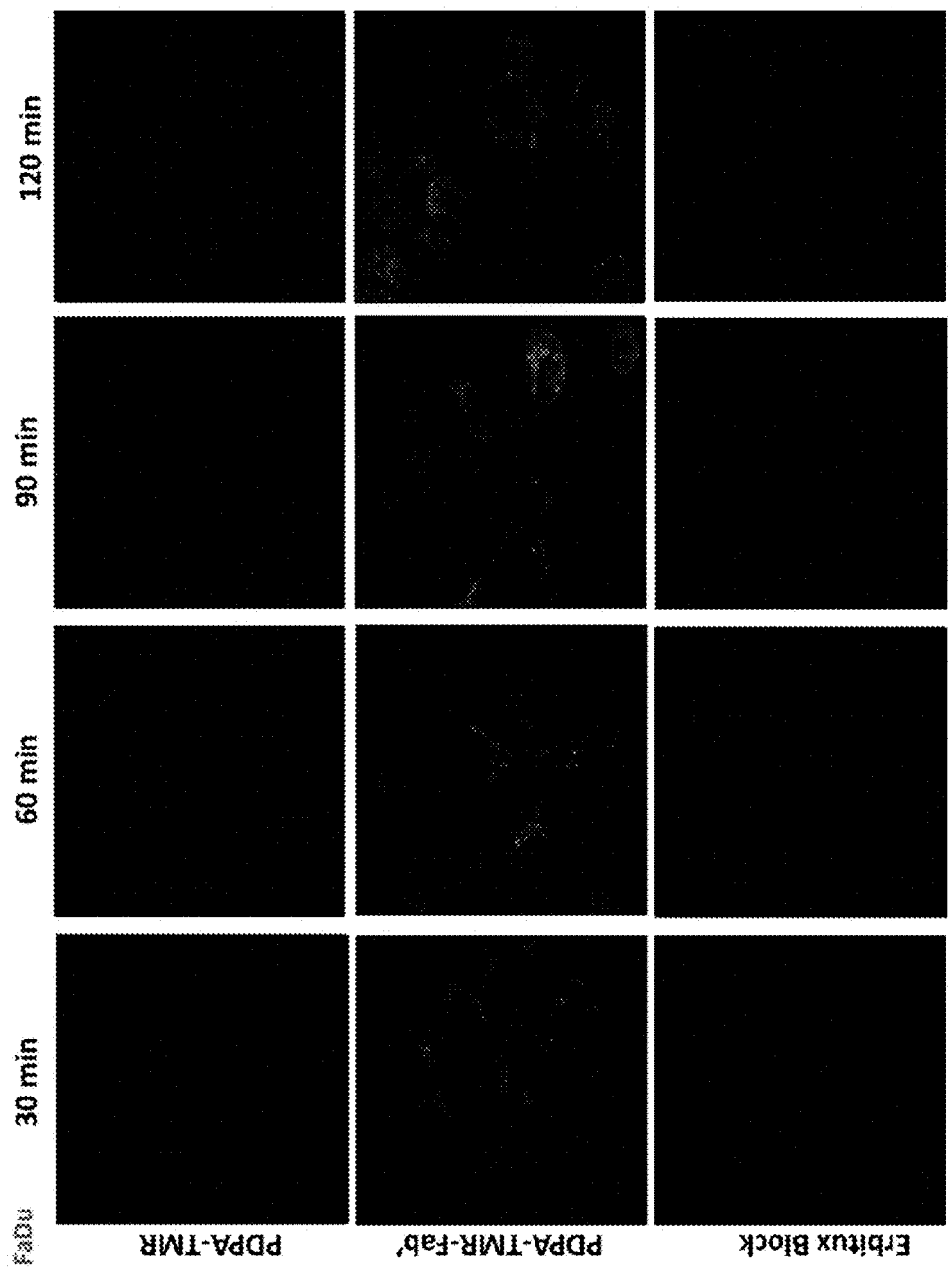
FIG. 46 Staining of FaDu cells at 30, 60, 90 and 120 minutes after exposure to a Fab' containing nanoprobe. The top row shows cells exposure to the nanoprobe without the Fab' fragment conjugated and the middle row shows cells exposure to the nanoprobe which contains a conjugated Fab' fragment. The bottom row shows cells exposure to a mixture of Erbitux antibody and the nanoprobe containing the Fab' fragment.
Figure 47:
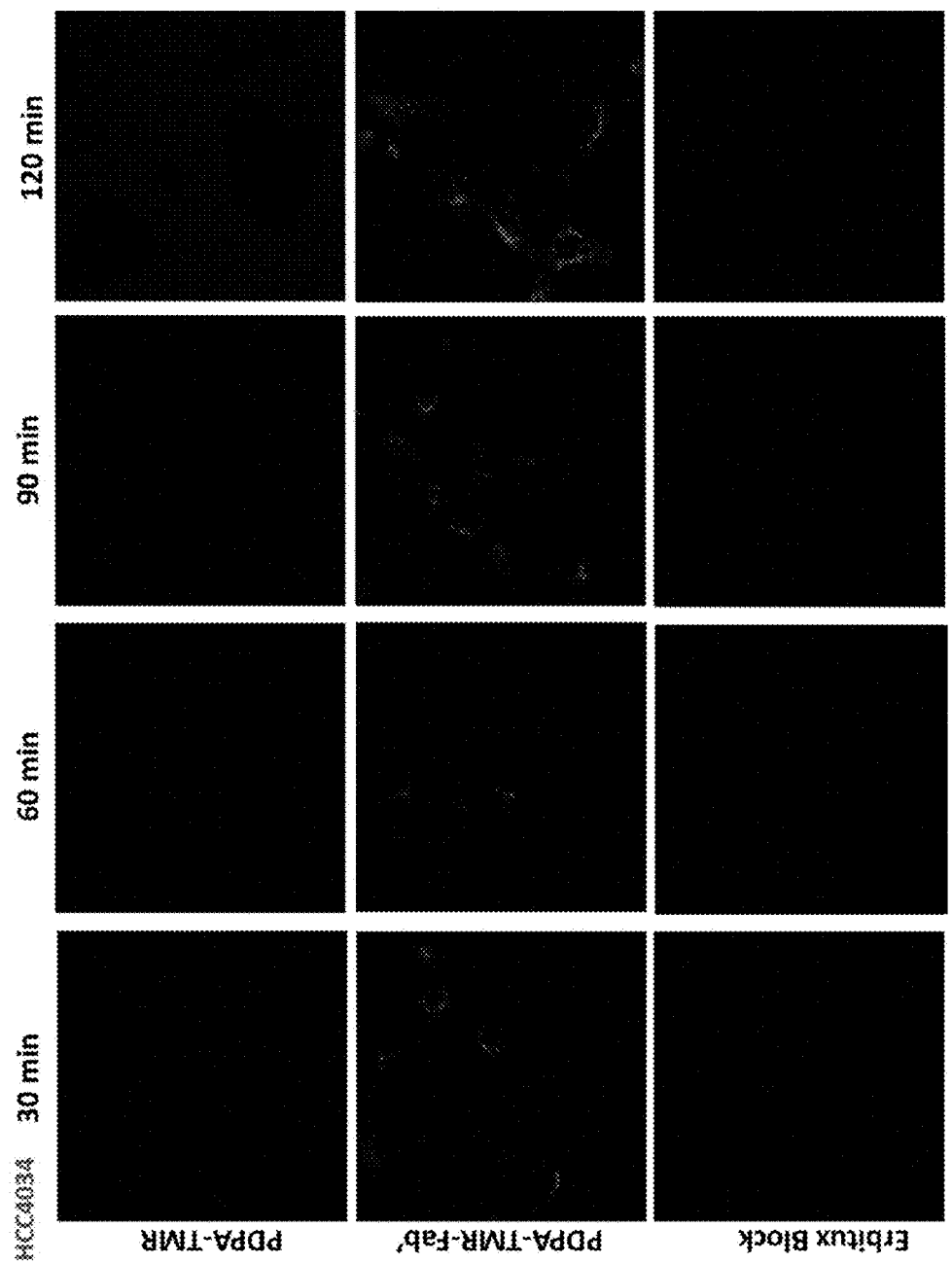
FIG. 47 Staining of HCC4034 cells at 30, 60, 90 and 120 minutes after exposure to a Fab' containing nanoprobe. The top row shows cells exposure to the nanoprobe without the Fab' fragment conjugated and the middle row shows cells exposure to the nanoprobe which contains a conjugated Fab' fragment. The bottom row shows cells exposure to a mixture of Erbitux antibody and the nanoprobe containing the Fab' fragment.
Figure 48:
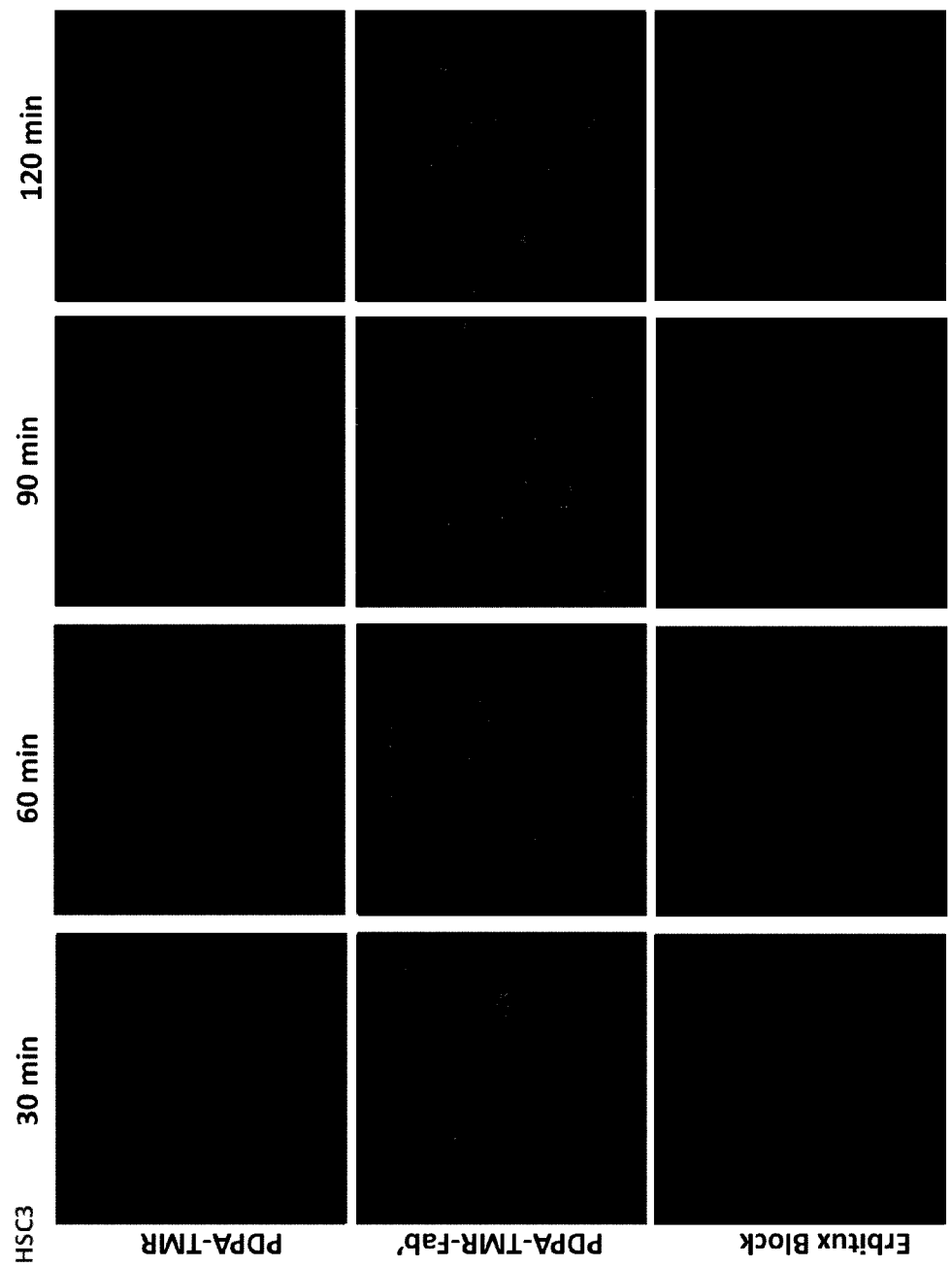
FIG. 48 Staining of HSC3 cells at 30, 60, 90 and 120 minutes after exposure to a Fab' containing nanoprobe. The top row shows cells exposure to the nanoprobe without the Fab' fragment conjugated and the middle row shows cells exposure to the nanoprobe which contains a conjugated Fab' fragment. The bottom row shows cells exposure to a mixture of Erbitux antibody and the nanoprobe containing the Fab' fragment.

At both 600× and 2,400× magnification, cancer cells were visible with the whole blood (FIGS. 40A & 40B). A similar study with Human HNC patients allowed visualization of a cell at 600× magnification (FIG. 41).

9. In Vitro, In Vivo and in Intro Imaging Using Functionalized PDPA-TMR-Fab' and PDPA-TMR-FA Nanoprobes of Different Cancer Cell Lines Furthermore, the nanoprobes as described above in Section 7 can be functionalized using different targeting moieties which modulate the selectivity of the probe for different cell types. Two different functionalized nanoprobes have also been synthesized to help more specifically target different cell types. A Fab' nanoparticle has been synthesized using Erbitux monoclonal antibody. The Erbitux antibody was cleaved in an acidic solution of pepsin. The reaction was heated at 37° C. for 1 hour and then quenched through additions of 1M Tris until the pH of the solution reached pH 6, which was followed by purification using FPLC to obtain the purified in F(ab')$_2$. The F(ab')$_2$ was added to 10 mM EDTA and 8 eq. of 1 mg/mL aqueous DTT. The reaction was heated to 37° C. for 4 hours and then purified using a PD-10 column to obtain the purified Fab' antibody fragment. The fragment was added to a solution containing of 10% PEG-PDPA-maleimide and allowed to stir overnight. The reaction mixture was purified and concentrated to 5 mg/mL by micro-ultrafiltration.

In order to identify the effect of adding the additional targeting moiety, the nanoprobes were incubated 7 different cell lines with a polymer concentration of 0.1 mg/mL at pH 7.4. The cells were then monitored using a confocal microscopy. As shown in FIGS. 42-48, the nanoprobe containing the Fab' fragment showed increased visualization of the target cells relative to the unfunctionalized nanoprobe. The PDPA-TMR showed little to no visualization of the cells while after 90 to 120 minutes, all 7 cell lines showed some fluorescence within some of the cells with cell lines, H2009 and HN5 (FIGS. 42 & 44), showing the brightest fluorescence after a 120 minutes. Additionally, a competition experiment was carried out using the Erbitux antibody. A 20-fold molar excess of the Erbitux and PDPA-TMR-Fab' were incubated with the cells for 2 hours. In the competition experiments, the nanoprobe no longer showed any visualization of the cells as the antibody had displaced the nanoprobe from the cell for all cell lines tested (FIGS. 42-48).

Figure 49:
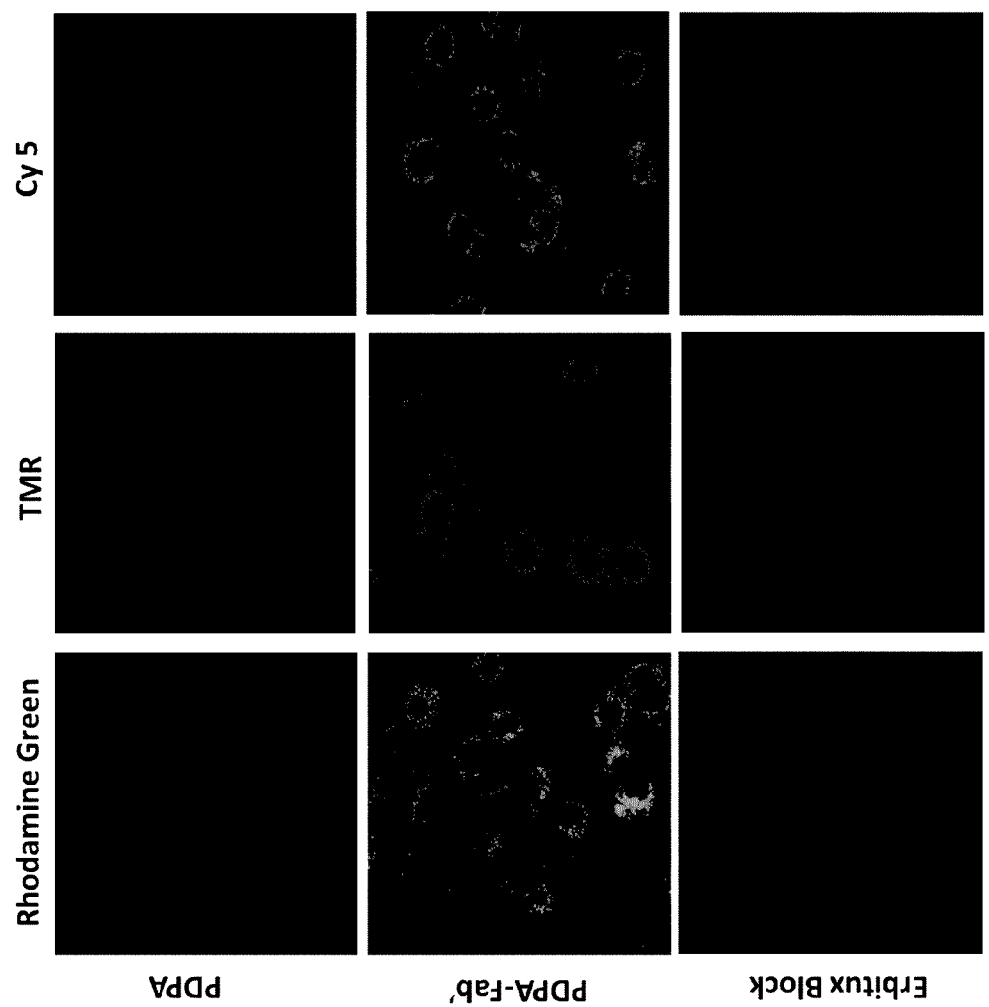
FIG. 49 Staining of HN5 cells with three different fluorophore containing nanoprobes. The left column contains a probe synthesized with Rhodamine Green, the middle column contains a probe synthesized with TMR and the right column contains a probe synthesized with Cy 5. The top row shows cells exposed to just PDPA, the middle row shows a nanoprobe which contains the Fab' fragment, and the bottom row shows cells exposure to a mixture of Erbitux antibody and the nanoprobe containing the Fab' fragment.

Using different fluorophores on the PDPA-Fab' probes still allowed for the visualization of the cells selective over the nanoprobe without the antibody fragment (FIG. 49). Additionally, the probe works in vivo allowing the imaging of HN5 tumors in tumor-bearing mice. The PDPA-TMR-Fab' was administered to the mice intravenously. The images shown in FIG. 50 are taken 12 hours after injection on the Maestro in vivo imaging system.

Figure 51:
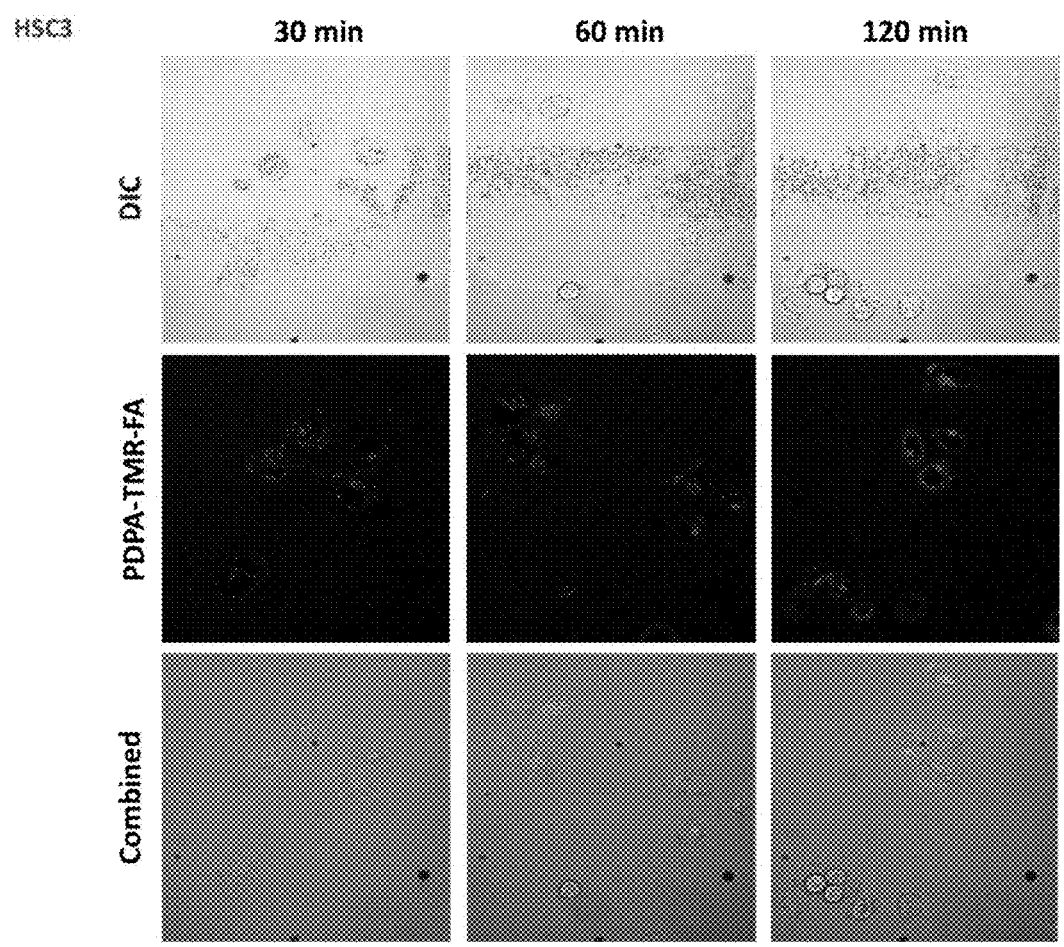
FIG. 51 Staining of A549 cells at 30, 60, and 120 minutes after exposure to a FA containing nanoprobe. The top two rows show two different imaging, the top being the differential interference contrast channel and the middle row showing the PDPA-TMR-FA channel. The bottom row is the combined image of both channels.

Similarly to the Fab' nanoprobe, a nanoprobe containing folic acid was synthesized by dissolving 10 equivalents of folic acid derivative containing a thiol with a micelle containing 10% PEG-PC7A-maleimide and 1 mM EDTA. The reaction was stirred overnight and then purified and concentrated to 5 mg/mL by micro-ultrafiltration. Using the same cell culturing and in vivo conditions described for the PDPA-TMR-Fab' nanoprobe, the PDPF-TMR-FA nanoprobe was exposed to HSC3 cells. As shown in FIG. 51, the cells clearly fluoresce in when exposed to the folic acid derivatized probe. Additionally, tumors present in the study mice were clearly visible with the addition of the probe in vivo (FIG. 52).

10. Use of Hybrid Micelles for pH Determination a. Method:

Dye conjugation: For dye conjugation, 50 mg of PEG-b-P(DPA-co-AMA3) or PEG-b-(PC7A-co-AMA3) was first dissolved in 2 mL of anhydrous DMF. Then, RhoG-NHS or TMR-NHS ester (1.5 equivalents to the molar amount of the primary amino group) was added. The reaction mixture was stirred at room temperature for two days. The polymer conjugates were purified by preparative gel permeation chromatography (PLgel Prep 10 μm 10E3 Å, 300×25 mm column by Varian, THF as eluent at 5 mL/min) to remove the free dye molecules. The resulting polymer conjugates were lyophilized and stored at −20° C.

Nanoprobe preparation: Ten milligrams of PEG-b-PC7A-RhoG and 10 mg of PEG-b-PDPA-TMR were dissolved in 1 mL THF. Then, the mixture was added into 4 mL of milli-Q water under sonication. The mixture was filtered 4 times to remove THF using the micro-ultrafiltration system.

Characterization of hybrid nanoprobe: The mean count rate (kcps) of the hybrid nanoprobes in different pH buffer solutions were obtained by dynamic light scattering analysis. The final polymer concentration were controlled at 1 mg/mL. The fluorescence spectrum of the hybrid nanoprobe were evaluated by Hitachi fluorometer (F-7500 model). The nanoprobe was diluted in 50 mM PBS buffer (pH 7.4) and excited at 490 nm, and the emission spectra were collected from 500 to 650 nm. Fluorescent images of hybrid nanoprobe solution (0.1 mg/mL) at different pH were captured on Maestro imaging system (CRI Inc) using "blue" and "green" filters.

b. Results:

The mean count rate of hybrid nanoprobe plotted as a function of pH was shown in FIG. 53a. The hybrid nanoprobe shows sequential dissociation at different pH. The hybrid nanoprobe displays two sharp pH transition point at pH 6.8 and pH 6.2. As shown in FIG. 53b, the spectra shows the FRET effect between Rhodamine Green and TMR dyes, indicating the formation of hybrid nanoprobe. Fluorescent images in FIG. 53c demonstrates that the dye-conjugated polymers can be sequentially activated at different pH value, indicating each copolymer still preserved its own pH activation profiles.

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Tsien, R. Y. *Nat. Rev. Mol. Cell. Biol.* 2003, 4, SS16.
Weissleder, R.; Pittet, M. J. *Nature* 2008, 452, 580.
Fernandez-Suarez, M.; Ting, A. Y. *Nat. Rev. Mol. Cell. Biol.* 2008, 9, 929.
Giepmans, B. N. G.; Adams, S. R.; Ellisman, M. H.; Tsien, R. Y. *Science* 2006, 312, 217.
Gross, S.; Piwnica-Worms, D. *Cancer Cell* 2005, 7, 5.
de Silva, A. P.; Gunaratne, H. Q. N.; Gunnlaugsson, T.; Huxley, A. J. M.; McCoy, C.; P.; Rademacher, J. T.; Rice, T. E. *Chem. Rev.* 1997, 97, 1515.
Zhang, J.; Campbell, R. E.; Ting, A. Y.; Tsien, R. Y. *Nat. Rev. Mol. Cell. Biol.* 2002, 3, 906.
Lee, S.; Park, K.; Kim, K.; Choi, K.; Kwon, I. C. *Chem. Commun.* 2008, 4250.
Kobayashi, H.; Choyke, P. L. Acc. *Chem. Res.* 2010, 44, 83.
Lovell, J. F.; Liu, T. W. B.; Chen, J.; Zheng, G. *Chem. Rev.* 2010, 110, 2839.
Ueno, T.; Nagano, T. *Nat. Methods* 2011, 8, 642.
Alberts, B.; Johnson, A.; Lewis, J.; Raff, M.; Roberts, K.; Walter, P. *Molecular Biology of the Cell;* 5th ed.; Garland Science: New York, 2008.
Maxfield, F. R.; McGraw, T. E. *Nat. Rev. Mol. Cell. Biol.* 2004, 5, 121.
Izumi, H.; Torigoe, T.; Ishiguchi, H.; Uramoto, H.; Yoshida, Y.; Tanabe, M.; Ise, T.; Murakami, T.; Yoshida, T.; Nomoto, M.; Kohno, K. *Cancer Treat. Rev.* 2003, 29, 541.
Nishi, T.; Forgac, M. *Nat. Rev. Mol. Cell. Biol.* 2002, 3, 94.
Webb, B. A.; Chimenti, M.; Jacobson, M. P.; Barber, D. L. *Nat. Rev. Cancer* 2011, 11, 671.
Kobayashi, H.; Ogawa, M.; Alford, R.; Choyke, P. L.; Urano, Y. *Chem. Rev.* 2010, 110, 2620.
Han, J. Y.; Burgess, K. *Chem. Rev.* 2010, 110, 2709.
Atkins, P.; De Paula, J. *Physical Chemistry;* Oxford University Press, 2009.
Casey, J. R.; Grinstein, S.; Orlowski, J. *Nat. Rev. Mol. Cell. Biol.* 2010, 11, 50.
Zhang, X.; Lin, Y.; Gillies, R. J. J. *Nucl. Med.* 2010, 51, 1167.
Srikun, D.; Albers, A. E.; Chang, C. J. *Chem. Sci.* 2011, 2, 1156.
Benjaminsen, R. V.; Sun, H. H.; Henriksen, J. R.; Christensen, N. M.; Almdal, K.; Andresen, T. L. *ACS Nano* 2011, 5, 5864.
Albertazzi, L.; Storti, B.; Marchetti, L.; Beltram, F. *J. Am. Chem. Soc.* 2010, 132, 18158.
Urano, Y.; Asanuma, D.; Hama, Y.; Koyama, Y.; Barrett, T.; Kamiya, M.; Nagano, T.; Watanabe, T.; Hasegawa, A.; Choyke, P. L.; Kobayashi, H. *Nat. Med.* 2009, 15, 104.
Li, C.; Xia, J. A.; Wei, X. B.; Yan, H. H.; Si, Z.; Ju, S. H. *Adv. Funct. Mater.* 2010, 20, 2222.
Almutairi, A.; Guillaudeu, S. J.; Berezin, M. Y.; Achilefu, S.; Frechet, J. M. J. *Am. Chem. Soc.* 2007, 130, 444.
Zhou, K.; Wang, Y.; Huang, X.; Luby-Phelps, K.; Sumer, B. D.; Gao, J. *Angew. Chem. Int. Ed.* 2011, 50, 6109-6114.
Dai, S.; Ravi, P.; Tam, K. C. *Soft Matter* 2008, 4, 435.
Gil, E. S.; Hudson, S. M. *Prog. Polym. Sci.* 2004, 29, 1173.
Zhou, K.; Lu, Y.; Li, J.; Shen, L.; Zhang, G.; Xie, Z.; Wu, C. *Macromolecules* 2008, 41, 8927.
Riess, G. *Prog. Polym. Sci.* 2003, 28, 1107.
Lee, E. S.; Shin, H. J.; Na, K.; Bae, Y. H. *J. Controlled Release* 2003, 90, 363.
Kairdolf, B. A.; Nie, S. *J. Am. Chem. Soc.* 2011, 133, 7268.
Ananthapadmanabhan, K. P.; Goddard, E. D.; Turro, N.J.; Kuo, P. L. *Langmuir* 1985, 1, 352.
Ruckenstein, E.; Nagarajan, R. *J. Phys. Chem.* 1975, 79, 2622.
Yezhelyev, M. V.; Qi, L.; O'Regan, R. M.; Nie, S.; Gao, X. *J. Am. Chem. Soc.* 2008, 130, 9006.
Yu, H.; Zou, Y.; Wang, Y.; Huang, X.; Huang, G.; Sumer, B. D.; Boothman, D. A.; Gao, J. *ACS Nano* 2011, 5, 9246.
Valeur, B. *Molecular fluorescence: principles and applications;* Wiley-VCH, 2002.

Lakowicz, J. R. *Principles of Fluorescence Spectroscopy;* 3rd ed.; Springer: New York City, 2006.
Demchenko, A. P. *Introduction to Fluorescence Sensing*; Springer Science: New York, 2008.
Lee, S.; Xie, J.; Chen, X. Y. *Curr. Top. Med. Chem.* 2010, 10, 1135.
West, W.; Pearce, S. *J. Phys. Chem.* 1965, 69, 1894.
López Arbeloa, I.; Ruiz Ojeda, P. *Chem. Phys. Lett.* 1982, 87, 556.
Valdes-Aguilera, O.; Neckers, D. C. *Acc. Chem. Res.* 1989, 22, 171.
Packard, B. Z.; Komoriya, A.; Toptygin, D. D.; Brand, L. *J. Phys. Chem. B* 1997, 101, 5070.
Ogawa, M.; Kosaka, N.; Choyke, P. L.; Kobayashi, H. *ACS Chem. Biol.* 2009, 4, 535.
Johansson, M. K.; Cook, R. M. *Chem. Eur. J.* 2003, 9, 3466.
Scheibe, G. *Z. Angew. Chem.* 1936, 49, 563.
Jelley, E. E. *Nature* 1936, 138, 1009.
Berezin, M. Y.; Achilefu, S. *Chem. Rev.* 2010, 110, 2641.
Weller, A. *Pure Appl. Chem.* 1968, 16, 115.
Wasielewski, M. R. *Chem. Rev.* 1992, 92, 435.
Vogel, S. S.; Thaler, C.; Koushik, S. V. *Sci. STKE* 2006, 2006, re2.
de Silva, A. P.; Gunaratne, H. Q. N.; McCoy, C. P. *Chem. Commun.* 1996, 2399.
Dale, T. J.; Rebek, J. J. *Am. Chem. Soc.* 2006, 128, 4500.
Diaz-Fernandez, Y.; Foti, F.; Mangano, C.; Pallavicini, P.; Patroni, S.; Perez-Gramatges, A.; Rodriguez-Calvo, S. *Chem. Eur. J.* 2006, 12, 921.
Tal, S.; Salman, H.; Abraham, Y.; Botoshansky, M.; Eichen, Y. *Chem. Eur. J.* 2006, 12, 4858.
Petsalakis, I. D.; Lathiotakis, N. N.; Theodorakopoulos, G. *J. Mol. Struct.: THEOCHEM* 2008, 867, 64.
Ohgaki, R.; van Ijzendoorn, S. C. D.; Matsushita, M.; Hoekstra, D.; Kanazawa, H. *Biochemistry* 2010, 50, 443.
Modi, S.; Swetha, M. G.; Goswami, D.; Gupta, G. D.; Mayor, S.; Krishnan, Y. *Nat. Nanotech.* 2009, 4, 325.
Nasongkla, N.; Bey, E.; Ren, J. M.; Ai, H.; Khemtong, C.; Guthi, J. S.; Chin, S. F.; Sherry, A. D.; Boothman, D. A.; Gao, J. M., *Nano. Lett.* 2006, 6, 2427-2430.
Kalyanasundaram, K.; Thomas, J. K., *J. Am. Chem. Soc.* 1977, 99, 2039-2044.
Winnik, F. M., *Chem. Rev.* 1993, 93, 587-614.
Demaurex, N. *News Physiol. Sci.* 2002, 17, 1-5.
Hanahan, D.; Weinberg, R. A., *Cell,* 2011, 144, 646-674.
Gatenby, R. A.; Gillies, R. J., *Nat. Rev. Cancer,* 2008, 8, 56-61.
Swartz, M. A.; et. al.; *Cancer Res.,* 2012, 72, 2473-2480.
Joyce, J. A., *Cancer Cell,* 2005, 7, 513-520.
Weis, S. M., Cheresh, D. A., *Nat. Med.,* 2011, 17, 1359-1370.
Folkman, J., *Nat. Rev. Drug Discovery,* 2007, 6, 273-286.
Webb, B. A.; Chimenti, M.; Jacobson, M. P.; Barber, D. L., *Nat. Rev. Cancer,* 2011, 11, 671-677.
Zhou, K. et. al., *J. Am. Chem. Soc.,* 2012, 134, 7803-7811.
Sonveaux, P., et. al., *J. Clin. Invest.,* 2008, 118, 3930-3942.
Gatenby, R. A.; Gillies, R. J., *Nat. Rev. Cancer,* 2004, 4, 891-899.
Kleiter, M. M. et. al., *Int. J. Radiat. Oncol. Biol. Phys.,* 2006, 64, 592-602.
Huang, X. et. al., *ACS Nano,* 2010, 4, 5887-5896.
Zhou, K. et. al., *Angew. Chem. Int. Ed.* 2011, 50, 6109-6114
Yang C. et. al., *Cancer Res.* 2009, 69, 7986-93.

The invention claimed is:

1. A pH-responsive system comprising:
   (a) a population of first nanoparticles, wherein the first nanoparticles comprise (i) a first block copolymer and (ii) a first fluorescent dye, and further wherein the first nanoparticles have a first pH transition point and a first emission spectra; and
   (b) a population of second nanoparticles, wherein the second nanoparticles comprise (i) a second block copolymer and (ii) a second fluorescent dye, and further wherein the second nanoparticles have a second pH transition point that differs from the first pH transition point of the first nanoparticles and a second emission spectra that differs from the first emission spectra of the first nanoparticles;
   wherein the population of first nanoparticles and the population of second nanoparticles are each independently a copolymer comprising:
   a) a hydrophilic polymer segment according to formula:

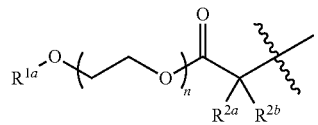

b) a hydrophobic polymer segment according to formula $A^1$; and
   c) a polymer segment according to formula $A^2$;
   or a pharmaceutically acceptable salt thereof; and stereoisomers, isotopic variants and tautomers thereof;
   wherein
   each $A^1$ and $A^2$ is independently selected from

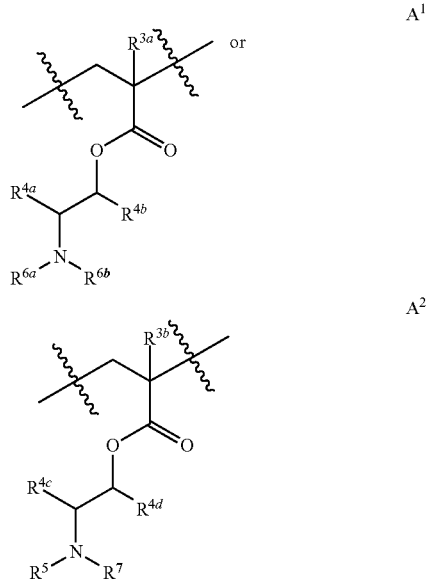

each $R^{1a}$ is independently H, substituted or unsubstituted alkyl, or

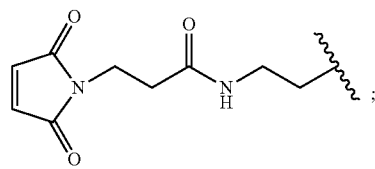 [SMILES: *CCNC(=O)CCN1C(=O)C=CC1=O]

each $R^{2a}$, $R^{2b}$, $R^{3a}$, $R^{3b}$, $R^{4a}$, $R^{4b}$, $R^{4c}$, $R^{4d}$, and $R^5$ is independently H or substituted or unsubstituted alkyl;

each $R^{6a}$, and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye selected from the group consisting of rhodamine, BODIPY, coumarin, and cyanine;

the subscript n is an integer between 10 to 200;

and wherein the copolymer is a random copolymer.

2. The pH-responsive system of claim 1, further comprising a population of third nanoparticles, wherein the third nanoparticles comprise (i) a third block copolymer and (ii) a third fluorescent dye, and further wherein the third nanoparticles have a third pH transition point that differs from the pH transition points of the first and second nanoparticles and a third emission spectra that differs from the emission spectra of the first and second nanoparticles;

wherein the population of third nanoparticles is a copolymer comprising:

a) a hydrophilic polymer segment according to formula:

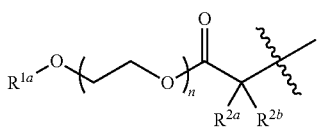

b) a hydrophobic polymer segment according to formula $A^1$; and c) a polymer segment according to formula $A^2$;

or a pharmaceutically acceptable salt thereof; and stereoisomers, isotopic variants and tautomers thereof;

wherein each $A^1$ and $A^2$ is independently selected from

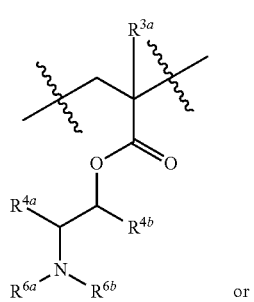

$A^1$ or

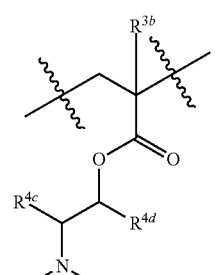

$A^2$ each $R^{1a}$ is independently H, substituted or unsubstituted alkyl, or

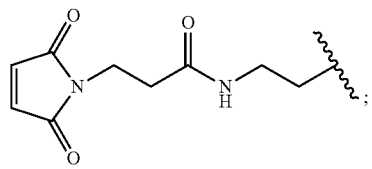 [SMILES: *CCNC(=O)CCN1C(=O)C=CC1=O]

each $R^{2a}$, $R^{2b}$, $R^{3a}$, $R^{3b}$, $R^{4a}$, $R^{4b}$, $R^{4c}$, $R^{4d}$, and $R^5$ is independently H or substituted or unsubstituted alkyl;

each $R^{6a}$, and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye selected from the group consisting of rhodamine, BODIPY, coumarin, and cyanine;

the subscript n is an integer between 10 to 200;

and wherein the copolymer is a random copolymer.

3. The pH-responsive system of claim 1, wherein the block copolymer of the first and/or second nanoparticles comprises at least two monomers with different hydrophobicities.

4. The pH-responsive system of claim 1, wherein the block copolymers of the first and/or second nanoparticles comprise different molar fractions of at least two monomers with different hydrophobicities.

5. The pH-responsive system of claim 1, wherein the first and second fluorescent dyes are pH-insensitive fluorescent dyes.

6. The pH-responsive system of claim 1, wherein the first and second fluorescent dyes have a Stokes shift of $\Delta\lambda<40$ nm.

7. The pH-responsive system of claim 1, wherein the pH transition points of the first and second nanoparticles are between pH 5.0 to pH 8.0.

8. The pH-responsive system of claim 1, wherein the emission spectra of the first and second nanoparticles are between 500-820 nm.

9. The pH-responsive system of claim 1, wherein the pH responses ($\Delta pH_{10-90\%}$) of the first and second nanoparticles are less than 1 pH unit.

10. The pH-responsive system of claim 1, wherein the first and/or second nanoparticles further comprises a targeting moiety.

11. The pH-responsive system of claim 10, wherein the targeting moiety binds a cell surface receptor.

12. A composition comprising a population of first nanoparticles and a population of second nanoparticles, each nanoparticle population having a pH transition point and an emission spectra, wherein the pH transition point and the emission spectra of the population of first nanoparticles and the population of second nanoparticles differ in pH transition point and the emission spectra;

wherein the population of first nanoparticles and the population of second nanoparticles are each independently a copolymer comprising:

a) a hydrophilic polymer segment according to formula:

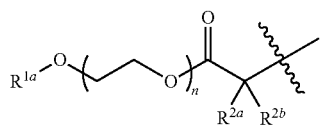

b) a hydrophobic polymer segment according to formula A¹; and c) a polymer segment according to formula A²;

or a pharmaceutically acceptable salt thereof; and stereoisomers, isotopic variants and tautomers thereof;

wherein each A¹ and A² is independently selected from

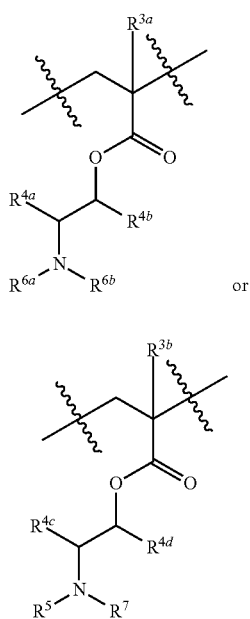

each $R^{1a}$ is independently H, substituted or unsubstituted alkyl, or

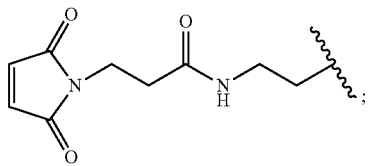 [SMILES: *CCNC(=O)CCN1C(=O)C=CC1=O]

each $R^{2a}$, $R^{2b}$, $R^{3a}$, $R^{3b}$, $R^{4a}$, $R^{4b}$, $R^{4c}$, $R^{4d}$, and $R^5$ is independently H or substituted or unsubstituted alkyl;

each $R^{6a}$, and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye selected from the group consisting of rhodamine, BODIPY, coumarin, and cyanine;

the subscript n is an integer between 10 to 200;

and wherein the copolymer is a random copolymer.

13. The composition of claim 12, wherein the A¹ has the formula:

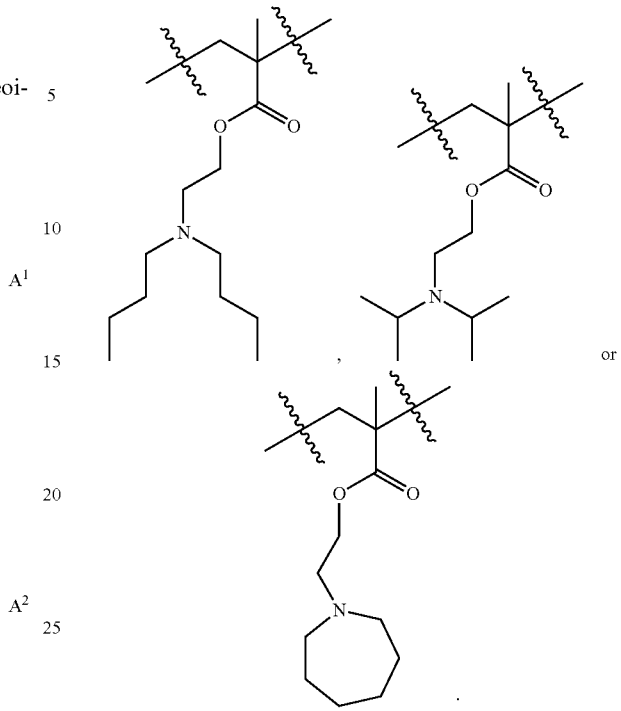

14. The composition of claim 12, wherein A² has the formula:

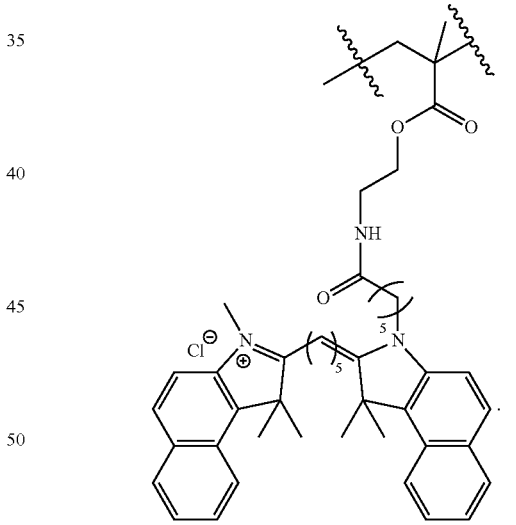

15. The composition of claim 12, wherein the population of first nanoparticles and/or population of second nanoparticles comprise block copolymers comprising different molar fractions of at least two monomers with different hydrophobicities.

16. The composition of claim 12, wherein the population of first nanoparticles and/or population of the second nanoparticles contain about 10% of a maleimide containing copolymer.

17. The composition of claim 12, wherein the population of first nanoparticles and/or population of the second nanoparticles comprise pH-insensitive fluorescent dyes having a Stokes shift of $\Delta\lambda < 40$ nm.

18. The composition of claim 12, wherein the pH transition point of the population of first nanoparticles and the population of second nanoparticles are between pH 5.0 to pH 8.0.

19. The composition of claim 12, wherein the emission spectra of the population of first nanoparticles and population of the second nanoparticles are between 500-820 nm.

20. The composition of claim 12, wherein the pH response ($\Delta pH_{10-90\%}$) of the population of first nanoparticles and the population of second nanoparticles is less than 1 pH unit.

21. The composition of claim 12, wherein the population of first nanoparticles and/or population of the second nanoparticles further comprises a targeting moiety.

22. The composition of claim 21, wherein the targeting moiety binds a cell surface receptor.

23. A composition comprising a first micelle population and a second micelle population, wherein each micelle population comprises a block copolymer and a fluorescent dye, and further wherein the first micelle population has a pH transition point and an emission spectra that differs from the pH transition point and emission spectra of the second micelle population;
wherein the first micelle population and the second micelle population are each independently a copolymer comprising
a) a hydrophilic polymer segment according to formula:

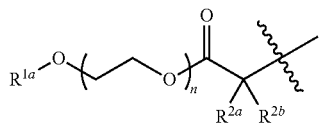

b) a hydrophobic polymer segment according to formula $A^1$; and
c) a polymer segment according to formula $A^2$;
or a pharmaceutically acceptable salt thereof; and stereoisomers, isotopic variants and tautomers thereof;
wherein
each $A^1$ and $A^2$ is independently selected from

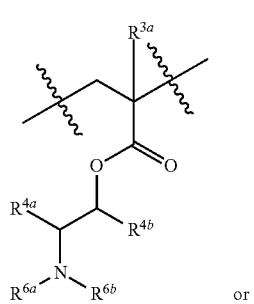

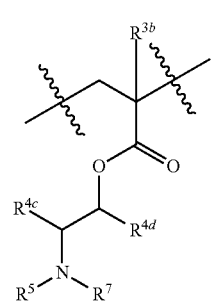

each $R^{1a}$ is independently H, substituted or unsubstituted alkyl, or

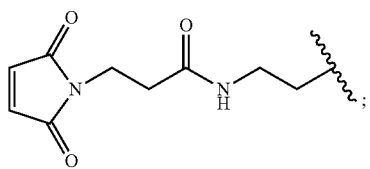 [SMILES: *CCNC(=O)CCN1C(=O)C=CC1=O]

each $R^{2a}$, $R^{2b}$, $R^{3a}$, $R^{3b}$, $R^{4a}$, $R^{4b}$, $R^{4c}$, $R^{4d}$, and $R^5$ is independently H or substituted or unsubstituted alkyl;

each $R^{6a}$, and $R^{6b}$ is independently substituted or unsubstituted alkyl, substituted or unsubstituted aryl, or substituted or unsubstituted heteroaryl; or $R^{6a}$, and $R^{6b}$ taken together with the N atom they are attached to form heterocycle;

$R^7$ is a moiety comprising a dye selected from the group consisting of rhodamine, BODIPY, coumarin, and cyanine;

the subscript n is an integer between 10 to 200;
and wherein the copolymer is a random copolymer.

24. A method of monitoring intracellular pH comprising:
(a) contacting a cell with a composition of claim 23; and
(b) detecting one or more fluorescent signals in the cell, wherein the detection of a fluorescent signal indicates that a micelle population comprising a corresponding fluorescent dye has reached its pH transition point and that the micelle population has disassociated.

25. A method of monitoring cell receptor cycling comprising:
(a) contacting a cell with a composition of claim 23 wherein each micelle population comprises a block copolymer, a fluorescent dye, and a receptor binding moiety;
(b) detecting in the cell or on its surface at least a first and a second fluorescent signal corresponding to the at least first and second fluorescent emission spectra, wherein the detection of the first and second fluorescent signal indicates that each micelle population comprising a corresponding fluorescent dye has reached its pH transition point and that the micelle population has disassociated; and
(c) determining the distribution of the at least first and second fluorescent signals in the cell or on the cell surface.

26. A method of measuring extracellular pH, comprising:
(a) contacting a collection of cells or their extracellular environment with a composition according to claim 23; and
(b) detecting a fluorescent signals in the collection of cells, wherein the detection of a fluorescent signal indicates that a micelle population comprising a corresponding fluorescent dye has reached its pH transition point and that the micelle population has disassociated.

27. A method of imaging a tumor comprising:
(a) contacting the tumor with a composition according to claim 23, wherein each micelle population comprises a block copolymer and a fluorescent dye, and further wherein the first micelle population has a pH transition point between about pH 6.5-7.4 and a first fluorescent emission spectra, the second micelle population has a pH transition point between about pH 5.9-6.4 and a second fluorescent emission spectra, and;

(b) detecting in the tumor a first and second fluorescent signal corresponding to the first and second fluorescent emission spectra, wherein the detection of first and second fluorescent signals indicates that the micelle population comprising a corresponding fluorescent dye has reached its pH transition point and the micelle population has disassociated.

28. A method of imaging circulating tumor cells comprising:
  (a) contacting a circulating tumor cell with a composition according to claim 23, wherein each micelle population comprises a block copolymer and a fluorescent dye, and has a pH transition point between about pH 5.9-6.4, and;
  (b) detecting a fluorescent signals in the circulating tumor cells, wherein the detection of a fluorescent signal indicates that a micelle population comprising a corresponding fluorescent dye has reached its pH transition point and that the micelle population has disassociated.

29. A method of imaging a tumor, a metastatic tumor or a sentinel lymph node of a tumor comprising:
  (a) contacting the tumor, metastatic tumor or sentinel lymph node of a tumor with a composition according to claim 23, wherein each micelle population comprises a block copolymer and a fluorescent dye, and further wherein the first micelle population has a pH transition point between about pH 6.5-7.4 and a first fluorescent emission spectra, the second micelle population has a pH transition point between about pH 5.9-6.4 and a second fluorescent emission spectra, and;
  (b) detecting in the tumor, metastatic tumor or sentinel lymph node of a tumor a first and second fluorescent signal corresponding to the first and second fluorescent emission spectra, wherein the detection of first and second fluorescent signals indicates that the micelle population comprising a corresponding fluorescent dye has reached its pH transition point and that the micelle population has disassociated.

30. The method of claim 27, wherein the tumor is an angiogenic tumor vasculature or a tumor that has metastasized to a lymph node in the regional area of the primary tumor.

31. The method of claim 28, wherein the circulating tumor cell is in lymphatic channels or the bloodstream.

* * * * *